United States Patent
Deering et al.

(10) Patent No.: US 11,284,993 B2
(45) Date of Patent: Mar. 29, 2022

(54) VARIABLE RESOLUTION EYE MOUNTED DISPLAYS

(71) Applicant: Tectus Corporation, Saratoga, CA (US)

(72) Inventors: Michael Frank Deering, Los Altos, CA (US); Alan Huang, Menlo Park, CA (US)

(73) Assignee: Tectus Corporation, Saratoga, CA (US)

( * ) Notice: Subject to any disclaimer, the term of this patent is extended or adjusted under 35 U.S.C. 154(b) by 289 days.

(21) Appl. No.: 15/974,904

(22) Filed: May 9, 2018

(65) Prior Publication Data
US 2018/0256316 A1 Sep. 13, 2018

Related U.S. Application Data

(63) Continuation of application No. 14/590,056, filed on Jan. 6, 2015, now Pat. No. 9,993,335.
(Continued)

(51) Int. Cl.
*A61F 2/16* (2006.01)
*G02B 27/01* (2006.01)
(Continued)

(52) U.S. Cl.
CPC .......... *A61F 2/1613* (2013.01); *A61F 2/1602* (2013.01); *G02B 13/0085* (2013.01); *G02B 13/16* (2013.01); *G02B 27/0093* (2013.01); *G02B 27/0172* (2013.01); *G02C 7/04* (2013.01); *G06F 3/012* (2013.01); *G06F 3/013* (2013.01);
(Continued)

(58) Field of Classification Search
None
See application file for complete search history.

(56) References Cited

U.S. PATENT DOCUMENTS

| 4,871,247 A | 10/1989 | Haynes |
| 5,467,104 A | 11/1995 | Furness, III et al. |

(Continued)

FOREIGN PATENT DOCUMENTS

| JP | H7-121114 A | 5/1995 |
| WO | WO 2016/014118 A1 | 1/2016 |
| WO | WO 2016/022665 A1 | 2/2016 |

OTHER PUBLICATIONS

Jones, R.J.M., "Direct Retinal Imaging and Virtual Displays," RTO HFM Specialists' Meeting on "Human Factors in the 21st Century," Paris France, Jun. 11-13, 2001, 8 pages.
(Continued)

*Primary Examiner* — Amare Mengistu
*Assistant Examiner* — Sarvesh J Nadkarni
(74) *Attorney, Agent, or Firm* — Fenwick & West LLP

(57) ABSTRACT

A display device (e.g., in a contact lens) is mounted on the eye. The eye mounted display contains multiple sub-displays, each of which projects light to different retinal positions within a portion of the retina corresponding to the sub-display. Additionally, a "locally uniform resolution" mapping may be used to model the variable resolution of the eye. Accordingly, various aspects of the display device may be based on the locally uniform resolution mapping. For example, the light emitted from the sub-displays may be based on the locally uniform resolution mapping.

19 Claims, 92 Drawing Sheets

7800 Cross-section through contact lens showing three foveal and six peripheral femto projectors as cylinders

Related U.S. Application Data

(60) Provisional application No. 61/924,924, filed on Jan. 8, 2014.

(51) Int. Cl.

| | | |
|---|---|---|
| *G02B 27/00* | (2006.01) | |
| *G06F 3/01* | (2006.01) | |
| *G09G 3/02* | (2006.01) | |
| *H04N 9/31* | (2006.01) | |
| *G02B 13/00* | (2006.01) | |
| *G02B 13/16* | (2006.01) | |
| *G02C 7/04* | (2006.01) | |
| *G09G 3/00* | (2006.01) | |

(52) U.S. Cl.
CPC ............ *G09G 3/02* (2013.01); *H04N 9/3129* (2013.01); *H04N 9/3197* (2013.01); *G02B 2027/0196* (2013.01); *G09G 3/001* (2013.01)

(56) References Cited

U.S. PATENT DOCUMENTS

| | | |
|---|---|---|
| 5,510,832 A | 4/1996 | Garcia |
| 5,621,424 A | 4/1997 | Shimada et al. |
| 5,680,231 A | 10/1997 | Grinberg et al. |
| 5,682,210 A | 10/1997 | Weirich |
| 5,712,721 A | 1/1998 | Large |
| 6,050,717 A | 4/2000 | Kosugi et al. |
| 6,120,460 A | 9/2000 | Abreu et al. |
| 6,215,593 B1 | 4/2001 | Bruce |
| 6,243,055 B1 | 6/2001 | Fergason |
| 6,307,589 B1 | 10/2001 | Maquire, Jr. |
| 6,312,393 B1 | 11/2001 | Abreu |
| 6,313,864 B1 | 11/2001 | Tabata et al. |
| 6,480,174 B1 | 11/2002 | Kaufmann et al. |
| 6,529,331 B2 | 3/2003 | Massof et al. |
| 6,570,386 B2 | 5/2003 | Goldstein |
| 6,614,408 B1 | 9/2003 | Mann |
| 6,851,805 B2 | 2/2005 | Blum et al. |
| 6,920,283 B2 | 7/2005 | Goldstein |
| 7,137,952 B2 | 11/2006 | Leonardi et al. |
| 7,522,344 B1 | 4/2009 | Curatu et al. |
| 7,542,210 B2 | 6/2009 | Chirieleison, Sr. |
| 7,626,562 B2 | 12/2009 | Iwasaki |
| 7,724,278 B2 | 5/2010 | Maguire, Jr. |
| 7,758,187 B2 | 7/2010 | Amirparviz |
| 8,087,777 B2 | 1/2012 | Rosenthal |
| 8,096,654 B2 | 1/2012 | Amirparviz et al. |
| 8,373,618 B2 | 2/2013 | Friedrich et al. |
| 8,430,310 B1 | 4/2013 | Ho et al. |
| 8,441,731 B2 | 5/2013 | Sprague |
| 8,446,341 B2 | 5/2013 | Amirparviz et al. |
| 8,482,858 B2 | 7/2013 | Sprague |
| 8,579,434 B2 | 11/2013 | Amirparviz et al. |
| 8,582,209 B1 | 11/2013 | Amirparviz |
| 8,608,310 B2 | 12/2013 | Otis et al. |
| 8,721,074 B2 | 5/2014 | Pugh et al. |
| 8,764,185 B1 | 7/2014 | Biederman et al. |
| 8,786,675 B2 | 7/2014 | Deering |
| 8,798,332 B2 | 8/2014 | Otis et al. |
| 8,827,445 B1 | 9/2014 | Wiser et al. |
| 8,870,370 B1 | 10/2014 | Otis et al. |
| 8,874,182 B2 | 10/2014 | Etzkorn et al. |
| 8,911,078 B2 | 12/2014 | Meyers |
| 8,922,898 B2 | 12/2014 | Legerton et al. |
| 8,960,898 B1 | 2/2015 | Etzkorn et al. |
| 8,971,978 B2 | 3/2015 | Ho et al. |
| 8,985,763 B1 | 3/2015 | Etzkorn et al. |
| 8,989,834 B2 | 3/2015 | Ho et al. |
| 9,039,171 B2 | 5/2015 | Groisman |
| 9,040,923 B2 | 5/2015 | Sprague et al. |
| 9,047,512 B2 | 6/2015 | Otis et al. |
| 9,054,079 B2 | 6/2015 | Etzkorn |
| 9,063,351 B1 | 6/2015 | Ho et al. |
| 9,111,473 B1 | 8/2015 | Ho et al. |
| 9,134,546 B2 | 9/2015 | Pugh et al. |
| 9,158,133 B1 | 10/2015 | Pletcher et al. |
| 9,161,712 B2 | 10/2015 | Etzkorn |
| 9,192,298 B2 | 11/2015 | Bouwstra et al. |
| 9,195,075 B2 | 11/2015 | Pugh et al. |
| 9,215,293 B2 | 12/2015 | Miller |
| 9,217,881 B2 | 12/2015 | Pugh et al. |
| 9,244,285 B2 | 1/2016 | Chen et al. |
| 9,271,677 B2 | 3/2016 | Leonardi |
| 9,282,920 B2 | 3/2016 | Ho et al. |
| 9,289,123 B2 | 3/2016 | Weibel et al. |
| 9,289,954 B2 | 3/2016 | Linhardt et al. |
| 9,298,002 B2 | 3/2016 | Border et al. |
| 9,298,020 B1 | 3/2016 | Etzkorn et al. |
| D754,861 S | 4/2016 | O'Driscoll et al. |
| 9,310,626 B2 | 4/2016 | Pugh et al. |
| 9,316,848 B2 | 4/2016 | Pugh et al. |
| 9,326,710 B1 | 5/2016 | Liu et al. |
| 9,332,935 B2 | 5/2016 | Etzkorn et al. |
| 9,341,843 B2 | 5/2016 | Border et al. |
| 9,366,872 B2 | 6/2016 | Honea et al. |
| 9,366,881 B2 | 6/2016 | Pugh et al. |
| 9,389,433 B2 | 7/2016 | Pugh et al. |
| 9,442,307 B2 | 9/2016 | Meyers |
| 2001/0035845 A1 | 11/2001 | Zwern |
| 2002/0039085 A1 | 4/2002 | Ebersole et al. |
| 2002/0089469 A1 | 7/2002 | Cone et al. |
| 2002/0113756 A1 | 8/2002 | Tuceryan et al. |
| 2002/0154214 A1 | 10/2002 | Scallie et al. |
| 2004/0046711 A1 | 3/2004 | Triebfuerst |
| 2004/0061663 A1 | 4/2004 | Reynolds et al. |
| 2004/0246588 A1 | 12/2004 | Grego |
| 2005/0024586 A1 | 2/2005 | Teiwes et al. |
| 2005/0264527 A1 | 12/2005 | Lin |
| 2005/0280603 A1 | 12/2005 | Aughey et al. |
| 2006/0007056 A1 | 1/2006 | Ou |
| 2006/0033879 A1 | 2/2006 | Covannon et al. |
| 2006/0038881 A1 | 2/2006 | Starkweather et al. |
| 2006/0044265 A1 | 3/2006 | Min |
| 2006/0227067 A1* | 10/2006 | Iwasaki ................ G02B 27/017 345/8 |
| 2006/0290882 A1 | 12/2006 | Meyers et al. |
| 2007/0188407 A1 | 8/2007 | Nishi |
| 2007/0205084 A1 | 9/2007 | Kobayashi et al. |
| 2007/0229397 A1 | 10/2007 | Sefton |
| 2008/0002262 A1 | 1/2008 | Chirieleison |
| 2008/0024392 A1 | 1/2008 | Gustafsson et al. |
| 2008/0309586 A1 | 12/2008 | Vitale |
| 2009/0163898 A1 | 6/2009 | Gertner et al. |
| 2009/0189830 A1* | 7/2009 | Deering ................ G09G 3/02 345/1.3 |
| 2009/0244477 A1* | 10/2009 | Pugh ................ B29D 11/00125 351/158 |
| 2009/0303159 A1 | 12/2009 | Gustafsson et al. |
| 2010/0001926 A1* | 1/2010 | Amirparviz .......... A61B 5/1455 345/7 |
| 2010/0085462 A1 | 4/2010 | Sako et al. |
| 2010/0234717 A1 | 9/2010 | Wismer |
| 2010/0302356 A1 | 12/2010 | Sinivaara |
| 2011/0043436 A1 | 2/2011 | Yamamoto |
| 2011/0102558 A1 | 5/2011 | Moliton et al. |
| 2014/0016097 A1 | 1/2014 | Leonardi et al. |
| 2014/0036172 A1* | 2/2014 | Trajkovska-Broach ..................... G02C 7/083 349/13 |
| 2014/0132904 A1* | 5/2014 | Bos .................. G02F 1/134309 349/139 |
| 2014/0192311 A1 | 7/2014 | Pletcher et al. |
| 2014/0204003 A1 | 7/2014 | Deering |
| 2014/0240665 A1 | 8/2014 | Pugh et al. |
| 2014/0327875 A1* | 11/2014 | Blum ................... A61F 2/1618 351/159.03 |
| 2015/0088253 A1 | 3/2015 | Doll et al. |
| 2015/0150510 A1 | 6/2015 | Leonardi et al. |
| 2015/0261294 A1 | 9/2015 | Urbach |
| 2015/0281411 A1 | 10/2015 | Markus et al. |
| 2015/0339857 A1 | 11/2015 | O'Connor et al. |
| 2015/0362750 A1 | 12/2015 | Yeager et al. |

(56) References Cited

U.S. PATENT DOCUMENTS

| | | | |
|---|---|---|---|
| 2015/0362752 A1 | 12/2015 | Linhardt et al. | |
| 2016/0030160 A1 | 2/2016 | Markus et al. | |
| 2016/0066825 A1 | 3/2016 | Barrows et al. | |
| 2016/0091737 A1* | 3/2016 | Kim | G02C 11/10 351/158 |
| 2016/0113760 A1 | 4/2016 | Conrad | |

OTHER PUBLICATIONS

Leonardi, M. et al., "Wireless Contact Lens Sensor for Intraocular Pressure Monitoring Assessment on Enucleated Pig Eyes," Acta Ophthamologica, 2009, pp. 433-437, vol. 87.

PCT International Search Report and Written Opinion, PCT/US2009/031902, dated Mar. 6, 2009, 8 Pages.

PCT International Search Report and Written Opinion, PCT/US2009/032024, dated Apr. 27, 2009, 9 Pages.

Sather, K., "Potential platform for superhuman vision in developmental UW," KING5.com, Jan. 17, 2008, 2 Pages, [online] [Retrieved on Jun. 13, 2008] Retrieved from the internet http://www.king5.eom/health/stories/NW_011708WAB_electronic_contacts_KS.2fdcdeaa . . . >.

United States Office Action, U.S. Appl. No. 12/359,211, dated Aug. 27, 2013, 8 pages.

United States Office Action, U.S. Appl. No. 12/359,211, dated Feb. 24, 2012, 7 pages.

United States Office Action, U.S. Appl. No. 12/359,211, dated Jan. 4, 2013, 9 pages.

United States Office Action, U.S. Appl. No. 12/359,211, dated Sep. 12, 2013, 19 pages.

United States Office Action, U.S. Appl. No. 12/359,211, dated Mar. 25, 2014, 33 pages.

United States Office Action, U.S. Appl. No. 12/359,951, dated Dec. 22, 2011, 13 pages.

United States Office Action, U.S. Appl. No. 12/359,951, dated Jul. 20, 2012, 12 pages.

U.S. Appl. No. 61/023,073, filed Jan. 23, 2008, Inventors Michael Frank Deering et al.

U.S. Appl. No. 61/023,833, filed Jan. 26, 2008, Inventor Michael Frank Deering.

United States Office Action, U.S. Appl. No. 14/590,056, dated Jun. 1, 2017, 10 pages.

* cited by examiner

800 Vertical cross section of human eye

1200 Close up of HMD Wavefronts

2100 A hexagon on its side

2110 A Hexagon on its side

2200 A hexagon on its end

2210 A Hexagon on its end

2600 The short diagonals of a hexagon on its end

2620 The short diagonal of a hexagon

2620

2620

2610 A Hexagon on its end

2700 Tiling of hexagons on their side

2710 A Tiling of hexagons on their side

2800 Tiling of hexagons on their end

2810 A Tiling of hexagons on their end

2900 The long pitch of a hexagonal tiling

2910 A tiling of hexagons

2920 The long pitch of a hexagonal tiling

3100 Even rows of a tiling of hexagons on their end

3110   Even rows of a hexagional tiling

3300 The first even row of a tiling of hexagons on their end

3310 The first even row of a hexagional tiling

3400 The first odd row of a tiling of hexagons on their end

3410
The first odd row of a hexagional tiling

3500 The first semi-column of a tiling of hexagons on their end

3510 The first semi-column of a hexagional tiling

3600 The second semi-column of a tiling of hexagons on their end

3700 The semi-column numbers of the first row of a tiling of hexagons on their end 3710 First row semi-column of a hexagional tiling 3800 The semi-column numbers of the second row of a tiling of hexagons on their end 3810
Second row semi-column of a hexagional tiling 3900 The integral addresses of a tiling of hexagons on their end 3910 Hexagon with 2D integeral address (0,0)

4000 The height unit-width hexagon in a of a tiling of hexagons on their end

4010 Height of a unit-width hexagon on its end

4100 The row to row pitch of a tiling of unit width hexagons on their end

4110 The pitch between even and odd rows of hexagons

4200 A 1-group of hexagons on their end

4210 A 1-group of hexagons on their end

4400 A 3-group of hexagons on their end

4410 A 3-group of hexagons on their end

4500 A 4-group of hexagons on their end

4510 A 4-group of hexagons on their end

4700 A square on its side

4710 A square on its side

4800 A square on its end

4810 A square on its end

4900 The long diagonals of a square on its side

4920 The long diagional of a square

4910 A square on its side

5200 The short diagonals of a square on its end

5220 The short diagional of a square

5210 A square on its end

5300 The long pitch of a square tiling

5320 The long pitch of a square tiling

5400 The short pitch of a square tiling

5420 The short pitch of a square tiling

5500 Locally uniform resolution mapping

5510 Square pixels on the ScreenSurface

5520 Polar wedges on the ViewPlane 5600 28 hexagonally shaped projectors in 7 circles of 4

5700 35 hexagonally shaped projectors in 7 circles of 5

5800 42 hexagonally shaped projectors in 7 circles of 6

5900 49 hexagonally shaped projectors in 7 circles of 7

6000 56 hexagonally shaped projectors in 7 circles of 8

6100 Foveal region of variable resolution projectors, then plus 7 fixed resolution projectors Variable resolution projectors 6110

Variable resolution projectors plus 7 fixed resolution projectors 6120

6200 Foveal region of a combination of variable and 13 fixed resolution projectors 6300 30 variable resolution plus 13 fixed resolution projectors 6400 49 and 55 hexagonally shaped projectors 49 hexagonally shaped projectors 6410

55 hexagonally shaped projectors 6420

6500 61 and 67 hexagonally shaped projectors 61 hexagonally shaped projectors 6510

67 hexagonally shaped projectors 6520

6600 A 3-group 7 hexagon wide fixed resolution 37 pixel projector

6700 A 7-group 15 hexagon wide fixed resolution 169 pixel projector

6800 A 15-group 31 hexagon wide fixed resolution 721 pixel projector

6900 A 31-group 63 hexagon wide fixed resolution 2,977 pixel projector

7000 A 63-group 127 hexagon wide fixed resolution 12,097 pixel projector

7100 A 5-group 11 hexagon wide variable resolution 91 pixel projector

7200 A 10-group 21 hexagon wide variable resolution 331 pixel projector

7300 A 20-group 41 hexagon wide variable resolution 1,261 pixel projector

7400 A 40-group 81 hexagon wide variable resolution 4,921 pixel projector

7800 Cross-section through contact lens showing three foveal and six peripheral femto projectors as cylinders 7900 Cross-section through contact lens showing three foveal and six peripheral femto projector optics 8200 Top view of display mesh with corner reflector tracking detail 8210 Tracker marker 8220 Tracker marker detail 8300 Display mesh top and side view 8310 Top view of display mesh 8320 Side view of display mesh 8400 Display mesh display controller die data to individual femto projector die wiring paths 8600 Detail of display mesh display controller die data to individual femto projector die wiring paths 8610 Wire bundle 8700 Femto projector blocking portions of contact lens optical zone 8800 The 43 femto projectors individually numbered 9200 Relationships to the ViewPlane

VARIABLE RESOLUTION EYE MOUNTED DISPLAYS

CROSS-REFERENCE TO RELATED APPLICATIONS

This application is a continuation of U.S. patent application Ser. No. 14/590,056, filed Jan. 6, 2015, now U.S. Pat. No. 9,993,335; which claims the benefit of U.S. Provisional Application No. 61/924,924, filed Jan. 8, 2014, which are both incorporated by reference in their entirety.

This application relates to U.S. patent application Ser. No. 12/359,211, "Eye Mounted Displays," by Michael Deering and Alan Huang, filed on Jan. 23, 2009, and U.S. patent application Ser. No. 12/359,951, "Systems Using Eye Mounted Displays," by Michael Deering, filed on Jan. 26, 2009. The subject matter of all of the foregoing is incorporated herein by reference in their entirety.

BACKGROUND OF THE INVENTION

1. Field of the Invention

This invention relates generally to visual display technology. More particularly, it relates to display technology for eye mounted display, and specifically to contact lens displays.

2. Description of the Related Art

More and more our technological society relies on visual display technology for work, home, and on-the-go use: document and productivity applications, text messages, email, internet access, voice calls, games, HDTV, video on demand, still and video cameras, etc. These services are delivered over different devices that mainly vary in size, for example, smartphones, dedicated digital cameras, dedicated portable game devices, tablets, laptops, desktops, TV sets, game consoles, and servers (including the cloud). What these all (but the last) have in common is a dedicated display, mainly constrained by the physical size of the particular device. Restrictions in size limit the possible field of view, which limits not just the resolution but scale of information and context available. Larger physical display sizes alleviate such limits, but rule out portability, and increases power requirements as well as cost. While there is some convergence in devices, e.g. smartphones are commonly used instead of dedicated small digital cameras, physical display size currently limits how far such convergence can go. For example, the electronics of a modern smartphone, tablet, and low power laptop are effectively identical, except for the physical display device and the incremental additional physical battery size required to power it. Thus there is a need for improvements in display technologies with respect to spatial resolution, quality, field of view, portability (both size and power consumption), cost, etc.

However, the current crop of display technologies makes a number of tradeoffs between these goals in order to satisfy a particular market segment. For example, direct view color CRTs do not allow direct addressing of individual pixels. Instead, a Gaussian spread out over several phosphor dots (pixels) both vertically and horizontally (depending on spot size) results. Direct view LCD panels have generally replaced CRTs in most computer display and TV display markets, but at the trade-offs of temporal lag in sequences of images, lower color quality, lower contrast, and limitations on viewing angles. Display devices with resolutions higher than the 1920×1024 HDTV standards are now available, but at substantially higher cost. The same is true for displays with higher dynamic range or high frame rates. Projection display devices can now produce large, bright images, but at substantial costs in lamps and power consumption. Displays for cell phones, tablets, handheld games, small still and video cameras, etc., must currently seriously compromise resolution and field of view. Within the specialized market where head mounted displays are used, there are still serious limitations in resolution, field of view, undo warping distortion of images, weight, portability, cosmetic acceptability, and cost.

The existing technologies for providing direct view visual displays include CRTs, LCDs, OLEDs, OLED on silicon, LEDs, plasma, SEDs, liquid paper, etc. The existing technologies for providing front or rear projection visual displays include CRTs, LCDs, DLP™, LCOS, linear MEMs devices, scanning laser, etc. All these approaches have much higher costs when higher light output is desired, as is necessary when larger display surfaces are desired, when wider useable viewing angles are desired, for stereo display support, etc.

Another general problem with current direct view display technology is that they are all inherently limited in the perceivable resolution and field of view that they can provide when embedded in small portable electronics products. Only in laptop computers (which are quite bulky compared to cell phones, tablets, hand held game systems, or small still and/or video cameras) can one obtain higher resolution and field of view in exchange for size, weight, cost, battery weight and life time between charges. Larger, higher resolution direct view displays are bulky enough that they must remain in the same physical location day to day (e.g., large plasma, LCD, or OLED display devices).

One problem with current rear projection display technologies is that they tend to come in very heavy bulky cases to hold folding mirrors. And to compromise on power requirement and lamp cost most use display screen technology that preferentially passes most of the light over a narrow range of viewing angles.

One problem with current front projection display technology is that they take time to set up, usually need a large external screen, and while some are small enough to be considered portable, the weight savings comes at the price of color quality, resolution, and maximum brightness. Many also have substantial noise generated by their cooling fans.

Current head mounted display technology have limitations with respect to resolution, field of view, image linearity, weight, portability, and cost. They either make use of display devices designed for other larger markets (e.g., LCD devices for video projection), and put up with their limitations; or custom display technologies must be developed for what is still a very small market. While there have been many innovative optical designs for head mounted displays, controlling the light from the native display to the device's exit pupil can result in bulky, heavy optical designs, and rarely can see-through capabilities (for augmented reality applications, etc.) be achieved. While head mounted displays require lower display brightness than direct view or projection technologies, they still require relatively high display brightness because head mounted displays must support a large exit pupil to cover rotations of the eye, and larger stand-off requirements, for example to allow the wearing of prescription glasses under the head mounted display.

Thus, there is a need for new display technologies to overcome the resolution, field of view, power requirements, bulk and weight, lack of stereo support, frame rate limitations, image linearity, and/or cost drawbacks of present display technologies

BRIEF DESCRIPTION OF THE DRAWINGS

The invention has other advantages and features which will be more readily apparent from the following detailed description of the invention and the appended claims, when taken in conjunction with the accompanying drawings, in which:

Figure 1:
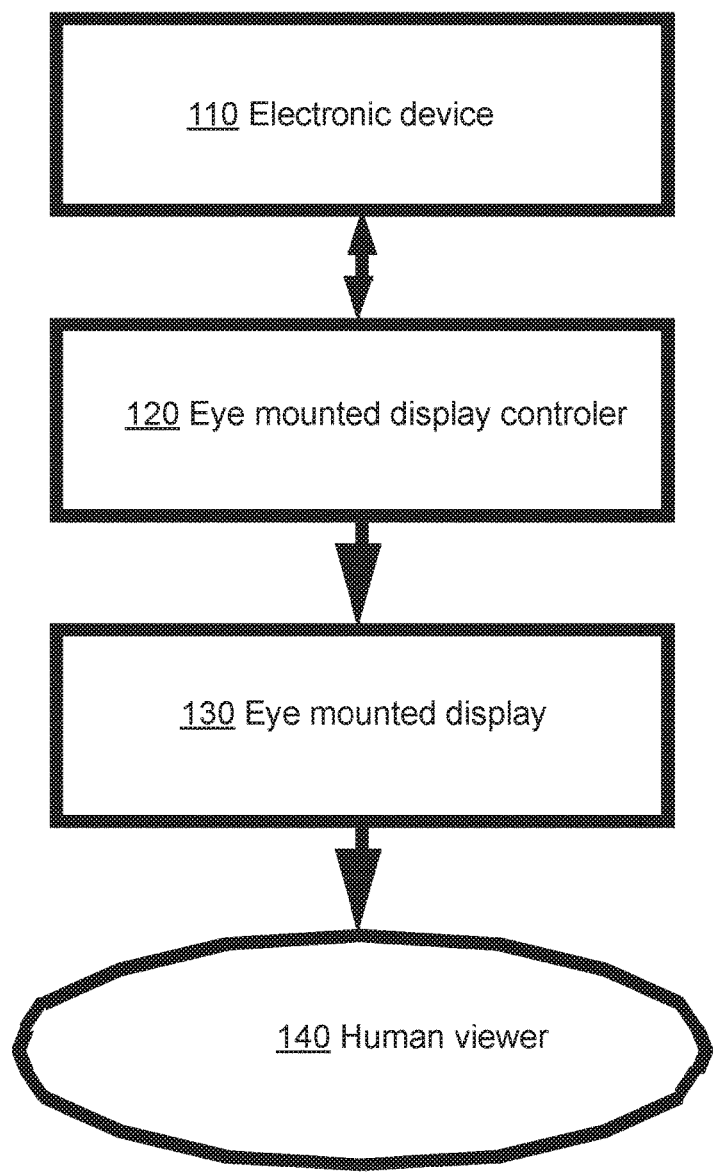
FIG. 1 is an electronic device desiring visual output, an eye mounted display controller, an eye mounted display, and a human user.

All figures include an element with a number the same as the figure number except multiplied by 100: this is always the title element for the figure.

DETAILED DESCRIPTION OF THE PREFERRED EMBODIMENTS

Outline

I. Overview
II. Anatomical and Visual Definitions
 II.A. Terminology
 II.B. Retinal Definitions
 II.C. Axis: Classical Optical vs. the Human Eye
 II.D. Important Retinal Neural Cell Types
III. Mathematical Definitions
 III.A. Mathematical Conventions
 III.B. Hexagonimania
 III.C. Mathematical Definitions of the ViewSphere and Related Concepts
 III.D. Scale Changes between the ScreenSurface and ViewSpaceVS
 III.E. Re-Definition of Resolution
IV. The Variable Resolution Nature of the Human Eye
V. Optical Function Required for Eye Mounted Displays
VI. Optical Function of a Contact Lens Display
VII. Variable Resolution Mappings for Contact Lens Displays
VIII. Means to Display Variable Resolution Pixels
 VIII.A. Pixel Tilings Overview
 VIII.B. Projector Tilings
 VIII.C. Pixel Tilings Details
 VIII.D. Sub-Sampling of Color for an Eye Mounted Display
 VIII.E. Computer Graphics Real-Time Variable Resolution Rendering
 VIII.F. Generation of Discrete Pixel Component Values from the Super-Sample Buffer
 VIII.G. Computer Graphics Real-Time Rendering of Arbitrary Pre-Inverse Distortion of Pixels
 VIII.H. Using Computer Graphics Real-Time Rendering of Arbitrary Pre-Inverse-Distortion of Pixels to Compensate for a Varity of Optical and Manufacturing Based Distortions
 VIII.I. Issues of Depth of Focus and Presbyopia.
IX. Physical Construction of the Display Mesh
 IX.A. Material Considerations
 IX.B. One Possible Solution: the Display Mesh
 IX.C. Wiring up the Display Mesh
 IX.D. Fabricating and Assembling the Display Mesh
X. Areas of Note I. Overview This patent relates to the optical elements of an eye mounted display, including how to construct a variable resolution display, how a computer graphics and/or video system can properly generate variable resolution pixels for such a display, and how the optical and structural elements may be fabricated and assembled.

An eye mounted display is a display device that is mounted to some exterior or interior portion of the human eye, and rotates along with rotations of the eye. The display can be hard fixed to the eye, or slide around some relative to the eye, much as current contact lenses do. The display can be mounted anywhere in the optical path of the human eye. It could be mounted offset from the cornea, allowing an air interface between the display and the cornea. It could be mounted on top of the tear layer of the cornea (much as current contact lenses are). It could be mounted directly on top of the cornea (but then would have to provide the biological materials to maintain the cornea cells). It could be mounted inside of, in place of, or to the posterior of the cornea. All of these mounting options discussed so far for eye mounted displays would be also more narrowly classified as cornea mounted displays (CMD's).

The eye mounted display could be mounted within the aqueous humor, between the cornea and the crystalline lens, just as present so called "inter-ocular" lenses are. Such an eye mounted display would be more narrowly defined as an inter-ocular mounted display.

Just as an eye mounted display could be mounted in front, inside, posterior to, or in place of the cornea, instead these options could be applied to the crystalline lens. These would be lens mounted displays.

Finally, an eye mounted display could be mounted on the surface of the retina itself. In this one case many less optical components are needed; the display pixels are placed right above the cones to be displayed to. Although such a "retina mounted display" would have some issues with how to best surgically implant it; such a display might also act as a pressure bandage and prevent (or slow down) macular degeneration.

For an eye mounted display to be effective, the overall display system has to know to high accuracy the orientation of the eye relative to the head at all times. Several types of devices can provide such tracking; for the special case of cornea mounted displays fixed in position relative to the cornea, the problem devolves to the much simpler problem of tracking the orientation (and movement direction and velocity) of the cornea display; special fiducial marks on the surface of the cornea mounted display can make this a fairly simple problem to solve. Other types of the eye mounted displays may require different solutions to the problem of tracking the orientation of the eye to sufficient accuracy.

Eye mounted displays have two properties that generally external display technologies cannot (easily) take advantage of. First, because the display is mounted right on the cornea, only the amount of light that actually will enter the eye (through the pupil) has to be produced. These savings are substantial; for an eye mounted display to produce the equitant retinal illumination as a 2,000 lumen video projector viewed from 8 feet away, the eye mounted display will only need to produce on one one-thousandth or less of a lumen: a factor of a million less photons.

A second inherent advantage of an eye mounted display is that the number of "pixels" that have to be generated can be matched to the much lower number of cones (and effective cone groupings in the periphery) (approximately 400,000) as opposed to having to produce the highest foveal resolution everywhere on the external display surface. (Technically, what has to be matched is the number of retinal midget ganglion neuron cells, of the "ON" type.) As an example, an eye mounted display with only 400,000 physical pixels can produce imagery that an external display may need 100 million or more pixels to equal (a factor of 200 less pixels).

In modern times, the human eye is easiest described as a kind of video camera—both video cameras and eyes capture photons over time impinging upon them from different directions in the physical world. But in virtually all man-made cameras (as well as displays), all pixels are the same size: they have effectively the same resolution; while the "pixels" of the human eye (called retinal receptor fields) vary in area by a factor of more than one thousand: the human eye not only is variable in its resolution, it is highly variably in its resolution. Despite holding great potential for improving display quality while simultaneously reducing the computational load, this variable resolution nature of the eye has for the most part not been exploited by any of our now obliquities video technology. There is a simple reason for this: up to now it has been very hard to do so. You can't record variable resolution video, you don't know where the end-viewers are going to look. You can't reduce the cost of a display for the same reason. And all of our video infrastructure is based on constant resolution. All of our technology for rendering real-time 3D images only knows how to do so for (what we think of as) constant resolution pixels.

The technology described here changes all that. An eye mounted display, such as a contact lens based display, one for each eye, has its physical output pixels always where the eye is looking—so the pixels can be manufactured of variable size, exactly matching the variable size of the eye's input pixels. A new rendering technology allows all the enormous advances in 3D graphics rendering architectures to work directly in variable resolution pixel space—where more than an order of magnitude less pixels have to be rendered.

An eye-mounted display, such as a contact-lens display, can be designed such that it can produce light from pixels that have been crafted to be in a space close to one-to-one with the location and size of the center portions of the retinal receptor fields of the human eye. Because this is a variable resolution space, only the position-based spatial frequencies that the retina can perceive need to be rendered—but one needs a renderer that can advantageously do so. Later we will describe how the traditional computer graphics pipeline of points in three dimensional space being projected into uniform planer two dimensional screen space for rendering can be extended to projecting into a two dimensional but non-uniform non-planer screen rendering space that does match the variable resolution and spherically curved surface of the human eye's retinal receptor fields.

Although the human eye has long since known to have a spherical imaging surface, most past analyses of the eye have used the more familiar mathematical planer projection model employed by most man-made cameras, projectors, and computer rendering. Here new mathematical techniques are developed to not only to understand imaging on a spherical surface, but also how to understand what it means when the pixels on the spherical surface are extremely variable in resolution. Now the concept of variable perceptual resolution can be precisely defined and modeled. This technique can be reversed and used to develop variable resolution pixel mappings with desired properties. A new mapping similar to that of spatially variant resolution follows when the constraint of local orientation preservation is applied; this "locally uniform resolution" mapping matches much of the variable resolution of the human eye. It is also used to create a tiled array of very small projectors, small enough to fit within a contact lens, that only have as many pixels as the human eye does.

A standard question is how a display device within a contact lens can generate images that will come into focus on the surface of the retina? One obviously cannot focus on images that are directly on top of one's cornea! The details of the types of optical wavefronts that can be normally focused on the retina, and how to generate them from within a contact lens are developed. The generation of the proper wavefronts involves a large number of small projectors, each containing several thousand pixels. How all these small projectors and their structural supports can be fabricated out of just four separate injection molded parts (or their equitant) is described. Techniques to allow computer graphics pre-distortion of the rendered images reduce or eliminate distortions due to the limits of fabrication and assembly techniques will be described.

FIG. 1 shows the solution in a general context. Element 110 is any form of electronic device that desires to have a visual output. Element 120 consists of all of the elements of an eye mounted display system that are required beyond the physical display device mounted on or in the eye itself. Element 130 is the physical display device that is mounted on or in the eye itself. Element 140 is the human viewer.

Figure 2:
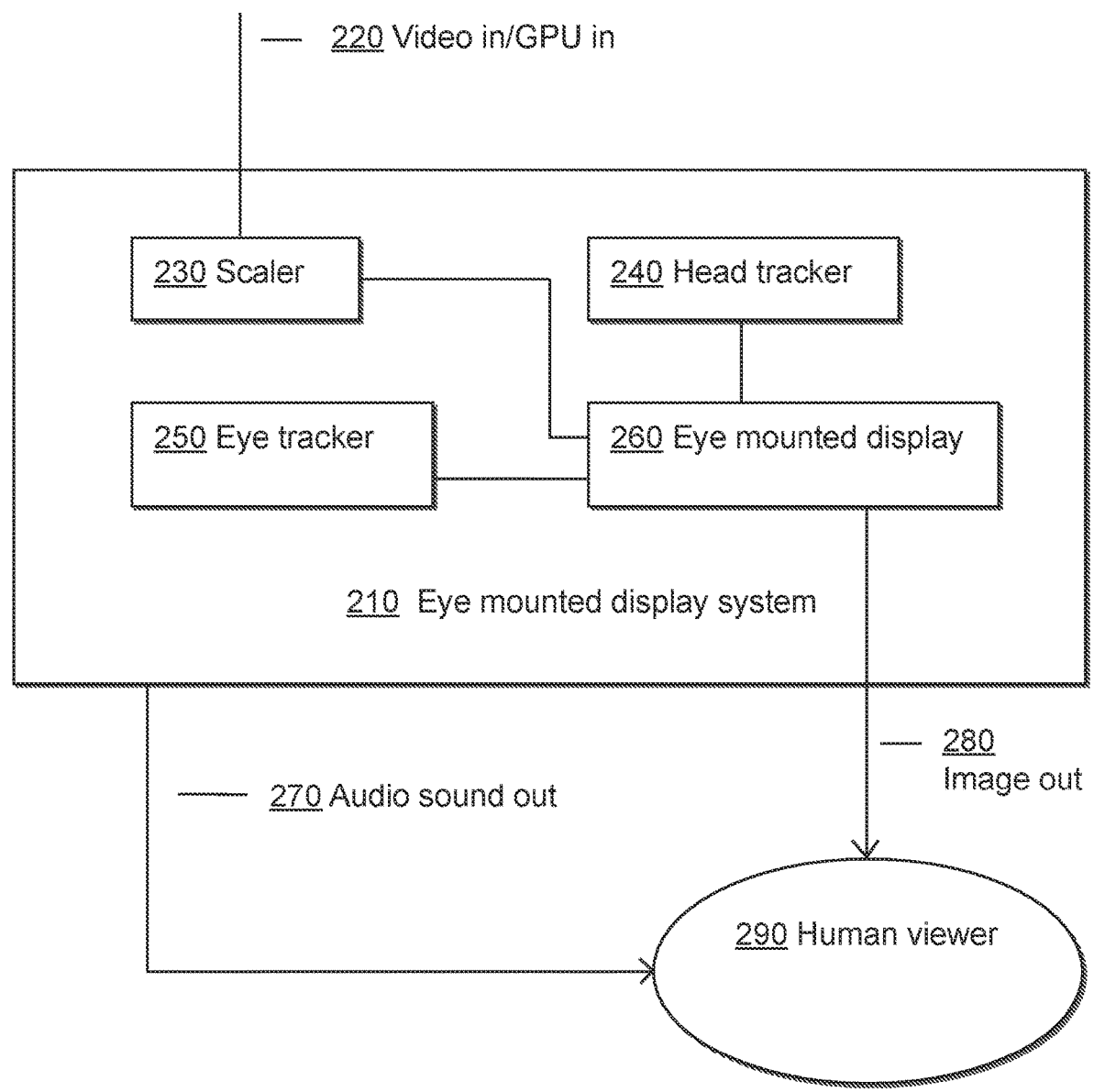
FIG. 2 is an eye mounted display system.

FIG. 2 is a logical diagram of a complete eye mounted display system element 210 along with the human viewer 290. The four most important sub-elements of the eye mounted display system element 210 are shown within it. Element 230, the scaler, is the subcomponent that converts either video streams or GPU instructions element 220 into a frame buffer of variable resolution samples, which are then converted into output pixels for the eye mounted display element 260. The position and orientation of the head of the human viewer element n is tracked by the head tracker element 240. The position and orientation of the eye of the human viewer element 290 is tracked by the eye tracker element 250. The eye mounted display element 260 produces a visual image element 280 that can be perceived by the human viewer element 290. Audio output element 270 is also produced for consumption by the human viewer element 290.

Figure 3:
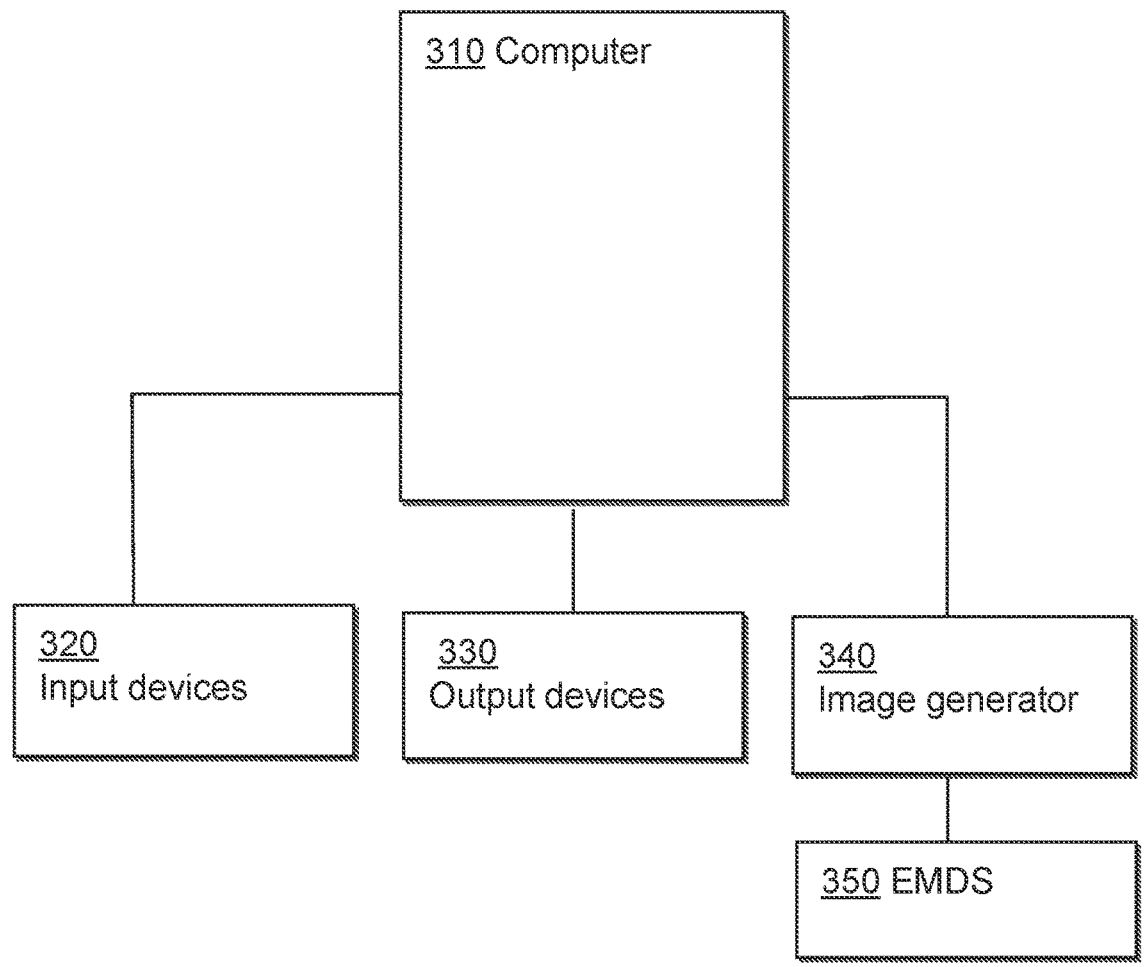
FIG. 3 is a large configuration of an eye mounted display system.

FIG. 3 shows an eye mounted display system element 350 in the context of a traditional computer element 310. The computer has input devices element 320, and output devices element 330, and an image generator element 340 (commonly a graphics card, or graphics chip, or portion of a chip dedicated to graphics). The standard video output of the image generator can be connected to the eye mounted display system element 350 for display to the human viewer. Alternately, the eye mounted display system element 350 can also serve as the image generator directly.

Figure 4:
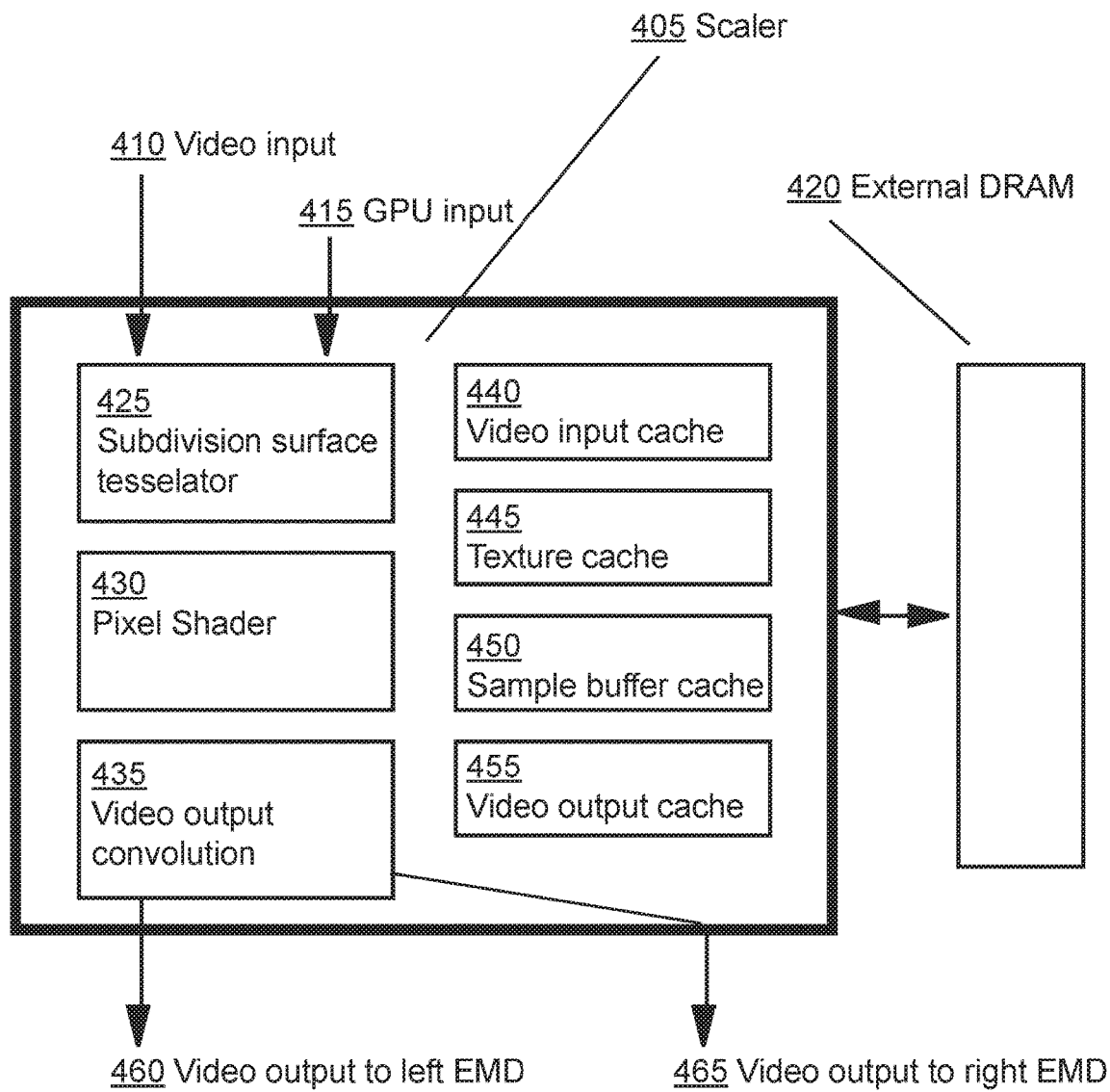
FIG. 4 is a block diagram of a scaler.

FIG. 4 shows a block diagram of a scaler element 405, which was element 230 of FIG. 2. The scaler can accept video input element 410, and optionally also accept graphics GPU input element 415. The scaler may contain a higher order surface tessellator element 425. It may also contain a pixel shader element 430. The scaler contains a video output convolver element 435. Video frames, textures, and other large data elements are preferably stored in an external bank of DRAM element 420. To speed access to this external data, preferably several caches are provided. Element 440 is a video input cache. Element 445 is a texture cache. Element 450 is a sample buffer cache. Element 455 is a cache of samples waiting to be convolved for video output. There are two (logical) video outputs, element 460 for the left eye, and element 465 for the right eye. They are "logical" because the scaler may not be connected directly to the eye mounted displays, but indirectly via other elements. Preferentially, the scaler element 405 is contained within a single chip.

II. Anatomical and Visual Definitions

This section defines several specialized anatomical and visual terms related to the human eye. They are precisely defined here because unfortunately their usage is not consistent within the literature.

II.A. Terminology

We have both left and right eyes. Internally they are not the same, but mirror images of each other (e.g., as is true for our left and right hands, etc.). In order to talk about anatomical features of the eye, the literature has adopted a terminology that is left/right eye agnostic. The term nasal means "in the direction of the nose," and due to the mirror symmetry, can describe the location of features of either eye. The opposite of nasal is the term temporal: "in the direction of the temple." While the eyes have are the same, not mirrored, in the vertical direction, still in the literature the terms superior and inferior are used for the directions up and down. To unambiguously define what is meant by front and back, the term anterior and posterior are defined to mean the front (where the light comes in the cornea) and rear (where the optic nerve leaves) of the eye, respectively.

Because the optics of the eye inverts the image on the retina (as with most man-made cameras), a location in visual space will correspond to an inverted (both horizontally and vertically) location on the inner surface of the eye (the retina). This means that the location of an anatomical feature on the retina is reversed depending upon whether one is asking for its location on the surface of the retina (as one is looking at the eye from behind the eye), or the location in visual space. A good example of all this is the blind spot. We have one in each eye. Looking out into the world, visually the blind spot of the right eye appears to the right of center (temporal), but physically its location on the retina is inverted, and thus is located to the left of center (nasal). The situation for the left eye is reversed, except the words temporal and nasal don't change.

Due to the eyes optics, the visual image isn't just inverted, but also somewhat magnified onto the retina. Thus visual eccentricity (the angle that a point in space makes relative to the visual axis) isn't exactly the same as retinal eccentricity (the retinal angle made between (the ray from the center of the retinal sphere to the center of the fovea) and (the ray from the center of the retinal sphere and the point on the surface of the retina that a point in space project to through the optics of the eye)). Because of this, it is important when locating an anatomical feature on the surface of the retina by describing its eccentricity, it is important to specify whether visual eccentricity or retinal eccentricity is being used, even when locating anatomical features relative to the physical retina itself. Many times in the literature distance along the surface of the retina will not be given in terms of either version of eccentricity, but in absolute distance units (generally millimeters: mm). Assuming a standard radius for the sphere that is the eye, such distances can be easily converted into retinal eccentricity. A problem is that many times the reference doesn't specify the physical radius of the particular eye in question. And even when some information is given, many times it is specified as the diameter of the eye. This is slightly ambiguous, as technically by diameter they mean axial length of the eye, which is not twice the radius of the spherical portion, but the distance from the front most bulge of the front of the center of the cornea, to the back of the eye at the posterior pole. The axial length is usually a bit longer than the spherical diameter.

Also, while the size of a circular anatomical feature on the retina centered on the fovea may be specified by a visual angular diameter, many times it is more important to think of it in terms of a maximum visual eccentricity from the center of the fovea, e.g. half the value of the diameter. To make this point, usually both visual angles will be specified.

Four figures depicting portions of the anatomy of the eye from the prior art are present first to give some context.

Figure 5:
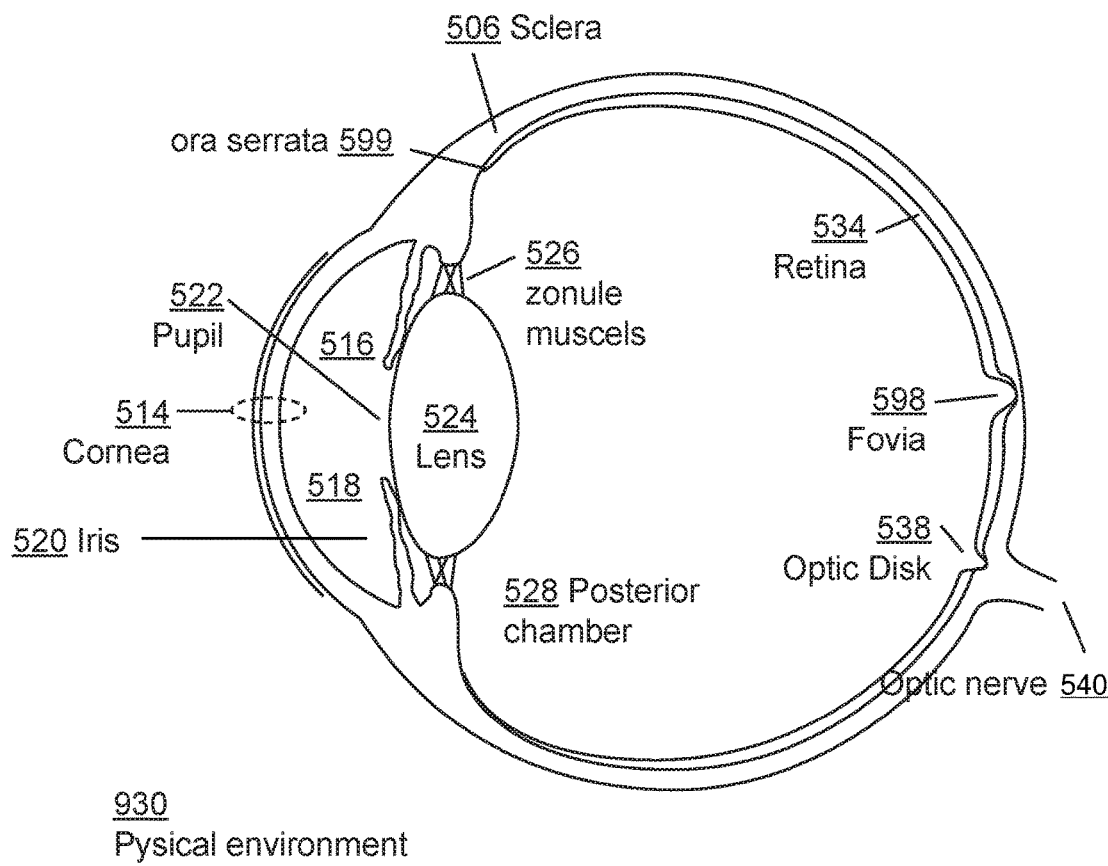
FIG. 5 (prior art) is a two dimensional cross section of the three dimensional human eye.

FIG. 5 shows a two dimensional horizontal cross section 500 through the three dimensional human eye. This cross section 500 shows many of the anatomical and optical features of the human eye that are relevant to the description of the invention. (Note: because the centers of the fovea 598 and the optic nerve 540 and optic disk 538 do not lie on exactly the same horizontal plane (more on this in a later section), the two dimensional horizontal cross section 500 is a simplification of the real anatomy. However, this simplification is standard practice in most of the literature; and so the slight inaccuracy usually does not have to be explicitly called out. It is mentioned here because of the highly tight match there must be between the eye coupled display and the real human eye.)

To simplify this description, optical indices of refraction of various gases, liquids, and solids will be stated for a single frequency (generally near the green visible optical frequency) rather than more correctly a specific function of optical frequency.

Figure 6:
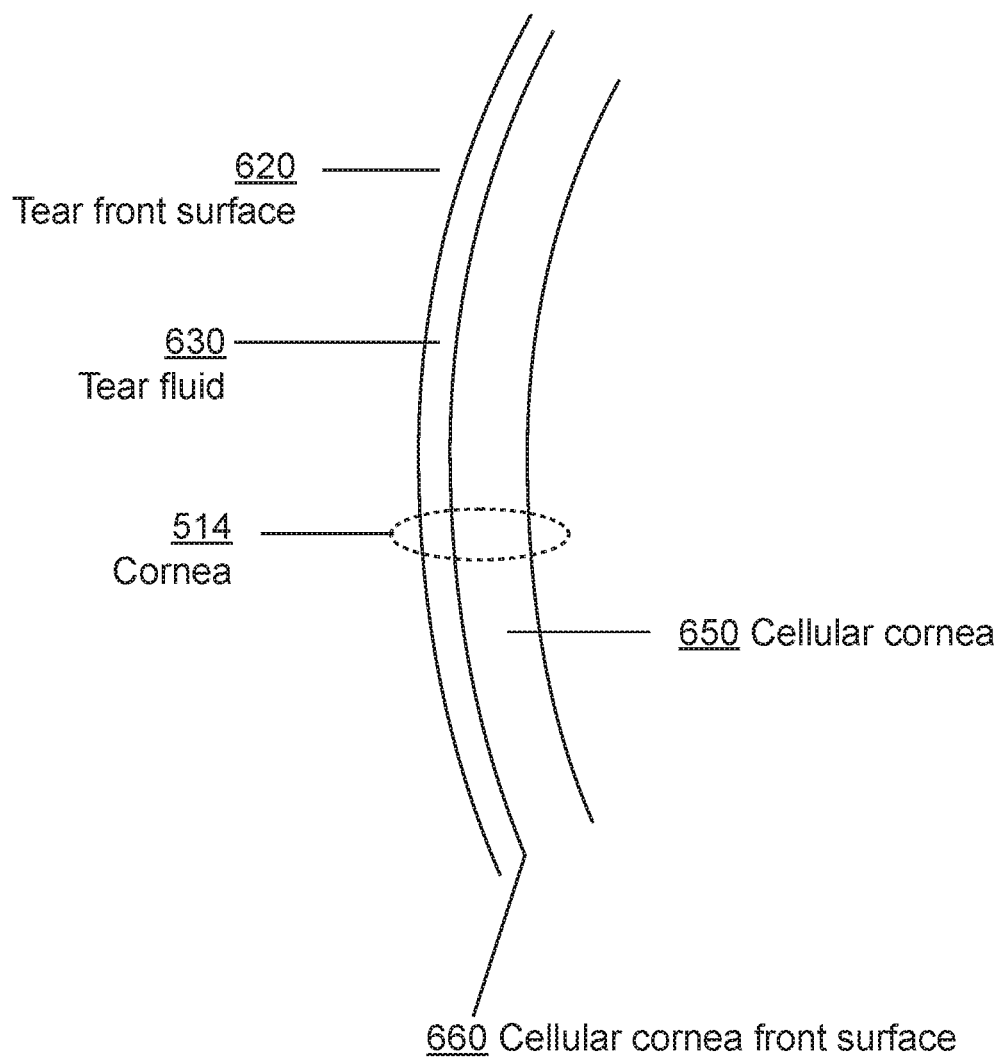
FIG. 6 (prior art) is a zoom into the corneal portion of the human eye.

The outer shell of the eye is opaque white surface called the sclera 506; only at a small portion in the front of the eye is the sclera 506 replaced by the clear cellular cornea 650 (see FIG. 6).

Figure 8:
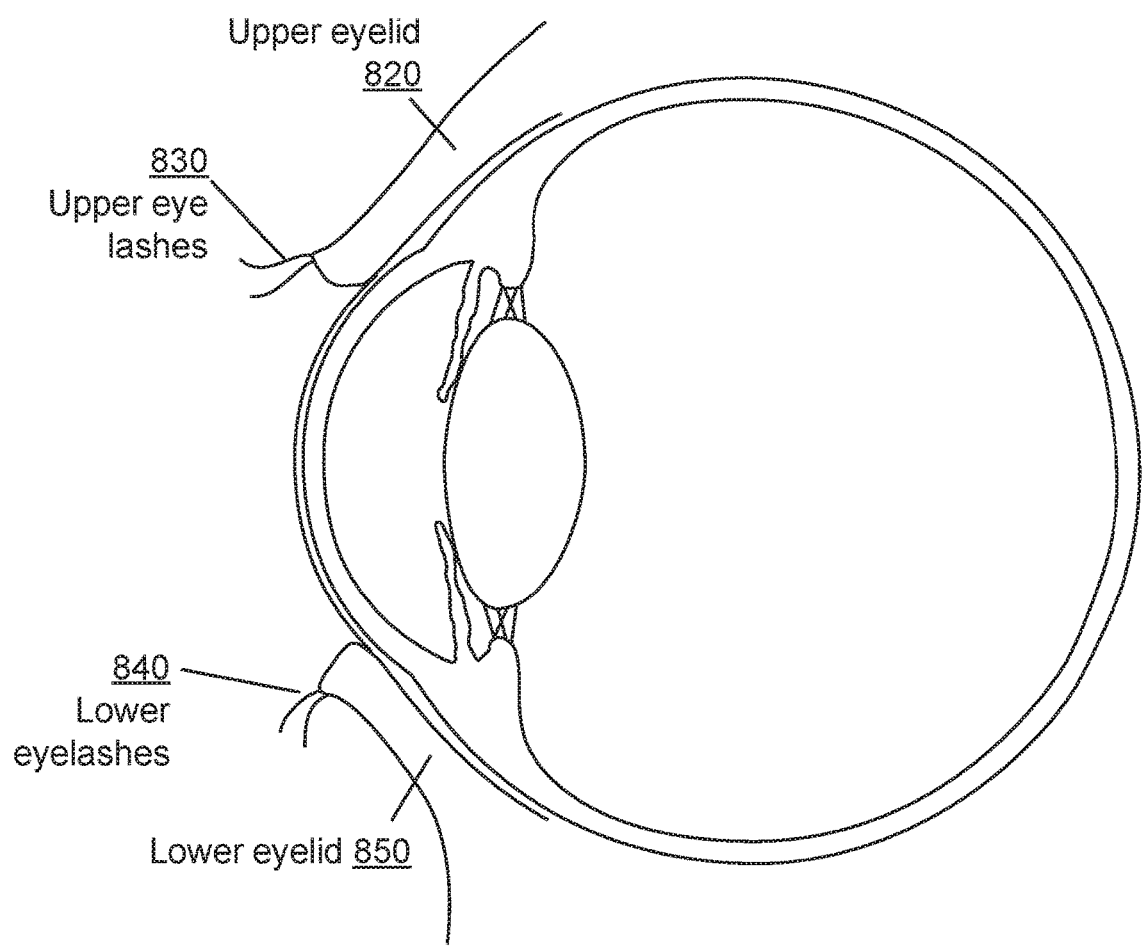
FIG. 8 (prior art) is a two dimensional vertical cross section of the three dimensional human eye.

FIG. 8 shows a two dimensional vertical cross section through the three dimensional human eye. The upper eye-lid 820 and the hairs attached to φ the upper eyelashes 830, along with the lower eye-lid 850 and lower eye-lashes 840, covers the entire eye during eye blinks, and redistribute the tear fluid 630 over the cellular cornea front surface 660 (see FIG. 6). Not always noticed is that when one looks down, the upper eye-lid 820 moves down to cover the exposed sclera 506 almost down to the cellular cornea 508, colloquially the eyes are "hooded".

The cellular cornea 650 is a fairly clear cell tissue volume whose shape allows it to perform the function of a lens in an optical system. Its shape is approximately that of a section of an ellipsoid; in many cases a more complex mathematical model of the shape is needed, and ultimately must be specific to a particular eye of a particular individual. The thickness near the center of the cellular cornea 650 is nominally 0.58 Millimeters.

FIG. 6 is a zoom into more detail of the cornea. The tissue at the front surface element 660 of the cellular cornea 650 is not optically smooth; a layer of tear fluid 630 fills in and covers these cellular corneal front surface 660 imperfections. Thus the front surface 620 of this tear fluid layer 630 presents an optically smooth front surface to the physical environment 910 (from FIG. 9); the combination of the cellular cornea 650 and the tear fluid layer 630 forms the physical and optical element called the cornea 514. While the physical environment 910 could be water or other liquids, gasses, or solids, for the purposes of this patent it will be assumed that the physical environment 910 is comprised of normal atmosphere at sea level pressures, so another name for 910 is "air".

The optical index of refraction of the cornea 514 (at the nominal wavelength) is approximately 1.376, significantly different from that of the air (e.g., the physical environment 910) at an optical index of 1.01, causing a significant change in the shape of the light wavefronts as they pass from the physical environment 910 through the cornea 514. Viewing the human eye as an optical system, the cornea 514 provides nearly two-thirds of the wavefront shape changing, or "optical power" of the system. Momentarily switching to the ray model of light propagation, the cornea 514 will cause a significant bending of light rays as they pass through.

Behind the cornea 514 lies the anterior chamber 516, whose boarders are defined by the surrounding anatomical tissues. This chamber is filled with a fluid: the aqueous humor 518. The optical index of refraction of the aqueous humor fluid 518 is very similar to that of the cornea 514, so there is very little change in the shape of the light wavefronts as they pass through the boundary of these two elements.

The next anatomical feature that can include or exclude portions of wavefronts of light from perpetrating deeper into the eye is the iris 520. The hole in the iris is the physical pupil 522. The size of this hole can be changed by the sphincter and dilator muscles in the iris 520; such changes are described as the iris 520 dilating. The shape of the physical pupil 522 is slightly elliptical (rather than a perfect circle), the center of the physical pupil 522 usually is offset from the optical center of the cornea 514; the center may even change at different dilations of the iris 520.

The iris 520 lies on top of the lens 524. This lens 524 has a variable optical index of refraction; with higher indices towards its center. The optical power, or amount of ability to change the shape of wavefronts of light passing through the lens 524 is not fixed; the zonules muscles 526 can cause the lens to flatten, and thus have less optical power; or loosen, causing the lens the bulge and thus have greater optical power. This is how the human eye accommodates to focusing on objects at different distances away. In wavefront terms, point source objects further away have larger radius to their spherical wavefronts, and thus need less modification in order to come into focus in the eye. The lens 524 provides the remainder of the modifications to the optical wavefronts passing through the eye; its variable shape means that it has a varying optical power. Because the iris 520 lies on top of the lens 524, when the lens 524 changes focus by expanding or contracting, the position of the iris 520 and thus also the physical pupil 522 will move towards or away from the cornea 514.

It is important to point out that this particular feature of the human eye is slowly lost in middle age; by the late forties generally the lens 524 no longer has the ability to change in shape, and thus the human eye no longer has the ability to change its depth of focus. This is called presbyopia; present solutions to this are separate reading from distant glasses, or bifocals, trifocals, etc. In some cases replacing the lens 524 with a manmade lens appears to restore much of the focus range of the younger eye. However, as will be discussed later, there are other ways to address the issue.

Behind the lens 524 lies the posterior chamber 528, whose boarders are defined by the surrounding anatomical tissues. This chamber is filled with a gel: the vitreous humor 530. In recent years it has been found that vitreous humor 530 is comprised not just of a simple gel, but also contains many microscopic support structures, such as cytoskeletons. The optical index of refraction of the rear of the lens 524 and the vitreous humor 530 gel are different; this difference is included in the modifications to the shape of input wavefronts of light to the lens 524 to the shape of the output wavefronts of light.

Figure 7:
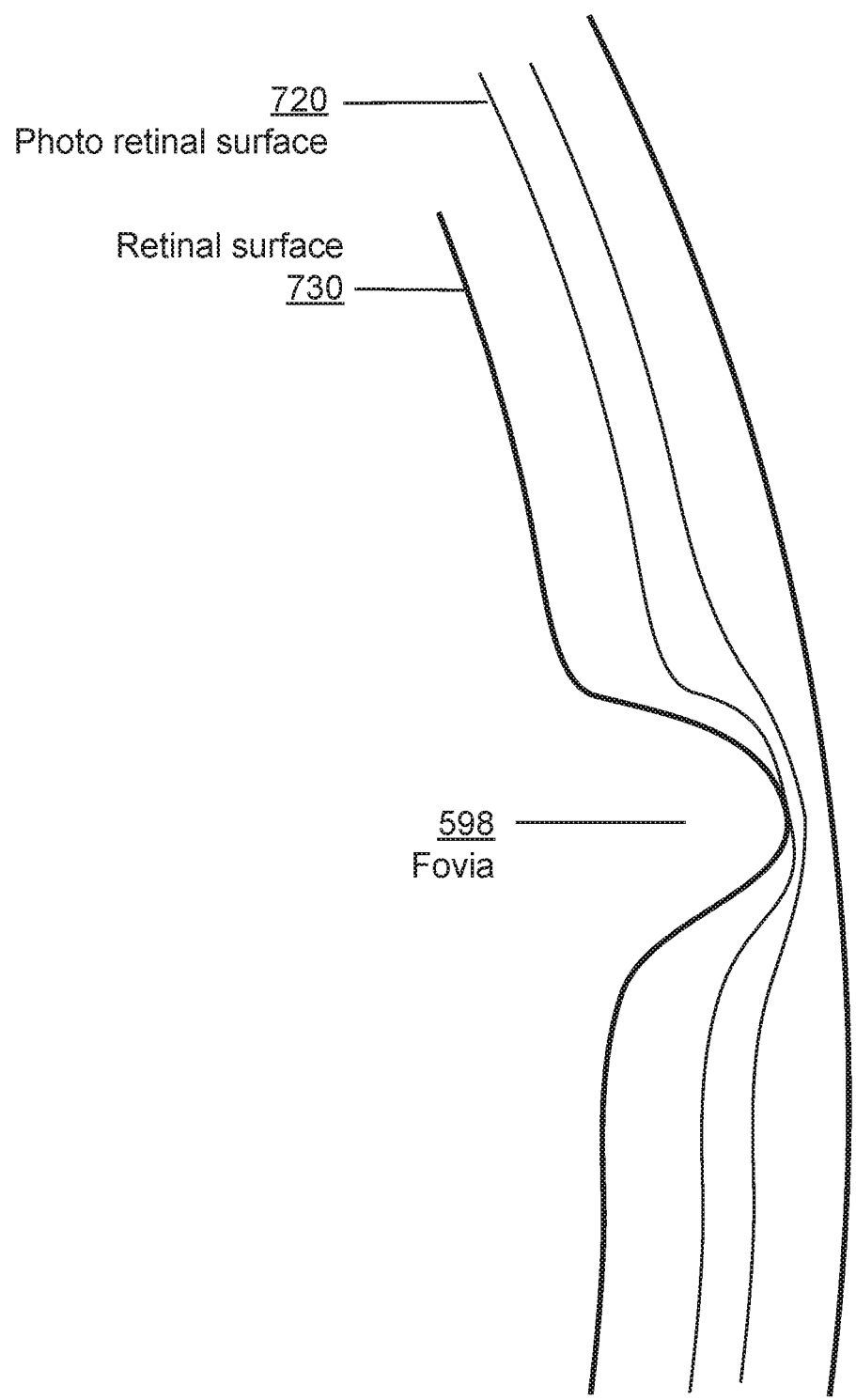
FIG. 7 (prior art) is a zoom into the foveal region of the retinal portion of the human eye.

The inside surface lining of the eye is comprised of various thin layers of neural cells that together form a truncated spherical shell of such cells that together are called the retina 534. It is shown in more detail in FIG. 7. The highest resolution portion of the retina is the fovea 598. The edge of the spherical truncation that forms the outer extent of the retina within the eye is an edge called the ora serrata 599. The anterior surface of the shell is bounded by the transition from the vitreous humor 530 to the retina; the rear of this thin shell bounded by the posterior surface of the pigment epithelium. The front surface of the shell is commonly defined as the retinal surface 730. However, when treating the retina as a photo sensitive surface, the same term "retinal surface" also commonly refers to a different surface: a sub-layer within the particular layer within the thin neural layers where photons are actually captured: the photo retinal surface element 720. In this document the term "retinal surface" will always refer to the photo retinal surface 720.

II.B. Retinal Definitions

The Retina is a Subset of a Sphere
  Definition of term: retina
  Definition of term: retinal surface
  Definition of term: point on the retinal surface
  The retina consists of several thin layers of neurons on the inner surface of the eye. It covers approximately 65% of the inner surface, from the rear forward. This portion of the eye is nearly spherical. The phrase retinal surface will be used when it is important to emphasize that the retina is a thin non-planer surface. The phrase a point on the retinal surface will be used to indicate that a particular location on the retina is meant; the fact that the retina, though thin, actually consists of several relatively well defined layers is below this level of abstraction.
  Definition of term: retinal sphere
  The retinal sphere is the best fit of a sphere to the retinal portion of the curved surface inner surface of the eye.
  Definition of term: center of the retinal sphere
  The center of the retinal sphere is the point located at the center of the retinal sphere.
  Definition of term: retinal radius
  The retinal radius is the radius of the retinal sphere. See the definition of the axial length for how these two terms differ. In this document, we will assume a default retinal radius of 12 mm. It is called the retinal radius rather than the eye radius because it is the inner radius of the non-zero thickness spherical shell of the eye that is of interest, not the radius of the outer shell (the sclera).
  Definition of term: corneal apex
  The corneal apex is the front most point on the front surface of the cornea; typically this is also the point through which the corneal optical axis passes.
  Definition of term: axial length
  The axial length of the eye is the distance measured from the corneal apex to the back of the eye at the posterior pole (thus this distance is measured along the corneal optical axis). The axial length is usually a bit longer than the diameter (twice the retinal radius) of the (mostly) spherical portion of the eye. Statistically, human eyes have an average axial length of 24 mm, but individually vary in size from 20 to 30 mm. The distribution of this variance is approximately Gaussian about 24 mm with a standard deviation of ±1 mm. Caution: when referring to the "diameter" of the (or an) eye, in the literature many times what is meant is the axial length of the eye, not twice the retinal radius. Convention: while 24 mm is usually used as the "standard" or default axial length of the eye, in this document we use 12 mm as the retinal radius, and the detailed model has an axial length of 23.94 mm.
  Definition of term: ora serrata
  On the inner surface of the eye, the edge where the retina ends is called to the ora serrata. It extends all the way around the inner front surface of the eye, but is not a line of constant retinal eccentricity. Instead its location varies in visual eccentricity from as little as 60° to as much as 105°. The exact shape is not well documented, but the gross details are. In the nasal direction the maximum visible visual eccentricity is close to 105°, but at the extreme, all you see is the side of your nose. In the superior and temporal directions, the maximum visible visual eccentricity is around 60°. In the inferior direction the maximum visible visual eccentricity is around 65°. There is considerable individual variation. The reason that each eye can see more of the world towards the nose is that that is where the stereo overlap between the two eyes lies.
  Definition of term: posterior pole
  The intersection of the optical axis of the cornea with the retinal surface is called the posterior pole. It is the center of the retina, as far as the axis of symmetry of the cornea (and thus the gross eye) is concerned. However, for most purposes the center of the retina is instead defined as the center of the fovea, which is located on the retinal surface, but in units of visual angle 2° inferior and 5° temporal from the posterior pole.
  Optical Elements of the Eye
  Definition of term: cornea
  The cornea is the front most transparent optical element of the eye. It is responsible for the first two-thirds of the optical power of the eye, most of the remainder is provided by the lens of the eye.
  Definition of term: lens
  Definition of term: crystalline lens
  The lens of the eye is also known as the crystalline lens. Usage of this phrase is considered mostly archaic in modern American English, but the usage is current in British English. In this document, sometimes the phrase crystalline lens will be used to avoid ambiguity when other lenses are present.
  Definition of term: accommodation
  Definition of term: accommodation mechanism
  The process of the eye dynamically changing the optical power of the lens to bring a point of visual attention into focus is called accommodation. accommodation is normally driven by vergence angle of the two eyes. That is, when the two eyes change their orientation such that the visual axis of the two eyes intersect at a point at a certain distance from the eyes, that is a very strong indication that the optical power of the two lenses should be changed so as to bring objects near that point into focus. In such a situation it is said that there is a change in the accommodation of the eyes, from wherever their previous focus was, to the current desired focus. The overall process is called the accommodation mechanism. The accommodation mechanism is not normally under conscious control; normally the vergence angle directly drives the focus of the eyes. This is a problem for stereo displays, as most cannot dynamically change the distance of optical focus of the display.
The Optic Nerve and the Optic Disc
  Definition of term: optic nerve
  Definition of term: lateral geniculate nucleus
  Definition of term: LGN
  Ganglion cells are located through the retina, with their dendritic end mostly placed locally to where their inputs from other retinal cells are. However, the other end of all ganglion cells (the axons) all head from there across the retina toward the same spot: the optic disc. The optic disc is a hole in the retina where all these extended length ganglion cells can pass through. When all these "nerve fibers" come together, they form the optic nerve. All communication from the eye to the rest of the brain is via the nerve fibers bundled into the optic nerve. From the back of the eye, most, but not all, of the nerve fibers head into the portion of the brain known as the lateral geniculate nucleus (LGN). There are actually two LGNs, a left and a right one.
  Definition of term: optic disc
  There is a hole in the surface of the retina where a large bundle of nerves from the retina become the optic nerve and exit through the back of the eye. This hole is called the optic disc, though its shape is elliptical: its size is approximately 1.5 mm horizontally and 2 mm vertically. Relative to the posterior pole (the end of the optical axis), on the surface of the retina the optic disc is centered vertically (0°), and located 10° nasal. Relative to the center of the fovea, the optic disc is located 2° superior, and 15° nasal.

Definition of term: blind spot

Visually, the lack of photoreceptors (rods or cones) caused within the optic disc results in what is called the blind spot. In visual space, relative to the visual axis, it is located 2° inferior, and 15° temporal.

The Macula

Definition of term: macula

Definition of term: macula lutea

The macula, also known as the macula lutea, is a circular disk of yellowish pigment on the retina centered on the fovea. The thickness of the macula diminishes with distance from the center of the fovea, but some of the same pigment that makes up the macula is found throughout the rest of the retina. Thus determining exactly where the macula ends is a subjective anatomy call; different sources express its diameter in visual space as anywhere from 5° to 20°, corresponding to a maximum visual eccentricity of between 2.5° and 10°. In addition to this, it is known the extent of the macula, as well as the peak thickness, is subject to a fair amount of individual variation.

One presumed function of the macula is to greatly reduce the amount of short wave length light (blue through ultraviolet) that reaches the central retina (that hasn't already been absorbed by the cornea and lens).

The Fovea

Definition of term: anatomical fovea

Definition of term: fovea centralis

The term "fovea" unfortunately has two different definitions. One is defined by anatomical features, which we will always refer to as the anatomical fovea. This anatomical definition, also known as the fovea centralis, is a circular area of the retina 5° of visual angle in diameter (1.5 mm), or a radius of 2.5° of visual eccentricity, within which most of the retinal neural layers are absent. This absence allows for best optical imaging quality to the photoreceptors present. The location of the anatomical fovea on the retina, relative to the posterior pole, is 2° superior and 5° nasal (there is some individual variation). In terms of anatomical features, the definition of the edge of the anatomical fovea is the location where the layers of retinal cells achieves their maximum density (thickness). From a resolution point of view, the term "fovea" has a different definition as a smaller region of the retina.

Definition of term: fovea

From a resolution point of view the term "fovea" indicates a region of visual space where the eye has its maximum resolution. In this document, we use the plain term fovea to indicate this visual definition. Specifically, the visual fovea is defined as a circular area of the retina 2° of visual angle in diameter (0.3 mm), or a radius of 1° of visual eccentricity, with the same center on the retina as the anatomical fovea.

Definition of term: center of the fovea

By the phrase the center of the fovea, we will always mean the point at the center of the highest resolution (smallest cones) portion of the anatomical fovea. Anatomically, this is the geometric center of the foveal maximum cone density zone.

Anatomically Defined Sub-Regions of the Fovea

Definition of term: foveal avascular zone

The foveal avascular zone is a circular sub-region of the anatomical fovea about 1.4° of visual angle across (0.4 mm), or a circle of 0.7° of visual eccentricity, anatomically defined as where even blood vessels are absent.

Definition of term: foveal rod-free zone

The foveal rod-free zone is a circular sub-region of the anatomical fovea about 1° of visual angle across (0.35 mm), or a circle of 0.5° of visual eccentricity, anatomically defined as where only cone photoreceptors are present, not rods.

Definition of term: foveal blue-cone-free zone

The foveal blue-cone-free zone is a circular sub-region of the anatomical fovea about 0.35° of visual angle across (0.1 mm), or a circle of 0.17° of visual eccentricity, anatomically defined as where no blue cones are present, only red cones and green cones.

Definition of term: foveola

The term foveola ("little fovea") atomically refers to a central portion of the anatomical fovea where no ganglion cell layer exists. But some authors define it differently, it can mean any one of the terms foveal avascular zone, foveal rod-free zone, or the foveal blue-cone-free zone. We will avoid the ambiguity by not using this term here, but the more specific ones instead.

Definition of term: foveal maximum cone density zone

Within a small very most central portion of the anatomical fovea, anatomically lies a circular sub-region of the anatomical fovea where the density of cones is at its maximum (for that individual). This is a region of approximately constant size cones that have the smallest size (highest resolution) found on the retina. This foveal maximum cone density zone is only four minutes of visual arc (1°/15) across (0.02 mm), or a circle of two minutes of visual eccentricity. This is well within the foveal avascular zone, foveal rod-free zone, and the foveal blue-cone-free zone, so in the foveal maximum cone density zone there are only red cones and green cones, no blood vessels, and no rods. The region is so small that it may contain less than 50 cones.

Definition of term: foveal maximum cone density

This is the per-individual peak cone density of their fovea, and it can vary by individual from as little as 150,000 cones/mm to as much as 350,000 cones/mm.

Definition of term: periphery

The rest of the retina outside the anatomical fovea is referred to as the periphery. It extends from the outside edge of the anatomical fovea, at 2.5° of visual eccentricity, all the way to the ora serrata, at 65° to 105° of visual eccentricity. Caution: when the visual fovea is the context, the term periphery can instead refer to the region outside this smaller region, e.g. extending from 1° of eccentricity out. Which is meant to be inferred from context.

II.C. Axes: Classical Optical Vs. the Human Eye

Optical Axes of Classical Optical Systems

In classical optics, the concept of "the optical axis" is well defined. Most classical optical systems are circularly symmetric (centered), making the optical axis easy to find: it is the axis of symmetry. Even most "off-axis" classical systems are really just a portion of a larger system that would have circular symmetry, and again the optical axis is self-evident. Quite often there is just one optical axis, which is why one can talk about "the" optical axis.

Optical Axes of the Human Eye

The human eye, however, is most certainly not a classical optical system, except in quite abbreviated form. The individual optical elements of the eye are mostly circularly symmetrical; the problem is that the individual optical axes are not aligned with each other. Much of this comes about because the axis of symmetry of the main image sensing component of the eye, the retina, is tilted by 5° relative to the main optical bending component of the eye, the cornea. Because of this, the axis of the pupil is offset from the corneal axis, and the axis of the lens is tilted relative to the cornea. The result is a decentered optical system, and concepts like the "optical axis" are ill-defined. To further complicate things, the center of rotation of the eye is not on any of the other axes, and its location actually changes during rotation.

Traditionally these issues are addressed by having different levels of approximation to optical models of the human eye. More recently some of the issues have been addressed by making changes or redefinitions in terminology (visual axis vs. line of sight).

Optical Models the Human Eye

All optical models of the human eye must be "simplified" models at some level, for example, very few contain an optical model of every photosensitive cone cell (let alone rod cell) in the eye. But even a simplified model can be quite useful for a given objective: fitting spectacles, or just understanding the image forming process. Some of the simplest sort of optical models are called schematic eyes, which are further divided into simple paraxial schematic eyes, and the more complex wide angle schematic eyes.

Definition of term: schematic eye

A schematic eye is an approximate model of the optics of the human eye, which has been simplified into a small number of classical optical components.

Definition of term: paraxial schematic eye

Definition of term: paraxial region

A paraxial schematic eye is a schematic eye which is explicitly restricted to be valid only within the paraxial region: optical angles less than 1°, where sin $[x] \approx x$.

Definition of term: wide angle schematic eye

A wide angle schematic eye is a schematic eye which is explicitly valid at nearly all angles, well beyond the paraxial region. In the human eye, this can extend to visual eccentricities past 90° (a field of view of 180°), up to 105° or more.

While any paper describing a particular optical model of the human eye can be said to define a schematic eye, there are a few well known historic schematic eyes that are commonly used as references. Most of these are paraxial schematic eyes, but a few are wide angle schematic eyes. Unfortunately from an axis point of view, pretty much all schematic eyes have a single optical axis, thus they are not very well suited for simulation of eyes with fovea's located properly at 5° off the corneal optical axis. One exception is [Deering, M. 2005. A Photon Accurate Model of the Human Eye. ACM Transactions on Graphics, 24, 3, 649-658], and that model will be used here.

The Axis of the Eye

Definition of term: optical axis of the cornea

The cornea is easily accessible from outside the eye, and from its shape its function as an optical element can be understood, including its principle optical axis. This axis is defined as a line through the center of the cornea, normal to the surface of the cornea there. Where the optical axis of the cornea hits the surface of the retina is called the posterior pole. Unfortunately the rest of the optical elements of the eye, including the pupil, the lens, and the spherical imaging plane (the retina), all have distinct, and different from each other, axis. Thus there is no single "optical axis of the eye." The term still arises in the literature, and sometimes is synonymous with optical axis of the cornea, and other times synonymous with the visual axis. We will avoid ambiguity by not defining or using the phrase "optical axis of the eye."

Definition of term: optical axis of the pupil

The optical axis of the pupil is defined to be a line through the center of "the hole in the iris." The orientation of the line is normal to the orientation of the inside edge of the iris. But this orientation isn't very well defined, and the lens can actually bulge through the iris. The center of the hole in the iris is not aligned with the optical axis of the cornea, it is generally decentered from it by 0.25 to 0.5 mm, and varies by individual. This decentering is required due to the resolution center of the retina (the center of the fovea) being 5° offset from the intersection of the optical axis of the cornea and the retina (the posterior pole). And not only that, but as the iris dilates (opens larger) the center of the hole can actually shift by 0.1 mm or more. Furthermore, the actual shape of the hole is not a perfect circle, but slightly elliptical (~6%). In most all the published schematic eyes, including wide angle schematic eyes, the optical axis of the pupil (and the optical axis of the lens) are assumed to be the same as the optical axis of the cornea. But for accurate modeling, the appropriate offset must be included.

Definition of term: optical axis of the lens

The optical axis of the lens is also decentered and tilted from that of the optical axis of the cornea, though by how much is still somewhat speculative. From an accurate optical modeling point of view, the decentering of the pupil is more important to include than decentering and/or tilting the lens.

Definition of term: visual axis

Definition of term: line of sight

From any given direction d towards the eye, a pencil of rays, all with the same direction, but offset in space, can hit the front surface of the cornea. After bending by the cornea's optical function, the pencil of rays will continue deeper into the eye, and many will hit the plane of the iris. However, of the original pencil of rays, only a subset will actually pass through the hole in the iris (the pupil), and continue even deeper into the eye. Label this subset pencil of rays all with the same direction d in object space that will end up passing through the pupil pd. The rays within any such pencil will still be offset in space from one another, generally in an elliptical cross section (as cut by a plane tangent to the center of the cornea). One can chose a single principle ray of each pencil ppd by choosing the ray at the center of the pencil. Then, over all directions d, (generally) only one of these principle rays will, after being further bent by the eye's lens, hit the surface of the retina at the exact center of the fovea. This one ray defines the visual axis.

Many times a different older definition of the visual axis is used: the ray in the visual world that ends up passing through the first nodal point of the eye's optics. Those who use the older definition now use the phrase line of sight to mean the same thing as the newer definition of the visual axis. But because even the line of sight has multiple older meanings, in this document the visual axis will always be used in its new form instead.

Definition of term: Eye Point

Definition of term: ViewPoint

The simple computer graphics view model is equivalent to pin-hole lens optics. That is, the only rays in object space that will be considered for making up the image plane are rays from any directions but that all pass through the same point: the Eye Point, or ViewPoint, which is the same location as the (infinitively small) pin-hole.

In real optical systems with lenses and non-infinitesimal entrance pupils, the situation is more complex, but the EyePoint is known to be located at the first nodal point of the optical system. Unfortunately, the last is true only for optical systems with rotational symmetry about a single shared optical axis. While this characterizes most man-made optical systems, the decentered and tilted elements of the optics of the human eye makes this not true there.

In the optical system of the human eye, the EyePoint will be located somewhere on the line defined by the visual axis. Referring to the construction of the visual axis, in theory all the principle rays ppd, if left to continue un-deflected by the eye's optics, would eventually intersect at a single point, and this would define the EyePoint. In practice, all the rays won't quite intersect at a single point, so the best one can do is chose the center of the narrowest waist in the envelope of such rays as they "almost intersect." These other locations in space within the envelope at its narrowest represent a more general concept of a "region" of EyePoints, and they are used in more complex computer graphics rendering models to correctly simulate depth of field effects.

Note that technically the EyePoint can move in and out slightly along the visual axis as accommodation changes. This is because as the eye's lens bulges or flattens to change focus, the location of narrowest point in the envelope are the rays cross will change as the optical power changes. One can also see from the definition of the EyePoint that if the center of the hole in the iris shifts laterally as the iris opens or closes, then both the visual axis and the EyePoint will shift laterally some as well.

Definition of term: center of the exit pupil of the eye

In an optical system with rotational optical symmetry, there is a theoretical single point that all the rays exiting from the optical system (e.g., those heading towards the imaging surface) will seem to have come from. In such classical optical systems, this is the second nodal point of the optical system. But once again, the human eye doesn't play by the same rules.

What we want to know is where, from points on the surface of the retina's point of view, do all the rays coming to the surface of the retina seem to come from? Again, the answer is a generalization that is based on finding the narrowest waist in the bundles of rays that emerge from the lens on the inside of the eye. This point is known as center of the exit pupil of the eye.

Definition of term: rotational center of the eye

The human eye center of rotation is not fixed; it shifts up or down or left or right by a few hundred microns over a ±20° rotation from straight ahead. The "standard" non-moving (average) center is given as a point on a horizontal plane through the eye, 13 mm behind the corneal apex, and 0.5 mm nasal to the visual axis.

Definition of term: retinal visual axis

The retinal visual axis is defined as ray from the center of the retinal sphere to the center of the fovea on the surface of the retina.

Definition of term: visual angle

The visual angle between two points in space is the angle between the ray from the Eye Point to the first point and the ray from the Eye Point to the second point. The visual angle between two rays in space with a common origin at the Eye Point is the angle between the two rays. The visual angle between a ray in space from the Eye Point and a point in space is the angle between the ray and the ray from the Eye Point to the point in space. Note that the visual angle between two points in space will not be exactly the same as the retinal angle of the two points on the surface of the retina that the optics of the eye project each point in space to.

Definition of term: visual eccentricity

The visual eccentricity of a point in space is the visual angle between that point and the visual axis. The visual eccentricity of a ray in space with its origin at the EyePoint is the angle between that ray and the visual axis. Note that the visual eccentricity of a point in space is not exactly the same as the retinal eccentricity of the point on the surface of the retina that the optics of the eye project the point in space to.

Definition of term: retinal angle

The retinal angle between two points on the surface of the retina is the angle between the ray from the center of the retinal sphere to the first point and the ray from the center of the retinal sphere to the second point. The retinal angle between two rays with a common origin of the center of the retinal sphere is the angle between them. The retinal angle between a ray from the center of the retinal sphere and a point on the surface of the retina is the angle between the ray and the ray from the center of the retinal sphere and the point on the surface of the retina. Note that the retinal angle between two points on the surface of the retina will not be exactly the same as the visual angle between two rays that reverse of the optics of the eye would project each point on the retina out to as rays in object space.

Definition of term: retinal eccentricity

The retinal eccentricity of a point on the surface of the retina is the retinal angle between that point and the retinal visual axis. The retinal eccentricity of a ray with its origin at the center of the retinal sphere is the angle between that ray and the retinal visual axis. Note that the retinal eccentricity of the point on the retina will not be exactly the same that the visual eccentricity that the inverse of the optics of the eye project that point out to as a ray in object space.

Definition of term: retinal distance

The retinal distance is a distance between two points on the surface of the retina along the great circle connecting them on the retinal sphere, measured in millimeters. If you know what the retinal radius is, then a retinal distance can be converted to a retinal angle. This can be converted to a visual angle, but only by a complex function of the eye model. When one of the two points on the retina is the center of the fovea, then the retinal distance, when the retinal radius is known, can be converted to retinal eccentricity (and then the conversion to visual eccentricity is a bit easier, though still not straight forward). When the distance between the two points is small relative to the retinal radius, then the great circle distance between the two points is effectively the same as their Euclidean distance. A good example of when this approximation apples is in specifying the size and spacing of retinal cones.

Definition of term: retinal exit pupil angle

The retinal exit pupil angle of a point on the retinal surface is defined as the angle between the ray from the center of the exit pupil of the eye to the point with the retinal visual axis. This angle is similar to the visual eccentricity, but like the retinal eccentricity, they are not related by a closed form expression. A common approximation is that tan [retinal exit pupil angle]=0.82·tan [visual eccentricity].

Definition of term: inter-pupillary distance

Simplistically, the inter-pupillary distance is just the distance between the (centers of) the two pupils of a viewer's two eyes. But this distance will change when the vergence angle between the two eye's change. In practice, the inter-pupillary distance is measured when the viewer is looking straight ahead and is focused on a point a great distance away (a vergence angle near zero).

Here we will more rigorously define the inter-pupillary distance as the distance between the rays of the visual axis of a viewer's left and right eyes, when the two rays are parallel and the eyes are looking straight ahead. Visually, this occurs when the viewer is looking at an object at an infinite distance. While objects can optically be placed at the equivalent distance to infinity, in practice distances of greater than two miles are indistinguishable, and even distance as little as thirty or forty feet are a good approximation.

One might think that certain anatomical measures would be provide the same value, e.g. the distance between the center of the retinal sphere of the viewer's two eyes, or the distance between the rotational center of the eye of the viewer's two eyes. However, due to the decentered nature of the optics of the eye, these anatomical measures are not quite equivalent.

Another complication to consider is that historically the inter-pupillary distance many times has been considered the purely horizontal distance between the centers of the pupils of the eyes. That is, a measurement made parallel to the ground when the viewer's head is perfectly upright. Unfortunately human eyes are not at the same level, usually one will be a little higher than the other relative to the upright skull. This height difference can be significant enough that it must be accurately measured. Along the same lines, the distance from the plane of symmetry of the skull to the left and right eyes also usually differs, and can also be significant enough that it must be accurately measured. What is ultimately required, rather than the historic inter-pupillary distance measurement, is the exact location relative to a fixed coordinate frame of the skull, is the 3D location of the left and right EyePoints when the eyes are at rotational rest, and the orientation of the visual axis relative to the same skull coordinate system under the same conditions. Here inter-pupillary distance was defined in such a way that it measures the true distance between the infinity directed visual axis of the viewer's two eyes, not just the horizontal component.

While in the general population a viewer's eyes tend to both point to the same location in space where attention is being directed, in people with strabismus, or similar conditions, the two eyes are not coordinated in the same way, and thus alternate means of measuring inter-pupillary distance need to be used.

Definition of term: vergence angle
Definition of term: angle of vergence

Under normal stereo viewing conditions, a viewer will orientate their eyes such that the left and right visual axis will intersect (or come very close to intersecting) at a point in space where attention is being directed. No such point exists in the special case of viewing at infinity, but in all other cases such a point will exist somewhere in physical space in front of the viewer. The definition of the vergence angle, or angle of vergence, is the angle made between the left and right visual axis from this point of intersection.

While the vergence angle is often associated with the current distance to the point of visual attention, the same vergence angle does not exactly correspond to the same distance in space, especially when the point towards the far left or right of the visual region of stereo overlap. However, to a first approximation, the vergence angle is a good estimate of the distance to the current point of visual fixation, and the focus system of the human eye, the accommodation mechanism, uses the current vergence angle to drive the current focus (e.g., at what distance should objects currently be in focus). That is, if you know a viewer's inter-pupillary distance, and the current vergence angle, then by simple trigonometry the distance to the current point of visual fixation is approximately:

$$\text{distance} = \frac{\text{inter-}pupillaryDistance}{\sin[vergenceAngle]} \quad (1)$$

In such a way, dynamically knowing the vergence angle of a viewer's eyes, one thus also known with high probability what the current depth of focus of their eyes are. This is important in display applications where the optical depth of field of the display must be dynamically adjusted to match what the human visual system is expecting.

For viewers with conditions like strabismus, vergence angle does not carry the same information.

Common Deficiencies of the Eye
Definition of term: myopia
Definition of term: myopic
Definition of term: high-myopic
Definition of term: near-sightedness Myopia, also called near-sightedness, occurs when the optical system of the eye causes distant objects to come into focus not on the surface of the retina, but at a location in front of it. A person with this condition will be able to bring objects relatively close to them into focus, but will not be able to do so for objects past some distance away. Such a person is said to be myopic. A severely nearsighted person is described a high myopic. The cause of myopia is usually an elongation of the eye, making it more ellipsoidal than spherical.

Definition of term: hypermetropia
Definition of term: hypermetropic
Definition of term: far-sightedness Hypermetropia, also called far-sightedness, occurs when the optical system of the eye causes near objects to come into focus not on the surface of the retina, but at a location in back of it. A person with this condition will be able to accurately focus on objects relatively far away, but will not be able to do so for objects closer than some distance. Such a person is said to be hypermetropic. The cause of hypermetropia is usually a foreshortening of the eye, making it more ellipsoidal than spherical. hypermetropia is not to be confused with presbyopia, a condition that naturally occurs with aging.

Definition of term: astigmatism
Definition of term: astigmatic

Astigmatism in general refers to an optical system whose main optical element does not possess circular symmetry. In the case of the eye, the main optical element is the cornea, and it normally is circularly symmetric. However, in cases where the cornea is more ellipsoidal than circular, circular symmetry no longer holds, and the eye is then considered astigmatic, and such a person is considered to have astigmatism. In such cases, the cornea no longer possess a single optical power, but a range of optical powers depending on the orientation of a stimulus to the eye. For the minority of cases in which the eye is astigmatic, but the fault is not the cornea (or entirely within the cornea), the problem then usually is the lens, and is generally an early indication of cataracts.

Definition of term: presbyopia

While the lens starts out in life as quite flexible and is easily changed in shape by the appropriate muscles when different optical powers are required, later in life (towards the age of forty) too many outer layers have been added to the lens and it starts to "harden", becoming less and less flexible, and thus possessing a lesser and lesser range of accommodation (focus). This (natural) condition is called presbyopia, it is why people generally require reading glasses later in life, even if their normal distance vision still does not require correction. For those who also require some form of optical correction, bifocals are one mechanism by which a single pair of glasses (or contact lens) can be support both distance and close up vision.

Definition of term: strabismus

Strabismus is a medical condition in which a person's two eyes do not always change their orientation in tandem with each other. Such people generally do not have stereo vision.

II.D Important Retinal Neural Cell Types

While the cornea and the lens of the human eye are constructed from modified skin cells, the light sensing and information processing cells of the retina are all specialized type of neurons: the brain literally begins inside the back of the eye. This section will define a few of the most important such cells that we will need to consider later.

Photoreceptors

Definition of term: photoreceptors

The first class of neural cells we will describe are photoreceptors, those neurons whose main purpose is to capture photons of light, turn each photon event into increments of electrical charge, and turn the summed voltage over a time span into the release of neural transmitter molecules that act as inputs to other retinal neural cells.

Definition of term: cone cell
Definition of term: cone
Definition of term: red cone
Definition of term: green cone
Definition of term: blue cone The cone cells, or just cones, are the daylight and indoor lighting sensitive photoreceptors of the eye. These photoreceptors neurons are active a moderately low to very high light levels, and pass a temporally normalized light level value to their output. The cone cells come three types with different spectral sensitivities to light: long wavelength, mid wavelength, and short wavelength, or now more commonly referred to as: red cones, green cones, and blue cones.

Definition of term: rod cell
Definition of term: rod

The rod cells, or just rods, are the nighttime and dark sensitive photoreceptors of the eye. These neurons are active at extremely low light levels, and become inactive as the light level approaches a moderately low level. Unlike cones, the output of rod cells is not temporally normalized; their outputs can always be read as a (time averaged) direct photon event count. The rod cells come in only one spectral sensitivity to light; they only "see" in black and white (shades of gray).

Horizontal Cells

Definition of term: horizontal cell

The horizontal cells connect to nearby cone cells. They appear to both input from and output to the cone cells they connect to. Their purpose appears to be to act as a contrast enhancer of the signal that the cone cells put out. Different types of horizontal cells exist with different preferences as to which color(s) of cone cells they connect to and from (some also connect to rods). Some have proposed that the horizontal cells eventually contribute to the surround portion of the midget ganglion cell receptor field, but the evidence is not conclusive.

Bipolar Cells

Definition of term: bipolar cell

The bipolar cells take their input(s) from photoreceptors, and output to one specific ganglion cell. Bipolar cells can be classed in one dimension as either those that invert their input or those that do not. In other dimensions, there are several types of bipolar cells, but we will be concerned with the subtypes that takes their input from a single cone cell.

Definition of term: cone bipolar cell

The cone bipolar cells take input from a single cone cell. One type takes it input from either a single red cone or green cone, another takes its input from a single blue cone. Each of these cone bipolar cell types come in both inverting and non-inverting forms.

Amacrine Cells

Definition of term: amacrine cell

The amacrine cells connect with both bipolar cells and ganglion cells, as well as each other. There are many different specialized types of amacrine cells. Currently it is thought that some of these are what forms the surround portion input to the midget ganglion cell receptor field out of the outputs of nearby cone bipolar cells.

Ganglion Cells

Definition of term: ganglion cell

The ganglion cells of the retina represent the final stage of retinal processing of visual information. So far all the other retinal cell types take in and send out "analog" values. For input, they have taking in quanta of light (photoreceptors), electrical potential (gap junctions), or quantities of neural transmitter molecules. These all are turned into electrical potential inside the cell, processed in some way, and then output, again in one (or more) of the same three ways. Ganglion cells are different. While they take their inputs in as neural transmitter molecules, their output is in the new form of pulses of action potentials for long distance signaling of effectively digital information to the brain proper. Ganglion cells are very long; they have one foot in the retina, but the other foot in the brain, usually at the LGN. The output of each ganglion cell heads from wherever it is located on the retina towards the exit out the back of the eye, the optic disc, where they become part of the optic nerve. The optic nerve heads into the brain, where most (though not all) ganglion cells have their other end terminate within the LGN.

Ganglion cells come in four different "sizes," which vary in how large of visual field they take in. We will only be interested in the smallest size, midget ganglion cells, because they are the determiner of resolution. Each of these come in an "OFF" and "ON" type, and are further differentiated by the color of the cones that they are indirectly connected to.

Definition of term: midget ganglion cell

The midget ganglion cells take input from cone bipolar cells, and, like most ganglion cells, send their output to the LGN.

Definition of term: retinal receptor field

The receptor field of a given neuron in the retina can be defined as the sub region of visual space over which increments or decrements of light can cause the output of that particular neuron to change. Most retinal receptor fields are fairly narrow in extent, their visual regions are between half a minute of arc to a few minutes of arc in visual angle diameter. While by the definition of receptor field, all retinal neurons have a receptor field, for simplicity in this document the phrase retinal receptor field, without further identification of the cell type involved, will refer to the receptor field of the last stage of high resolution processing in the retina, e.g. the midget ganglion cell receptor field. The center portion of this receptor field will sometimes also (loosely) be referred to as "the pixels of the eye."

Definition of term: midget ganglion cell receptor field

Midget ganglion cells have a receptor field characterized by a small central field and a larger surround field. It is important to note that the surround field includes the region of the center field as a sub field.

Up to about 6° of visual eccentricity, each midget ganglion cell central receptor field takes input from only one cone bipolar cell output, which in turn is connected to only one cone cell (and therefore of only one color type). Between 6° and 12° of visual eccentricity, each midget ganglion cell central receptor field takes as input either one or two cone bipolar cell outputs. The proportion of input connections to one vs. two cone bipolar cells varies smoothly from mostly one just above 6° to mostly two just below 12°. Between 12° and 16°, the number of midget ganglion cell central receptor field inputs from different cone bipolar cell outputs smoothly varies from two to three in a similar manner. This process continues at increasing visual eccentricities, and by 45° of visual eccentricity, the number of pooled inputs is twenty one. How is this overall function characterized? Analysis of anatomical midget ganglion cell density counts reveals that the number of midget ganglion cells present on the retina at a particular visual eccentricity is approximately constant. This means that the implied mapping is close to that of LocallyUniformResolution.

What about the surround portion of the midget ganglion cell receptor field? When the center portion is just one cone bipolar cell, the surround appears to be from just the inverted version of that cell again, plus from the inverted version of the (approximately) six cone bipolar cells whose input cone cells are the immediate neighbors of the cone cell input to the central cone bipolar cell. When the center portion of the receptor field is from multiple cone bipolar cells, then the surround appears to be from a proportionately larger number of cone bipolar cells with inputs from close neighboring cone cells. It is presently thought that a single amacrine cell takes its input from the multiple (inverted) cone bipolar cell outputs, and the single amacrine cell output is connected to the input of a single midget ganglion cell in order to form the surround portion of the midget ganglion cell receptor field.

Definition of term: midget ganglion cell processing

The processing of a midget ganglion cell is to subtract the value of its surround field from its central field, or vice versa. Because the output of midget ganglion cells is in the digital pulse code format (used by most of the rest of the brain) which can only represent positive numbers, midget ganglion cells whose central receptor field input comes from one or more cone bipolar cells of the "ON" type subtract the value of their surround input from that of the center input, and clip if below zero. E.g., they only send out pulses if the result of the subtraction is a positive number. Midget ganglion cells whose central receptor field input comes from one or more cone bipolar cells of the "OFF" type subtract the value of their central input from that of the surround input, and clip if below zero. E.g., they only send out pulses if the result of the subtraction the other way would have been a negative number. Since each midget ganglion cell has a direct line to the brain (at the LGN) through its other end, that means that in principle each "pixel" of the retina takes two neural fibers in the optic nerve to transmit its value to the brain, because of the need to encode values into only positive numbers. As the output of midget ganglion cells form the majority of neurons in the optic nerve, this in essence means that the number of neural fibers in the optic nerve represents an approximate double count of the number of "pixels" actually sensed by the eye. In actuality, this is only strictly true for the "ON" and "OFF" pairs of midget ganglion cells below 6° of visual eccentricity. Above this, the pairing is no longer exact, as the "ON" and "OFF" sets of midget ganglion cells separately choose when and how they connect to more than one cone bipolar cell. In fact, the ratio of the density of "ON" midget ganglion cells to "OFF" midget ganglion cells in the periphery appears to be about 1.7:1 (1.3:1 difference in linear resolution). Some perceptual experiments appear to confirm that this ratio effects human perceptual resolution.

III. Mathematical Definitions

III.A Mathematical Conventions

Mathematical Conventions on Variable Names

Traditional mathematical notation heavily relays on the convention that all variable names are a single character in length. They may have (multiple) subscripts or superscripts, be "primed", "tildiaded", boldfaced, etc., but there is only one base character. When a mathematician runs out of letters in the alphabet, he just starts using letters from another alphabet. When this isn't sufficient, subscripting is added, even if that means subscripted subscripts. In computer science, variable names can be arbitrarily long, but (usually) don't include spaces between multiple words that make up a long name, instead either the "under-bar" "_" is used, or the first character of the each name (not always including the first) is capitalize. In this document we will generally use multiple character variable names, with the first letter of a word uppercased convention. Occasionally, in relatively informal equations, phrases with spaces between words will be used for variables, when there is little or no possibility of ambiguity.

Mathematical Conventions on Multiplication

Traditional mathematical notation for multiplication heavily relays on the convention that all variable names are a single character in length. Because multiplication is so common, the traditional convention is that two variables right next to each other (e.g. usually with no space between them) indicates an implicit multiplication.

But because we are not adhering to the single character variable name convention in this document, we always will have to include an explicit multiplication operator symbol of some sort. For ordinary multiplication (e.g. of scalars, or multiplication of something else by scalars), we will use the centered small dot "·" to indicate multiplication. (Computer science usually uses the asterisk "*" (or occasionally the centered star: "*") for multiplication, or even "mul".) The centered small dot is the normal mathematical notation for multiplication when an explicit multiplication operator symbol is required.

A problem arises in multiplication of objects other than by scalars. Dot products and cross products of vectors can use their traditional operator symbols: ● and x. But for matrix multiplication, there is no standard convention of what symbol should represent the matrix multiplication operator when an explicit operator is required. Sometimes the small dot is used, sometimes the cross product symbol is used. Since we have to make a choice here, the cross product symbol "x" will be used. While this is slightly less common than the choice of the small dot, it reinforces the semantics that matrices are being multiplied here, not scalars.

Another issue with matrix multiplication is the semantics of the order of their composition under multiplication. With scalars, multiplication is commutative: x·y·z=z·y·x, so in mathematics the order in which scalars are multiplied is irrelevant. In computer science, because of rounding, the order in which numbers are multiplied can be relevant, so the default order of application is in general left to right, though optimizing compilers are allowed to use the commutatively property to re-shuffle the application order in most circumstances. However matrix multiplication is in general not commutative, so the order makes a difference. This is important because matrix multiplication is defined to operate right to left, not left to right. The reason for this is that matrices are considered transforms, which are considered mappings, which have associated mapping functions. So for example, assume that you have three spaces: A, B, and C. Then assume that the transform between points in the first to points in the second is AtoB( ), and the transform between points in the second to points in the third is BtoC( ). Now the transform between points in the first to points in the third is defined by the application of BtoC on the results of applying AtoB: BtoC(AtoB)→AtoC( ), or BtoC° AtoB→AtoC. This makes perfect sense when the transforms are viewed as functions. But the mathematical convention is that even when transforms are not viewed as functions, but as transforms to be multiplied, the order that the transform names appear in stays the same: BtoC×BtoA→AtoC, e.g. matrix multiplication obeys the right to left rules of functional composition. While it can be argued that the other way around makes more logical sense, e.g. AtoB×BtoC→AtoC, in this document we will use the standard mathematical order in equations.

A note on inverse matrices. The traditional notation for the inverse of a matrix (or a transform) is the name of the matrix to the minus one power, e.g. if you have the matrix M, its inverse is $M^{-1}$. However, one of the advantages of our long naming style is that most transforms are named in the form of the spaces that they transform from and to, e.g., for spaces A and B, the transform is generally AtoB. This means that the inverse usually has a well-defined name, in this case it would be BtoA. So in many cases we will just use the direct name of the inverse, rather than applying the inverse operator to the original matrix.

III.B Hexagonimania

This section offers a (brief) introduction to the properties of hexagons and tilings of hexagons. We will need the equations derived here to compare data about cones and their hexagonal tiling from different sources that use different definitions of the size of cones, and the spacing of hexagonal lattices. Almost always, by hexagon, we mean a six sided polygon in which all the sides have exactly the same length. The exceptions are the "hexagonally shaped" cones of the retina, in which not only do not all the sides share the same length, but sometimes have 5, 7, 8 or 9 sides instead of 6! (Statistically, the average number of sides of retinal cones appears to be about 6.2.)

Individual Hexagons

The Orientation of a Hexagon

To apply the terms "width" or "height" to a hexagon, you have to know which of the two main possible orientations of the hexagon are being referred to.

Definition of term: hexagon on its side

Definition of term: hexagon on its end

Figure 21:
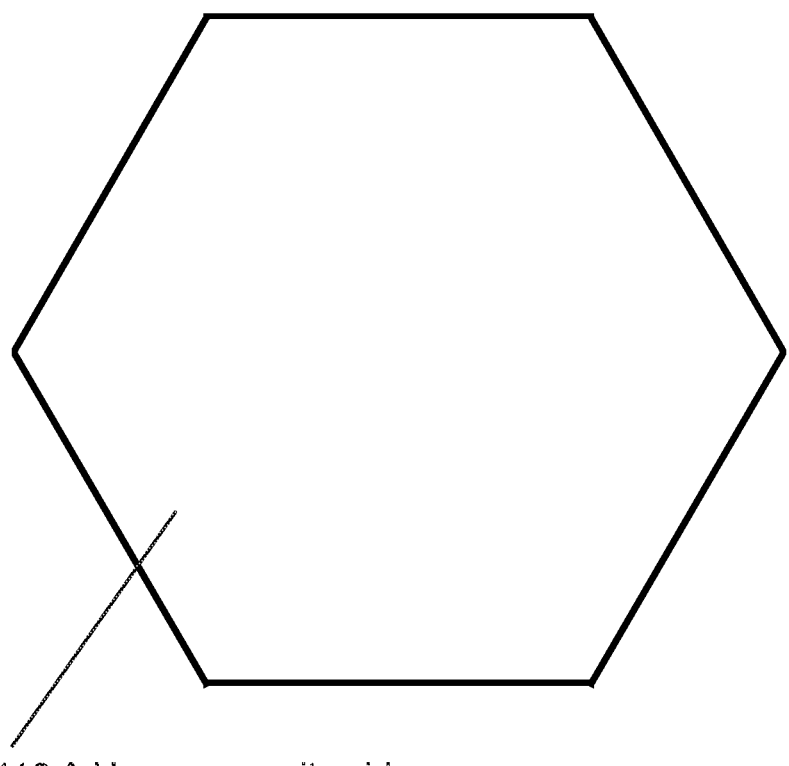
FIG. 21 shows a hexagon on its side.
Figure 22:
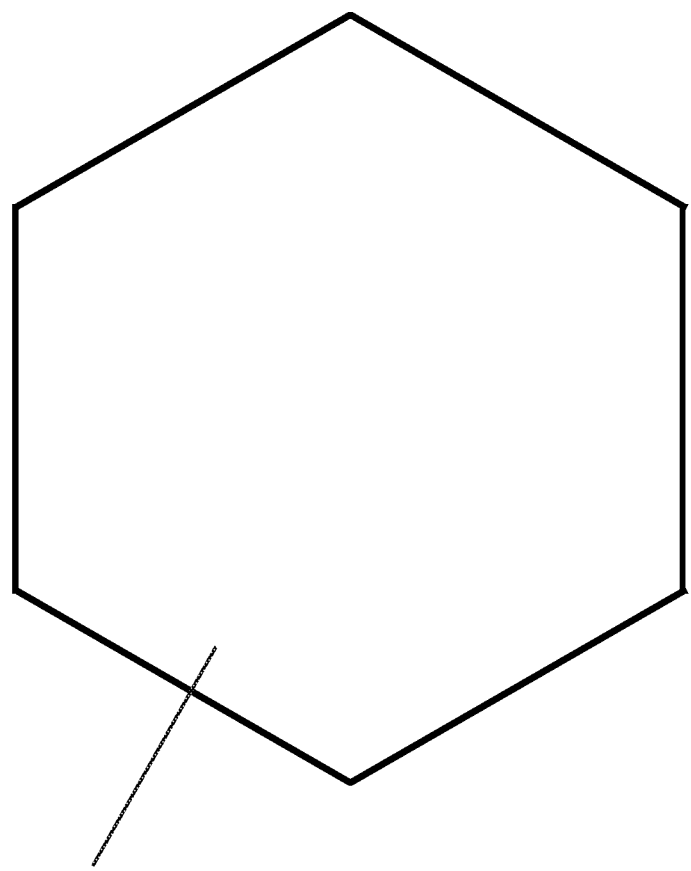
FIG. 22 shows a hexagon on its end.

As shown in FIG. 21, we define a hexagon on its side as a regular hexagon 2110 "resting" with one side aligned with horizontal axis. As shown in FIG. 22, we define a hexagon on its end as the case in which a regular hexagon 2210 is balanced on one of its corners.

To avoid ambiguity, it is better when possible to use non-orientation specific terms, so we introduce several.

The Diagonals of a Hexagon

Definition of term: LongDiagonal

Definition of term: Short Diagonal

Figure 23:
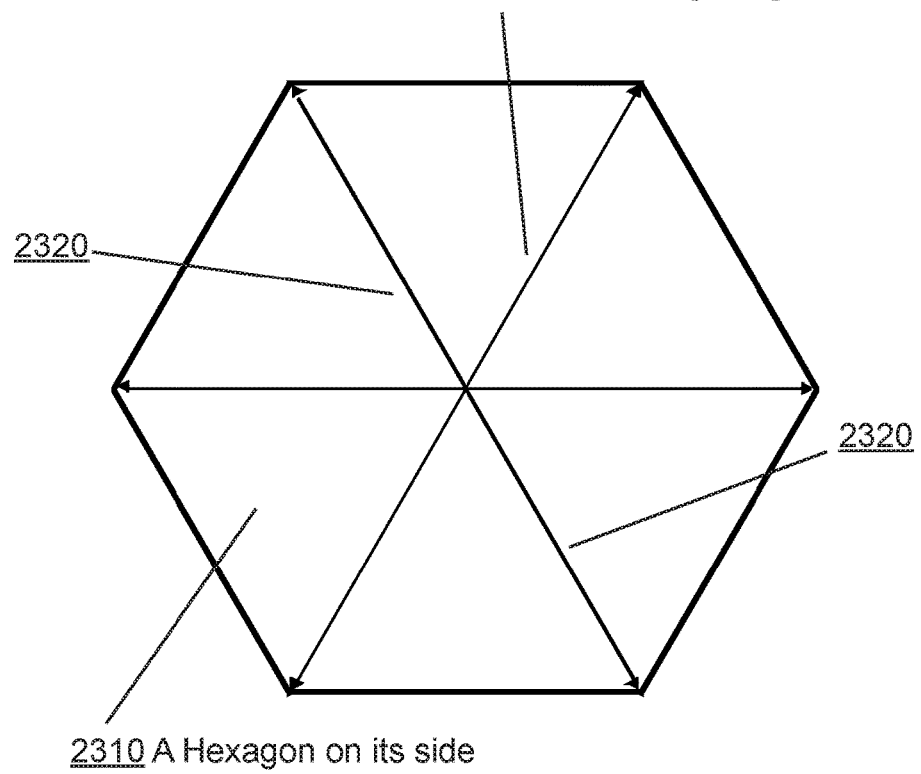
FIG. 23 shows the long diagonals of a hexagon on its side.
Figure 24:
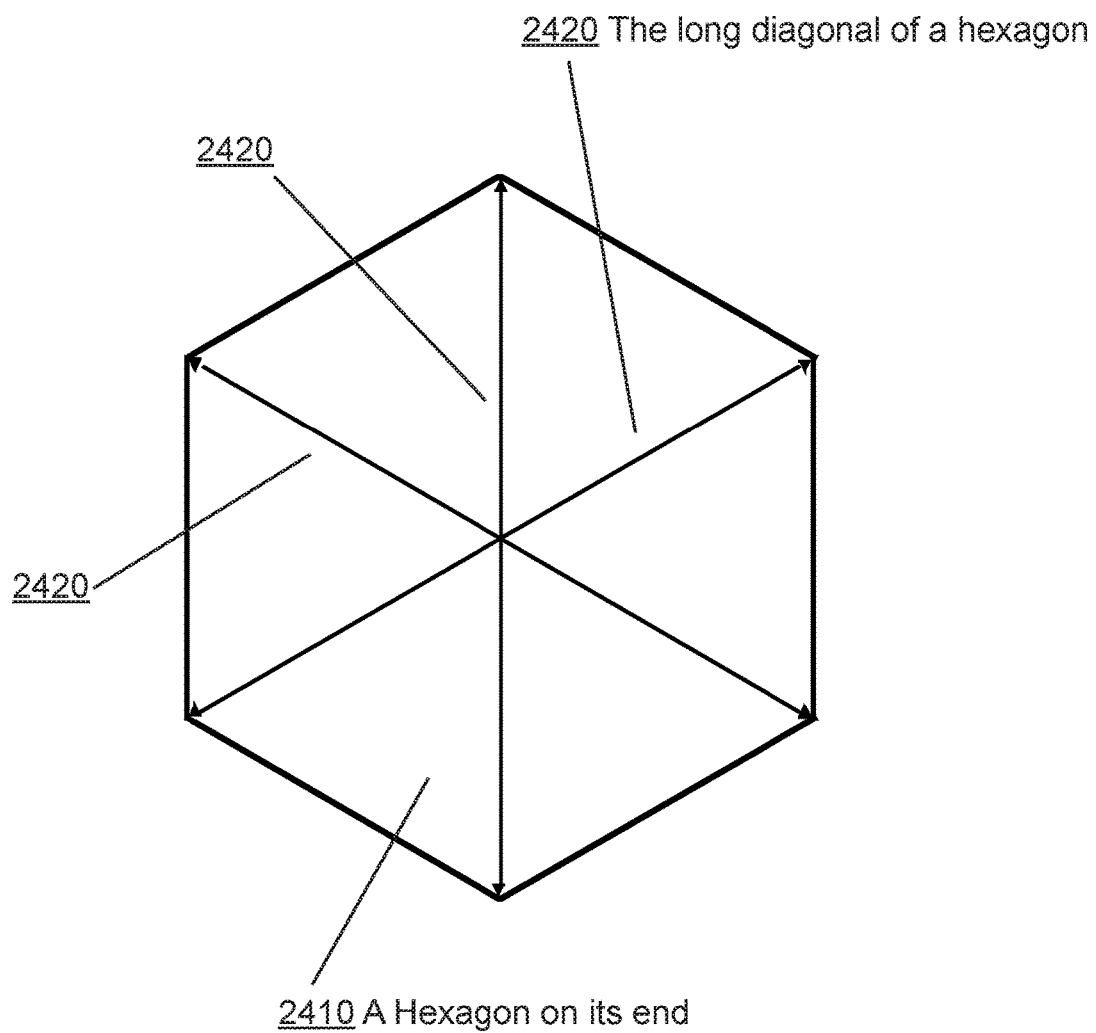
FIG. 24 shows the long diagonals of a hexagon on its end.
Figure 25:
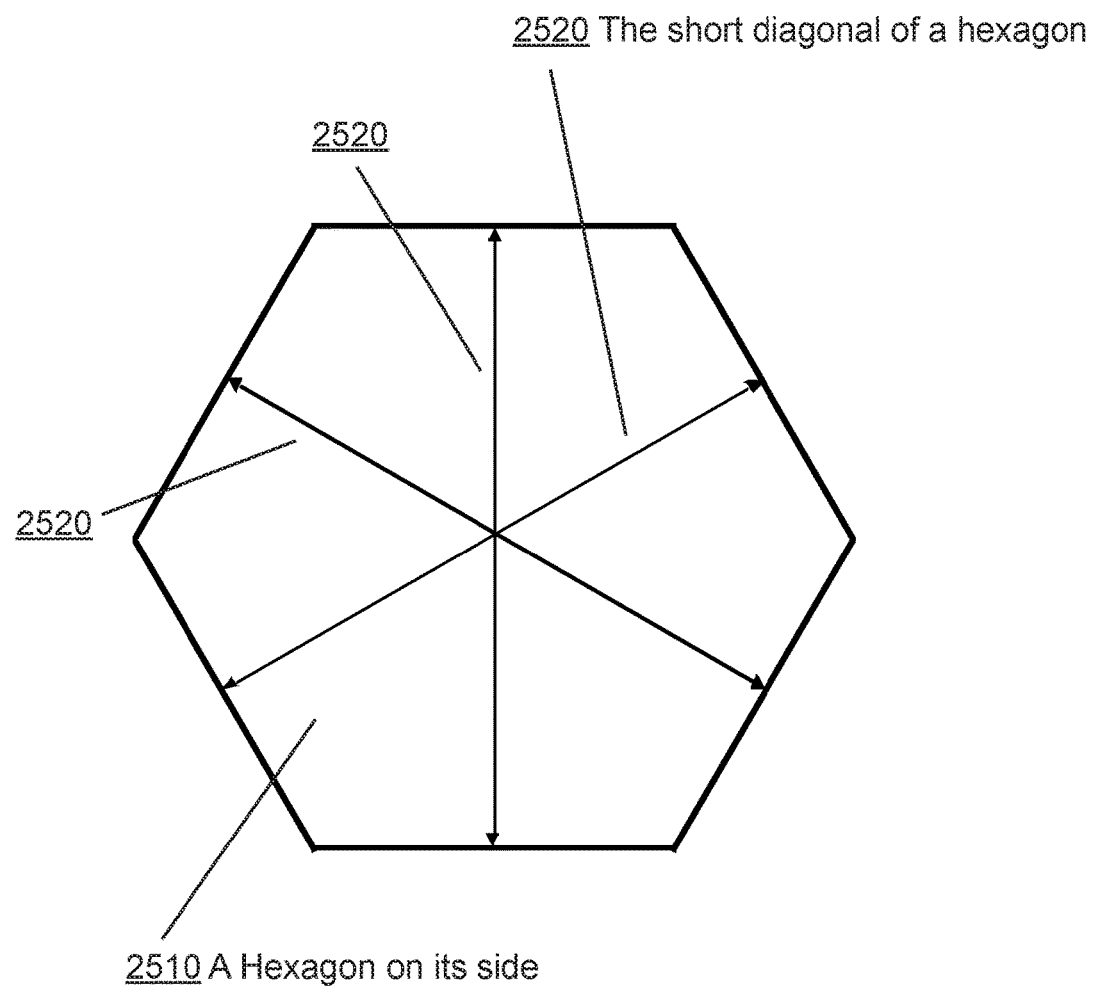
FIG. 25 shows the short diagonals of a hexagon on its side.
Figure 26:
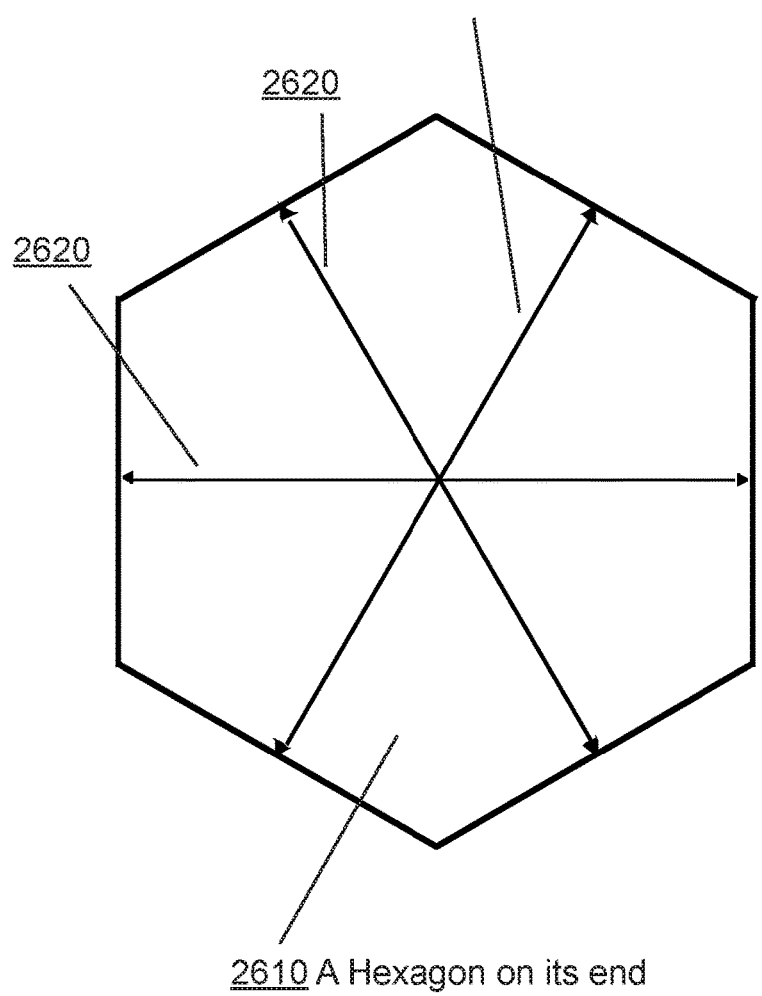
FIG. 26 shows the short diagonals of a hexagon on its end.

We define the LongDiagonal of a hexagon as the longest line segment of any orientation that can be drawn across the hexagon. FIG. 23 shows the long diagonal element 2320 of a hexagon on its side element 2310. FIG. 24 shows the long diagonal element 2420 of a hexagon on its end element 2410. We define the ShortDiagonal of a hexagon as the shortest line segment of any orientation that can be drawn across the hexagon. FIG. 25 shows the short diagonal element 2520 of a hexagon on its side element 2510. FIG. 26 shows the short diagonal element 2620 of a hexagon on its end element 2610. The numerical relationship between the ShortDiagonal and the LongDiagonal of a hexagon is:

$$\frac{ShortDiagonal}{LongDiagonal} = \frac{\sqrt{3}}{2} \qquad (2)$$

$$ShortDiagonal = \frac{\sqrt{3}}{2} \cdot LongDiagonal \qquad (3)$$

$$LongDiagonal = \frac{2}{\sqrt{3}} \cdot ShortDiagonal \qquad (4)$$

Tilings of Hexagons

The Orientation of Tilings of Hexagons

Definition of term: tiling of hexagon on their sides

Definition of term: tiling of hexagon on their ends

Figure 27:
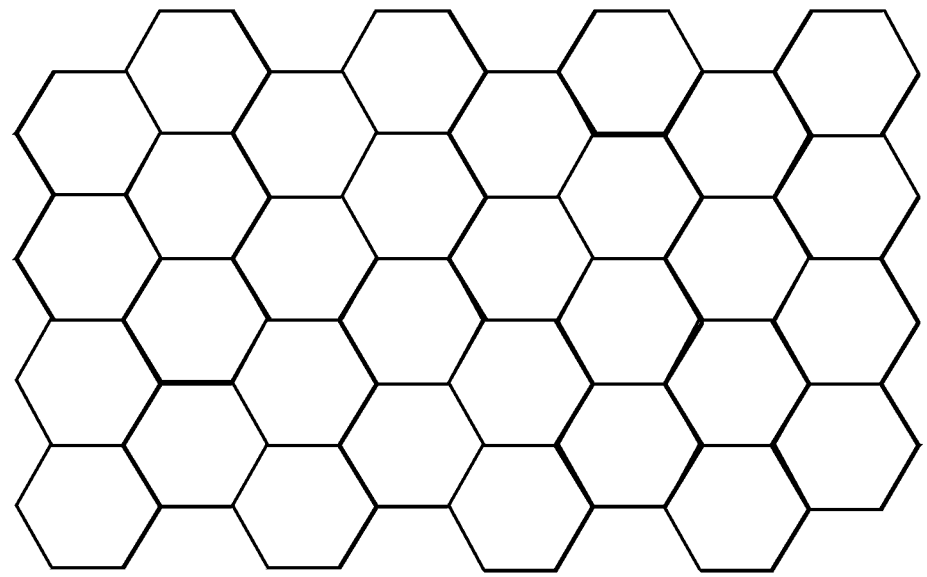
FIG. 27 shows a tiling of hexagons on their side.
Figure 28:
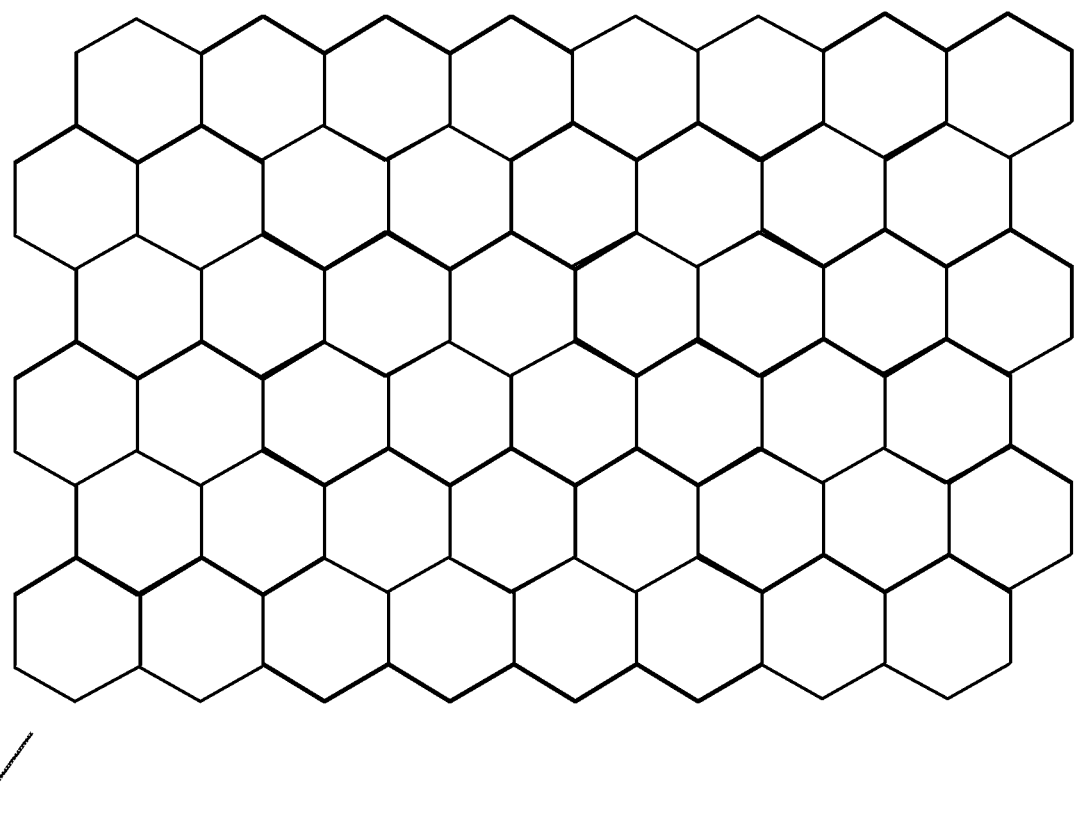
FIG. 28 shows a tiling of hexagons on their end.

Just as lone hexagons have two main possible orientations, the same is true when they gang up. In FIG. 27, we show a tiling of hexagons on their sides 2710, and in FIG. 28, we show a tiling of hexagons on their ends 2810.

The Pitch Between Hexagons in Tilings of Hexagons

Definition of term: long pitch

Definition of term: short pitch

Figure 29:
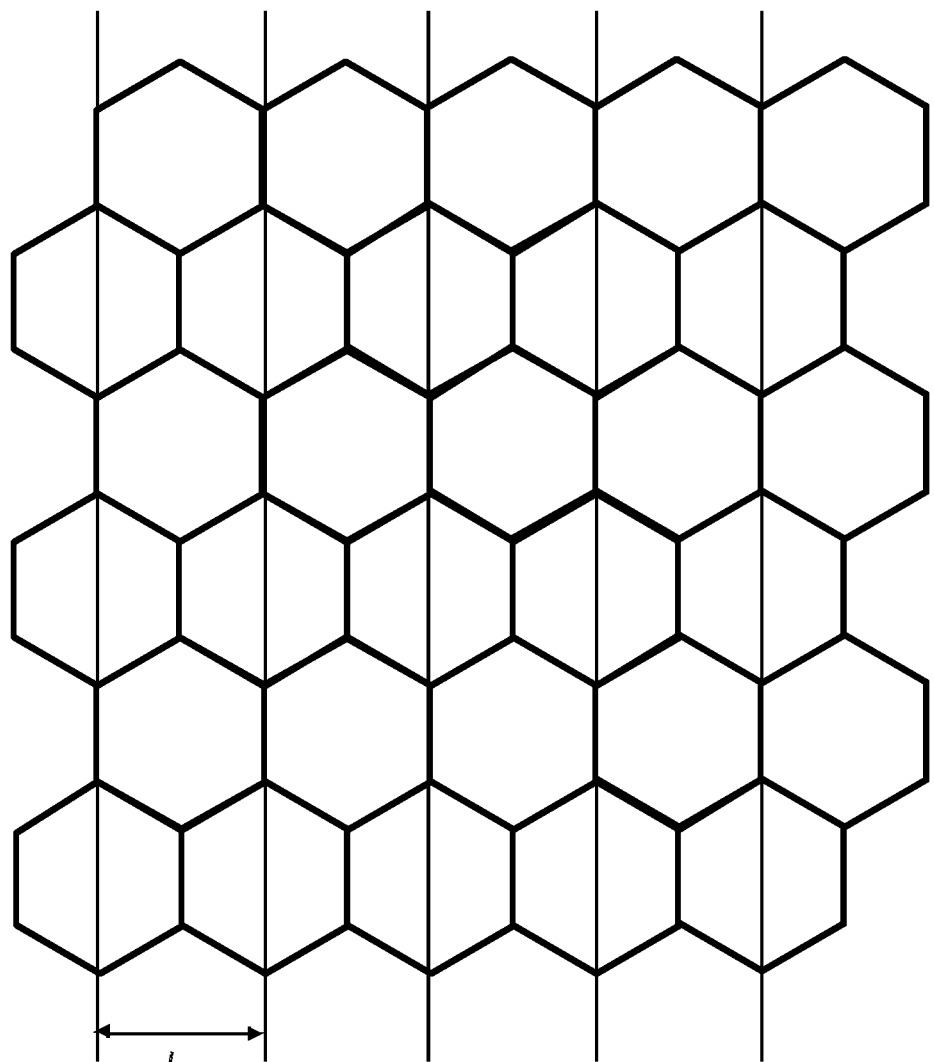
FIG. 29 shows the long pitch of a hexagonal tiling.
Figure 30:
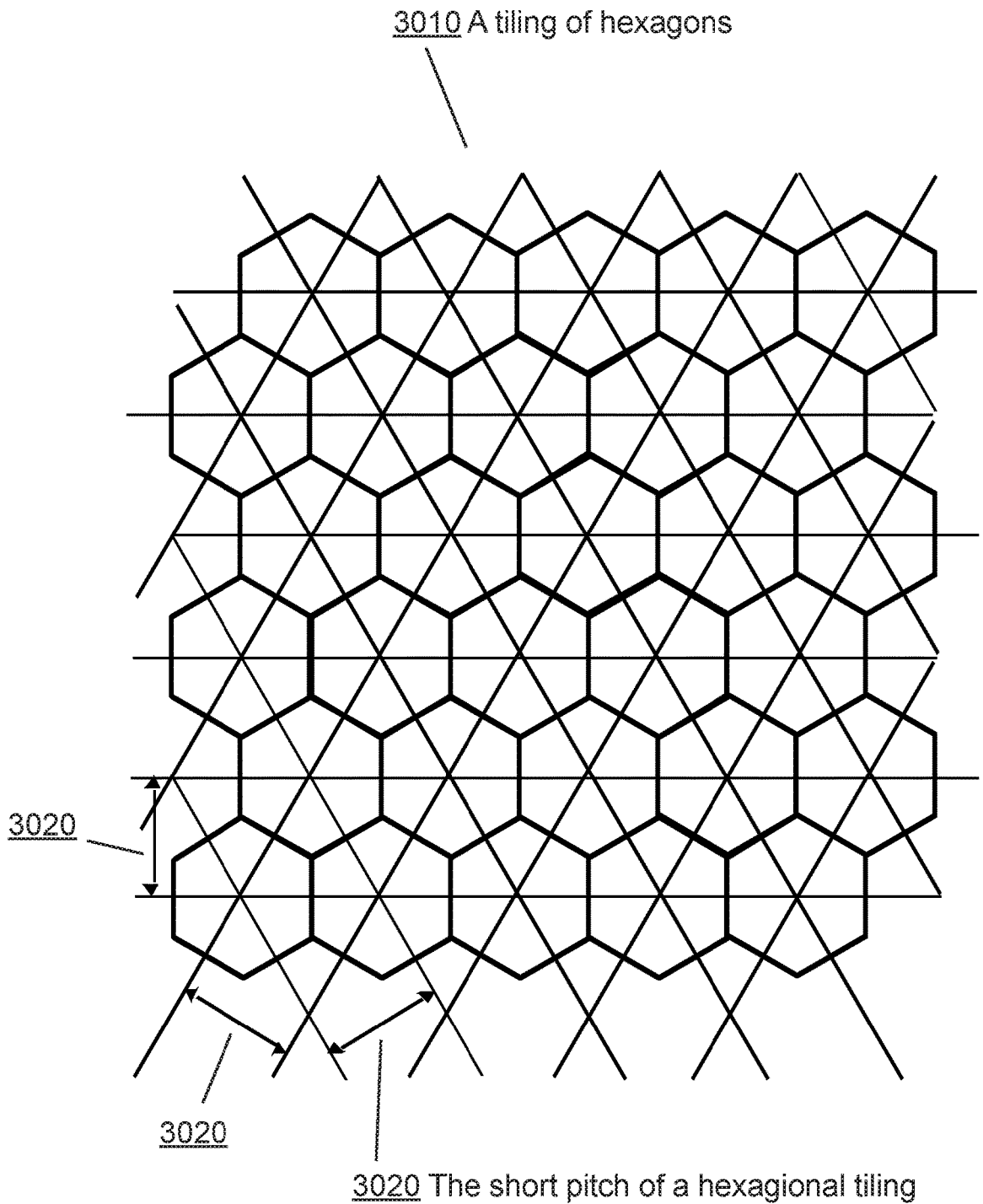
FIG. 30 shows the short pitch of a hexagonal tiling.

Regardless of the orientation of a tiling of hexagons, there are two different "pitches" to a hexagonal tiling. In FIG. 29 we define the longer of the two: the long pitch 2920 of a hexagonal tiling 2910 is the distance between left right neighboring hexagons in a tiling when that tiling is viewed as a tiling of hexagons on their end. In FIG. 30 we define the shorter of the two: the short pitch 3020 of a hexagonal tiling 3010 is the distance between adjacent hexagons diagonally in a tiling when that tiling is viewed as a tiling of hexagons on their end. FIG. 30 shows diagonals up and to the right, and also the symmetrically equivalent diagonals up and to the left, and those vertically apart, which all have the same short pitch. The long pitch turns out to be the same as the short diagonal of a hexagon, so we will generally just use the term short diagonal instead. The relationship between the ShortPitch and the ShortDiagonal is:

$$ShortPitch = \frac{3}{4} \cdot LongDiagonal = \frac{\sqrt{3}}{2} \cdot ShortDiagonal \qquad (5)$$

$$ShortDiagonal = \frac{2}{\sqrt{3}} \cdot ShortPitch \qquad (6)$$

The Rows and Semi-Columns of Tilings of Hexagons on their End

Hexagonal tilings don't have the simple row-column relationship that tilings of squares (and rectangles) do. However, we can define some close equivalents.

The Rows of Tilings of Hexagons on their End

Figure 31:
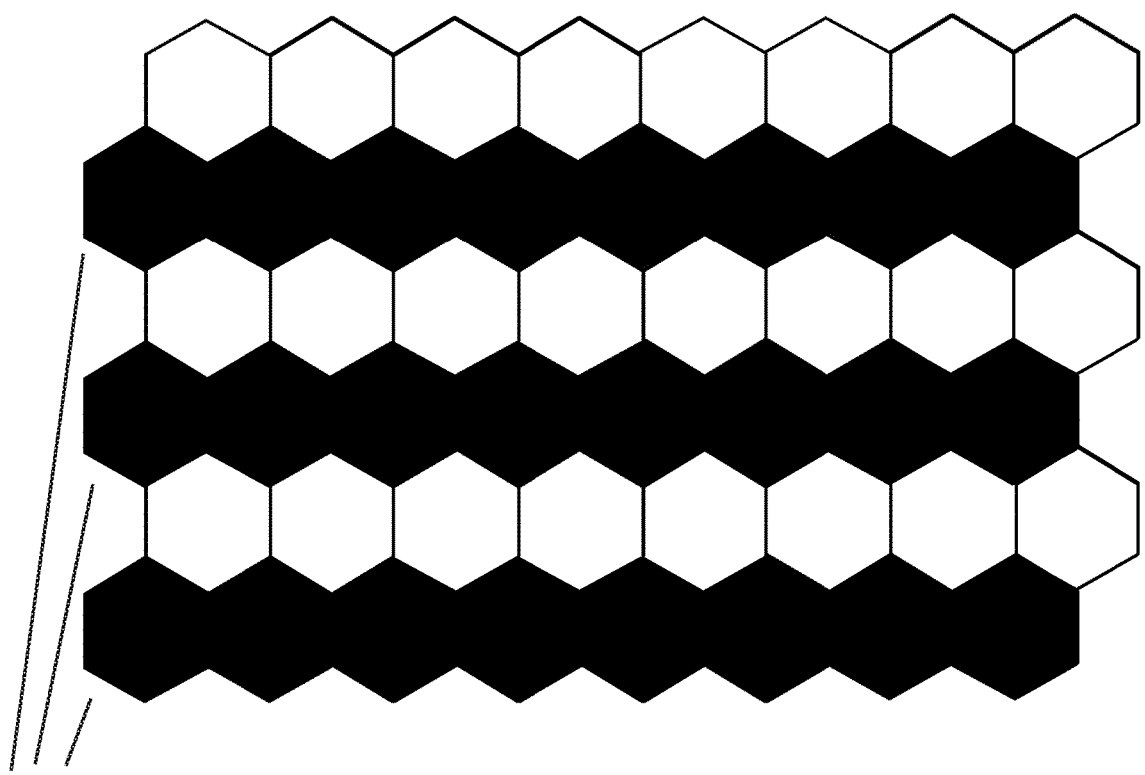
FIG. 31 shows the even rows of a tiling of hexagons on their end.
Figure 32:
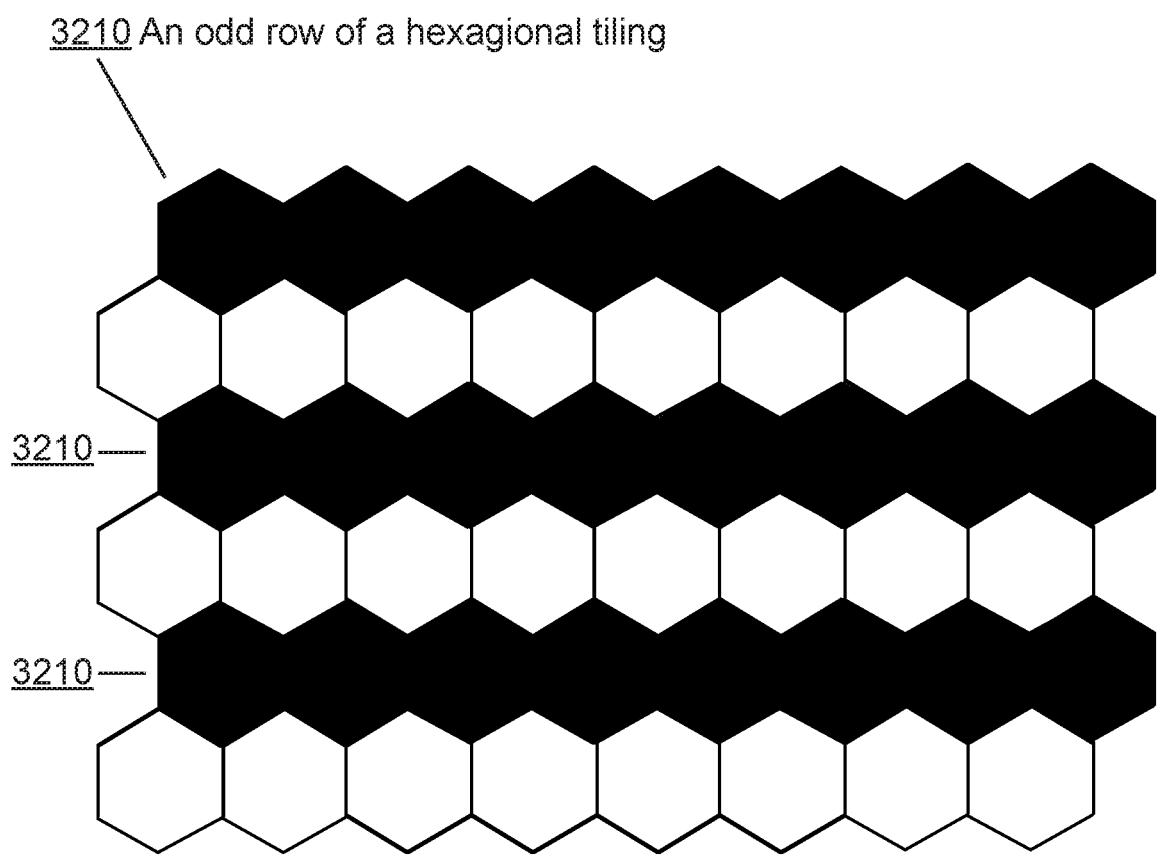
FIG. 32 shows the odd rows of a tiling of hexagons on their end.
Figure 33:
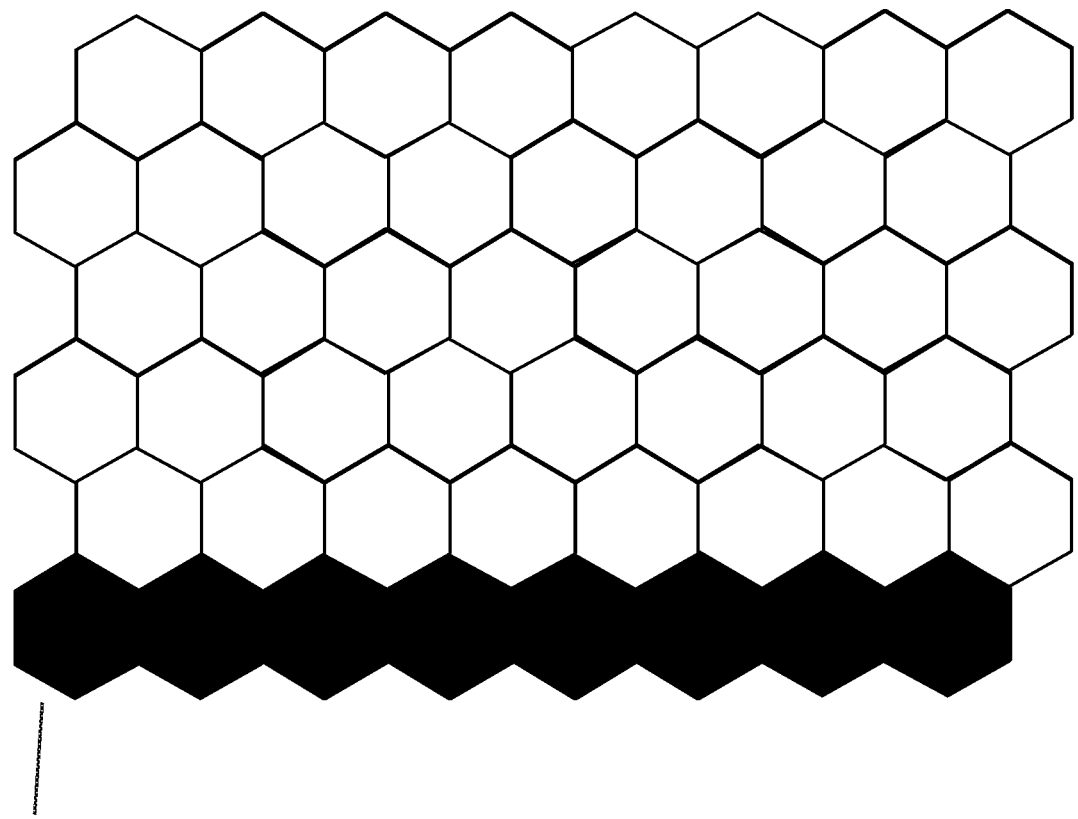
FIG. 33 shows the first even row of a tiling of hexagons on their end.
Figure 34:
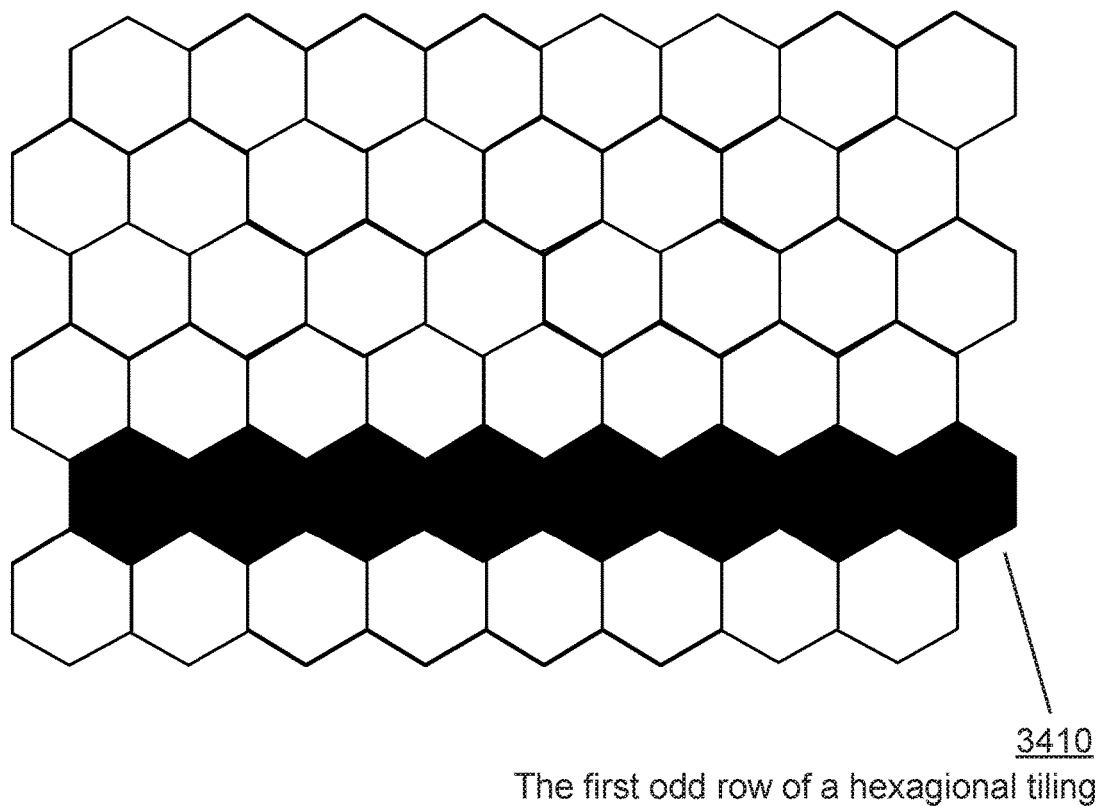
FIG. 34 shows the first odd row of a tiling of hexagons on their end.

In a tiling of hexagons on their end, we can see what looks something like the rows of squares in a tiling of squares, but in the hexagonal tiling, ever other row is offset by half a hexagon from its neighbors above and below. We will call these rows of hexagons (in a tiling of hexagons on their end), but will differentiate between even and odd rows. FIG. 31 shows examples of the even rows of a tiling of hexagons on their end, element 3110. FIG. 32 shows examples of the odd rows of a tiling of hexagons on their end, element 3210. We will call the bottommost even row of hexagons the first even row, as shown in FIG. 33 element 3310. We will call the bottommost odd row of hexagons the first odd row, as shown in FIG. 34 element 3410.

The Semi-Columns of Tilings of Hexagons on their End

Figure 35:
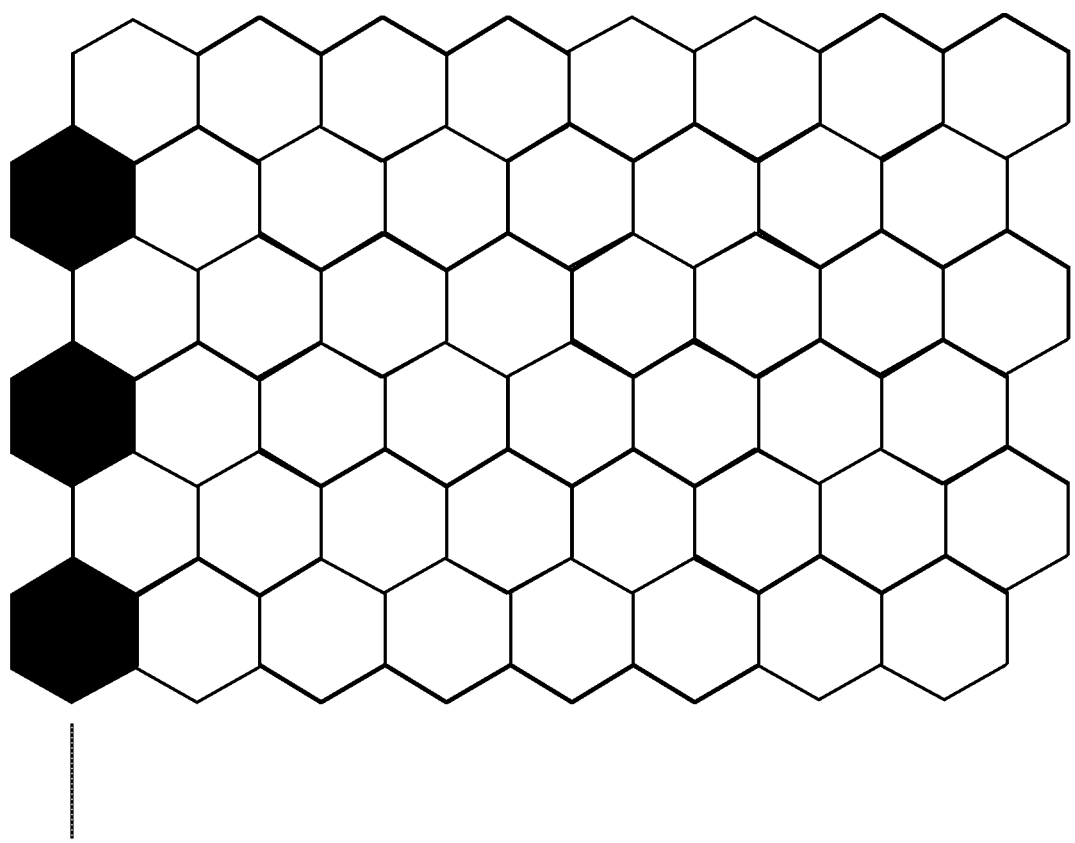
FIG. 35 shows the first semi-column of a tiling of hexagons on their end.
Figure 36:
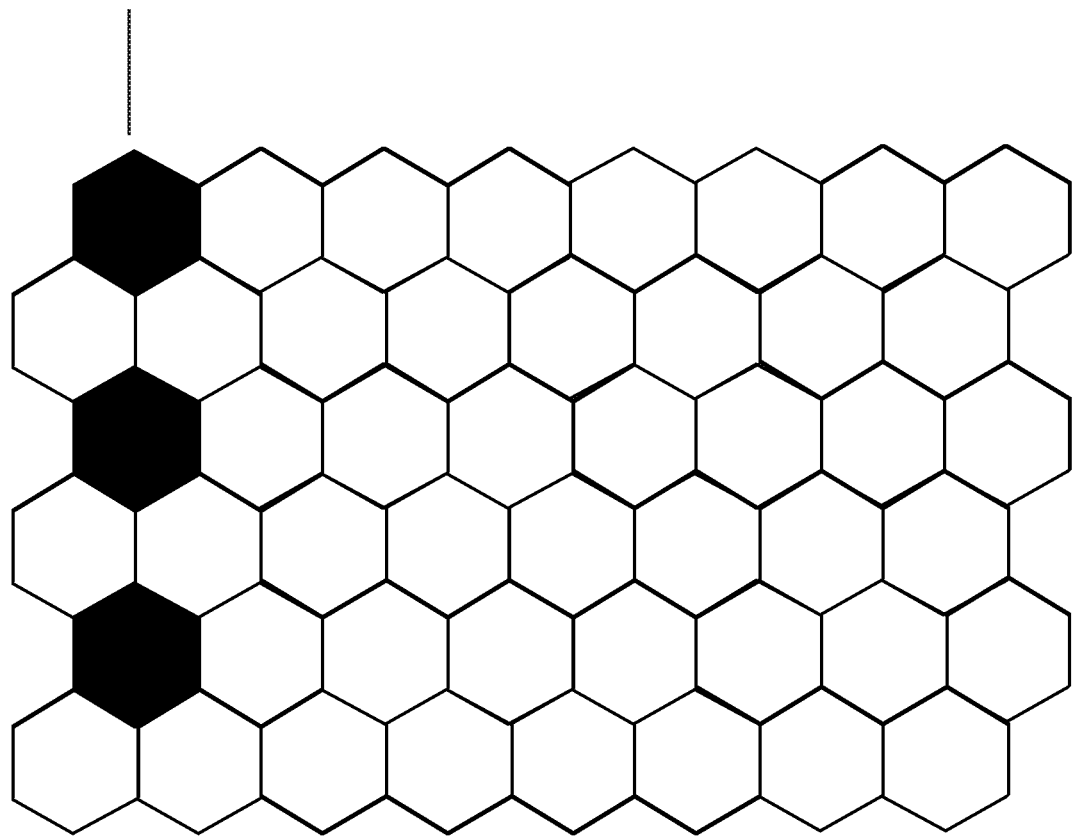
FIG. 36 shows the second semi-column of a tiling of hexagons on their end.

One has to squint a bit harder, but a partial equivalent to columns exist in tilings of hexagons on their end: semi-columns. FIG. 35 shows the first semi-column 3510 of a tiling of hexagons on their end. FIG. 36 shows the second semi-column 3610 of a tiling of hexagons on their end.

Figure 37:
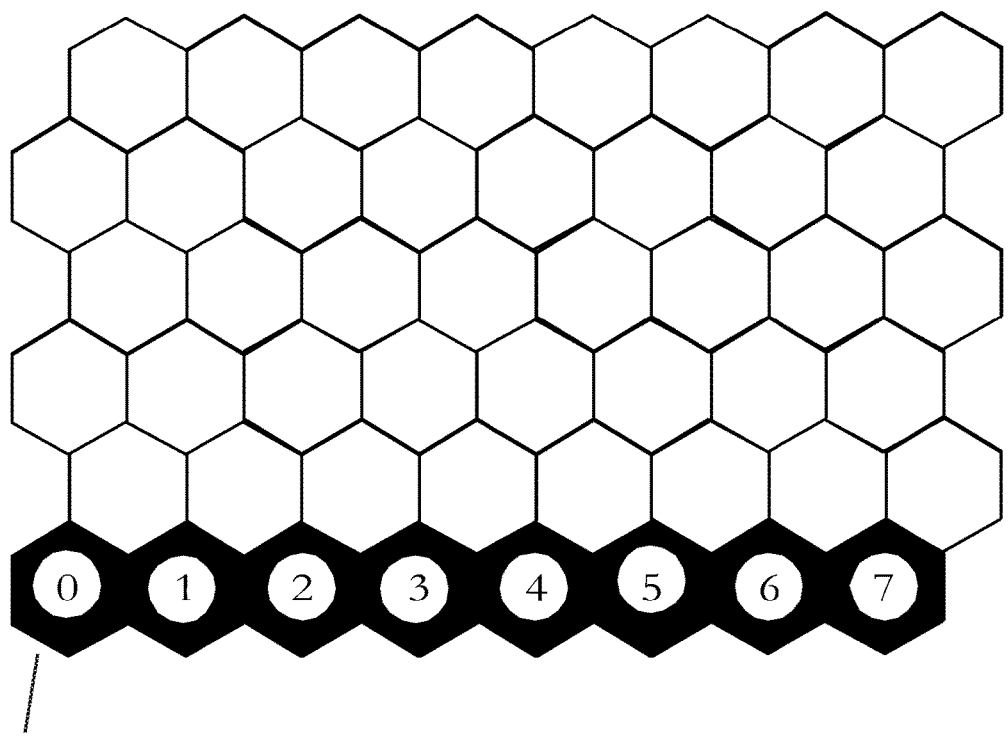
FIG. 37 shows the semi-column numbers of the first row of a tiling of hexagons on their end.
Figure 38:
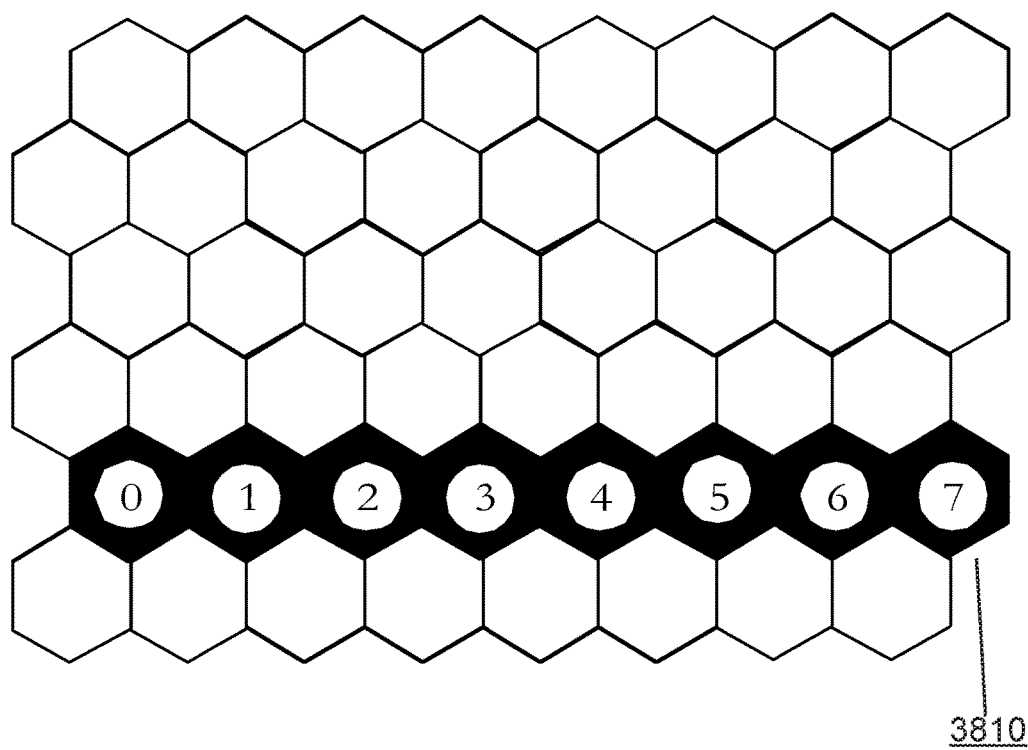
FIG. 38 shows the semi-column numbers of the second row of a tiling of hexagons on their end.

We can now assign semi-column numbers to both even and odd rows of tilings of hexagons on their end. FIG. 37 shows numbers (element 3710) for the first eight semi-columns for even rows of hexagons on their end. FIG. 38 shows numbers (element 3810) for the first eight semi-columns for odd rows of hexagons on their end.

Integral Row, Semi-Column Addresses of Tilings of Hexagons on their End

Figure 39:
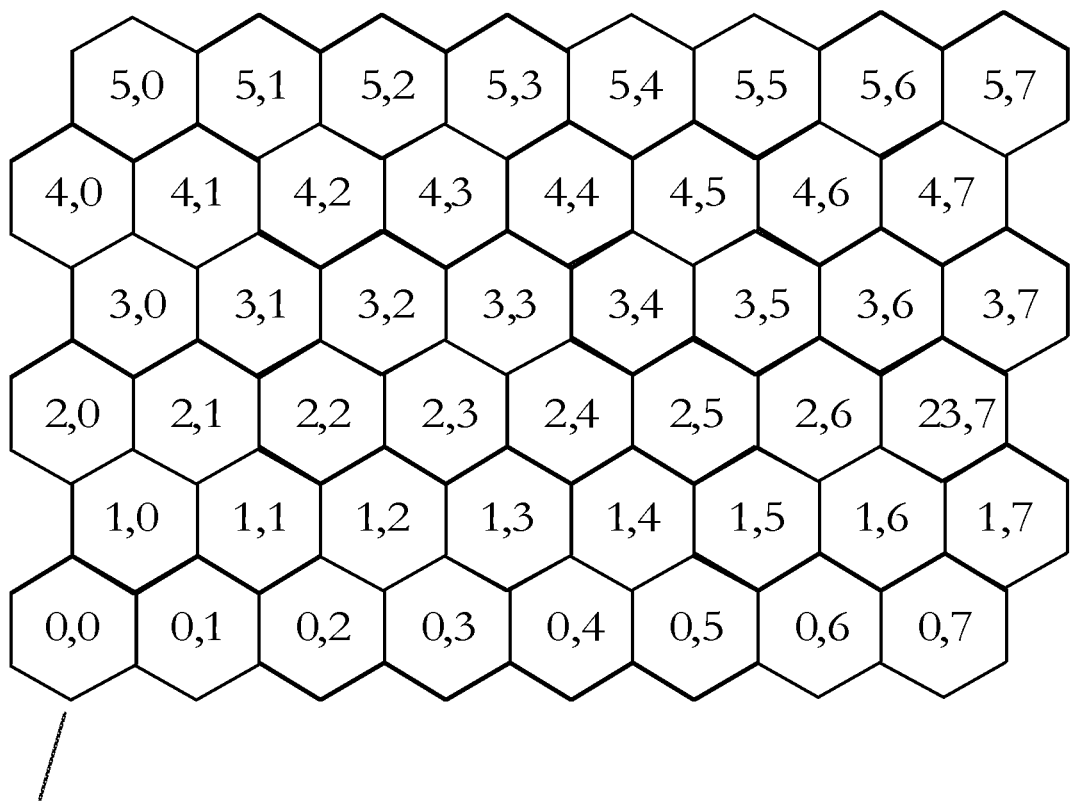
FIG. 39 shows the integral addresses of a tiling of hexagons on their end.

Numbering the first even row of a tiling of hexagons on their end 0, then the first odd row as 1, and so on, we can finally assign a unique 2D integral address to each hexagon. This is shown in FIG. 39. For example, element 3910 is the hexagon with the unique 2D integral address of (0,0).

Conversion from Rectangular to Hexagonal Coordinates

This sub-section will define how 2D (u, v) points from Cartesian coordinate system on $\Re 2$ can be identified with a particular unique (uu, vv) integral hexagon address. For this definition we will assume that the within the uv Cartesian space each hexagonal pixel shape on its end has a width of unity, e.g. the short diagonal is one.

Because the width of all hexagons is one, all the points within all the leftmost hexagons of all even rows have a u address in the range of [0 1]. All points within all the second leftmost hexagons in all the even rows have a u address in the range of [1 2), and so on. We associate with each hexagon in even rows an integer uu semi-column address that is derived from the floor[ ] of their u address range. This is the first of the unique two integer pixel address for even row hexagons.

Figure 40:
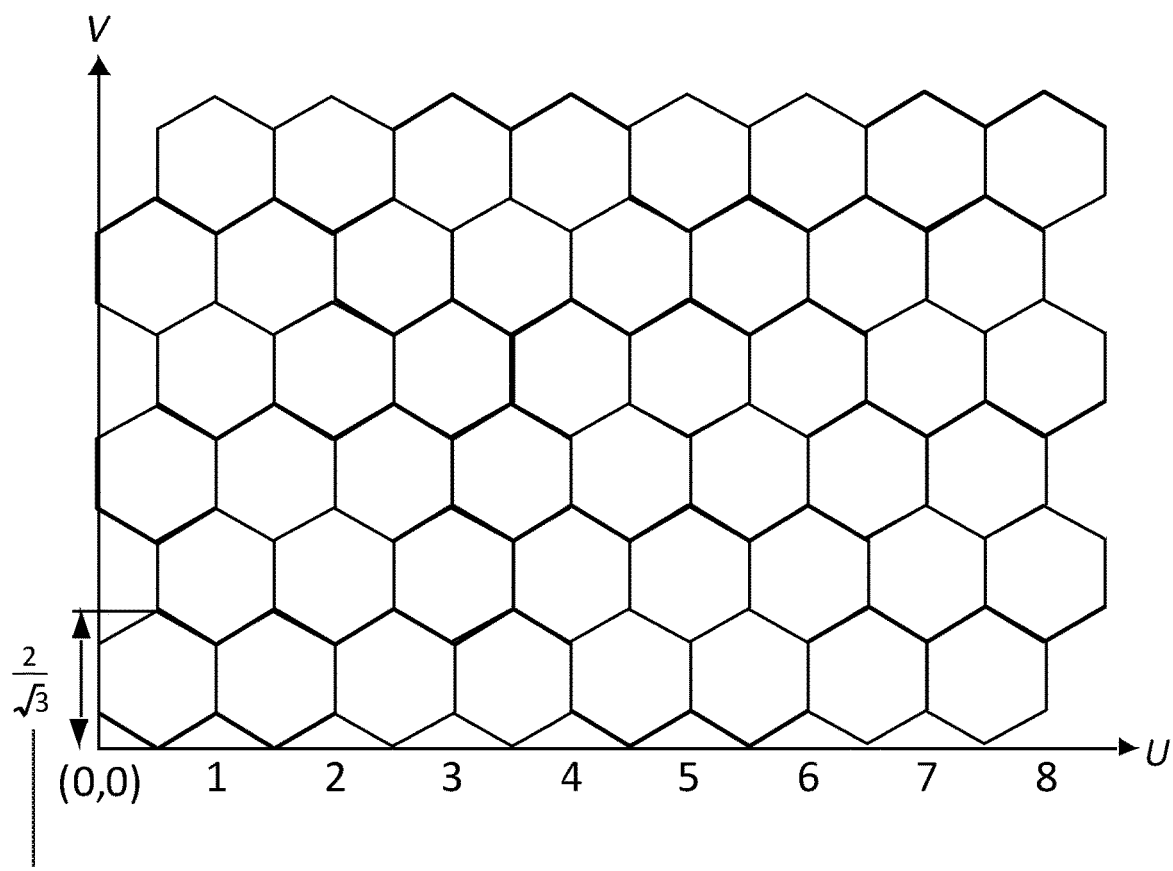
FIG. 40 shows the height of a unit-width hexagon in a tiling of hexagons on their end.

The situation with all odd row hexagons is similar, but shifted to the right by ½. Thus all the points within all the leftmost hexagons of all even rows have a u address in the range of [½ 1½). All points within all the second leftmost hexagons in all the odd rows have a u address in the range of [1½ 2½), and so on. We associate with each hexagon in odd rows an integer uu semi-column address that is derived from the floor[ ] of their u address range. This is the first of the unique two integer pixel address for odd row hexagons. This is shown graphically in FIG. 40, where the height of a unit-wide hexagon on its end is shown as $2/\sqrt{3}$ (element 4010).

Figure 41:
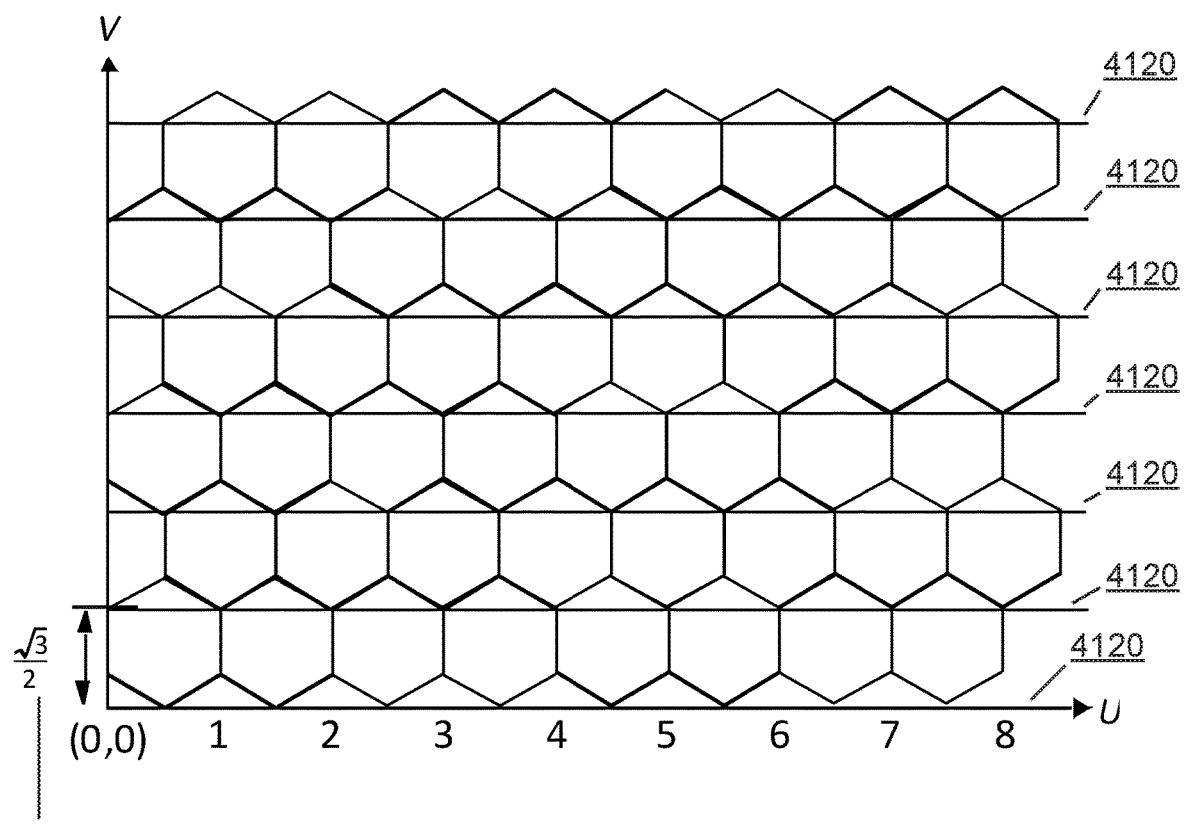
FIG. 41 shows the row to row pitch of a tiling of unit width hexagons on their end.

As shown in FIG. 41, the pitch 4110 between adjacent even and odd rows of hexagons is the short pitch of the tiling, which for a unit short diagonal hexagon is $\sqrt{3}/2$. Consider the set of horizontal lines with v axis intercept of $n \cdot \sqrt{3}/2$, where n is a positive integer. Just as the positive u axis contains the bottom most points of all the hexagons in the first row, the horizontal lines parameterized by n contain the bottommost points of all the hexagons of the n-th row, starting with n=0 (the positive u axis), for both even and odd rows of hexagons. These lines are also shown in FIG. 41, as element 4120. The integer n is the integer vv address for each hexagon, which is the second of the unique two integer pixel address for hexagons. This completes the assigning of unique two integer pixel addresses to each hexagon in the tiling.

Each point (u v) in the Cartesian space lies within a unique hexagon of the tiling, which is pretty much the definition of "tiling the plane." The algorithm for converting a given (u v) Cartesian space point to a unique (uu vv) hexagon id is straight forward, if slightly laborious to detail. The algorithm is well known from the literature, so it will not be repeated here. The function CarToHex[ ] is the notation used to indicate this process. Thus we have:

$$uu[u,v] = \text{CarToHex}[u,v] \cdot uu \quad (7)$$

$$vv[u,v] = \text{CarToHex}[u,v] \cdot vv \quad (8)$$

The equivalent integer pixel address computing for a square tiling is (floor[u] floor[v]). Because the function is destructive, no (unique) inverse exists.

Properties of Hexagons and Tilings of Hexagons

The Area of a Hexagon

The area of a hexagon can be expressed either in terms of its ShortDiagonal, its LongDiagonal, or its ShortPitch.

$$\text{area} = \frac{3}{4} \cdot LongDiagonal \cdot ShortDiagonal \quad (9)$$

$$= \frac{3}{8} \cdot \sqrt{3} \cdot LongDiagonal^2 = \frac{\sqrt{3}}{2} \cdot ShortDiagonal^2$$

$$\text{area} = ShortPitch \cdot ShortDiagonal = \frac{2}{\sqrt{3}} \cdot ShortPitch^2 \quad (10)$$

Sometimes we need to know the diameter of a circle with the same area as a hexagon, or vice versa. Narrowly defining the diameter of a hexagon to be the diameter of the circle with the same area as a hexagon, we can relate these:

$$\text{area} = \pi \cdot \left(\frac{diameter}{2}\right)^2 \quad (11)$$

$$diameter = \sqrt{\frac{4 \cdot area}{\pi}} \quad (12)$$

$$diameter = \sqrt{\frac{4 \cdot \frac{\sqrt{3}}{2} \cdot ShortDiagonal^2}{\pi}} = \sqrt{\frac{2 \cdot \sqrt{3}}{\pi}} \cdot ShortDiagonal \quad (13)$$

$$ShortDiagonal = \sqrt{\frac{\pi}{2 \cdot \sqrt{3}}} \cdot diameter \quad (14)$$

$$ShortPitch = \sqrt{\frac{\pi \sqrt{3}}{8}} \cdot diameter \approx 0.85 \cdot diameter \quad (15)$$

$$diameter = \sqrt{\frac{8}{\pi \cdot \sqrt{3}}} \cdot ShortPitch \quad (16)$$

Many times, rather than be given an area, we are given a density of hexagons per unit area. We need to be able to convert density to and from our linear measurements:

$$density = \frac{1}{area} \quad (17)$$

-continued $$\text{density} = \frac{\sqrt{3}}{2} \cdot \frac{1}{ShortPitch^2} \quad (18)$$

$$\text{density} = \frac{2}{\sqrt{3}} \cdot \frac{1}{ShortDiagonal^2} \quad (19)$$

$$\text{density} = \frac{1}{\pi} \cdot \left(\frac{2}{\text{diameter}}\right)^2 = \frac{4}{\pi \cdot \text{diameter}^2} \quad (20)$$

Inverting:

$$\text{area} = \frac{1}{\text{density}} \quad (21)$$

$$ShortPitch = \sqrt{\frac{\sqrt{3}}{2} \cdot \frac{1}{\text{density}}} \quad (22)$$

$$ShortDiagonal = \sqrt{\frac{2}{\sqrt{3}} \cdot \frac{1}{\text{density}}} \quad (23)$$

$$\text{diameter} = \sqrt{\frac{4}{\pi \cdot \text{density}}} \quad (24)$$

Resolution of Hexagons Vs. Squares

Theorem: If you define the resolution of a given pixel shape to be limited by the lowest resolution cross-section of the pixel (e.g., a line across the pixel at any angle: choose the longest diagonal of the pixel shape), then hexagonal pixels are 30% more efficient than square pixels. That is, to achieve at least a given worse case resolution within a given region, 30% less hexagonal shaped pixels are needed than rectangular shaped pixels.

Proof: The area of a hexagon whose LongDiagonal is one is $3/8 \cdot \sqrt{3} \approx 0.65$. (The area of a unit circle is $$\frac{\pi}{4} \approx 0.79.)$$

A square with me same worse case resolution is a square with a diagonal of length one. The area of a square with a diagonal of length one is ½. Thus the amount of area covered by a hexagon whose LongDiagonal is one relative to the amount of area covered by a square with a diagonal of length one is $3/4 \cdot \sqrt{3} \approx 1.3$.

Hexagonal Shaped Tilings of Hexagons

So far we have talked about hexagonal tilings that extend infinitely across the plane. But we will also need to create tilings of hexagonally shaped groups of hexagonal tilings.

Definition of term: n-group of hexagons

Figure 42:
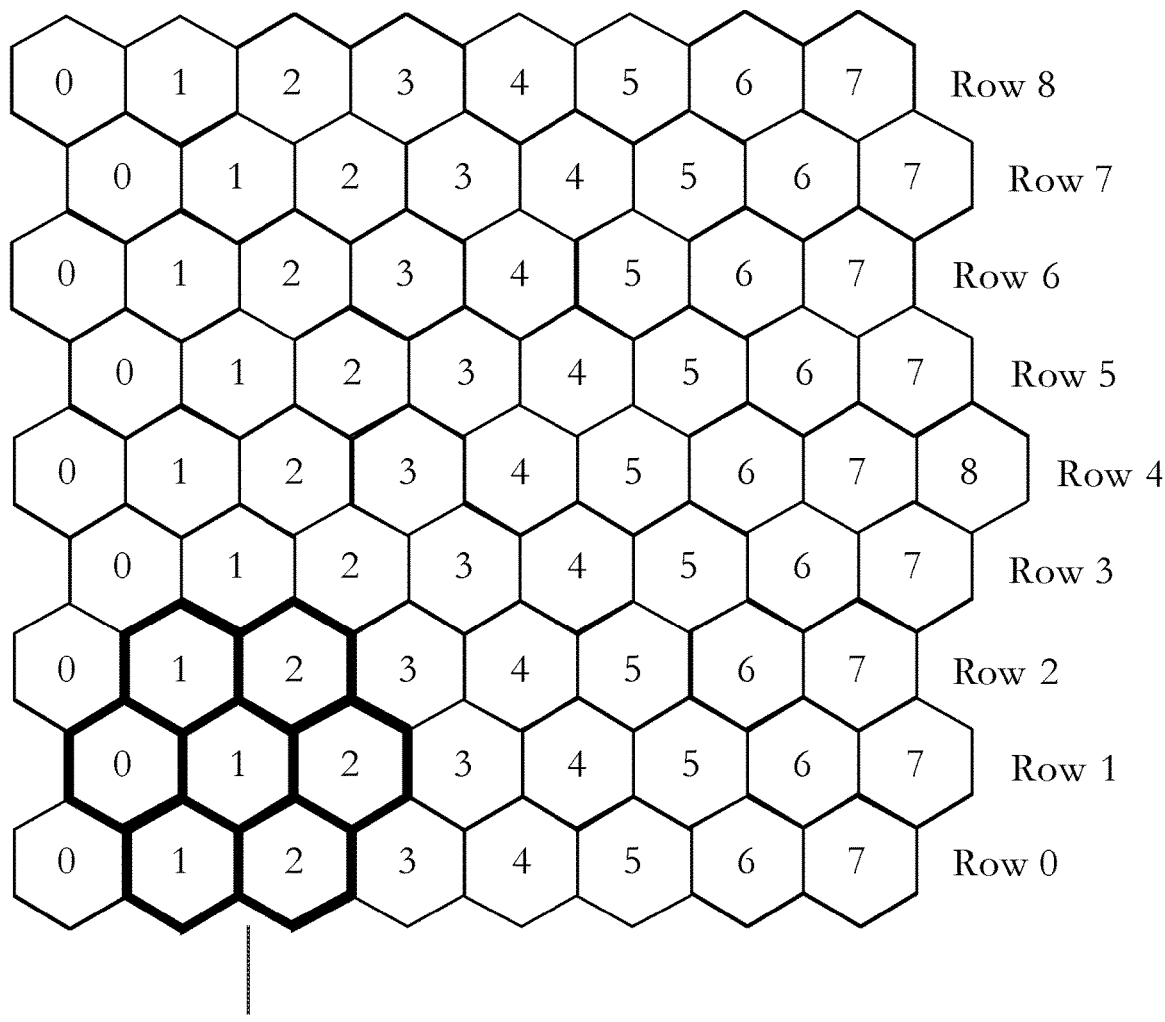
FIG. 42 shows a 1-group of hexagons their end
Figure 43:
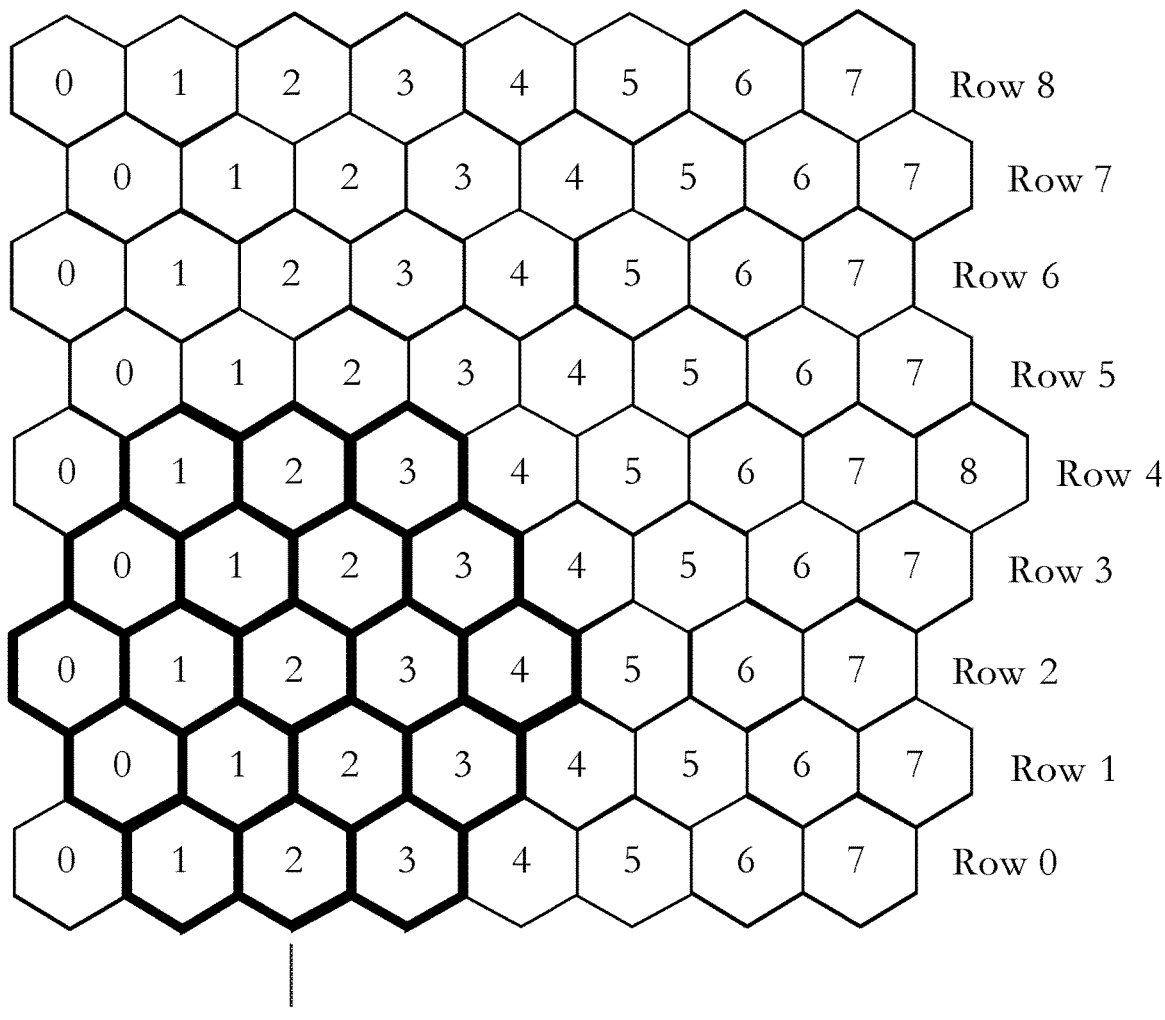
FIG. 43 shows a 2-group of hexagons their end
Figure 44:
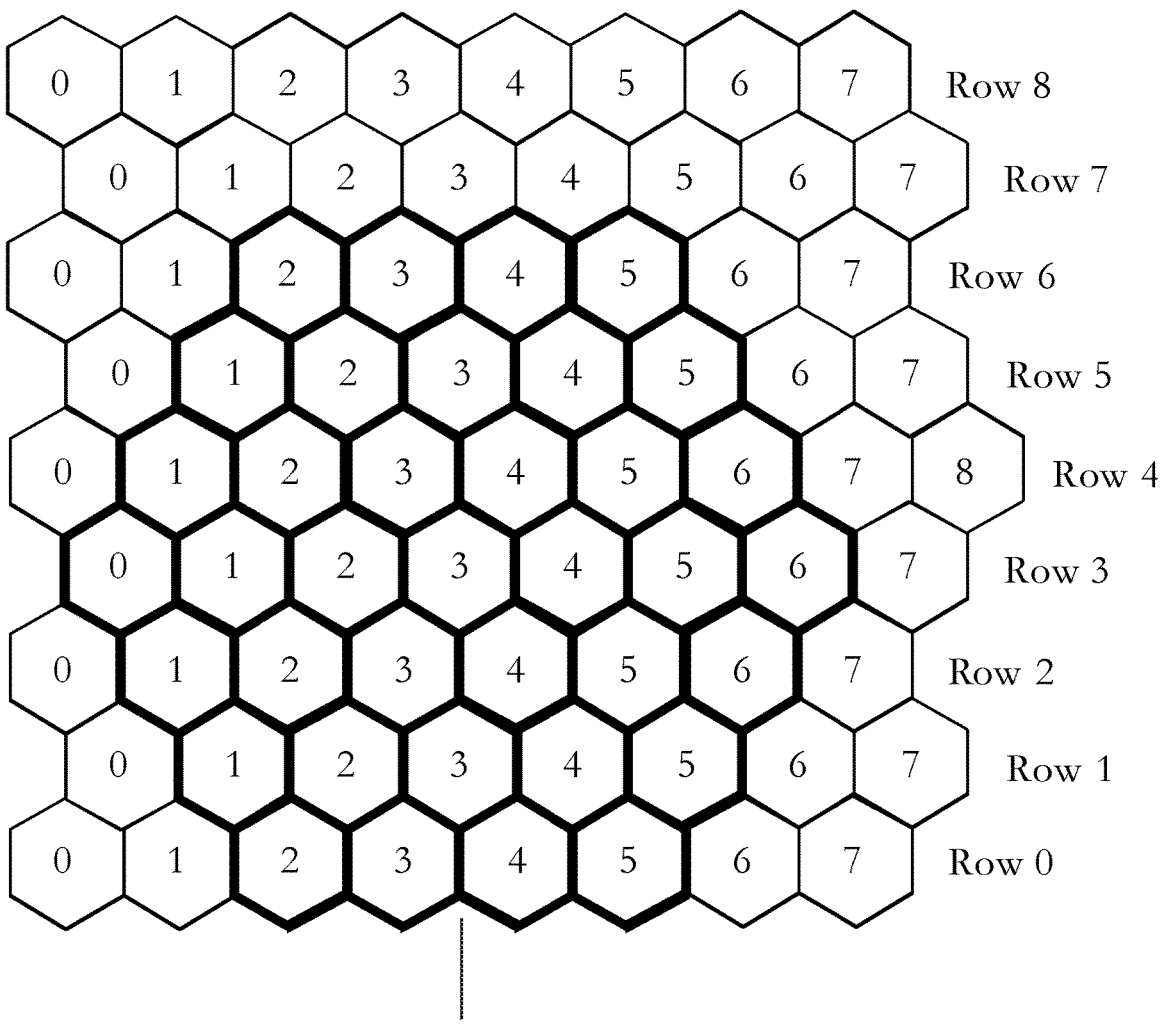
FIG. 44 shows a 3-group of hexagons their end
Figure 45:
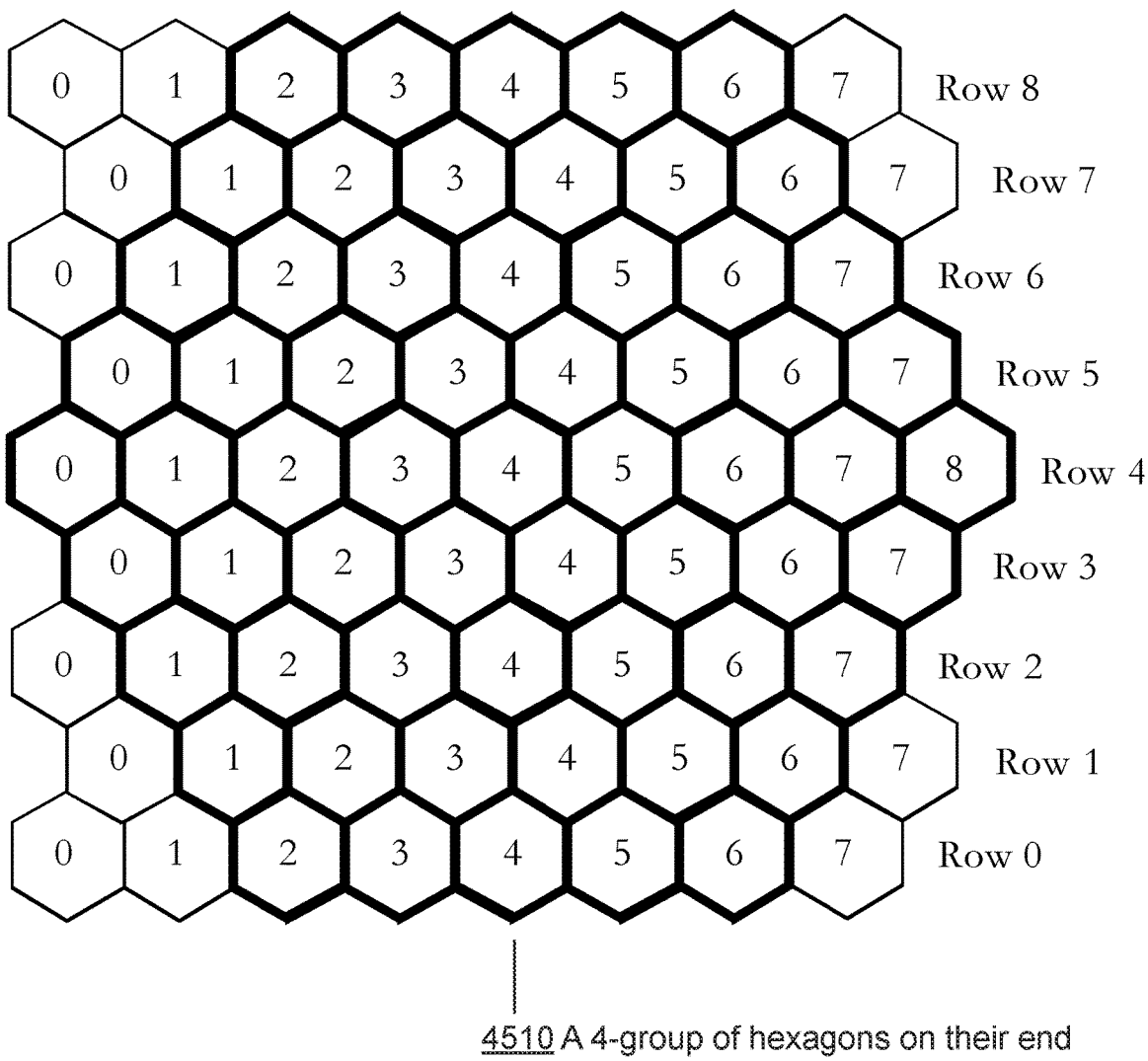
FIG. 45 shows a 4-group of hexagons their end

We define an n-group of hexagons to be, for positive integer's n, a single hexagon on its end surrounded by n layers of hexagons on their end. A 0-group of hexagons thus consists of a single hexagon on its end. We illustrate this concept for n from 1 to 4 by example: FIG. 42 shows a 1-group of hexagons 4210. FIG. 43 shows a 2-group of hexagons 4310. FIG. 44 shows a 3-group of hexagons 4410. And FIG. 45 shows a 4-group of hexagons 4510. In general, an n-group of hexagons will have 2·n+1 hexagons across its widest row. The number of hexagons inside an n-group of hexagons is given by the following equation:

$$\text{NumberOfHexagons} = 1 + 3 \cdot n \cdot (n+1) \quad (25)$$

Figure 46:
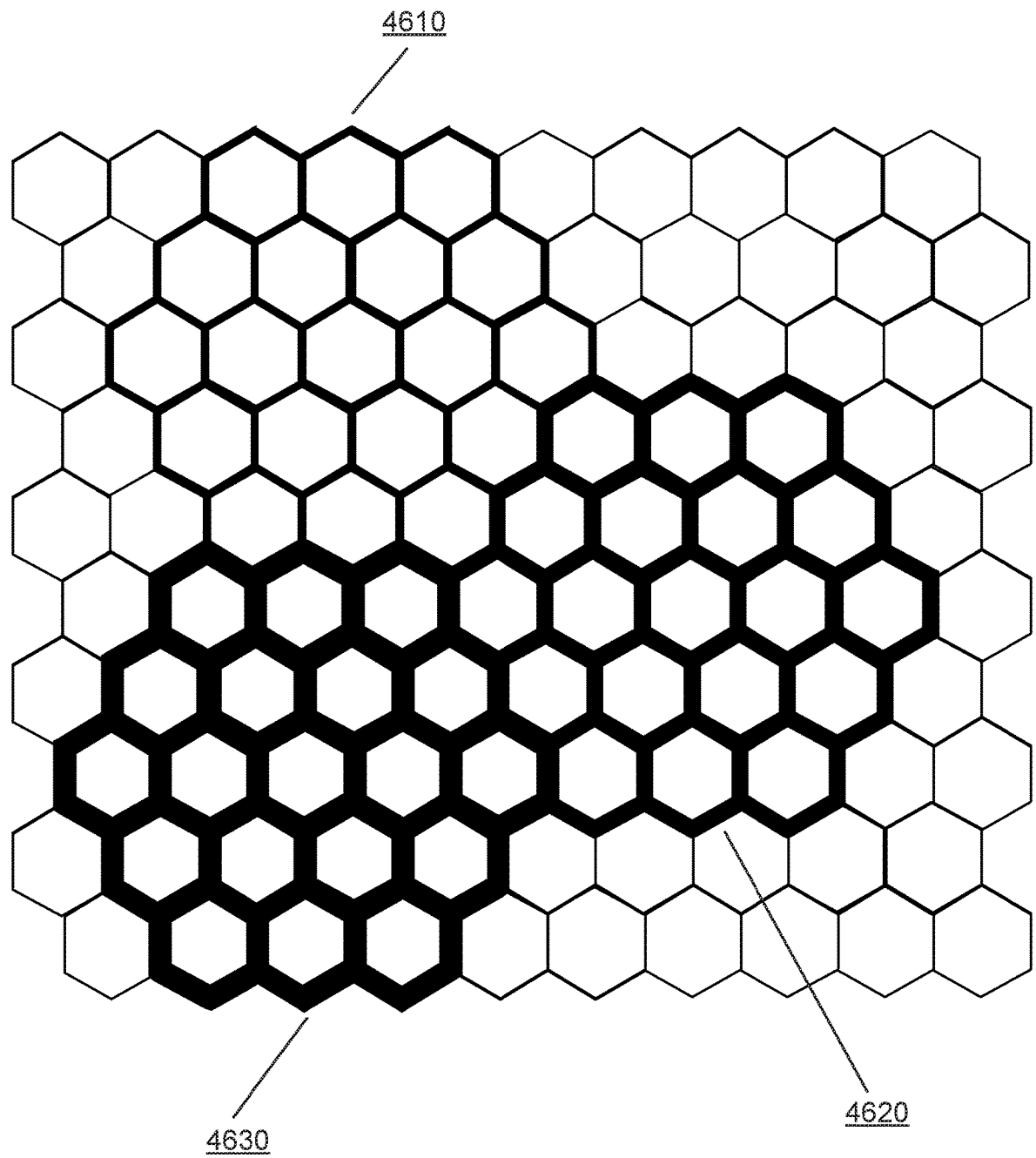
FIG. 46 shows a hexagonal tiling of three 2-groups of hexagons on their end.

A very important property of n-group of hexagons on their end is that they tile the plane like hexagons on their side. This is illustrated in FIG. 46, where three 2-group of hexagons, 4610, 4620, and 4630, are shown partially tiling the plane. This prosperity will be used later to tile a variable resolution space with several hexagonally shaped projectors, each have hexagonal shaped pixels composed as an n-group of hexagons.

Brief Notes on Square Tilings

The Orientation of a Square

Figure 47:
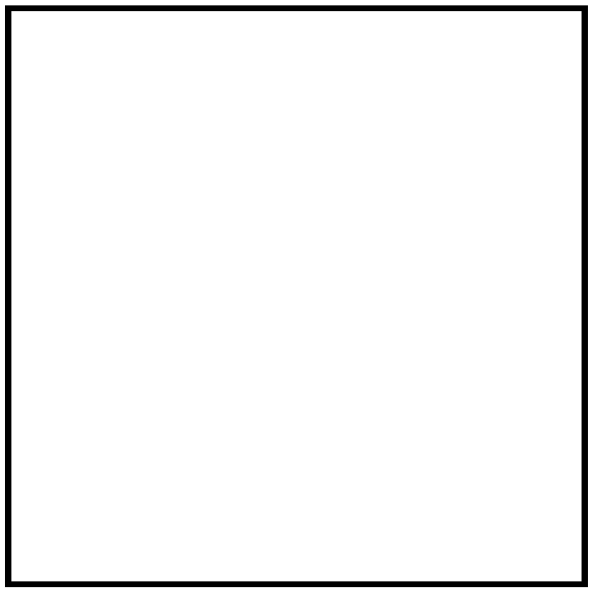
FIG. 47 shows a square on its side.
Figure 48:
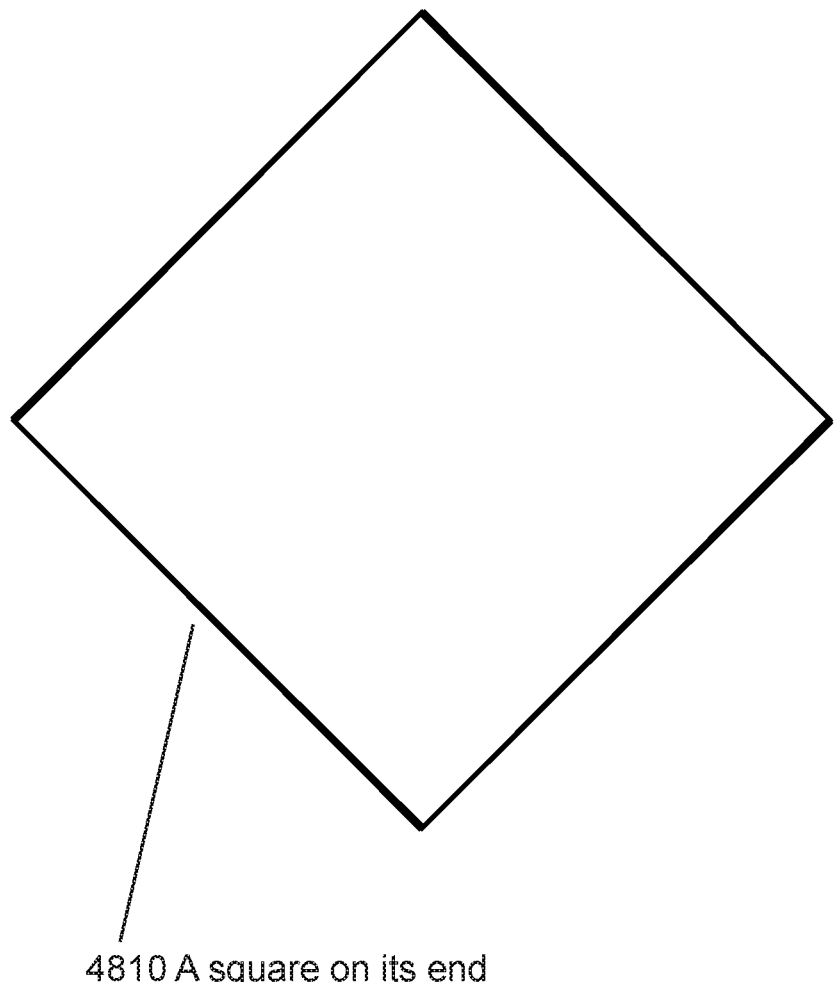
FIG. 48 shows a square on its end.

Squares are often viewed as having only one orientation: flat end down (a square on its side: FIG. 47, element 4710). But a diamond orientation is perfectly reasonable: squares (oriented) on its end (FIG. 48, element 4810). (The square in repose.) But we will deal mostly with squares on their side. Here the width and height are well defined, and are of course the same.

The Diagonals of a Square

Figure 49:
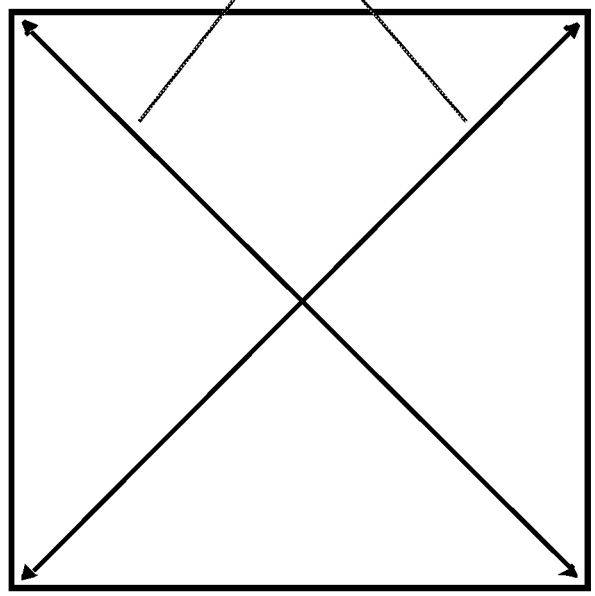
FIG. 49 shows the long diagonals of a square on its side.
Figure 50:
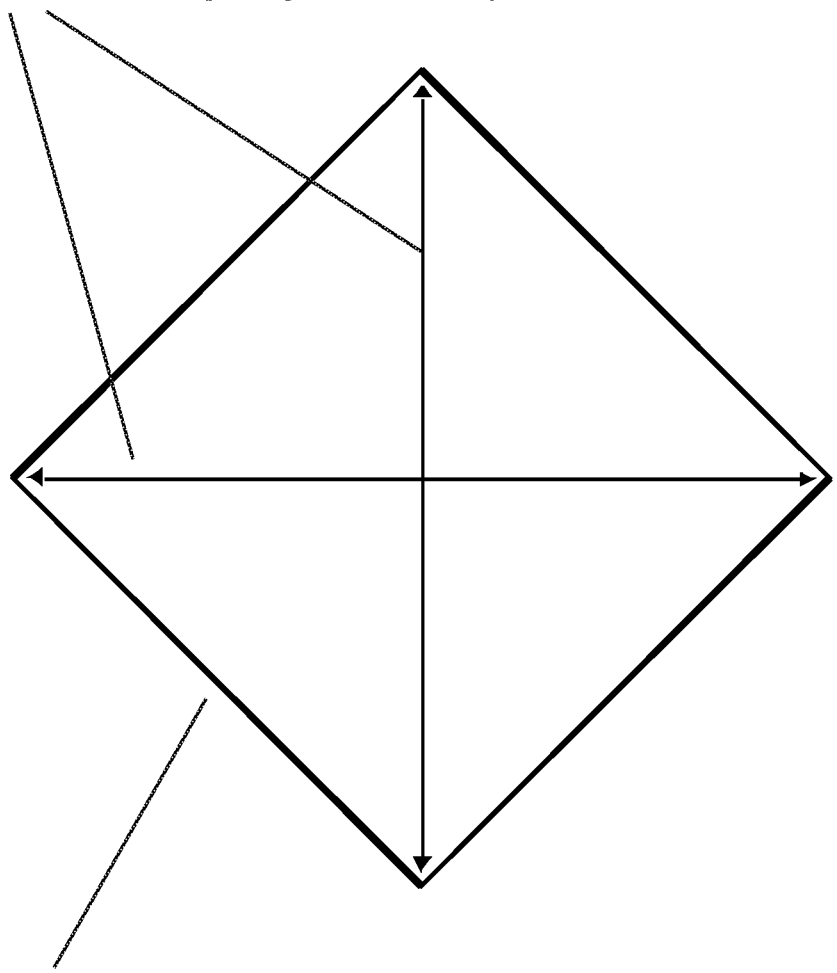
FIG. 50 shows the long diagonals of a square on its end.
Figure 51:
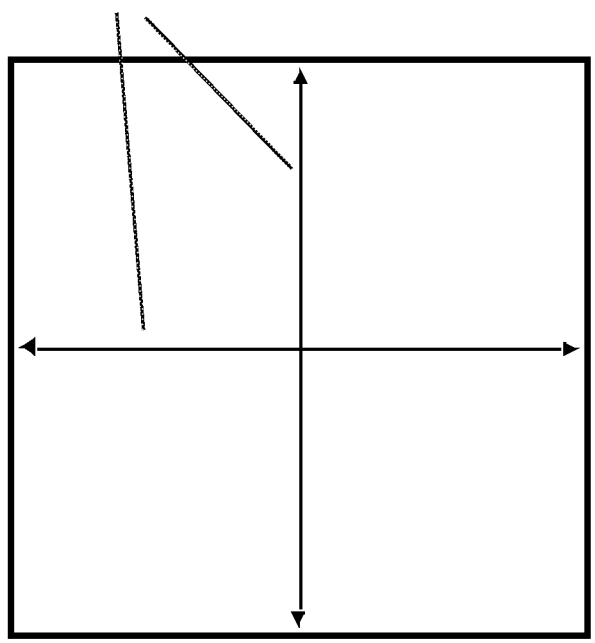
FIG. 51 shows the short diagonals of a square on its side.
Figure 52:
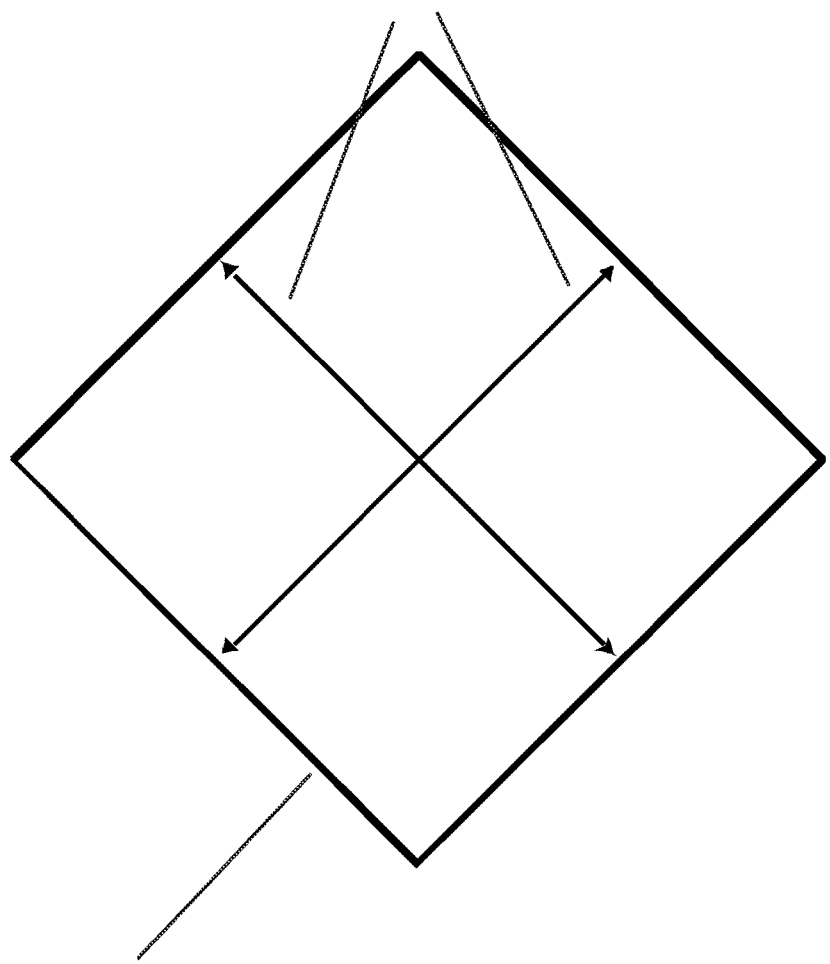
FIG. 52 shows the short diagonals of a square on its end.

Like many other pixel shapes, the square has by our definition both a long diagonal and a short diagonal. The long diagonal is just the diagonal of the square; the short diagonal of a square is just one edge. FIG. 49 shows the long diagonal element 4920 of a square on its side element 4910. FIG. 50 shows the long diagonal element 5020 of a square on its end element 5010. FIG. 51 shows the short diagonal element 5120 of a square on its side element 5110. FIG. 52 shows the short diagonal element 5220 of a square on its end element 5210. The ratio of the long diagonal to the short diagonal is $\sqrt{2}$.

The Pitches of a Tilling of Squares

Figure 53:
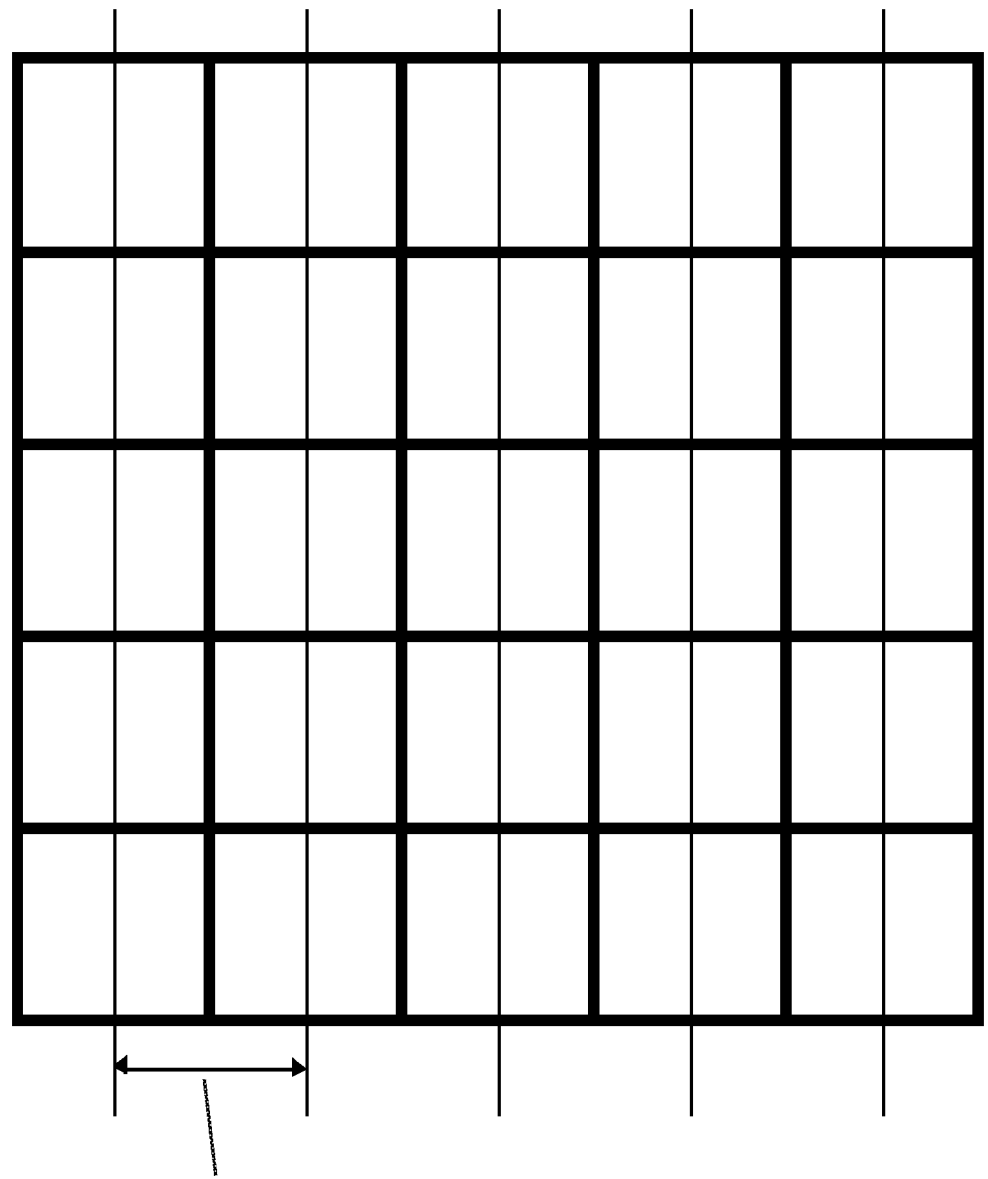
FIG. 53 shows the long pitch of a square tiling.
Figure 54:
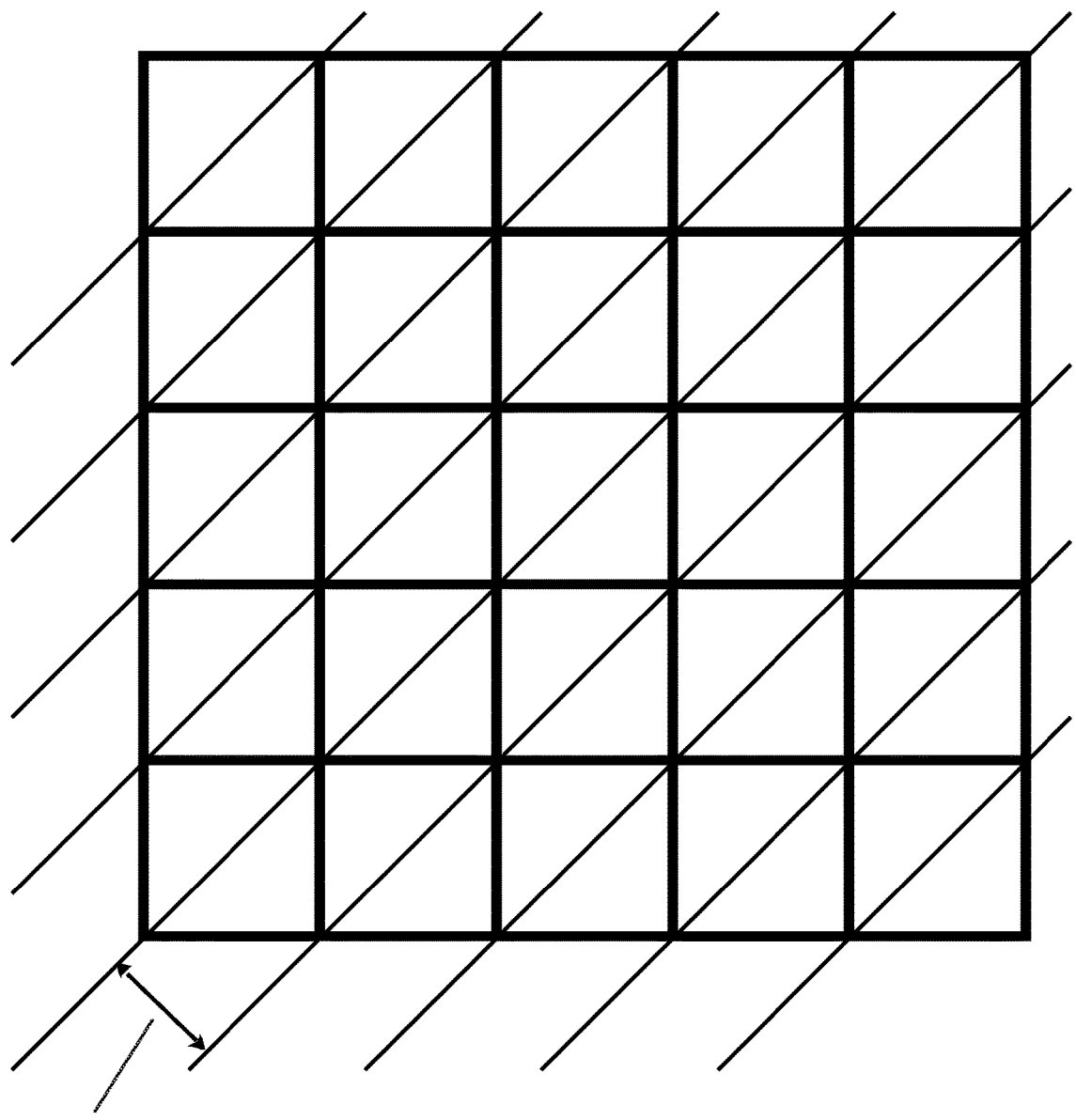
FIG. 54 shows the short pitch of a square tiling.

The long pitch of a tilling of squares is the same as its short diagonal: just the length of a side (FIG. 53 element 5320). The short pitch of a tilling of squares is half the length of the long diagonal: $\sqrt{2}/2 \approx 0.707$ (FIG. 54 element 5420). This also the ratio between the short diagonal and the long diagonal.

The Area of a Square

The area of a square is the square of its side length.

III.C. Mathematical Definition of the Viewsphere and Related Concepts

INTRODUCTION

The following describes a combined mathematical coordinate system model from both the visual sciences ("object space," "visual space") and computer graphics ("camera space", "view space"). The model is inherently variable resolution, and can be used both to describe the variable resolution cones and retinal receptor fields of the human eye and organization of the visual cortex as well as variable resolution contact lens displays and variable resolution computer graphics renderers.

Several spaces and coordinate systems will be described, defined by their mapping to ViewSpace. To model variable resolution spaces, and how they map to ViewSpace, we will introduce a general class of manifolds called ScreenSurfaces.

Formalized Mappings: Manifolds

ScreenSurfaces are Manifolds

For the general class of objects we are about to define as ScreenSurfaces, we need to define more than a mapping function to ViewSpace. In fact, we will need the full semantics of what are called manifolds. Thus ScreenSurfaces are defined to be manifolds.

Manifolds

A manifold is a mathematical object, modeled on an affine space X, with two associated parts. In our case, the manifold will always be called a ScreenSurface, or referred to by a name assigned to mean a particular ScreenSurface: a named ScreenSurface. The affine space X will always be ViewSpaceVS, which will be defined to be a subset of ViewSpace. The first part of a manifold is a Hausdorff topological space M, which in our case will be a sub-portion of $\Re 2$ called the surface of the ScreenSurface manifold. The second part of a manifold is an atlas containing one or more charts, in our case, usually only one or two charts. A chart is a pair consisting of an open set in the ScreenSurface surface, and a map ScreenSurfaceToViewSpaceVS (shorthand name sv) that takes points from the open set to ViewSpaceVS. Manifolds also have a degree of continuity; here we shall only assume that a first derivative exists, except at the boundaries between charts (this last is not standard). The first element of the atlas will be the general variable resolution mapping to ViewSpaceVS. If a second chart exists, it will always be referred to as the EndCap chart. It will be defined on its own open set in the ScreenSurface surface, and a map EndCap·ScreenSurfaceToViewSpaceVS (shorthand EndCap·sv) that takes points from the end-cap's open set to ViewSpaceVS. This second chart will always be a polar end-cap to, among other things, cover the degeneracy that occurs in spherical coordinates at the north pole.

The ScreenSurface's surface is the surface on which we wish to perform pixel and sample rendering for computer graphics applications, or image analysis on for biological modeling and image processing applications.

Both mappings have defined inverses: ViewSpaceVSToScreenSurface (shorthand name vs) that takes points from ViewSpaceVS to their open sets.

While formally each part of the ScreenSurface should be referred to as <ScreenSurface name>.<part-name>, sometimes, in context, the ScreenSurface name will be used to refer to the part.

So a named ScreenSurface will primarily be used as a (formal) named mapping.

Named Objects of ViewSpace

This section will describe several spaces, surfaces, and mappings related to ViewSpace, which is just a well-defined form of object space. These will be used both for visual science purposes for real eyeballs, and to describe the semantics of the generalized computer graphics view model.

Definition of term: ViewSpace

In the model described here, the term ViewSpace takes the place of the traditional "camera space" of computer graphics. It can also be considered a well-defined form of visual science object space. The coordinate axis of ViewSpace are the same as the traditional "camera space": the X and Y axis represent horizontal and vertical directions, the positive Z axis represents the general direction of greater depth from the origin. Because positive values of Z represent distance, ViewSpace is a left handed coordinate system. The origin of ViewSpace will be the EyePoint or ViewPoint of the perspective transform that will be defined. In the following, the character c will be used as a shorthand for ViewSpace, because here ViewSpace is the replacement of the older concept of camera space. The individual coordinate components of ViewSpace will be denoted by x, y, and z. (Sometimes, when another space is involved that also used named coordinates x, y, and sometimes z, individual coordinate components of ViewSpace will be denoted by X, Y, and Z for clarity.)

Definition of term: ViewSphere

The ViewSphere is defined to be the two dimensional closed surface of the unit sphere in ViewSpace centered at the origin. The ViewSphere is the surface upon which the three dimensional world of objects in ViewSpace coordinates usually will be projected onto. No special character is defined for this space, as it is an abstract space, character names will be assigned to particular coordinate systems defined on the surface of the ViewSphere. (Even though the ViewSphere as defined is a surface, we still will usually refer to "the surface of the ViewSphere" to reinforce this point.)

A three dimensional embedding of the ViewSphere into three dimensional ViewSpace will be defined; see ViewSpaceVS. One existing standard reference two dimensional coordinate system will be defined for the surface of the ViewSphere; see VisualCoordinates.

Definition of term: VisualField

We define the term VisualField, in the context of any chart with an associated mapping to the ViewSphere, to be region of the ViewSphere surface that is the image (range) of the mapping (as limited by its chart). The term VisualField, in the context of a particular atlas of charts, refers to the region of the ViewSphere surface that is the union of the images of mappings (constrained by their charts) for all charts in the specific atlas. In a mapping modeling the human eye, the VisualField would be just the visual field of the eye, with the outer edge of the valid region on the ViewSphere being the ora serrata (as transformed into visual eccentricity from retinal eccentricity). In simpler cases the outer edge will be defined by a constant angle of visual eccentricity, though the projection mapping of traditional rectangular external displays are bounded by "barrel distorted" sort of rectangle on the surface of the ViewSphere. The VisualField of any given mapping onto the ViewSphere almost always will map to less than the total 4πc steradian surface area of the entire ViewSphere. This remaining region of the ViewSphere still exists, it is just considered outside the particular VisualField.

Definition of term: ViewSpaceVS

The ViewSpaceVS is defined to be the set of three dimensional points in ViewSpace that are the embedding of the two dimensional points of the ViewSphere into three dimensional ViewSpace. (We could have called this space "ViewSphereEmbededInViewSpace," but for a shorter name, we let the "VS" after "ViewSpace" stands for "ViewSphere.") In the following, the character v will be used as a shorthand for ViewSpaceVS. The individual coordinate components of ViewSpaceVS will be denoted by x, y, and z.

Definition of term: ViewSpaceToViewSpaceVS

Definition of term: cv

ViewSpaceToViewSpaceVS is the mapping of points from anywhere in ViewSpace to points in ViewSpaceVS. The mapping from three dimensional points in ViewSpace to three dimensional points in ViewSpaceVS is many to one. But if the mapping ViewSpaceToViewSpaceVS is used to map all of ViewSpaceVS, the results is just exactly ViewSpaceVS again, which is the definition of a projection mapping (even though it ends in a three dimensional space, not a two dimensional space), and in particular a perspective mapping. The mapping itself is straightforward: treat all 3D points in ViewSpace as vectors from the origin; the normalization of any such vector produces the desired mapped corresponding point in ViewSpaceVS. Note that ViewSpaceToViewSpaceVS is not a normalization, it is a mapping from ViewSpace to ViewSpace that happens to be defined using normalization. Given that ViewSpaceToViewSpaceVS is rather awkward to use in equations, we will let the shorthand cv stand for it. To avoid confusion, in the equation below we will use XYZ for the location of the original point in ViewSpace. Now cv is defined as:

$$\text{ViewSpaceToViewSpaceVS·}x[X,Y,Z] = X/\sqrt{X^2+Y^2+Z^2} \quad (26)$$

$$\text{ViewSpaceToViewSpaceVS·}y[X,Y,Z] = Y/\sqrt{X^2+Y^2+Z^2} \quad (27)$$

$$\text{ViewSpaceToViewSpaceVS·}z[X,Y,Z] = Z/\sqrt{X^2+Y^2+Z^2} \quad (28)$$

Because of the destructive nature of the projective transform, we can't reverse this mapping. But we will note that points in ViewSpaceVS are by definition points in ViewSpace.

Note our convention here of denoting the individual components of a mapping by {mapping-name}.{component-name}. In some future cases, two (or more) different sets of coordinate component names will be used for different coordinate frames defined on the same space. Most of these will be defined on two dimensional coordinate frames. Alternate coordinate component names will never be used for changes of coordinate frame that change the number of dimensions.

The following will define one specific and one general two dimensional coordinate systems on the ViewSphere. Transforms will be defined between these, as well as transforms from either two dimensional space to ViewSpaceVS and to ViewSpace.

Definition of term: VisualCoordinates
Definition of term: eccentricity

We inherit the VisualCoordinates system from the Visual Sciences. It is a two dimensional longitude $\phi$ and a co-latitude $\theta$ coordinate system defined on the ViewSphere. The co-latitude $\theta$ is called the eccentricity. Visual coordinates differ from the standard convention for spherical coordinates in two ways. First, rather than "latitude," "co-latitude" is used. This means that $\theta=0°$ is not at the equator, but at the north pole. Second, the usual convention is that the variable $\theta$ is the longitude, and that $\phi$ is the latitude. Visual coordinates reverses these two, because the eye is mostly symmetrical in longitude, thus the main angle of interest is generally the co-latitude (eccentricity), and the variable $\theta$ is used for that, while $\phi$ is used for longitude. In the following, the character z will be used as a shorthand for VisualCoordinates. The two coordinate components for VisualCoordinates will be $\phi$ and $\theta$. Note that VisualCoordinates is just a coordinate frame for the points from the 2D space of the ViewSphere, not the coordinate frame.

Definition of term: ViewSpaceVSToVisualCoordinates
Definition of term: vz

Given the above definitions, following our naming conventions, the mapping that takes 3D points from ViewSpaceVS to 2D points on the ViewSphere as represented in the VisualCoordinates system is named ViewSpaceVSToVisualCoordinates. Its shorthand name is vz. The definition is:

$$vz\cdot\phi[x,y,z] = a\tan2[y,x] \quad (29)$$

$$vz\cdot\theta[x,y,z] = \cos^{-1}[z] \quad (30)$$

where a tan 2[y,x] is the is the angular component of the rectangular coordinates to polar coordinates transform of x and y.

Convention:

while most implementations of a tan 2[y,x] return results in the range of $[-\pi+\pi)$, in this document the a tan 2[ ] function is defined to return results in the range of $[0\ 2\pi)$. This is because we will many times specifically need the results to be in this form, but the conversion from the range of $[-\pi+\pi)$, to $[0\ 2\pi)$ involves conditionals: if $\theta>=0$, then $\theta$, else $2\pi+\theta$. For the times when this specific form is not needed, either form will work, so we will just always use the $[0\ 2\pi)$ form.

Definition of term: VisualCoordinatesToViewSpaceVS
Definition of term: zv

The inverse mapping of ViewSpaceVSToVisualCoordinates is VisualCoordinatesToViewSpaceVS, with a shorthand name of zv. The definition of this mapping is:

$$zv\cdot x[\phi,\theta] = \cos[\phi]\cdot\sin[\theta] \quad (31)$$

$$zv\cdot y[\phi,\theta] = \sin[\phi]\cdot\sin[\theta] \quad (32)$$

$$zv\cdot z[\phi,\theta] = \cos[\theta] \quad (33)$$

Note again that the VisualCoordinates are not "the" ViewSphere coordinates; points on the ViewSphere surface can be expressed in many different 2D coordinate systems. The one-to-one mapping defined by the equations above show that both xyz ViewSpaceVS coordinates as well as $\phi\theta$ VisualCoordinates can be used to represent points located on the ViewSphere surface. (Why didn't we just define xyz as an alternate transformation of VisualCoordinates, and not have to have created ViewSpaceVS? Because this breaks the restriction on coordinate names causing a change in the dimensionality of the space. This is why VisualCoordinates exists as a separate space from any 2D space defined on the surface of the ViewSphere.)

Definition of term: ScreenSurface

As described above, a ScreenSurface is a manifold whose primary use is to define how points are mapped from the ScreenSurface's two dimensional surface to ViewSpaceVS (or a surrogate for ViewSpaceVS, e.g. VisualCoordinates), as well as the inverse mapping. The chart aspects of the manifold only come up when dealing with the EndCap portion of the manifold.

The two dimensional surface associated with a ScreenSurface manifold is called a surface rather than a plane because more complex screen geometries will be considered than the simple planer model of the traditional (simple) computer graphics view model. Another way of saying this is that there will not always exist a linear, let alone planer, embedding of a ScreenSurface's surface into ViewSpace. In the following, the character s will be used as a shorthand for the generic ScreenSurface. The two coordinate components for the ScreenSurfaces surface will usually be the pair u and v, denoting that the (0, 0) origin of the coordinate system is located at the lower left of the space, but the pair x and y will be used to denote a transformed coordinate system in which the (0, 0) origin is located at the center of the space, and the pair radius and angle will be used to indicate a transformed general polar coordinate system (with a centered origin). (See ScreenSurfaceCoordinates.) We will never use $\theta$ to denote the angle of a polar coordinate system: $\theta$ will always denote eccentricity (though note that visual eccentricity and retinal eccentricity are not exactly the same).

Definition of term: ViewSpaceVSToScreenSurface
Definition of term: vs

The mapping that takes points from ViewSpaceVS to points on the ScreenSurface. Its shorthand name is vs. The mapping will have different definitions depending on details of the form of the perspective projection being employed, expressly including possibilities for projections points on the ScreenSurface will have considerable variable resolution on the ViewSphere.

Definition of term: ScreenSurfaceToViewSpaceVS
Definition of term: sv

The inverse mapping of ViewSpaceVSToScreenSurface is

ScreenSurfaceToViewSpaceVS, with a shorthand name of sv.

Definition of term: VisualCoordinatesToScreenSurface
Definition of term: zs

The mapping that takes points from VisualCoordinates to points on the ScreenSurface is VisualCoordinatesToScreenSurface. Its shorthand name is zs. This is the portion of the mapping ViewSpaceVSToScreenSurface that starts from VisualCoordinates rather than from ViewSpaceVS. The relationship is:

ViewSpaceVSToScreenSurface=VisualCoordinatesToScreenSurface×ViewSpaceVSToVisualCoordinates Thus:

VisualCoordinatesToScreenSurface=ViewSpaceVSToScreenSurface×VisualCoordinatesToViewSpaceVS $$zs = vs \times zv$$

Definition of term: ScreenSurfaceToVisualCoordinates
Definition of term: sz

The inverse mapping of VisualCoordinatesToScreenSurface is ScreenSurfaceToVisualCoordinates, with a shorthand name of sz. This is the portion of the mapping ScreenSurfaceToViewSpaceVS that stops at VisualCoordinates, rather than going all the way to ViewSpaceVS. The relationship is:

ScreenSurfaceToViewSpaceVS=VisualCoordinatesToViewSpaceVS×ScreenSurfaceToVisualCoordinates Thus:

ScreenSurfaceToVisualCoordinates=ViewSpaceVSToVisualCoordinates×ScreenSurfaceToViewSpaceVS $$sz = vz \times sv$$

By using the ViewSpaceToViewSpaceVS transform, we can define transforms from ViewSpace to either of the 2D ViewSphere coordinate systems. Because no inverse of ViewSpaceToViewSpaceVS exists, these new transforms also do not have inverses.

Definition of term: ViewSpaceToVisualCoordinates
Definition of term: cz

The mapping that takes points from ViewSpace to points on the VisualCoordinates.

The shorthand name for ViewSpaceToVisualCoordinates is cz. It is defined as the multiplication of ViewSpaceVSToVisualCoordinates with ViewSpaceToViewSpaceVS, and is given by:

$$\phi = cz \cdot \phi[x, y, z] = \operatorname{atan2}[y, x] \tag{34}$$

$$\theta = cz \cdot \theta[x, y, z] = \cos^{-1}\left[\frac{z}{\sqrt{x^2 + y^2 + z^2}}\right] \tag{35}$$

No (unique) inverse exists.

Definition of term: ViewSpaceToScreenSurface
Definition of term: cs

The mapping that takes points from ViewSpace to points in VisualCoordinates. The shorthand name for ViewSpaceToScreenSurface is cs. It is defined as the multiplication of ViewSpaceVSToScreenSurface with ViewSpaceToViewSpaceVS. No inverse exists.

Summary of Mapping Notation

Single characters have been associated with the four spaces associated with the view mapping (along with hints to remember them):

| | |
|---|---|
| c: ViewSpace | ('c' because ViewSpace is similar to "camera space") |
| v: ViewSpaceVS | ('v' because this is the "view" space we most use) |
| z: VisualCoordinates | ('z' because "visual" is pronounced "vizual") |
| s: ScreenSurface | ('s' for "screen") |

Now the nine transformations between the spaces are just the appropriate pairing of the individual characters for the spaces:

cv=ViewSpaceToViewSpaceVS
cz=ViewSpaceToVisualCoordinates
cs=ViewSpaceToScreenSurface
vz=ViewSpaceVSToVisualCoordinates
zv=VisualCoordinatesToViewSpaceVS
vs=ViewSpaceVSToScreenSurface
sv=ScreenSurfaceToViewSpaceVS
zs=VisualCoordinatesToScreenSurface
sz=ScreenSurfaceToVisualCoordinates Screen Surface Coordinates Definition of term: ScreenSurfaceCoordinates
Definition of term: ScreenWidth
Definition of term: SW
Definition of term: ScreenHeight
Definition of term: SH The topological space associated with every ScreenSurface manifold is always a portion of $\Re 2$. Most of the time, that portion is a fixed size rectangle. Here, when this is true, we define four specific 2D ScreenSurfaceCoordinates systems on that rectangular surface portion. What is important about two of these four coordinate systems is that they define integral specifically shaped equal size pixels to their tiling of the ScreenSurface's surface: they define pixel spaces.

2D Cartesian uv Lower Left Origin Coordinate System

The first is a two dimensional Cartesian uv coordinate. The range of the u coordinate is defined to be [0, ScreenWidth), where ScreenWidth will commonly be abbreviated to SW. The range of the v coordinate is defined to be [0, ScreenHeight), where ScreenHeight will commonly be abbreviated to SH. Thus this is a rectangular portion, but in many times topologically it will be defined to be a strip: for any given v coordinate, for a given u coordinate $u_0$ in the range [0, ScreenWidth), all u coordinates outside of the range [0, ScreenWidth) for which $u_0$=u mod ScreenWidth are the same points. Note that in this coordinate system, the origin (0,0) is located at the lower left corner of the rectangle.

2D Cartesian xy Centered Origin Coordinate System

The second is an offset version of the first coordinate system. To differentiate it from the first, the coordinate components are x and y. The range of the x coordinate is defined to be [−ScreenWidth/2, ScreenWidth/2). The range of the y coordinate is defined to be [−ScreenHeight/2, ScreenHeight/2). This coordinate system is still a rectangular portion, but the origin (0, 0) is located at the center of the rectangle. It is related to the previous coordinate system via the transforms:

$$x[u,v] = u - SW/2 \tag{36}$$

$$y[u,v] = v - SH/2 \tag{37}$$

and the inverse is:

$$u[x,y] = x + SW/2 \qquad (38)$$

$$v[x,y] = y + SH/2 \qquad (39)$$

The coordinate system is an intermediate one not used for purposes of rendering, so integral pixels are not defined for it. (This would have involved negative integer pixel coordinates, which we wish to avoid.)

2D Polar Angle Radius Coordinate System

The third coordinate system is the polar form of the second coordinate system, with coordinate components angle and radius. The range of the angle coordinate is defined to be $[-\pi, +\pi)$ (and wraps around past this). The range of the radius coordinate is defined to be [0, ScreenHeight). The origin of this coordinate system is the same as that of the xy coordinate system. However, this coordinate system is a circular portion of the ScreenSurface. It is related to the xy coordinate system via the transforms:

$$\text{angle}[x,y] = a\tan 2[y,x] \qquad (40)$$

$$\text{radius}[x,y] = \sqrt{x^2 + y^2} \qquad (41)$$

and the inverse is:

$$x[\text{angle}, \text{radius}] = \text{radius} \cdot \cos[\text{angle}] \qquad (42)$$

$$y[\text{angle}, \text{radius}] = \text{radius} \cdot \sin[\text{angle}] \qquad (43)$$

The coordinate system is an intermediate one not used for purposes of rendering, so integral pixels are not defined for it. (This would have involved quantizing the angle, which would be contrary to the purposes for which the coordinate system was created.)

2D Hexagonal Lower Left Origin Coordinate System

The fourth specific 2D ScreenSurfaceCoordinates coordinate system defined on a rectangular portion of the surface is a hexagonal grid. It is a tiling of hexagons on their end, relative to the Cartesian uv space orientation. All pixels have the same shape and size (within the coordinate system). In this case, all the pixels have a hexagonal shape. Setting the scale of the hexagonal pixels relative to the uv Cartesian space is a complex issue, and will be left to be described later.

The mapping from Cartesian u v space coordinates to uu vv hexagonal ids is as described by equations (7) and (8).

There are some "holes" in this tiling on the four sides of the tiling of the rectangle. If, as is many times the case, the u address "wraps around" at SW, then the holes on the left and right side are covered. The "holes" on the top and bottom of the rectangle are usually dealt with by the domain side of the chart with the associated mapping that is using hexagonal coordinates.

Again, the hexagons described in the address labeling method were arbitrarily chosen to have unit width in the space we were working in. The precise scale change between the Cartesian uv space and the space that the hexagons are defined is not yet fixed.

Notation Notes

In the future, we will use our convention of letting the choice of coordinate component name determine which of these three coordinate systems are being referred to. In some equations, that means that there will be an implicit change of coordinate systems. We will always use the coordinate name angle, and never use the symbol θ. Here θ is exclusively reserved to denote eccentricity.

In the future, we will be comparing different ScreenSurface mappings. In such cases, references to SW and SH will be ambiguous; we will use the terminology <ScreenSurface Name>·SH (and ·SW, ·u, . . . ), where <ScreenSurface Name> is a particular named ScreenSurface, to make it clear which parameters are being referred to.

III.D. Scale Changes Between the ScreenSurface and ViewSpaceVS

Note that three of our four coordinate systems (ViewSpace, ViewSpaceVS, VisualCoordinates) have a fixed definition, and thus the transformations to and from any of the three to any other of the three are also fixed, e.g. we know what all these transforms are (when they exist). So far we have not yet defined any specific (named) instance of a ScreenSurface: thus far it is only an abstraction. The whole point was to set up framework to examining properties (including visual properties) of any arbitrary mapping (and related information) we are given to define a particular ScreenSurface manifold.

Soon, we will define the all-important property of resolution in terms of distance on the surface of the ViewSphere. But first we will need to develop a way to relate the size of a pixel in a particular ScreenSurface surface ($\Re 2$) to distance on the ViewSphere. Let d be a tangent vector in the tangent space to the ScreenSurface surface. If we were dealing with a mapping $f$ from ScreenSurface to $\Re 1$, the directional derivative $\nabla_d f$ would tell us how much the change in scale would be between the derivative in $\Re 1$ off in the direction d relative to unity (the normalized length of d). But unfortunately we want to compute this property for mappings, especially including sv, which maps to $\Re 3$, not $\Re 1$. So we will develop a differential operator for that scale change in higher dimensional image (range). We will call this function the directional magnitude derivative, and denote it by $\nabla_d f$. This can be distinguished from the ordinary directional derivative when the mapping (whether in bold or not) is known to be to $\Re 2$ or $\Re 3$, not $\Re 1$. (When $f$ is a mapping to vectors, e.g. a vector field, the same notation has been used to denotes a connection, but here $f$ is always a mapping to points.) The closest existing mathematical concept to this is the determinant of the Jacobian, but this measures the ratio of the area or volume change caused by a mapping, not the absolute value of the linear scale change in a given direction. So in the next subsection we will go into a considerable amount of mathematical detail to develop the function we want. In the end, it will turn out to be expressible as the length of a vector of ordinary directional derivatives. Once developed, we will mainly use the function symbolically, and only occasionally actually compute it.

Tangent Spaces and how to Use them (The following is summary of some of the material and mostly uses the notation found in [Dodson, C. T. J., and Poston, T. 1997, Tensor Geometry, The Geometric Viewpoint and its Uses., 2nd Ed., Springer].)

Given a space X, we will denote by d[x,y] the difference function between two points x∈X and y∈X, and the image of d is a vector space, which we will denote by T. We will denote by $d_x[y]$ the difference function between an arbitrary point y and always the point x, this produces a vector in the vector space T.

Given a space X and a point x∈X, the tangent space to X at x is denoted by $T_x X$. The contents of $T_x X$ are the vectors $d_x[y]$ for all possible y∈X, thus $T_x X$ is a space with the same number of dimensions as X. The elements of $T_x X$ are called tangent vectors.

Given two spaces, X and X', which can have different numbers of dimensions, and which have difference functions d and d', let $f$ be a mapping from X to X'. We denote a derivative off at x∈X, as $D_x f$. $D_x f$ is a map from the tangent space $T_x X$ to the tangent space $T_{f[x]} X'$. $d'_{f[x]}$ is the difference function between an arbitrary point in X' and always the point $f[x] \varepsilon X'$, and produces a tangent vector result in the tangent vector space T'. We denote its inverse as $d'^{-1}_{f[x]}$. It is a map that takes a vector from T' to a tangent vector in $T_{f[x]}X'$. Given t as a tangent vector in $T_xX$, we can now define $D_xf[t]$ as:

$$D_x f[t] = \lim_{h \to 0} d'^{-1}_{f[x]}\left[\frac{d'[f[x], f[x+h \cdot t]]}{h}\right] \quad (44)$$

Now we will impose the coordinate frames $(b_0 \ldots b_n)$ on X and $(c_0 \ldots c_n?)$ on X's. This means:

$$D_x f[b_j] = \frac{\partial f^i}{\partial x^j} \cdot c_i \quad (45)$$

$$D_x f[t] = \frac{\partial f^i}{\partial x^j} \cdot c_i \cdot t^j \quad (46)$$

Where $f^i$ are the coordinate component functions off, and $t^j$ are the coordinate components of the tangent vector t (and we are assuming that the summation convention is being used.) The partial derivatives expressed as a matrix is the Jacobian matrix of the map $f$ at x. We will only be interested in maps from $\Re 2$ to $\Re 2$, from $\Re 2$ to $\Re 2$, and from $\Re 2$ to $\Re 3$, so we will write out all three:

$$D_x f[t] = \begin{bmatrix} \frac{\partial f^1}{\partial x^1}[x] & \frac{\partial f^1}{\partial x^2}[x] \\ \frac{\partial f^2}{\partial x^1}[x] & \frac{\partial f^2}{\partial x^2}[x] \end{bmatrix} \text{ when } f: \Re 2 \to \Re 2 \quad (47)$$

$$D_x f[t] = \begin{bmatrix} \frac{\partial f^1}{\partial x^1}[x] & \frac{\partial f^1}{\partial x^2}[x] & \frac{\partial f^1}{\partial x^3}[x] \\ \frac{\partial f^2}{\partial x^1}[x] & \frac{\partial f^2}{\partial x^2}[x] & \frac{\partial f^2}{\partial x^3}[x] \end{bmatrix} \quad (48)$$

when $f: \Re 3 \to \Re 2$ $$D_x f[t] = \begin{bmatrix} \frac{\partial f^1}{\partial x^1}[x] & \frac{\partial f^1}{\partial x^2}[x] \\ \frac{\partial f^2}{\partial x^1}[x] & \frac{\partial f^2}{\partial x^2}[x] \\ \frac{\partial f^3}{\partial x^1}[x] & \frac{\partial f^3}{\partial x^2}[x] \end{bmatrix} \text{ when } f: \Re 2 \to \Re 3 \quad (49)$$

We now have the first part of what we want: given that we have a mapping $f$ between two spaces, we have a function $D_xf[t]$ that, for a given point x in the first space, will take us from a tangent vector to the first space t to a tangent vector to the second space. Now all that is left is to take the ratio of the length of the second tangent vector to the length of the first. First we note that the squared length of the second vector is:

$$D_x f[t] \cdot D_x f[t] = \quad (50)$$

$$\left(\frac{\partial f^i}{\partial x^j}[x] \cdot c_i \cdot t^j\right) \cdot \left(\frac{\partial f^k}{\partial x^l}[x] \cdot c_k \cdot t^l\right) = \sum_i \left(\sum_j \frac{\partial f^i}{\partial x^j}[x] \cdot t^j\right)^2$$

Definition of term: directional magnitude derivative
Definition of term: $\nabla_d f$ $$\nabla_d f[x] = \frac{|D_x f[x]|}{|d|} = \quad (51)$$

$$\frac{\sqrt{D_x f[d] \cdot D_x f[d]}}{\sqrt{d \cdot d}} = \frac{1}{|d|} \cdot \sqrt{\sum_i \left(\sum_j \frac{\partial f^i}{\partial x^j}[x] \cdot t^j\right)^2}$$

Equation (51) above is our formal definition of the directional magnitude derivative in the most general case. We have changed the name of the tangent vector t to d, because it is now used as a tangent direction vector (e.g., its magnitude doesn't matter anymore). (Note that d is different from d, the difference function.) In the future, we will elide the argument point x, because it is generally clear from context.

One should note that where $d'=D_xf[d]$.

$$\nabla_{d'} f^{-1} = \frac{1}{\nabla_d f} \quad (52)$$

This just means that when a tangent vector to the second space is mapped by $\nabla_d f^{-1}$ back into a tangent vector to the first space at a given point, the relative scale change is reversed.

It is interesting to note that we can alternately define the directional magnitude derivative $\nabla_d f$ in terms of the ordinary directional derivative. Here's the definition when the image off produces two dimensional points, and three dimensional points:

$$\nabla_d f = |\langle \nabla_d f^1 \nabla_d f^2 \rangle| \quad (53)$$

$$\nabla_d f = |\langle \nabla_{d'}^1 \nabla_d f^2 \nabla_d f^3 \rangle| \quad (54)$$

Where $\nabla_d f^k$ is just the ordinary directional derivative on the scalar valued function $f^k$ in the direction d. Seeing that both definitions involve a square root, it is clear that our directional magnitude derivative only produces positive results.

The ordinary directional derivative is defined in the tangent space to the manifold described by $f$. The vector $\nabla f$ also lies on the tangent space, and points in the direction of the steepest increase in $f$ at a given point, with $|\nabla f|$ indicating the rate of the change in this direction. The ordinary directional derivative can be defined as the dot product of the vector $\nabla f$ with the unit vector in the direction d, or $|\nabla f|$ times the cosine of an angle between $\nabla f$ and d. At angles of 90°, e.g. when d is orthogonal to $\nabla f$, $\nabla_d f$ will be 0; at angles greater than 90°, it will be negative.

In terms of differentials, the directional magnitude derivative can be thought of as the ratio between the length of a (infinitesimal step) in the image off to the length of the (infinitesimal) step in the domain off in the direction d that caused it. Not only is this always positive, but it can be greater than zero everywhere (or almost everywhere).

We will use a special case of the Jacobian. When we map the pixel unit vectors u and v in the tangent space to the ScreenSurface surface at a the ScreenSurface surface point p to their corresponding vectors u' and v' in the tangent space to ViewSpaceVS at the ViewSpaceVS point p', then 1/|u'xv'| is the density of ScreenSurface surface pixels at the point p' (assuming a square pixel tiling, the equation has to be adjusted for hexagonal tilings).

As was mentioned, we will frequently be using the directional magnitude derivative of the mapping sv, or its inverse vs. But the ViewSpaceVS direction vector stated will sometimes be θ, e.g. $\nabla_\theta$ vs. What does this mean? Well, it just means that we want use the direction of the θ axis, but expressed in ViewSpaceVS coordinates. That's just $D_x zv[\theta]$, and in $\nabla_\phi$ vs φ will be $D_x zv[\phi]$. Yes, in general these will not be unit length vectors in ViewSpaceVS, but since the vectors are only being used for their directions, this isn't an issue.

Definition of term: visual longitudinal direction
Definition of term: longitudinal direction
Definition of term: φ
Definition of term: retinal longitudinal direction We will use the phrase visual longitudinal direction, or just longitudinal direction, or the boldface symbol φ, to indicate for a given point on the ViewSphere, in what direction does the (local) longitude increase, and the eccentricity (locally) not change at all. When talking about the physical RetinalSphere, we will refer to the retinal longitudinal direction.

Definition of term: visual eccentricity direction
Definition of term: eccentricity direction
Definition of term: θ
Definition of term: retinal eccentricity direction We will use the phrase visual eccentricity direction, or just eccentricity direction, or the boldface symbol θ, to indicate for a given point on the ViewSphere, in what direction does the (local) eccentricity increase, and the longitude (locally) not change at all. When talking about the physical RetinalSphere, we will refer to the retinal eccentricity direction.

More Comments on the Semantics of the ViewSphere

In most physical eyes, the physical position of the retina is best understood as a spherical imaging surface that corresponds to a portion of the rear portions of ViewSpaceVS; this is why there is an inversion of the image on the retina. However, consistent with the traditional ViewPlane, the mathematical convention is that the spherical view surface is in the front portions of ViewSpaceVS. What front portions of ViewSpaceVS is used is dependent on the "eye" being modeled. However, the limitation to points in the frontal portions is not a limitation to points with positive z values, as the field of view of even a single eye can include points of easily greater than 90° of eccentricity from the direction of highest resolution, without implying that the field of view is anywhere greater than, or even near 180°.

An Example ScreenSurface: The ViewPlane

Definition of term: ViewPlane
Definition of term: FOV

The "view plane" traditionally used in computer graphics will be our first example of a ScreenSurface manifold. The mapping portion is called planer because it can be linearly embedded in ViewSpace as a section of a plane. We will refer to this particular ScreenSurface as the ViewPlane. The ViewSpace embedding of the ViewPlane is rectangular portion of a plane orthogonal to the z axis, and in simple view models, also centered on the z axis. In more complex view models, the center of the rectangle is offset from the z axis, see [Deering, M. 1992: High Resolution Virtual Reality. In proceedings of SIGGRAPH 1992, pp. 195, 202] for a view model in which the decentering is based on head-tracking and stereo display. For the purposes of our example here, we will assume no such z axis offset.

The horizontal angular field of view from the center of ViewSpace through the left and right edges of the rectangle is denoted by the term FOV (in units of radians). We will assume square pixels, e.g. that the aspect ratio of the rectangle defined in ScreenSurface coordinates SW/SH is the same as the aspect ratio defined in ViewSpace by sin [horizontal angular field of view/2]/sin [vertical field of view/2]. Thus the vertical field of view does not need to be specified, it is fixed as $2 \cdot \sin^{-1}[\sin [FOV/2] \cdot SH/SW]$.

The cs mapping for the ViewPlane is given by:

$$u = ViewPlane.cs.u[X, Y, Z] = \frac{X}{Z} \cdot \frac{SW/2}{\tan[FOV/2]} + \frac{SW}{2} \quad (55)$$

$$v = ViewPlane.cs.v[X, Y, Z] = \frac{Y}{Z} \cdot \frac{SW/2}{\tan[FOV/2]} + \frac{SH}{2} \quad (56)$$

The use of SW in the equation for cs·v is not a typo, it is a consequence of mandating square pixels.

Occasionally, instead of uv, we will need to use an xy centered coordinate system. This shouldn't cause confusion, as the cs mapping by definition lands on the ScreenSurface, and we are just using a transformed version of the uv coordinates. In this case, the cs mapping is defined as (here for clarity we will use XYZ for the three ViewSpace coordinates):

$$x = ViewPlane.cs.x[X, Y, Z] = \frac{X}{Z} \cdot \frac{SW/2}{\tan[FOV/2]} \quad (57)$$

$$y = ViewPlane.cs.y[X, Y, Z] = \frac{Y}{Z} \cdot \frac{SW/2}{\tan[FOV/2]} \quad (58)$$

We will also sometimes need to use the radius and angle polar coordinate frame for the ViewPlane ScreenSurface. Now the cs mapping is defined as:

$$\begin{aligned} radius &= ViewPlane.cs.radius[X, Y, Z] \\ &= \sqrt{cs.x[X, Y, Z]^2 + cs.y[X, Y, Z]^2} = \frac{SW/2}{\tan[FOV/2] \cdot Z} \cdot \sqrt{X^2 + Y^2} \end{aligned} \quad (59)$$

$$\begin{aligned} angle &= ViewPlane.cs.angle[X, Y, Z] \\ &= a\tan2[cs.y[X, Y, Z], cs.x[X.Y.Z]] = a\tan2[Y, X] \end{aligned} \quad (60)$$

Note that the angle defined here is the same longitude as defined in

VisualCoordinates:

$$ViewPlane \cdot cs \cdot angle[X,Y,Z] = cz \cdot \phi[X,Y,Z] \quad (61)$$

As with the cv mapping, because of the destructive nature of the cs mapping, no unique inverse for cs (sc) exists (though we will define a particular one later). Note also that this mapping is defined only for fields of view less than 180°. As will be seen later, not all cs mappings have this field of view limitation.

Because ViewSpaceVS is a subset of ViewSpace, the mapping for vs is the same as that for cs:

$$u = ViewPlane.vs.u[X, Y, Z] = ViewPlane.cs.u[X, Y, Z] \quad (62)$$
$$= \frac{X}{Z} \cdot \frac{SW/2}{\tan[FOV/2]} + \frac{SW}{2}$$

$$v = ViewPlane.zs.v[X, Y, Z] = ViewPlane.cs.v[X, Y, Z] \quad (63)$$
$$= \frac{Y}{Z} \cdot \frac{SW/2}{\tan[FOV/2]} + \frac{SH}{2}$$

And to xy coordinates:

$$x = ViewPlane.vs.x[X, Y, Z] = \quad (64)$$
$$ViewPlane.cs.x[X, Y, Z] = \frac{X}{Z} \cdot \frac{SW/2}{\tan[FOV/2]}$$

$$y = ViewPlane.vs.y[X, Y, Z] = \quad (65)$$
$$ViewPlane.cs.y[X, Y, Z] = \frac{Y}{Z} \cdot \frac{SW/2}{\tan[FOV/2]}$$

And to radius angle coordinates:

$$ViewPlane.vs.radius[X, Y, Z] = ViewPlane.cs.radius[X, Y, Z] \quad (66)$$
$$= \sqrt{cs.x[X, Y, Z]^2 + cs.y[X, Y, Z]^2}$$
$$= \frac{SW/2}{\tan[FOV/2] \cdot Z} \cdot \sqrt{X^2 + Y^2}$$

$$ViewPlane.vs.angle[X, Y, Z] = ViewPlane.cs.angle[X, Y, Z] \quad (67)$$
$$= a\tan2[cs.y[X, Y, Z], cs.x[X.Y.Z]]$$
$$= a\tan2[Y, X]$$

However this time the inverse of the mapping, the mapping sv, does exist. Defining the point P in ViewSpace coordinates using the uv ViewPlane coordinates as:

$$P = \left\{ \frac{u - SW/2}{SW/2} \cdot \tan[FOV/2], \frac{v - SH/2}{SW/2} \cdot \tan[FOV/2], 1 \right\} \quad (68)$$

or, alternately, using the centered xy ViewPlane coordinates:

$$P = \left\{ \frac{x}{SW/2} \cdot \tan[FOV/2], \frac{y}{SW/2} \cdot \tan[FOV/2], 1 \right\} \quad (69)$$

or, alternately, using the polar radius angle ViewPlane coordinates:

$$P = \left\{ \frac{radius \cdot \cos[angle]}{SW/2} \cdot \tan[FOV/2], \right. \quad (70)$$
$$\left. \frac{radius \cdot \sin[angle]}{SW/2} \cdot \tan[FOV/2], 1 \right\}$$

and then using ViewSpaceToViewSpaceVS (cv), then sv is:

$$x = sv.x[u, v] = \frac{P.x}{|P|}, y = sv.y[u, v] = \frac{P.y}{|P|}, z = sv.z[u, v] = \frac{P.z}{|P|} \quad (71)$$

The ViewPlane can be embedded into ViewSpace as a plane orthogonal to the z axis, but at any arbitrary point on the z axis. The z value of this point determines the scale of the mapping. In the past, the character D (roughly analogous to focal length) was sometimes used to denote this z distance. Using D as a parameter, a family of mappings from ViewPlane (a ScreenSurface) to ViewSpace, sc, exists as an embeddings:

$$x = \quad (72)$$
$$sc.x[u, v] = \frac{u - SW/w}{SW/2} \cdot \tan[FOV/2] \cdot D = \frac{x}{SW/2} \cdot \tan[FOV/2] \cdot D$$

$$y = \quad (73)$$
$$sc.x[u, v] = \frac{v - SW/2}{SW/2} \cdot \tan[FOV/2] \cdot D = \frac{y}{SW/2} \cdot \tan[FOV/2] \cdot D$$

$$x = sc.x[u, v] = D \quad (74)$$

(Where the x and y on the right hand side are the xy ViewPlane coordinates.)

Definition of term: ViewPlaneEmbededInViewSpace
Definition of term: ViewPlaneToViewPlaneEmbeddedIn-ViewSpace
Definition of term: ViewPlane·sp In order to have a unique mapping, fixing the value of D to 1 creates an embedding in which the embedded ViewPlane is tangent to the north pole of the ViewSphere. We will adopt this as a convention, which will allow for a unique mapping from any point in ViewSpace to a point on the plane z=1 in ViewSpace. We will call this plane the ViewPlaneEmbededInViewSpace. (In this sense, it is analogous to ViewSpaceVS, which, as mentioned before, could have been called "ViewSphereEmbededInViewSpace.") We will use the character p as a shorthand for the ViewPlaneEmbededInViewSpace space. With this definition, we can define the mapping that goes from the ScreenSurface ViewPlane (when D=1) back to ViewPlaneEmbededInViewSpace: ViewPlaneToViewPlaneEmbeddedInViewSpace, or with our short naming conventions, sp, which for clarity we will usually prepend the name of the ScreenSurface to: ViewPlane·sp.

So ViewPlane·sp, for the mapping to ViewPlaneEmbededInViewSpace from the uv Cartesian coordinates centered at the lower left of the ScreenSurface is:

$$x = ViewPlane.sp.x[u, v] = \frac{u - SW/2}{SW/2} \cdot \tan[FOV/2] \quad (75)$$

$$y = ViewPlane.sp.y[u, v] = \frac{v - SW/2}{SW/2} \cdot \tan[FOV/2] \quad (76)$$

$$z = ViewPlane.sc.z[u, v] = 1 \quad (77)$$

and then the mapping ViewPlane·sp from the xy Cartesian coordinates centered at the center of the ScreenSurface:

$$x = ViewPlane.sp.x[x, y] = \frac{x}{SW/2} \cdot \tan[FOV/2] \quad (78)$$

$$y = ViewPlane.sp.y[x, y] = \frac{y}{SW/2} \cdot \tan[FOV/2] \quad (79)$$

$$z = ViewPlane.sp.z[x, y] = 1 \quad (80)$$

and then the mapping ViewPlane·sp from the (normal) radius angle polar coordinates of the ScreenSurface:

$$x = ViewPlane.sp.x[\text{radius, angle}] = \frac{\text{radius}}{SW/2} \cdot \cos[\text{angle}] \quad (81)$$

$$y = ViewPlane.sc.y[\text{radius, angle}] = \frac{\text{radius}}{SW/2} \cdot \sin[\text{angle}] \quad (82)$$

$$z = ViewPlane.sc.z[\text{radius, angle}] = 1 \quad (83)$$

The first two sets of equations define a rectangular portion of the plane ViewPlaneEmbededInViewSpace, the third a circular portion.

Definition of term: ViewSpaceToViewPlaneEmbededInViewSpace
Definition of term: ViewPlane·cp We can now state the traditional 3D perspective mapping equation (independent of how many pixels there are) as the mapping ViewSpaceToViewPlaneEmbededInViewSpace, short name ViewPlane·cp:

$$x = ViewPlane.cp.x[X, Y, Z] = \frac{X}{Z} \quad (84)$$

$$y = ViewPlane.cp.x[X, Y, Z] = \frac{Y}{Z},$$

$$ViewPlane.cp.z[X, Y, Z] = 1$$

As with the cv mapping, because of the destructive nature of the cp mapping, no unique inverse for cp (pc) exists. But also as with ViewSpaceVS, points in ViewPlaneEmbededInViewSpace are also points in ViewSpace.

Definition of term: ViewPlaneEmbededInViewSpaceToVisualCoordinates
Definition of term: ViewPlane·pz Since ViewPlaneEmbededInViewSpace is a subset of ViewSpace, the mapping for ViewPlaneEmbededInViewSpaceToVisualCoordinates, short name ViewPlane·pz, is the same as that for ViewPlane·cz:

$$\phi = ViewPlane.pz.\phi[x, y, z] = ViewPlane.cz.\phi[x, y, z] = a\tan2[y, x] \quad (85)$$

$$\theta = ViewPlane.pz.\theta[x, y, z] = \quad (86)$$
$$ViewPlane.cz.\theta[x, y, z] = \cos^{-1}\left[\frac{z}{\sqrt{x^2 + y^2 + z^2}}\right]$$

Figure 92:
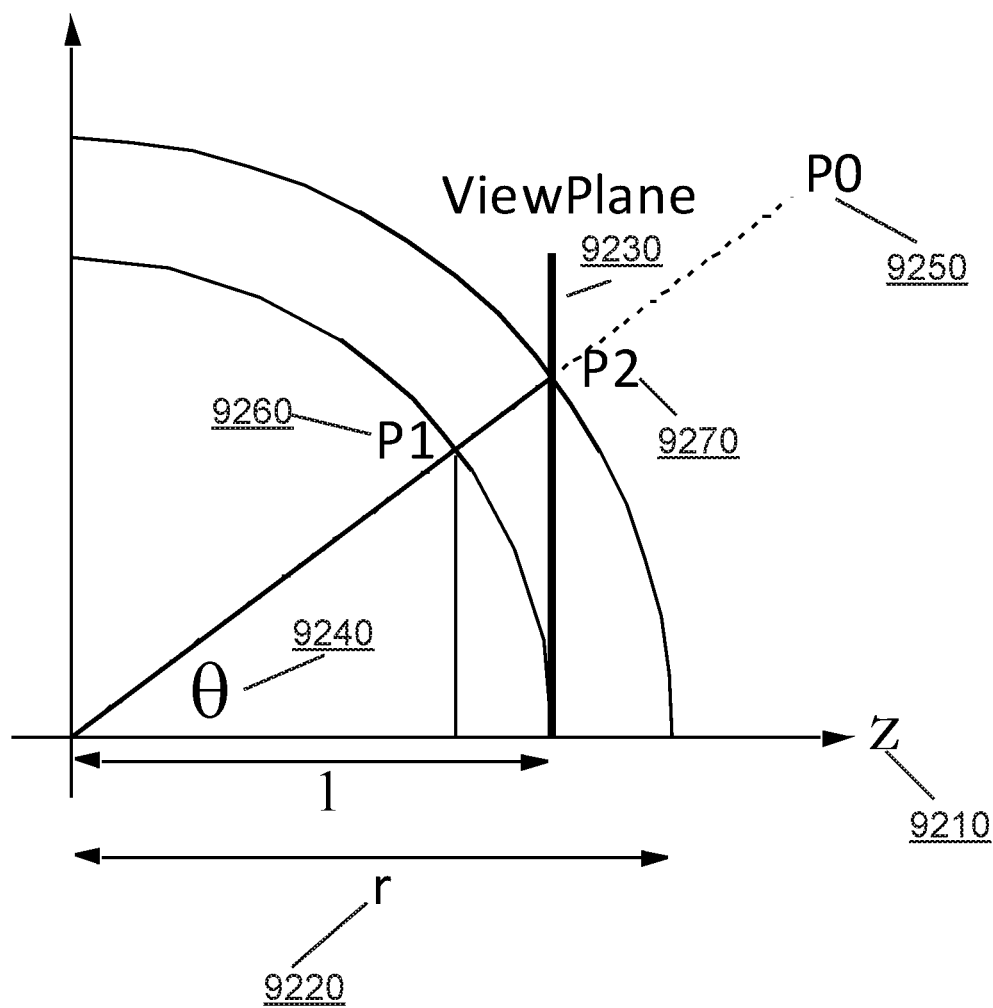
FIG. 92 shows the relationships between several geometric points, distances, and angles, between the ViewPlane and the ViewSphere in space.

Converting from ViewPlane (ScreenSurface) Coordinates to its Equivalent in VisualCoordinates This sub-section will derive an equation for converting a point given in ViewSpace coordinates to (the polar form of) ViewPlaneEmbededInViewSpace coordinates. An illustration of the relationship of the geometric elements involves is shown in FIG. 92.

Given: the positive z axis of ViewSpace is 9210, the ViewPlane is 9230, P0 9250 is the original point in xyz ViewSpace coordinates, P1 9260 is the projection of P0 onto the ViewSphere in xyz ViewSpaceVS coordinates, θ 9240 is the eccentricity of P1 in VisualCoordinates, P2 9270 is the projection of P0 onto the ViewPlaneEmbededInViewSpace, in radius, angle ViewPlaneEmbededInViewSpace coordinates (not ViewPlane), and r 9220 is the radius of the origin centered sphere that passes through P2, and P3 is P2 in radius, angle ViewPlane coordinates (not ViewPlaneEmbededInViewSpace).

Then:

$$\theta = cz.\theta[P0] = \cos^{-1}\left[\frac{P0.z}{\sqrt{P0.x^2 + P0.y^2 + P0.z^2}}\right] \quad (87)$$

$$\phi = cz.\phi[P0] = a\tan2[P0.y, P0.x] \quad (88)$$

$$P1.z = zv.z[\phi, \theta] = \cos[\theta] \quad (89)$$

$$P1.radius = \sqrt{zv.x[\phi, \theta]^2 + zv.y[\phi, \theta]^2} = \sin[\theta] \quad (90)$$

$$r = 1/P1.z = 1/\cos[\theta] \quad (91)$$

$$P2.radius = r \cdot \sin[\theta] = \frac{1}{\cos[\theta]} \cdot \sin[\theta] = \tan[\theta] \quad (92)$$

$$P2.radius = \tan\left[\cos^{-1}\left[\frac{P0.z}{\sqrt{P0.x^2 + P0.y^2 + P0.z^2}}\right]\right] \quad (93)$$

$$P3.angle = P2.angle = cz.\phi[P0] = a\tan2[P0.y, P0.x] \quad (94)$$

$$P3.radius = \frac{SW/2}{\tan[FOV/2]} \cdot P2.radius = \frac{SW/2}{\tan[FOV/2]} \cdot \tan[\theta] \quad (95)$$
$$= \frac{SW/2}{\tan[FOV/2]} \cdot \tan\left[\cos^{-1}\left[\frac{P0.z}{\sqrt{P0.x^2 + P0.y^2 + P0.z^2}}\right]\right]$$

Restating this, when the ScreenSurface is the ViewPlane, the cs mapping from ViewSpace to radius angle polar ViewPlane coordinates is:

$$cs.radius[x, y, z] = \quad (96)$$
$$\frac{SW/2}{\tan[FOV/2]} \cdot \tan\left[\cos^{-1}\left[\frac{P0.z}{\sqrt{P0.x^2 + P0.y^2 + P0.z^2}}\right]\right]$$

$$cs.angle[x, y, z] = a\tan2[y, x] \quad (97)$$

Restating this from VisualCoordinates:

$$cs.radius[\phi, \theta] = \frac{SW/2}{\tan[FOV/2]} \cdot \tan[\theta] \quad (98)$$

$$cs.angle[\phi, \theta] = \phi \quad (99)$$

Comments on the ViewPlane

A previously very important reason that the traditional ViewPlane has been so extensively used in software and effectively all hardware 3D graphics systems is the property that straight lines in ViewSpace transform into straight lines in 2D ViewPlane coordinates. Any shading, lighting, texturing etc. on the line would not transform linearly, but that isn't a concern when the line display "color" is just black or glowing green. What was a benefit is that transformed 3D lines and triangles can be rendered in ViewSpace with (appropriate) 2D line and triangle drawing algorithms, and if pixels need to be Z-buffered (e.g., triangles are not pre-sorted in painter's order or the equivalent), then values proportional to 1/w can be linearly interpolated to produce a "z" value to be z-buffered. This had the advantage of avoiding what were expensive division operations per pixel drawn, though multiply per ViewSpace interpolated values (color, texture address(es), etc.) are still required. However, now that complete complex shaders are executed at least once per drawn pixel, the division saving is no longer relevant. The "last straw" will come when all geometric primitives are always evaluated at least once per pixel. As of that point the only operation that still might be performed in 2D is the interpolation of color and z from micro-triangle vertices to perturbed sub-pixel sampling locations. As mentioned earlier, the graphics pipeline described in this system assumes that all geometric primitives are sub-divided or the equivalent until they fall below a specified maximum size relative to the local variable resolution pixel size.

III.E. Re-Definition of Resolution

To define what we will mean by variable resolution, we first must have an appropriate definition of resolution. With the concept of the ViewSphere established, we can now formally define linear preceptorial resolution, or just resolution:

Definition of term: linear preceptorial resolution
Definition of term: resolution
Definition of term: visual spatial frequency The standard definition of visual spatial frequency will be used as the definition of linear perceptual resolution, or just resolution. This is defined as the spatial frequency in cycles per radian with a half wavelength corresponding to a given perceptual distance on the ViewSphere. The perceptual distance between two points on the surface of the ViewSphere is their "angular" distance on the great circle connecting the two points. Thus all resolution measurements are made by in some way mapping two points to the surface of the ViewSphere. Table 1 expresses common examples of resolution in more convenient units of cycles per degree.

TABLE 1

Resolution examples.

| Example | Cycles/Degree |
|---|---|
| 20/10 rare best vision | 60 |
| 20/20 typical vision | 30 |
| 20/30 frequently used vision | 20 |
| 2K digital cinema | 30 |
| 4K IMAX ™ | 25 |
| 1920 × 1080 HDTV | 30 |
| 1280 × 720 HDTV | 20 |
| Sony ™ HMZ-T1 HMD | 12 |

The Resolution Equation

Given our definition of perceptual resolution, we are now in a position to extend the definition to the concept of variable resolution.

The perceptual resolution of a point on the ScreenSurface in the direction d is defined as the frequency of the corresponding perceptual distance on the ViewSphere: our directional magnitude derivative of sv:

$$rez = \frac{1}{2 \cdot \nabla_d sv} \quad (100)$$

This is the resolution equation. The resolution equation tells us the "resolution at a pixel." Because this function will not necessary have the same value in both the horizontal and vertical unit pixel directions (u and v), we cannot assume even approximately square pixels on the ViewSphere. In fact, we will have to fight a bit to get them.

Note that this definition of resolution is based on the assumption that the highest perceivable spatial frequency is that given by the Nyquist limit of one cycle per two pixels. This will be modified in a later section.

Note that the this variable resolution equation gives the resolution relative to a point, not the resolution of a pixel edge or diagonal, as the distance is actually measured in the tangent space. This is the most correct symbolic equation. But sometimes the del operator can't be easily applied, for example, because the mapping is a table. In this case an accurate numerical alternative is available. Assume that you want to compute the resolution subtended by two points $P_0$ and $P_1$ on the ScreenSurface. First use the sv mapping to obtain the two corresponding ViewSpace points on the surface of the ViewSphere. These points by definition also represent normal vectors. This allows the great circle distance between them to be computed. Thus the corresponding resolution is:

$$rez = \frac{1}{2 \cdot \cos^{-1}[sv[P_0] \cdot sv[P_1]]} \quad (101)$$

This is the discreet resolution equation. The points $P_0$ and $P_1$ could represent two corners of a pixel, i.e. their difference is the unit vector u or v or the non-unit vector u+v. This last case is worth noting. The resolution function has its lowest value $1/(2 \cdot |\nabla sv|)$, e.g. the longest spatial wavelength, in the direction of $\nabla sv$. But this is for a radius one pixel distance. The lowest resolutions for square pixel tiling's of the ScreenSurface are effectively always found by measuring one of their diagonals, e.g. in the direction u+v or u−v, when the results have been properly scaled by the path length $\sqrt{2}$. Proponents of rectangular tilings like to point out that the human visual system is not as sensitive to 45° features. How large this effect is, is not the point. But, for example, when variable resolution is applied to contact lens displays, generally the mappings are rotationally symmetric (e.g. diagonals of pixels will appear at all orientations around the display, including horizontal and vertical). This is an area where proponents of hexagonal tiling's get support for their point of view, because the hexagonal maximum wavelength is lower relative to that of a square pixel of the same area. The lowest resolution of a hexagon per unit area is higher than that of a square, for example, 30% fewer hexagons are needed to tile a region of the plane than squares for a given desired minimum resolution. Both the cones and the receptor fields of the eye use six-way symmetry. Note that later mentions of "unity aspect ratio" have to do with equal directional derivatives, not the specific pixel tiling.

Orthogonal Longitude Eccentricity Mappings

Definition of term: OrthogonalLongitudeEccentricity

We start with the case where sz·φ[u, v] is purely a function of u, and sz·θ[u, v] is purely a function of v: OrthogonalLongitudeEccentricity mappings. This simply means that the mapping equations for longitude and the eccentricity are independent of each other: the equations are orthogonal. It is very important to note that this class of mappings preserves the pixel structure of any Pixel Space of the surface associated with the surface.

Linearly Longitudinal Mappings

Definition of term: LinearlyLongitudinal

Next we consider the case of an OrthogonalLongitudeEccentricity mapping with the additional constraints that sz·φ [u, v] is a fixed linear function of u: LinearlyLongitudinal mappings. This just means that the mapping equation for u is linear in longitude. Thus zs·φ and its inverse sz·θ must be:

$$u = zs.u[\phi, \theta] = \phi \cdot \frac{SW}{2\pi} \quad (102)$$

-continued $$\phi = sz.\phi[u, v] = u \cdot \frac{2\pi}{SW} \quad (103)$$

This component of the mapping distributes SW pixels equally around the $2\pi$ radians of longitude, regardless of the eccentricity.

Because the circle of points with a constant $\phi$ (but all possible values of $\theta$) on the ViewSphere is always a great circle, and thus has a radius of 1 and a circumference of $2\pi$, we have $\nabla_v sv = \nabla_v sz$, and by inversion, also $\nabla_\theta vs = \nabla_\theta zs$. However the circle of points with a constant $\theta$ (but all possible values of $\phi$) on the ViewSphere is not a great circle (except the single case of $\theta = \pi$), but instead has a radius of $\sin[\theta]$ and a circumference of $2\pi \cdot \sin[\theta]$. This means that $\nabla_\theta sv = \sin[\theta] \cdot \nabla_u sz$ Taking this into account, for the perceptual distance in the direction u we have:

$$\nabla_u sv = \sin[\theta] \cdot \frac{2\pi}{SW} \quad (104)$$

and by equation (52) for the inverse, which is linear pixel density (pixels per radian):

$$\nabla_\phi vs = \frac{1}{\sin[\theta]} \cdot \frac{SW}{2\pi} \quad (105)$$

What about $\nabla_u sv$? It still can be any general function of $\theta$. In this LinearlyLongitudinal case it dynamically controls the aspect ratio of the approximately rectangular region of the ViewSphere that square regions of the ScreenSurface map onto.

$$AspectRatio = \frac{\nabla_u sv}{\nabla_v sv} = \frac{\sin[\theta]}{\nabla_v sv} \cdot \frac{2\pi}{SW} \quad (106)$$

In this way the resolution can be set in the v direction to whatever is desired, but in the u direction it must follow equation (103).

When we do have an equation for $\nabla_u sv$, by equation (52) we also have the equation for $\nabla_\theta vs$, we can then obtain the equation for v simply by integration:

$$v = vs \cdot v[\theta] = \int_{\theta_{min}}^{\theta} \nabla_\theta vs \cdot d\theta' \quad (107)$$

Where $\theta_{min}$ is defined next.
Definition of term: $\theta_{min}$
Definition of term: $\theta_{max}$ $\theta_{min}$ is smallest value of $\theta$ used for a particular LinearlyLongitudinal mapping, $\theta_{max}$ is largest. In many cases $\theta_{max} = FOV/2$. The chart (as described in VisualCoordinates) associated with a particular LinearlyLongitudinal mapping many times only includes the region of the ViewSphere defined by values of e such that $\theta_{min} \leq \theta < \theta_{max}$. For portions of the ViewSphere outside this region, mappings from other charts in the overall atlas of charts have to be used instead of the LinearlyLongitudinal mapping. In most cases, $\theta_{max}$ represents the outer edge of the atlas of mappings, so no additional chart (and associated mapping) for that portion of the ViewSphere need be present. More details of what values $\theta_{min}$ may take on and why, and what sort of chart and associated mapping is used for this "north pole" region will be covered later in the discussion on end-caps.

Equations (102) through (107) describe all LinearlyLongitudinal mappings.
Locally Uniform Resolution Now we will consider LinearlyLongitudinal mappings with the additional restriction that the mappings are locally uniform, and therefore so is the resolution, e.g. square regions on the ScreenSurface map to an approximately square regions on the ViewSphere: shape is locally preserved. Locally uniform resolution mappings occurs when the local value of resolution is invariant of the direction chosen:

$$\nabla_v sv = \nabla_u sv \quad (108)$$

Such mappings are a strict subset of LinearlyLongitudinal mappings. Thus equation (105) is now also the value for $\nabla_\theta vs$, the resolution in the $\theta$ direction varies as the inverse sine of the eccentricity:

$$rez = \frac{1}{\sin[\theta]} \cdot \frac{SW}{4\pi} \quad (109)$$

Applying equation (107) to obtain the v component:

$$v = vs.v[\theta] = \frac{SW}{2\pi} \cdot \int_{\theta_{min}}^{\theta} \frac{1}{\sin[\theta']} \cdot d\theta' \quad (110)$$
$$= \left(\frac{SW}{2\pi} \cdot \log_e\left[\tan\left[\frac{\theta}{2}\right]\right]\right) - \frac{SW}{2\pi} \cdot \log_e\left[\tan\left[\frac{\theta}{2}\right]\right]$$

Definition of term: Locally Uniform Resolution
Definition of term: LUR

Combined with equation (102) we now have a complete sv mapping. Equations (102) and (110) comprise the locally uniform mapping (a named ScreenSurface) also referred to as LUR. Note that LUR mapping is unique; it is the only one that obeys all of the constraints. Several properties of this mapping including its uniqueness make it quite valuable for use in variable resolution systems. For example, equation (110) is the inner loop of perceptual resolution driven hardware renderers. And with appropriately set parameters of $\theta_{min}$ and SW, it also fits much of the observed visual resolution capabilities of the human eye and visual system.

Figure 55:
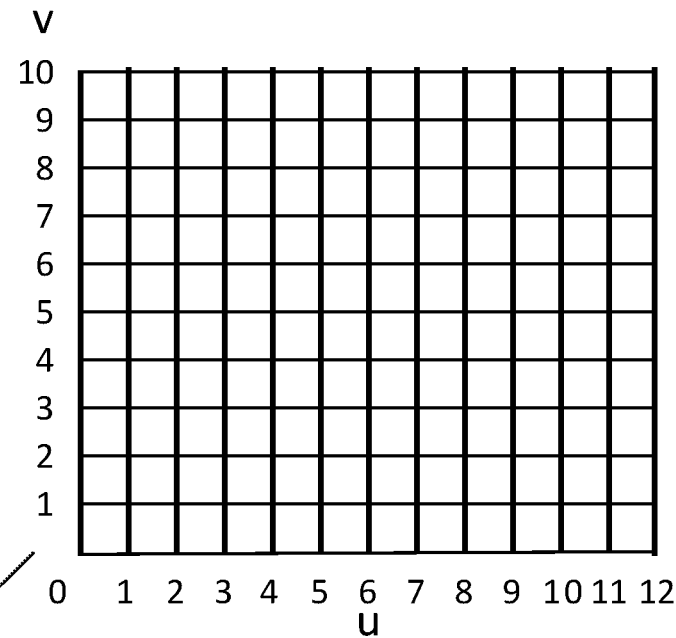
FIG. 55 shows the locally uniform resolution mapping.
Figure 55:
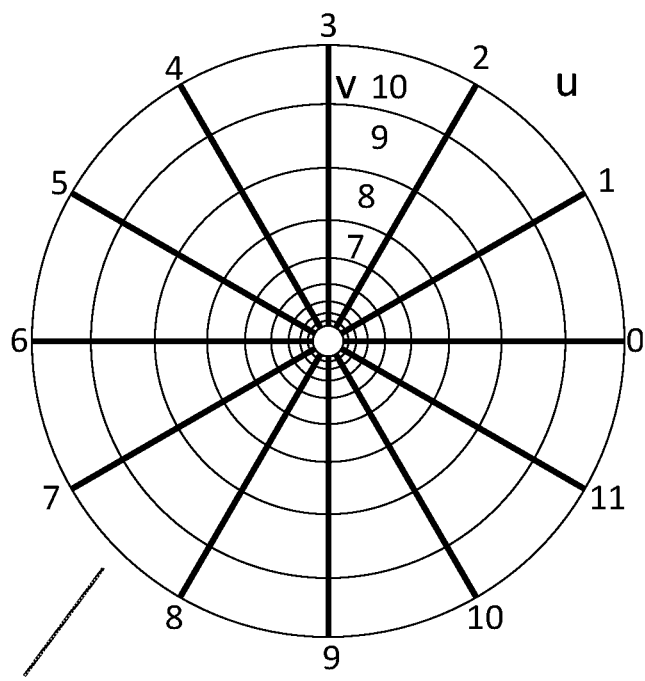

FIG. 55 shows this mapping both on the ScreenSurface, where it is just ordinary square pixels element 5510, and on the standard orthographic ViewPlane projection, where it is a log half angle polar mapping: uniform rotation and $\log_e[\tan[\theta/2]]$ mapping in radius element 5520. Locally, shapes and therefore orientations on the ScreenSurface are preserved on the surface of the ViewSphere. Local preservation of relative lengths and angles between vectors directly follows from this.

By combining in the standard mapping from ViewSpace to VisualCoordinates, cz, we can obtain the complete transform from ViewSpace to the ScreenSurface for the LocallyUniformResolution mapping:

$$u = cz.u[x, y, z] = \text{atan2}[y, x] \cdot \frac{SW}{2\pi} \quad (111)$$

$$v = cz.v[x, y, z] \quad (112)$$
$$= \log_e\left[\tan\left[\frac{\cos^{-1}\left[\frac{z}{\sqrt{x^2+y^2+z^2}}\right]}{2}\right]\right] \cdot \frac{SW}{2} - \log_e\left[\tan\left[\frac{\theta_{min}}{2}\right]\right] \cdot \frac{SW}{2\pi}$$

This can be simplified by collecting up the second constant term as $v_{min}$:

$$v_{min} = \log_e\left[\tan\left[\frac{\theta_{min}}{2}\right]\right] \cdot \frac{SW}{2\pi} \quad (113)$$

We can now restate cz as:

$$u = cz.u[x, y, z] = \text{atan2}[y, x] \cdot \frac{SW}{2\pi} \quad (114)$$

$$v = cz.v[x, y, z] = \log_e\left[\tan\left[\frac{\cos^{-1}\left[\frac{z}{\sqrt{x^2+y^2+z^2}}\right]}{2}\right]\right] \cdot \frac{SW}{2\pi} - v_{min} \quad (115)$$

Algorithm for Conversion to ScreenSpace
Traditional pipeline computation:

$1/Pv \cdot z \rightarrow w$ $Pv \cdot x * w * SW/2 + SW/2 \rightarrow Ps \cdot u,$ $Pv \cdot y * w * SW/2 + SH/2 \rightarrow Ps \cdot v$ Variable Resolution Pipeline with constants: $Z_{max}$=cos $[\theta_{min}]$, $v_{min}$=log [tan [[$\theta_{min}$/2] ]*SW/2π, and D=SW/sin $[\theta_{min}]$:
Computation:

$Pv \cdot z/\text{sqrt}[Pv \cdot x^2 + Pv \cdot y^2 + Pv \cdot z^2] \rightarrow z'$ If $z' > Z_{max}$: // End cap $D*Pv \cdot x \rightarrow Ps \cdot u,$ $D*Pv \cdot y \rightarrow Ps \cdot v$ else // locally uniform resolution mapping $a \tan 2[Pv \cdot y, Pv \cdot x]*(SW/2\pi) \rightarrow Ps \cdot u,$ $\log [\tan [a \cos [z'/2]]]*(SW/2\pi) - v_{min} \rightarrow Ps \cdot v$ From a hardware point of view, a key insight is that the function: $\log_e[\tan [a \cos [x]/2]]$ can be implemented as a single fast dedicated hardware function unit.
Log-Polar Coordinates and Spatial Variant Resolution
Definition of term: LogPolar
Definition of term: SpatialVarientResolution
Two dimensional LogPolar coordinates are a variation of standard polar coordinates in which the radius component is a function of the $\log_e[\ ]$ of a scaling of the standard polar coordinates radius, while the polar coordinates angle component of both are the same. SpatialVarientResolution is effectively the same concept.
A general introduction to LogPolar mappings of the ViewPlane is [Araujo, H, Dias J. M. 1996. "An introduction to the log-polar mapping," in Proceedings of the 2nd Workshop Cybernetic Vision, December 1996, pp. 139-144.].
Especially when the parameter a (to be described below) is included, the LogPolar mapping has also been referred to as spatial variant resolution. The main reference is [Wallace 1994: Wallace, R. et al. 1994. Space Variant Image Processing. International Journal of Computer Vision 13, 71-90.].
LogPolar/SpatialVarientResolution mappings have been of interest because (with the appropriate constants) they appear to closely match how visual information is physically mapped into the brain's visual cortex, and also because they also have proved to be an efficient space to perform certain image processing tasks in. This class of spaces has several properties of interest, most of which are described in the two references given above. One in common with most of those taught here is that LogPolar mappings are LinearlyLongitudinal. This means that all points of a particular longitude in VisualCoordinates fall onto the same vertical line on the ScreenSurface. While LogPolar mappings are not (even locally) shape-preserving, the mappings can be said to be angle preserving in the sense that differences in "angle" (visual longitude, see below) between two points are preserved by the mapping. Locally "shape" preserving would mean that angles between local vectors are preserved. That is, if points A, B, and C are points in the original image quite close to each other, then the angle between the local vectors $\overrightarrow{AB}$ and $\overrightarrow{AC}$ (e.g. $\cos^{-1}[\overrightarrow{AB} \cdot \overrightarrow{AC}]$) should have the same value both before and after the mapping is applied. This is not true for LogPolar mappings, but it is true for the LocallyUniformResolution mapping. Also, the LocallyUniformResolution mapping preserves the ratio of the lengths of the vectors: the ratio $|\overrightarrow{AB}|/|\overrightarrow{AC}|$ has the same value both before and after the mapping is applied; again this does not hold for the LogPolar mappings.

In our terminology, the LogPolar mapping is a specific ScreenSurface mapping. However, the way that LogPolar mappings have been defined in the literature are not in the form of any of the mappings we have been using to define ScreenSurface mappings. That is, they are not given as a mapping from a ScreenSurface to ViewSpace, or to ViewSpaceVS, or to VisualCoordinates. Instead, the standard definitions of the LogPolar mapping is given as a mapping from ViewPlane ScreenSurface centered xy coordinates to an un-normalized radius and angle:

$$\text{angle} = a\tan 2[\text{ViewPlane} \cdot y, \text{ViewPlane} \cdot x] \quad (116)$$

$$\text{radius} = \log_e[\sqrt{\text{ViewPlane} \cdot x^2 \text{ViewPlane} \cdot y^2}|] \quad (117)$$

The angle is in units of radians, not pixels, and the radius is in units of $\log_e$[pixel distance in ViewPlane coordinates]. To fully define what is meant by the LogPolar mapping, we will first have to normalize them using the values of LogPolar·SW, LogPolar·FOV, and ViewPlane·SW.
The FOV of the two spaces, however, is generally the same, though the VisualField of a LogPolar mapping is a circle cut out of the (squarish) ViewPlane mapping's ScreenSurface. In cases where the ScreenSurface surface is defined by the equation θ<FOV/2, we have $\theta_{max}$=FOV/2.
Even though one is derived from the other, the LogPolar mapping is a different instance of a ScreenSurface than the ViewPlane mapping, and (effectively) they will always have their own different values of SW and SH. Thus, when necessary, we will differentiate them by explicitly referring to ViewPlane·SW, LogPolar·SW, and LogPolar·SH. Since the mapping is defined on a circular sub-region of the ViewPlane, the utilized portion of the ViewPlane is a square region, and so ViewPlane·SW and ViewPlane·SH can be considered the same.
By inspection, LogPolar is a LinearlyLongitudinal mapping, so we know what the u (longitude) component is in various other spaces:

$$u = LogPolar.cs.u[X, Y, Z] = \frac{LogPolar.SW}{2\pi} \cdot \text{atan2}[Y, X] \quad (118)$$

$$u = ViewPlaneToLogPolar.u[x, y] = \frac{LogPolar.SW}{2\pi} \cdot \text{atan2}[y, x] \quad (119)$$

-continued $$u = ViewPlaneEmbeddedInViewSpaceToLogPolar.u[x, y] \quad (120)$$
$$= \frac{LogPolar.SW}{2\pi} \cdot atan2[y, x]$$

$$u = LogPolar.zs.u[\phi, \theta] = \frac{LogPolar.SW}{2\pi} \cdot \phi \quad (121)$$

The v component will be a little harder to obtain.

Since the $\log_e[\ ]$ returns negative numbers for inputs less than 1, most LogPolar mappings define the circular region of the ViewPlane with a radius less than 1 to be outside the main LogPolar chart. The minimum LogPolar·v coordinate value of 0 is defined to be at this radius. This is equivalent to the use of a $\theta_{min}$ value set to the eccentricity subtended by a one pixel radius in the ViewPlane:

$$\theta_{min} = \tan^{-1}\left[\frac{\tan[FOV/2]}{Viewplane.SW/2}\right] \quad (122)$$

The problem with this definition of $\theta_{min}$ is that the shape of the LogPolar mapping is dependent on both the number of pixels in the ViewPlane ScreenSurface as well as the FOV. This means that changing the number of pixels doesn't just change the sampling density, it also changes the shape of the radius mapping function. And changing the FOV doesn't just change the extent of the VisualField and the sampling density, it also changes the shape of the radius mapping function. While much of the existing literature defines the LogPolar mapping in this shifting way, we will normalize our definition of the LogPolar mapping by taking $\theta_{min}$ as a fixed constant, and not dependent on either the ViewPlane·SW or the FOV.

Past work apparently has been able to accept the shape change because of the use of the $\log_e[\ ]$ function means that the change in shape of the mapping is just a shift along the radius axis, and the shift is quite small for even large scale changes: a scale factor of two will only offset the destinations of points into the LogPolar representation by less than a pixel in radius (as $\log_e[2]\approx0.7$). But when arguing over different LogPolar fits of the visual cortex, people are concerned about such small offsets and small differences in the value of a (to be described).) The equation above can be used to convert the assumptions of other work into our normalized form.

We can convert from the radial distance in ViewPlane coordinates to a function of visual eccentricity via the previously developed equation (but only for the non-normalized version of $\theta_{min}$ defined above):

$$ViewPlane.zs.radius[\phi, \theta] = \frac{ViewPlane.SW/2}{tab[FOV/2]} \cdot \tan[\theta] = \frac{\tan[\theta]}{\tan[\theta_{min}]} \quad (123)$$

We know that the final form of the equation for the v component of the LogPolar mapping will be of the form:

$$v = LogPolar.zs.v[\phi, \theta] = k1 \cdot \log_e\left[k2 \cdot \frac{\tan[\theta]}{\tan[\theta_{min}]}\right] \quad (124)$$

Where k1 and k2 are constants to be determined.

We know we want LogPolar·zs·v[$\theta_{min}$]=0, so k2 must be a value that sets the expression inside the $\log_e[\ ]$ function to be 1 when $\theta=\theta_{min}$, which happens when k2=1, so k2 vanishes. This leaves us with:

$$v = LogPolar.zs.v[\phi, \theta] = k1 \cdot \log_e\left[\frac{\tan[\theta]}{\tan[\theta_{min}]}\right] \quad (125)$$

k1 is harder. We would like to keep $\nabla_\theta$LogPolar·sv·v as close to $\nabla_\phi$LogPolar·sv·u as possible, so let's take a look at them:

$$\nabla_e LogPolar.sv.v = \frac{d}{dv} \cdot LogPolar.sv.v = \frac{2}{\sin[2\cdot\theta]} \cdot k1 \quad (126)$$

Since the LogPolar mapping is LinearlyLongitudinal, the scale change in the direction is:

$$\nabla_\phi LogPolar.sv.v = \frac{1}{\sin[\theta]} \cdot \frac{LogPolar.SW}{2\pi} \quad (127)$$

Here we see the fundamental difference between the LogPolar mapping and the LocallyUniformResolution mapping. LocallyUniformResolution mapping has, by definition, the same directional magnitude derivative in all directions from a given point. The LogPolar mapping cannot be made to do so. In fact, the derivation of the unique LocallyUniformResolution mapping proves that it is the only mapping that can have this property.

We can, however, come close, at least for small eccentricities. For small values of $\theta$, sin[$\theta$]≈$\theta$. So the following setting of k1 will make $\nabla_\theta$LogPolar·sv·v≈$\nabla_\phi$LogPolar·sv·u, for small values of $\theta$:

$$k1 = \frac{LogPolar.SW}{2\pi} \quad (128)$$

so now we have:

$$v = LogPolar.zs.v[\phi, \theta] = \frac{LogPolar.SW}{2\pi} \cdot (\log_e[\tan[\theta]] - \log_e[\tan[\theta_{min}]]) \quad (129)$$

and:

$$\nabla_e LogPolar.sv.v = \frac{2}{\sin[2\cdot\theta]} \cdot \frac{LogPolar.SW}{2\pi} = \frac{1}{\cos[\theta]} \cdot \frac{1}{\sin[\theta]} \cdot \frac{LogPolar.SW/2}{2\pi} \quad (130)$$
$$= \frac{\nabla_\phi LogPolar.sv.v}{\cos[\theta]}$$

Unfortunately, the scale in the θ direction will differ from that in φ direction as θ gets larger, e.g. by 1/cos [θ]. For (relatively) small FOVs, this isn't off by much, as a FOV of 60° will have a maximum visual eccentricity of 30°, and 1/cos [30°]≈1.15. This isn't too bad, especially compared to other factors that have to be taken into consideration when deeply modeling the optics of the eye, such as converting from visual eccentricity to retinal eccentricity. But by a FOV of 90°, the ratio raises to about 1.4, and goes completely of the chart as one approaches 180°: at a FOV of 170°, the ratio is up to 11.5! As the maximum visual eccentricity of the human can be over 105°, any form of the LogPolar mapping becomes undefined.

Summarizing, we can now define:
Definition of term: LogPolar·zs $$u = LogPolar.zs.u[\phi, \theta] = \frac{LogPolar.SW}{2\pi} \cdot \phi \qquad (131)$$

$$v = LogPolar.zs.v[\phi, \theta] = \frac{SW}{2} \cdot \log_e[\tan[\theta]] - \frac{SW}{2\pi} \cdot \log_e[\tan[\theta_{min}]] \qquad (132)$$

and derivatives in the φ and θ directions:

$$\nabla_\phi LogPolar.sv.v = \frac{1}{\sin[\theta]} \cdot \frac{LogPolar.SW}{2\pi} \qquad (133)$$

$$\nabla_\theta LogPolar.sv.v = \qquad (134)$$
$$\frac{1}{\cos[\theta]} \cdot \frac{1}{\sin[\theta]} \cdot \frac{LogPolar.SW}{2\pi} = \frac{\nabla_\phi LogPolar.sv.v}{\cos[\theta]}$$

The inverses of these particular mappings and mappings to and from other known coordinate systems can be easily derived using the previous space conversion mappings. Though, as described, the mappings to and from the ViewPlane are problematic for the reasons mentioned.

Definition of term: LogPolar·SH
Note that LogPolar·SH is defined by:

$$LogPolar.SH = \frac{SW}{2\pi} \cdot \log_e[\tan[\theta_{max}]] - \frac{SW}{2\pi} \cdot \log_e[\tan[\theta_{min}]] \qquad (135)$$
$$= \frac{SW}{2\pi} \cdot \log_e\left[\frac{\tan[\theta_{max}]}{\tan[\theta_{min}]}\right]$$

In the past, when attempts were made to fit the LogPolar mapping to known data about the human eye and visual system resolution as a function of visual eccentricity, different k1 constants have been used, different values of $\theta_{min}$ (usually 1° or a little more) are used, and often an offset a is added inside the $\log_e[$ $]$ term, which, when greater than 1, also eliminates the undefined radius 1 hole in the mapping. The latter is useful when building physical lens based implementations of the mapping. So we have a modified radius function:

$$radius = \log_e[\sqrt{ViewPlane \cdot x^2 ViewPlane \cdot y^2} + a] \qquad (136)$$

This is back in the un-normalized form, because this is the space in which a is usually defined. This form is harder to analyze, as a closed form of the derivative doesn't exist.

The methods described in this document are more general, and have been referred to as variable resolution. The phrase "spatial variant resolution" is more specific than that of "variable resolution," in that it tells one in what way does the resolution vary (by space). But as presently the term "space variant resolution" is tightly identified with LogPolar representations, in this document the more general techniques will continue to be referred to as variable resolution.

The previously mentioned match of LogPolar representations to the human visual system are for areas outside the central foveal region, a region approximately two degrees of visual angle across (e.g., all of the retina inside about one degree of eccentricity). Thus many existing models that use LogPolar mapping elsewhere switch to a more constant high resolution mapping for the foveal region; thus the full model consists of a chart of two maps: a LogPolar mapping outside of one degree of eccentricity, and a constant density EndCap mapping inside one degree of eccentricity. The actual cut point between the two maps is generally parameterized by a constant that is effectively the same as the $\theta_{min}$ constant. But as previously mentioned, when the application is to perform the LogPolar mapping optically, it is usually easier to not use an end-cap, but a value of the parameter a larger than 1.

Comparing the Log-Polar Mapping with the Locally Uniform Resolution Mapping

In the last section we have already compared many aspects of the LogPolar mapping with LocallyUniformResolution. Both are LinearlyLongitudinal mappings, so they have the same equation for zs·u and $\nabla_\theta$LogPolar·sv·u. But while the LocallyUniformResolution mapping has the same equation for $\nabla_\theta$LocallyUniformResolution·sv·v as $\nabla_\phi$LocallyUniformResolution·sv·u, which is why the mapping is locally shape preserving (as well as locally visual angle preserving), the LogPolar mapping does not. The effect can be kept small for small eccentricities, but blows up at larger ones, and is ill defined at or beyond a FOV of 180°, while the LocallyUniformResolution mapping is well defined for FOVs approaching 360° (even though at eccentricities above 90° the resolution starts going up again!).

Since such a superior mapping exists, why was the LogPolar mapping ever proposed in the first place, and why have so many researchers continued to use it?

In all likelihood, the LogPolar mapping was first proposed because those involved were using the traditional flat projection plane common to most manmade optical systems: cameras with flat planes of film, and newer digital cameras of flat light sensitive imaging chips. We still don't have the technology to make doubly curved surface semi-conductor imaging or display chips. With film, there have been some exceptions. The most notable is probably the 200 inch Mount Palomar Telescope, which has a spherically curved film plate and specially produced spherically curved film! However the reason for this was to reduce spherical aberrations of the telescope's optical system. The field of view is considerably narrower than that of the eye.

If one is only familiar with the planer projection model, or is forced to use it for technical reasons, then applying a $\log_e$ function to the radius of a polar coordinate representation of the ViewPlane seems like a natural step. The only still or video images most people can get are all produced with the planer projection model. It's the "if all you have is a hammer, every problem looks like a nail" sort of situation.

Even when restricted to a planer image acquisition surface, there still are tricks that can be played with the optics. The common example are "fisheye" lenses. (This is amusing, because the human eye is basically a fish eye adapted to use in air, and has a wider field of view than most any "fisheye" lens.) This name covers a number of different ways that the radius function can be manipulated optically. Some lenses have been specially designed so that their radius manipulation implements the ViewPlane to LogPolar mapping optically, making optimal use of the pixels on the planer imaging device at the focal plane of the optics. This is one quite valid reason for using the LogPolar mapping: it can be relatively inexpensively be actually implemented with existing technology, and can result in considerable computational savings for some image processing and computer vision tasks. The fact that it might not completely accurately model the human visual system's representation is irrelevant, and the slightly non-uniform local resolution of the mapping can be worked around.

There are less excuses when it comes to modeling the human eye. It has long been known that the eye has a spherical imaging surface—in analyzing it, one should start with a spherical projection, like the ViewSphere. But the basic mathematical techniques behind such mappings are not widely understood, and mainly applied in a few niches, such as computer rendering for hemispherical dome displays, and some of the associated video projection techniques. The combination of using a spherical projection and variable resolution appears just to never have come up before. More details about how well the LocallyUniformResolution mapping can fit the known properties of the human eye and visual system will be discussed in a later section.

Later several techniques for building practical LocallyUniformResolution mapping based displays and cameras using today's existing technological techniques will be discussed. Not too many years ago, not all of these techniques were practical, which could be another reason why the mapping hasn't been explored before.

It should be noted that being confined to using imaging devices on the ViewPlane is not a legitimate impediment to using the LocallyUniformResolution mapping rather than the LogPolar mapping. Below is the definition of the LocallyUniformResolution mapping in terms of ViewPlane coordinates:

Definition of term: LocallyUniformResolution·ps $$u = LocallyUniformResolution.ps.u[ViewPlane.x, ViewPlane.y] \qquad (137)$$
$$= \frac{LocallyUniformResolution.SW}{2\pi} \cdot atan2[ViewPlane.y, ViewPlane.x]$$

$$v = LocallyUniformResolution.ps.v[ViewPlane.x, ViewPlane.y] \qquad (138)$$
$$= \frac{SW}{2\pi} \cdot \log_e\left[\tan\left[\tan^{-1}\left[\frac{\sqrt{ViewPlane.x^2 + ViewPlae.y^2}}{SW/2} \cdot \tan\left[\frac{FOV}{2}\right]\right]/2\right]\right] - \frac{SW}{2\pi} \cdot \log_e[\tan[\theta_{min}]]$$

As previously mentioned, this radius transform can also be implemented completely optically for existing planer image plane image capture devices.

End Caps

There is a singularity present at v=0 where the resolution goes to infinity in LinearlyLongitudinal mappings. Most real variable resolution LinearlyLongitudinal mappings effectively switch to another mapping dependency on θ at about 1°. We have defined the end cap takeover angle as $\theta_{min}$. The alternative mapping most simply is just near constant resolution, or only varies by a small additional factor.

A very simple way to "implement" this is to add an additional chart called EndCap to the atlas of mappings for a particular named ScreenSurface (which, remember, is a manifold). The surface for this EndCap chart is will be the set of points that the inverse of its mapping function takes the set of all points on the ViewSphere with z values above cos [$\theta_{min}$] to. The mapping function for this EndCap chart can be bound by defining a specific mapping of ScreenSurface surface to or from any of the well-defined coordinate systems. In the example we will give here we will do this by defining the EndCap·vs mapping. (Note that this denotes a different vs mapping than the one of the primary chart of the ScreenSurface. EndCap is the name of the second chart, it is not a named ScreenSurface, it is just a component of any ScreenSurface, e.g. the full name is <named ScreenSurface>·EndCap. When no chart name is specified (as we have been doing up till now), the convention is that the primary (first) chart is being implicitly referenced.) There are a number of different mappings that can work well for endcaps, but the simplest is just an orthographic projection, which has the advantage of being simple to implement in hardware. Here we define:

$$EndCap.vs.u[x, y, z] = x \cdot \frac{EndCap.SW}{\sin[\theta_{min}]} \qquad (139)$$

$$EndCap.vs.v[x,y,z] = y \cdot \frac{EndCap.SW}{\sin[\theta_{min}]} \qquad (140)$$

Note that the ScreenWidth here is that of this second mapping, not the first, and here ScreenHeight equals ScreenWidth (this is a square patch over a round hole). Again the domain of this mapping in this ScreenSurface is only those points which map via sv to a z value greater than cos [$\theta_{min}$]. The resolution of the primary mapping at this boundary will be a constant when a LinearlyLongitudinal mapping is being used. Thus to ensure first order continuity between the two charts, the value of EndCap·SW can be adjusted so that the EndCap mapping will have the same resolution at the boundary. (Orthographic projection has a slightly varying resolution in the region over the north pole, but for any given eccentricity the resolution will be constant. We will not give the equation to force the matching of the resolution of the two charts at the boundary here.) Order one continuity in resolution at the boundary means that there will be order one continuity in both mapped pixel size and sample density. In practice, second order continuity at the boundary can be achieved by special casing the sampling patterns in all the boundary pixels to smooth the changes When modeling the eye's retina, the EndCap mapping is that of the fovea, which is quite different from the mapping outside the fovea. Also, the foveal mapping actually varies by as much as a factor of three in peak resolution by the individual. Most contact lens' displays can't use such variable foveal resolution maps, because slight shifts in the alignment of the contact lens on the cornea correspondingly shifts the peak foveal resolution point all about the foveal portion of the display and beyond. Instead, a constant high resolution map is required.

A feature of some mappings, in particular the LocallyUniformResolution mapping, is that they are well defined past 90°. The only difference is that the resolution can get higher again past 90°. This actually happens on the human eye, where portions of the visual field do reach as much as 105°. There, the density of retinal cones does go up.

The end cap technique basically put a cap on the north pole. Most mappings do not need to be defined anywhere up to $180°-\theta_{min}$. But when required, the singularity at the south pole can be capped as well, using exactly the same methods. In the sequel, when such one or two caps are needed, they are implicitly assumed to be defined, and will only be called out as necessary. Also, there is nothing too special about 1°; for any given real mapping, generally a workable angle somewhere in the range of one half to ten degrees can be found for $\theta_{min}$. Again, besides the orthographic end cap mapping, many others can be defined, most with better continuity.

VisualCoordinates to Retinal ScreenSurfaces
Overview

This chapter introduces the concept of the RetinalSphere, which physical space for points on the surface of the physical retina. Additional coordinate systems and two new ScreenSurface manifolds defined on the RetinalSphere support the physical and visual modeling of retinal cones and retinal midget ganglion cells. But the most critical detail, the derivation of a specific primary mapping function for each of these manifolds, will be left to a still later section.

SUMMARY

This chapter first defines a new two dimensional physical space: the RetinalSphere, corresponding to the physical world points on the surface of the retina.

ViewSpaceRS will be defined as the embedding of the RetinalSphere into ViewSpace.

RetinalCoordinates will be defined as a coordinate frame for ViewSpaceRS.

RetinalCones will be a new named ScreenSurface manifold defined for modeling retinal cones.

RetinalMidget will be a new named ScreenSurface manifold defined for modeling retinal midget ganglion cells.

The conversion from RetinalCoordinates to VisualCoordinates (RetinalCoordinatesToVisualCoordinates) cannot be expressed as a closed form equation, due to the non-linear effects of the eye's optics in the eccentricity direction. Instead, a table interpolation will have to be used.

If, later down the line, any specific mapping's definition involves concatenation with the table based RetinalCoordinatesToVisualCoordinates conversion, then that mapping will have to be considered as table based as well.

Defined ScreenSurface Spaces and their Mappings
  Definition of term: RetinalSphere
  The RetinalSphere is defined to be the two dimensional closed surface of a sphere in ViewSpace, with a radius equal to the retinal radius (default 12 mm), centered at the origin. The RetinalSphere represents the eye's physical retinal surface. No special character is defined for this space, as it is just S2, a character name will be assigned to a particular coordinate system defined on the surface of the Retinal-Sphere. (Even though the RetinalSphere as defined is a surface, we still will usually refer to "the surface of the RetinalSphere" to reinforce this point.)

The RetinalSphere is not just magnified version of the ViewSphere. Points on the surface of the ViewSphere represent the projection of any points that lie on a straight line in ViewSpace from the origin of ViewSpace through a given point on the ViewSphere to that same point. Points on the surface of the RetinalSphere represent the physical locations in space of certain retinal neurons. The optics of the eye cause points in ViewSpace that project to a specific point on the surface of the ViewSphere to be optically imaged onto a different, non-corresponding point on the surface of the RetinalSphere. Points on the surface of the RetinalSphere correspond to where light is physically projected by the cornea and the lens; points on the surface of the ViewSphere correspond to the angles that the light would have come in at if there were no optics present and that the light would have intersected (or nearly) the EyePoint. (The Retinal-Sphere is a particular formalization of what was defined anatomically as the retinal sphere.)

A three dimensional embedding of the RetinalSphere into three dimensional ViewSpace will be defined; see ViewSpaceRS. One existing standard reference two dimensional coordinate system will be defined for the surface of the RetinalSphere; see RetinalCoordinates.

The actual mapping caused by the eye's optics between points on the surface of the ViewSphere to points on the surface of the RetinalSphere will be defined later, in particular it will be in the form of a mapping from VisualCoordinates to RetinalCoordinates.

Definition of term: ViewSpaceRS

ViewSpaceRS is defined to be the set of three dimensional points in ViewSpace that are the embedding of the two dimensional points of the RetinalSphere into three dimensional ViewSpace. (We could have called this space "RetinalSphereEmbededInViewSpace", but for a shorter name, we let the "RS" after "ViewSpace" stands for "Retinal-Sphere".) The individual coordinate components of ViewSpaceRS will be denoted by x, y, and z Definition of term: RetinalCoordinates
Definition of term: r RetinalCoordinates is a coordinate system for the surface of the RetinalSphere. It is akin to VisualCoordinates, in that both used the same longitude eccentricity angular parameterizations of their respective sphere's surface. To differentiate the angular parameters for RetinalCoordinates from those of VisualCoordinates, the upper case Greek letters will be used: retinal longitude will be denoted by $\Phi$, and retinal eccentricity will be denoted by $\Theta$.

The shorthand name for the RetinalCoordinates is r. Because the conversion between VisualCoordinates and RetinalCoordinates is fairly well defined, RetinalCoordinates (like VisualCoordinates) is not a ScreenSurface (this is why it can have a separate shorthand name).

Definition of term: VisualCoordinatesToRetinalCoordinates

Definition of term: zr

While there is no (accurate) closed form equation relating VisualCoordinates to RetinalCoordinates, any particular wide angle schematic eye can be raytraced to produce a numeric solution. Longitude is preserved, so we have:

$$RetinalCoordinates.\Phi = \frac{VisualCoordinatesTo}{RetinalCoordinates.\Phi[\phi, \theta]} \quad (141)$$
$$= \phi$$

But the equation for eccentricity is table based:

$$RetinalCoordinates.\Theta = \frac{VisualCoordinates}{ToRetinalCoordinates.\Theta[\phi, \theta]} \quad (142)$$
$$= VisEccToRetEcc[\theta]$$

where the table VisEccToRetEcc[ ] will be defined in a later section.

The shorthand name for this mapping is zr.

Definition of term: RetiniCoordinatesToVisualCoordinates

Definition of term: rz

RetinalCoordinatesToVisualCoordinates is the inverse of VisualCoordinatesToRetinalCoordinates. The shorthand name for this conversion is rz. Again, longitude is preserved, so we have:

$$VisualCoordinates.\phi = \frac{RetinalCoordinatesTo}{VisualCoordinates.\phi[\Phi, \Theta]} \quad (143)$$
$$= \Phi$$

But again the equation for eccentricity is table based:

$$VisualCoordinates.\theta = \frac{RetinalCoordinatesTo}{VisualCoordinates.\theta[\Phi, \Theta]} \quad (144)$$
$$= RetEccToVisEcc[\Theta]$$

where the table RetEccToVisEcc[ ] will be defined in a later section.

Definition of term: RetinalCones

RetinalCones is a named ScreenSurface for the retinal cones. It is used to map a uniform array of equal size cones on a 2D surface to their physical instances on the RetinalSphere, or other coordinate systems.

Definition of term: RetinalCones·sr

The mapping of RetinalCones to RetinalCoordinates is defined by RetinalCones·sr.

Definition of term: RetinalCones·rs

The mapping of RetinalCoordinates to RetinalCones is defined by RetinalCones·rs, which is the inverse of RetinalCones·sr.

Definition of term: RetinalCones·sz

The mapping of RetinalCones to VisualCoordinates is defined by RetinalCones·sz. This is defined by the concatenation of the mapping RetinalCones·sr with the conversion RetinalCoordinatesToVisualCoordinates.

Definition of term: RetinalCones·zs

The mapping of VisualCoordinates to RetinalCones is defined by RetinalCones·zs, which is the inverse of RetinalCones·sz.

Definition of term: RetinalMidget

RetinalMidget is a named ScreenSurface for the retinal midget ganglion cells. It is used to map a uniform array of equal size midget ganglion cells on a 2D surface to their physical instances on the RetinalSphere, or other coordinate systems.

Definition of term: RetinalMidget·sr

The mapping of RetinalMidget to RetinalCoordinates is defined by RetinalMidget·sr.

Definition of term: RetinalMidget·rs

The mapping of RetinalCoordinates to RetinalMidget is defined by RetinalMidget·rs, which is the inverse of RetinalMidget·sr.

Definition of term: RetinalMidget·sz

The mapping of RetinalMidget to VisualCoordinates is defined by RetinalMidget·sz. This is defined by the concatenation of the mapping RetinalMidget·sr with the conversion RetinalCoordinatesToVisualCoordinates.

Definition of term: RetinalMidget·zs

The mapping of VisualCoordinates to RetinalMidget is defined by RetinalMidget·zs, which is the inverse of RetinalMidget·sz.

IV. The Variable Resolution Nature of the Human Eye

The human eye, like digital cameras, is comprised of a large number of discrete light catching "pixels," called retinal photoreceptors. The retina has two types of photoreceptors: the night-vision photoreceptive rods, and the daylight and indoor lighting sensing photoreceptive cones. While there are many more rods (approximately eighty to one hundred twenty million) in the eye than cones (approximately five to six million); the rods trade-off increased light sensitivity for lower resolution, so much so that they provide less visual resolution than the cones do. So for the purposes of understanding the uppermost resolution limits of the eye, and how to optimally display to it, it is the resolution capabilities of the cones that must be understood.

In most man-made cameras, all the pixels are of the same size, and spaced the same amount apart from each other. But the cones of the human eye vary quite a bit in size, and more importantly, the spacing between them varies even more. Furthermore, the "pixels" that are carried out the back of the eye by the optic nerve to the rest of the brain represent the results of retinal processing that groups the outputs of many cones together, making the "effective pixel size" even larger. What this means is that the human eye does not have anywhere near uniform resolution across its field of view. In fact, the "area" of a pixel on the optic nerve can vary by a factor of one thousand from the highest resolution portion of the eye (the center of the fovea) to the lowest (the far periphery). Putting it another way, while the eye has as many as six million individual retinal cone photoreceptors, there are less than one third of a million optic nerve fibers for carrying "pixel data." If an eye mounted display (specifically including contact lens displays) can be engineered to vary the size of the discrete light producing pixels to match the resolution of the portion of the retina that the particular pixel will display to, then there is the opportunity to only need similarly small numbers of them; and therefore potentially also only the need to render similarly small numbers of them for use on the display. This represents a considerable savings over the current art.

These "pixels of the optic nerve" are the outputs of the retinal midget ganglion cells. Each such cell has an associated visual receptor field, with a field center input from one or more cone cells, and a larger surround input from (approximately) seven or (many) more cone cells. It is the combined visual field of all the cones that contribute to the center field that effectively determines what you could call the "visual pixel size" that the retinal midget ganglion cells detect. To understand how this size varies across the visual field of the human eye, several other factors must be taken into account first. So we will briefly identify the relevant factors, followed by a detailed sub-section on each factor. As we get into the details, we will finally start defining most of the specific mapping equations for the retinal spaces.

The "visual pixel size" mostly varies with eccentricity. The variation in size is approximately circularly symmetric around the center of the retina; the smallest size (highest resolution) occurs inside the fovea, the largest size (lowest resolution) occurs at the far periphery.

The retinal image is magnified. Because of the optics of the eye, the visual image is magnified on the surface of the retina. This means that any given visual eccentricity maps to a greater retinal eccentricity, by a factor of as much as 1.38, though the actual amount of magnification varies, and is becomes somewhat lower at larger eccentricities. By contrast, the retinal longitudinal angle is the same as the visual longitudinal angle. This is important, as it means that the retinal angle in the eccentricity direction caused by the local spacing between cones will be larger than the corresponding visual angle. In other words, from the visual side the cones look slightly flattened (approximately an ellipse with a ratio of major to minor axes of 1.38).

Cones are not always "flat-on" to the local surface of the retina. To gather the maximum amount of light, cones actively point in the direction of the center of the exit pupil of the eye as it appears from their individual location on the surface of the retina, e.g. not the same direction in general as the normal to the (local) surface of the retina. This cause the cones to look slightly "squashed" from the visual side, though not enough to cancel out the opposite effect caused by the retinal image magnification.

The retinal size of cones is governed by several functions. The retinal size of the cones is governed within the fovea by one constant and one function, and outside the fovea grows larger with increased eccentricity by a different function, and then becomes constant again.

The spacing between cones is governed by two functions. Inside the sub portion of the fovea with less than 0.7° visual eccentricity, the foveal rod-free zone, there are no rods, only cones, and therefore the spacing between cones is determined by the size of the cones. Outside the foveal rod-free zone, rods start appearing between the individual cones, and the spacing between individual cones grows by a different function, which is greater than that determined by the size of the cones.

The number of cones that contribute to the center input of retinal midget ganglion cells varies with eccentricity. Inside a visual eccentricity of 6°, each midget ganglion cell obtains its center input from precisely one cone cell, so the visual pixel size of the midget ganglion cell is the same as that of the underlying cone cells. Outside this region, the center input to midget ganglion cells start to come from more than one cone cell, with the number of such cones increasing more and more with increasing visual eccentricity.

Now we will go into more details on each of these factors.

"Visual Pixel Size" Mostly Varies with Eccentricity

To a first approximation, the resolution mapping of the human eye is an OrthogonalLongitudeEccentricity mapping. Actually, it is almost a LinearlyLongitudinal mapping. That is, the preceptorial resolution of the human eye drops off with increasing visual eccentricity in almost the same way regardless along which longitude the drop off is measured. While there is no longitudinal difference in the drop off within the foveal region, in fact, outside the fovea, the drop off is somewhat slower in the nasal direction and the temporal direction than it is in the superior or oblique direction. The drop off in the nasal direction is slightly slower than in the temporal direction. The fact that slightly higher resolution is preserved in the nasal quadrant is because that is where the stereo overlap between the two eyes is.

This same slightly perturbed longitudinally symmetry is also present in the distribution of the size of cones, and the spacing between cones.

The Retinal Image is Magnified

The purpose of this sub-section is define the RetinalCoordinates conversion to and from VisualCoordinates.

Because of the optics of the eye, retinal eccentricity is not the same as visual eccentricity. Optical effects cause the visual image to be magnified on the surface of the retina. This means that any given visual eccentricity maps to a greater retinal eccentricity. The amount of magnification is not a constant, and itself varies with visual eccentricity. There is no closed form equation for the exact relationship, instead the magnification has to be found by explicit ray tracing of an optical model of the eye. And because there is no one "standard" wide angle optical model of the human eye, there is no standard conversion table; different authors end up using different magnifications. Fortunately, because of the symmetries of the eye, retinal longitude is the same as visual longitude.

In this document to have a consistent conversion from visual eccentricity to the corresponding retinal eccentricity (and the reverse), we will use the result of ray tracing the particular eye model of [Deering, M. 2005. A Photon Accurate Model of the Human Eye. ACM Transactions on Graphics, 24, 3, 649-658]. In table 2 below the conversion factor is given for every one degree of visual eccentricity that the corresponding retinal eccentricity is, followed by the current magnification factor.

TABLE 2

Table of retinal eccentricities corresponding to visual eccentricities.

| Visual Eccentricity | Retinal Eccentricity | Retinal/Visual |
| --- | --- | --- |
| 0° | 0.000° | 1.380 |
| 1° | 1.380° | 1.380 |
| 2° | 2.759° | 1.379 |
| 3° | 4.138° | 1.379 |
| 4° | 5.517° | 1.379 |
| 5° | 6.895° | 1.379 |
| 6° | 8.273° | 1.379 |
| 7° | 9.650° | 1.379 |
| 8° | 11.026° | 1.378 |
| 9° | 12.402° | 1.378 |
| 10° | 13.776° | 1.378 |
| 11° | 15.149° | 1.377 |
| 12° | 16.521° | 1.377 |
| 13° | 17.892° | 1.376 |
| 14° | 19.261° | 1.376 |
| 15° | 20.628° | 1.375 |
| 16° | 21.994° | 1.375 |
| 17° | 23.358° | 1.374 |
| 18° | 24.720° | 1.373 |
| 19° | 26.079° | 1.373 |
| 20° | 27.437° | 1.372 |
| 21° | 28.792° | 1.371 |
| 22° | 30.145° | 1.370 |
| 23° | 31.495° | 1.369 |
| 24° | 32.843° | 1.368 |
| 25° | 34.187° | 1.367 |
| 26° | 35.529° | 1.367 |
| 27° | 36.868° | 1.365 |
| 28° | 38.203° | 1.364 |
| 29° | 39.535° | 1.363 |
| 30° | 40.863° | 1.362 |
| 31° | 42.188° | 1.361 |
| 32° | 43.509° | 1.360 |
| 33° | 44.826° | 1.358 |
| 34° | 46.140° | 1.357 |
| 35° | 47.448° | 1.356 |
| 36° | 48.753° | 1.354 |
| 37° | 50.053° | 1.353 |
| 38° | 51.348° | 1.351 |
| 39° | 52.639° | 1.350 |
| 40° | 53.924° | 1.348 |
| 41° | 55.205° | 1.346 |
| 42° | 56.480° | 1.345 |
| 43° | 57.749° | 1.343 |
| 44° | 59.013° | 1.341 |

TABLE 2-continued

Table of retinal eccentricities corresponding to visual eccentricities.

| Visual Eccentricity | Retinal Eccentricity | Retinal/Visual |
|---|---|---|
| 45° | 60.271° | 1.339 |
| 46° | 61.523° | 1.337 |
| 47° | 62.769° | 1.336 |
| 48° | 64.009° | 1.334 |
| 49° | 65.242° | 1.331 |
| 50° | 66.468° | 1.329 |
| 51° | 67.687° | 1.327 |
| 52° | 68.899° | 1.325 |
| 53° | 70.103° | 1.323 |
| 54° | 71.300° | 1.320 |
| 55° | 72.489° | 1.318 |
| 56° | 73.670° | 1.316 |
| 57° | 74.843° | 1.313 |
| 58° | 76.007° | 1.310 |
| 59° | 77.162° | 1.308 |
| 60° | 78.308° | 1.305 |
| 61° | 79.445° | 1.302 |
| 62° | 80.572° | 1.300 |
| 63° | 81.689° | 1.297 |
| 64° | 82.796° | 1.294 |
| 65° | 83.892° | 1.291 |
| 66° | 84.977° | 1.288 |
| 67° | 86.051° | 1.284 |
| 68° | 87.113° | 1.281 |
| 69° | 88.163° | 1.278 |
| 70° | 89.200° | 1.274 |
| 71° | 90.225° | 1.271 |
| 72° | 91.236° | 1.267 |
| 73° | 92.233° | 1.263 |
| 74° | 93.216° | 1.260 |
| 75° | 94.185° | 1.256 |
| 76° | 95.137° | 1.252 |
| 77° | 96.074° | 1.248 |
| 78° | 96.994° | 1.244 |
| 79° | 97.897° | 1.239 |
| 80° | 98.782° | 1.235 |
| 81° | 99.648° | 1.230 |
| 82° | 100.495° | 1.226 |
| 83° | 101.322° | 1.221 |
| 84° | 102.127° | 1.216 |
| 85° | 102.910° | 1.211 |
| 86° | 103.670° | 1.205 |
| 87° | 104.405° | 1.200 |
| 88° | 105.115° | 1.194 |
| 89° | 105.799° | 1.189 |
| 90° | 106.454° | 1.183 |
| 91° | 107.080° | 1.177 |
| 92° | 107.674° | 1.170 |
| 93° | 108.236° | 1.164 |
| 94° | 108.762° | 1.157 |

The mapping functions based on this table to and from visual eccentricities and retinal eccentricities will be called VisEccToRetEcc[ ] and RetEccToVisEcc[ ]. They can be assumed to be piecewise linear interpolation between entries of the table above.

This retinal magnification has some important implications.

Generally it means that you can't convert from retinal eccentricities to visual eccentricities without using the mapping function. But you can convert visual longitude to retinal longitude, because they are the same:

RetinalLongitude=VisualLongitude (145)

which means:

VisualCoordinatesToRetinalCoordinates·Φ[ϕ,θ]=zr·Φ[ϕ,θ]=ϕ (146)

RetinalCoordinatesToVisualCoordinates·ϕ[Φ,Θ]=rz·ϕ[Φ,Θ]=Φ (147)

where we have used upper case angles for the VisualCoordinates to avoid confusion.

When converting purely longitudinal angles, the retinal angle and visual angle are the same.

Assuming the retinal radius is the default 12 mm, we can convert the retinal distance between any two points on the surface of the retina (as measured along the great circle connecting the two points) into a retinal angle:

$$RetinalAngle = \frac{RetinalDistance}{12 \text{ mm}} \quad (148)$$

The retinal angle is in units of radians. But it is handy to know how many degrees in retinal and visual arc in longitude are equivalent to 1 mm:

$$RetinalAngle[1 \text{ mm}] = \frac{(180°/\pi) \cdot \text{mm}}{12 \text{ mm}} \approx 4/77° \quad (149)$$

It is also handy to know how many millimeters on the surface of the retina are equivalent to one degree of retinal arc:

$$RetinalDistance[1° of retinal arc] = 12 \text{ mm} \cdot 1° \cdot \frac{\pi}{180°} \approx 0.209 \text{ mm} \quad (150)$$

When the retinal angle and the retinal distance are only in the longitudinal direction, these results also apply to visual longitude:

$$VisualLongitudinalAngle = \frac{RetinalLongitudinalDistance}{12 \text{ mm}} \quad (151)$$

$$VisualLongitudinalAngle[1 \text{ mm}] = \frac{(180°/\pi) \cdot \text{mm}}{12 \text{ mm}} \approx 4.77° \quad (152)$$

$$RetinalDistance[1° of visual longitudinal arc] = \quad (153)$$
$$12 \text{ mm} \cdot 1° \cdot \frac{\pi}{180°} \approx 0.209 \text{ mm}$$

These also would be the conversions for visual eccentricity, if it were not for the optical distortion.

In the eccentricity direction, we have to use the table:

RetinalEccentricity=VisEccToRetEcc[VisualEccentricity] (154)

VisualEccentricity=RetEccToVisEcc[RetinalEccentricity] (155)

which means:

$$\begin{aligned}VisualCoordinatesTo\\RetinalCoordinates.\Theta[\phi, \theta]\end{aligned} = zr.\Theta[\phi, \theta] \quad (156)$$
$$= VisEccToRetEcc[\theta]$$

$$\begin{aligned}RetinalCoordinatesTo\\VisualCoordinates.\theta[\Phi, \Theta]\end{aligned} = rz.\theta[\Phi, \Theta] \quad (157)$$
$$= RetEccToVisEcc[\Theta]$$

where we have used upper case angles for the RetinalCoordinates to avoid confusion.

For angles less than 30°, VisEccToRetEcc[θ]≈1.38·θ:

$$zr\text{-}\Theta[\phi,\theta] = VisEccToRetEcc[\theta] \approx 1.38 \cdot \theta 0 \leq \theta < 30° \quad (158)$$

and thus also:

$$rz.\theta[\Phi, \Theta] = RetEccToVisEcc[\Theta] \approx \frac{\Theta}{1.38} \quad 0 \leq \Theta < 30° \cdot 1.38 \quad (159)$$

Now we have:

$$RetinalDistance[1°ofvisualeccentricity] = 1.38 \cdot 12 \text{ mm} \cdot 1° \cdot \frac{\pi}{180°} \quad (160)$$
$$\approx 0.289 \text{ mm}$$

So we see the effect of the squashing in the visual eccentricity direction. For visual eccentricities less than 30°: 1° of visual longitudinal corresponds to 0.209 mm on the surface of the retina, while 1° of visual eccentricity corresponds to 0.289 mm on the surface of the retina. And all this is assuming a 12 mm retinal radius. It can be seen why various authors, assuming different retinal radii, and perhaps trying to use a single "average" conversion constant for converting from visual angles to retinal angles, have used 0.200, 0.250, 0.291, and 0.300 mm all for supposedly the same conversion factor. (And different wide field schematic eyes will ray trace out slightly different conversion tables.)

Generally, all this means that you can't convert a visual angle to a retinal angle, unless you know the visual eccentricity of the location where the visual angle is measured, and in what direction the visual angle is, and that the visual angle is relatively small in extent.

What the retinal magnification means for a square region on the retina, such as a bounding box around a circularly symmetric cone, is that it will become squashed in visual space in the visual eccentricity direction, e.g. a rectangle that is (for low visual eccentricities) about 0.72 times less tall than wide. This mean, in principle, that there could be 1.38 times more resolution in the visual eccentricity direction than in the visual longitudinal direction. We will consider this point in more detail later.

It also means that if one has a function of retinal eccentricity, as are some we are about to develop, re-parameterizing the function to be based on visual eccentricity isn't simple.

Summary: Equations (146) and (156) have defined the conversion VisualCoordinatesToRetinalCoordinates, and equations (147) and (157) have defined the inverse of that conversion: RetinalCoordinatesToVisualCoordinates. An approximate linear mapping reasonable for visual eccentricities less than 30° was defined for the eccentricity components of these conversions in equations (158) and (159).

From these, mapping to and from various other spaces of interest can be constructed by compositing the appropriate existing mappings.

Cones are not Always "Flat-On" to the Local Surface of the Retina

This subsection does not modify the mapping between the RetinalSurface and VisualCoordinates, but because the results show that the aspect ratio of cones on the surface of the retina is not unity, it will affect the mappings of cone cells and midget bipolar cells to the RetinalSurface, and thus also to VisualCoordinates.

To gather the maximum amount of light, cones actively point (e.g., biological motors actively steer them over the course of a day) in the direction of the center of the exit pupil of the eye as it appears from their individual location on the surface of the retina. At any appreciable retinal eccentricity, this will be a somewhat different direction than the local normal to the surface of the retina is at the location of the cones. Because of this, at higher eccentricities the cones are slightly flattened relative to the local surface of the retina. This has the effect of slightly squashing the visual height of cones, but this only partially counters the effect of the retinal magnification, and only at relatively large eccentricities. This doesn't change general conversions of visual eccentricity to retinal eccentricity, or vice versa, but it does change the properties of the assumed hexagonal pitch of cone centers. The amount of this squashing is given by the cosine of the angle between the ray from a given cone to the center of the retinal sphere and the ray from the cone to the center of the exit pupil of the eye. There exist approximate closed form equations describing the amount of local tilt parameterized by (visual or retinal) eccentricity, but ray traced based tables give better estimates.

The Retinal Size of Cones is Governed by Several Functions

The purpose of this sub-section is to define a function for a circle equitant diameter of retinal cone cells as a function of visual eccentricity. This function will be used in the next sub-section to define a portion of the RetinalCones manifold mappings to and from VisualCoordinates.

As previously described, the retinal size of cones is (almost) only a function of eccentricity. The specific "retinal size" of cones we will compute is their equivalent circle's diameter in millimeters on the retinal surface. (The equations we have developed can convert this measure of "size" to measures of the underlying hexagonal tiling: the short diagonal and the short pitch.) The function for ConeDiam[θ°] can be broken up into three different functions over three different ranges of visual eccentricity. The argument θ° is visual eccentricity, in units of degrees. (The full name of the function really is RetinalConeDiameterinMM[ ], but we will keep it short.)

Inside the foveal maximum cone density zone, e.g. within two minutes of visual eccentricity, the size of cones is determined by the maximum cone density of the particular individual, which can range from 125,000 cones/mm² to 350,000 cones/mm². Since no rods appear between cones here, the cone size and the cone spacing is the same, and can be computed from the rule relating the density of hexagons to their equivalent circle diameter (in units of mm on the surface of the retina):

$$ConeDiam[\theta°] = \sqrt{\frac{4}{\pi \cdot FovealMaximumConeDensity}} \quad 0° \leq \theta° < 1°/30 \quad (161)$$

Between two minutes and 1° of visual eccentricity, the density of cones drops from that of the individual foveal maximum cone density to about 50,000 cones/mm², regardless of individual variation.

$$ConeDiam[\theta°] = \sqrt{\frac{4}{\pi \cdot ConeDensity[\theta°]}} \quad 1°/30 \leq \theta° < 1° \quad (162)$$

Where:

$$CorneDensity[\theta°] = \qquad (163)$$
$$FovealMaximumConeDensity \cdot \left(1 - \frac{\theta° - 1°/30}{1° - 1°/30}\right) +$$
$$50{,}000 \cdot \left(\frac{\theta° - 1°/30}{1° - 1°/30}\right)$$

This purely linear fall-off is an approximation, in part because while no rods appear between cones for visual eccentricities below 0.7°, this equation applies both to this limited range and beyond out to 1°.

From 1° of visual eccentricity all the way out to the ora serrata, the diameter of cones was modeled by [Tyler, C. 1997. Analysis of Human Receptor Density, in Basic and Clinical Applications of Vision Science, Ed. V. Kluwer Academic Publishers, 63-71] as:

$$ConeDiam[\theta°] = (0.005 \text{ mm}/°) \cdot (0.2° + \theta°)^{1/3} \quad 1° \le \theta° < \text{ora serrata} \qquad (164)$$

Note again that while the results of ConeDiam[θ° ] is defined in the retinal space, as distance in mm on the RetinalSurface, the parameter to the function is visual eccentricity, not retinal eccentricity, and is in units of degrees, not radians. This is the form in which we will eventually want this component of the mapping function in, so we won't show the re-parameterization as a function of retinal eccentricity.

The Spacing Between Cones is Governed by Two Functions

The purpose of this sub-section is define the directional magnitude derivative of the RetinalCones manifold mapping to ViewSphereVS.

As previously described, the spacing between cones is (almost) only a function of eccentricity.

Inside the sub portion of the fovea with less than 0.7° visual eccentricity, the foveal rod-free zone, there are no rods, only cones, and therefore the spacing between cones is determined by the size of the cones. Outside the foveal rod-free zone, rods start appearing between the individual cones, and the spacing between individual cones grows by a different function, which is greater than that determined just by the size of the cones.

In both cases, the local spacing between cones is a function of the local density of cones. Here we assume that the cones keep a relative hexagonal tiling of their centers, even though the cones themselves don't directly abut once enough rods start interspersing between them. This means that we can use our previously developed equation for converting from density and the short pitch of the underlying hexagonal tiling. Because for now we are defining resolution by the Nyquist limit, the uppermost resolution of a hexagonal tiling is determined by the ShortPitch, although this resolution will only occur in the local direction of the ShortPitch within the local tiling. Restating the relationship between the density of hexagons and the length of the ShortPitch:

$$RetinalConeShortPitchInMM = \qquad (165)$$
$$\sqrt{\frac{\sqrt{3}}{2} \cdot \frac{1}{RetinalConeDensityPerMM2}}$$

This equation can be used to determine the ShortPitch of cone spacing given a cone density function of visual eccentricity in units of degrees:

$$RetinalConeShortPitchInMM[\theta°] = \qquad (166)$$
$$\sqrt{\frac{\sqrt{3}}{2} \cdot \frac{1}{RetinalConeDensityPerMM2[\theta°]}}$$

Where the density is measured in units of cones/mm², so the ShortPitch will be in units of mm of length, thus the long names.

Now we need to define the cone density function. Between 0° and 1° of visual eccentricity, the density of cones will be assumed to be the same as was assumed when determining the size of cones above, so we have:

$$RetinalConeDensityPerMM2[\theta°] = FovealMaximumConeDensity \qquad (167)$$
$$0° \le \theta° < 1°/30$$

$$RetinalConeDensityPerMM2[\theta°] = \qquad (168)$$
$$FovealMaximumConeDensity \cdot \left(1 - \frac{\theta° - 1°/30}{1° - 1°/30}\right) +$$
$$50{,}000 \cdot \left(\frac{\theta° - 1°/30}{1° - 1°/30}\right)$$
$$1°/30 \le \theta° < 1°$$

Between 1° and 20° of visual eccentricity, we will use the [Tylor 1997] model of cone density:

$$RetinalConeDensityPerMM2[\theta°] = 50{,}000 \cdot \theta^{°-2/3} \quad 1° \le \theta° < 20° \qquad (169)$$

At 20° of visual eccentricity, the density of cones by the equation above will have fallen to ~6,800 cones/mm². From 20° of visual eccentricity, out to 60° of visual eccentricity, we will follow Tyler's suggestion that cone density fall off linearly from the previous to ~6,800 cones/mm² to 4,000 cones/mm²:

$$RetinalConeDensityPerMM2[\theta°] = \qquad (170)$$
$$50{,}000 \cdot 20^{°-2/3} \cdot \frac{(60° - \theta°)}{40°} + 4{,}000 \cdot \frac{(\theta° - 20°)}{40°}$$
$$20° \le \theta° < 60°$$

At 60° of visual eccentricity, the density of cones by the equation above will have fallen to 4,000 cones/mm². From 60° of visual eccentricity, out to the edge of the ora serrata, we will keep the cone density constant at 4,000 cones/mm²:

$$RetinalConeDensityPerMM2[\theta°] = 4{,}000 \quad 60° \le \theta° < \text{ora serrata} \qquad (171)$$

Equations (167), (168), (169), (170), and (171) allow equation (166) to define the ConeShortPitch in units of mm for the entire range of possible visual eccentricities. We would prefer to have the ConeShortPitch in units of visual angle, so first we need to convert the output from units of mm on the surface of the retina to a retinal angle in units of radians by dividing by the (default) retinal radius:

$$ConeShortPitchInRetinalAngleInRadians[\theta°] = \qquad (172)$$
$$\frac{RetinalConeShortPitchInMM[\theta°]}{12 \text{ mm}}$$

Now we need to convert from the retinal angle to the visual angle. But this conversion depends on the direction of the short pitch, as well as the visual eccentricity.

In the purely longitudinal direction, the retinal angle and the visual angle are the same, so we get:

$$ConeShortPitchInVisualLongitudinalAngleInRadians[\theta°] = \frac{RetinalConeShortPitchInMM[\theta°]}{12\ mm} \quad (173)$$

In the purely eccentricity direction, the visual angle will be minified by:

$$ConeShortPitchInVisualEccentricityAngleInRadians[\theta°] = \frac{\theta°}{VisEccRetEcc[\theta°]} \cdot \frac{RetinalConeShortPitchInMM[\theta°]}{12\ mm} \quad (174)$$

How do we take a function that gives us the short pitch of a cone at any eccentricity and use it to construct the RetinalCones manifold? As described earlier, we start with the directional magnitude derivative. Since we are using our mappings to define resolution, and because the highest resolution that a hexagonal array of cones can perceive described by their short pitch, we can take the short pitch function in each angular direction and define them to be the directional magnitude derivatives in those directions:

$$\nabla_\phi RetinalCones \cdot sv \cdot \phi[\phi, \theta] = \quad (175)$$
$$ConeShortPitchInVisualLongitudinalAngleInRadians[\theta°] = \frac{RetinalConeShortPitchInMM[\theta°]}{12\ mm}$$

$$\nabla_\theta RetinalCones \cdot sv \cdot \phi[\phi, \theta] = \quad (176)$$
$$ConeShortPitchInVisualEccentricityAngleInRadians[\theta°] = \frac{\theta°}{VisEccToRetEcc[\theta°]} \cdot \frac{RetinalConeShortPitchInMM[\theta°]}{12\ mm}$$

Note that the mapping that we are taking the directional magnitude derivative of is sv, e.g. RetinalCones·surfaceToViewSphereVS. That is because a visual angle is an angle on the ViewSphere, which even if taken in the longitudinal direction should still be based on the distance between two points on the surface of the ViewSphere as measured along the great circle that connect them, not any longitudinal angle in VisualCoordinates.

For our purposes here, these directional magnitude derivatives are the results we will want for use in the next section. So we don't need to follow through with the integration of the piecewise defined functions. It is enough to observe that the results of such integration will be linear functions of $\theta°$, linear functions of $\theta°^2$, and a function of $\theta°^{1/3}$. This all shows what we already know: while the density of cones goes down with increasing visual eccentricity, e.g. the spacing between the cones gets larger, the actual number of cones straddling any particular visual eccentricity on the ViewSphere goes up.

We will also note that a full specification of the Cones mapping would require the creation of an EndCap mapping for the foveal maximum cone density zone.

The Number of Cones that Contribute to the Center Input of Retinal Midget Ganglion Cells Varies with Eccentricity The purpose of this sub-section is to define the directional magnitude derivative of the Retinal Midget manifold mapping to ViewSphereVS. Once we have this, we can then compare how close to a locally uniform resolution mapping the RetinalMidget mapping is. But first we will obtain an equation for how many cone cells there are, on average, feeding into the center field of midget ganglion cells, as a function of visual eccentricity.

Inside a visual eccentricity of 6°, each midget ganglion cell obtains its center input from precisely one cone, so the underlying tiling of the midget ganglion cells is the same as the tiling of the underlying cones (which we are still assuming to be hexagonal):

$$MidgetShortPitchVisualLongitudonalAngleInRadians[\theta°] = \quad (177)$$
$$ConeShortPitchVisualLongitudonalAngleInRadians[\theta°]$$
$$0° \le \theta° < 6°$$

$$MidgetShortPitchVisualEccentricityAngleInRadians[\theta°] = \quad (178)$$
$$ConeShortPitchVisualEccentricityAngleInRadians[\theta°]$$
$$0° \le \theta° < 6°$$

Beyond 6° of visual eccentricity, the center input to midget ganglion cells start to come from more than one cone cell, with the number of such cones increasing more and more with increasing eccentricity. [Dacey, Dennis M. "The Mosaic of Midget Ganglion Cells in the Human Retina, The Journal of Neuroscience, December 1993, 13(12): 5334-5355] studied the diameters of midget ganglion cells and fit an equation to his anatomical measurements (from 0.5° to 75° of visual eccentricity). The equation gives the diameter of midget ganglion cells expressed as a visual angle in units of minutes of arc as a function of visual eccentricity measured in units of degrees:

$$VisAngDiameterInArcMin[\theta°] = \quad (179)$$
$$2.1 + 0.058 \cdot \theta° - 0.022 \cdot \theta°^2 - 0.00022 \cdot \theta°^3$$
$$0.5° \le \theta° < 75°$$

Dacey's empirical data about the location of midget ganglion cells on the retinal surface was measured in units of retinal distance from the center of the fovea in millimeters (rdist). To convert these distances to visual eccentricities, he used a simplified formula of:

$$\theta° = 0.1 + 3.4 \cdot rdist° + 0.035 \cdot rdist°^2 \quad (180)$$

where $\theta°$ is visual eccentricity in units of degrees.

Dacey measured the diameter of a midget ganglion cell by empirically drawing a polygon around its dendritic field, then calculating the polygon's area, and calculating the diameter of the circle that would have the same area (just as we have done in the hexagon case). This diameter is a (short) retinal distance measured at a particular retinal eccentricity. How he converted this retinal distance to a visual angle is not explicitly stated. From his plots it looks like he obtained the local conversion factor from retinal angle to visual angle using the derivative of equation (180). This is the correct conversion for converting a retinal distance in the eccentricity direction to a visual angle in the eccentricity direction, and represents the highest possible resolution. However, it is not the correct conversion in the longitudinal direction, where the conversion factor is a constant 0.209 mm/°. So we will use his diameter only as a measure in the eccentricity direction.

First we need to convert the output from visual angle in units of minutes of arc to visual angle in units of radians:

$$VisAngDiameterInRadians[\theta°] = \qquad (181)$$
$$\frac{\pi}{60 \cdot 180} \cdot (2.1 + 0.058 \cdot \theta° + 0.022 \cdot \theta°^2 - 0.00022 \cdot \theta°^3)$$

We can convert this to the length of the ShortPitch of the underlying hexagonal tilling via the relationship:

$$MidgetShortPitch = \frac{\sqrt{\pi}}{2} \cdot \sqrt{\frac{\sqrt{3}}{2}} \cdot diameter \approx 0.825 \cdot diameter \qquad (182)$$

Therefore (and since this equation is only good in the eccentricity direction):

$$MidgetShortPitchVisualEccentricityAngleInRadians[\theta°] = \qquad (183)$$
$$\frac{\sqrt{\pi}}{2} \cdot \sqrt{\frac{\sqrt{3}}{2}} \cdot \frac{\pi}{60 \cdot 180}$$
$$(2.1 + 0.058 \cdot \theta° + 0.022 \cdot \theta°^2 - 0.00022 \cdot \theta°^3)$$

Figure 89:
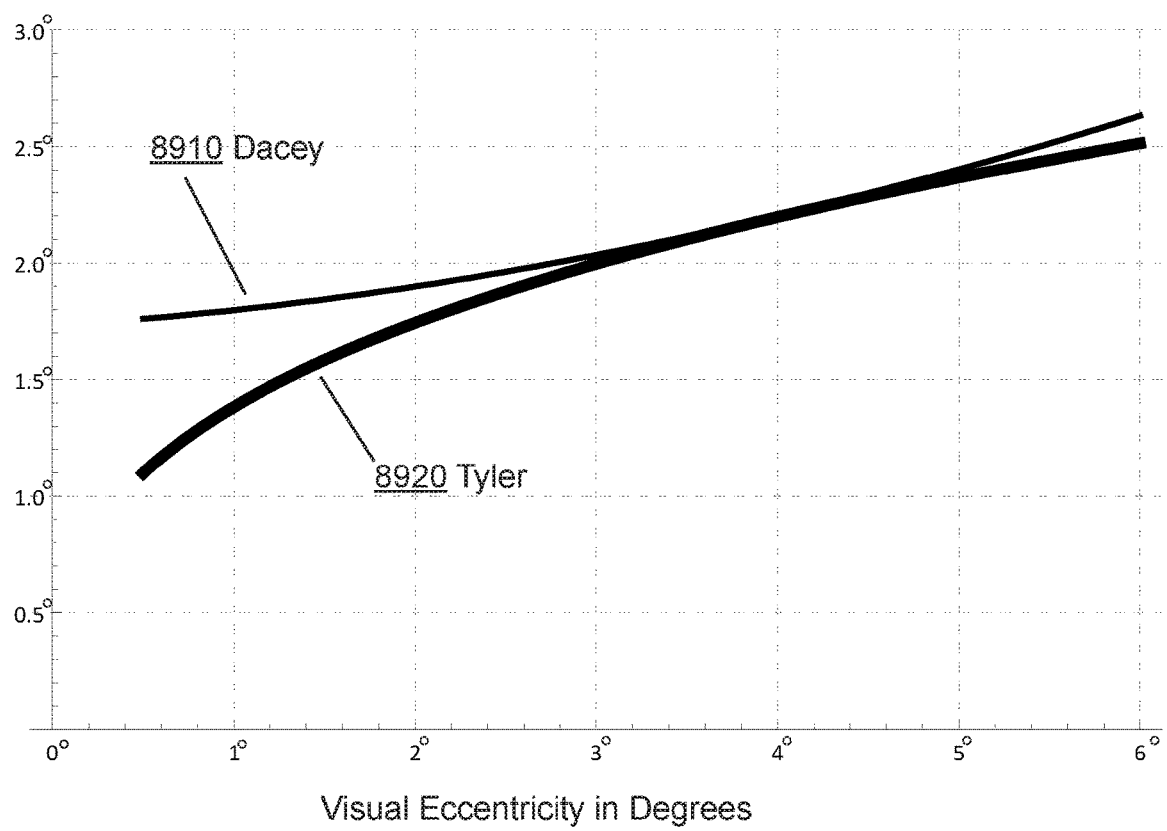
FIG. 89 shows the ratio of cone short pitch models of Dacey and Taylor, from 0.5° to 6°.

Below a visual eccentricity of 6°, our modified Dacey's equation also is (should be) an equation for the short pitch of the tiling of cones on the retina. Thus Dacey's fitting of a curve to empirical data about midget ganglion cell density in the 0.5° to 6° range of visual eccentricity should be comparable to Tyler's fitting of Oesterberg's empirical data about the cone cell density in the same range. Simple inspection of their equations shows that they can't match exactly, Tyler's is curve to the ⅓$^{rd}$ power of the visual eccentricity; Dacey's is a cubic polynomial in the visual eccentricity. FIG. 89 shows a plot of the predicted cone short pitch measured in minutes of arc in the visual eccentricity direction against degrees of visual eccentricity for Tyler, the thick line, element 8920, and for Dacey, the thin line, element 8910. Because the two equations predict different absolute cone short pitches, in this plot they have been normalized to meet at 4°, where the two curves are tangent. Some of this difference is due to converting between longitudinal direction and eccentricity direction cone diameters. Both curves predict similar straight lines, though Tyler's seems to be predicting some of the ramp up to foveal densities better.

With the above caveat, we will now proceed to use the square of the ratio of Dacey's equation to that of Tyler's in the range of 4° to 48° to see what they predict about how many cones, on average, feed into a single midget ganglion cell center input at a given visual eccentricity θ° (in units of degrees). We need take the square of the ratio of midget ganglion cell ShortPitch to ConeShortPitch. Because the two models should not predict more cones than midget ganglion cells at 6°, this time we normalize the results of each function at that angle:

$$ConesPerMidgetCenter[\theta°] = \qquad (184)$$
$$\left( \frac{\frac{MidgetShortPitchVisualEccentricityAngleInRadians[\theta°]}{ConeShortPitchVisualEccentricityAngleInRadians[\theta°]} \cdot}{\frac{ConeShortPitchVisualEccentricityAngleInRadians[6°]}{MidgetShortPitchVisualEccentricityAngleInRadians[6°]}} \right)^2$$

In Table 3 below, we show at which visual eccentricities in units of degrees does the number of cone cells per single midget ganglion cell receptor field center achieve successive integer values, given the two models.

TABLE 3

Visual eccentricity vs. number of cone inputs to midget ganglion center field.

| Visual Eccentricity | Number of Cones |
| --- | --- |
| 6.0° | 1 |
| 12.3° | 2 |
| 15.8° | 3 |
| 18.5° | 4 |
| 20.8° | 5 |
| 22.9° | 6 |
| 24.7° | 7 |
| 26.4° | 8 |
| 28.1° | 9 |
| 29.6° | 10 |
| 31.1° | 11 |
| 32.6° | 12 |
| 34.0° | 13 |
| 35.4° | 14 |
| 36.8° | 15 |
| 38.2° | 16 |
| 39.6° | 17 |
| 41.1° | 18 |
| 42.5° | 19 |
| 44.0° | 20 |
| 45.6° | 21 |
| 47.3° | 22 |

Figure 90:
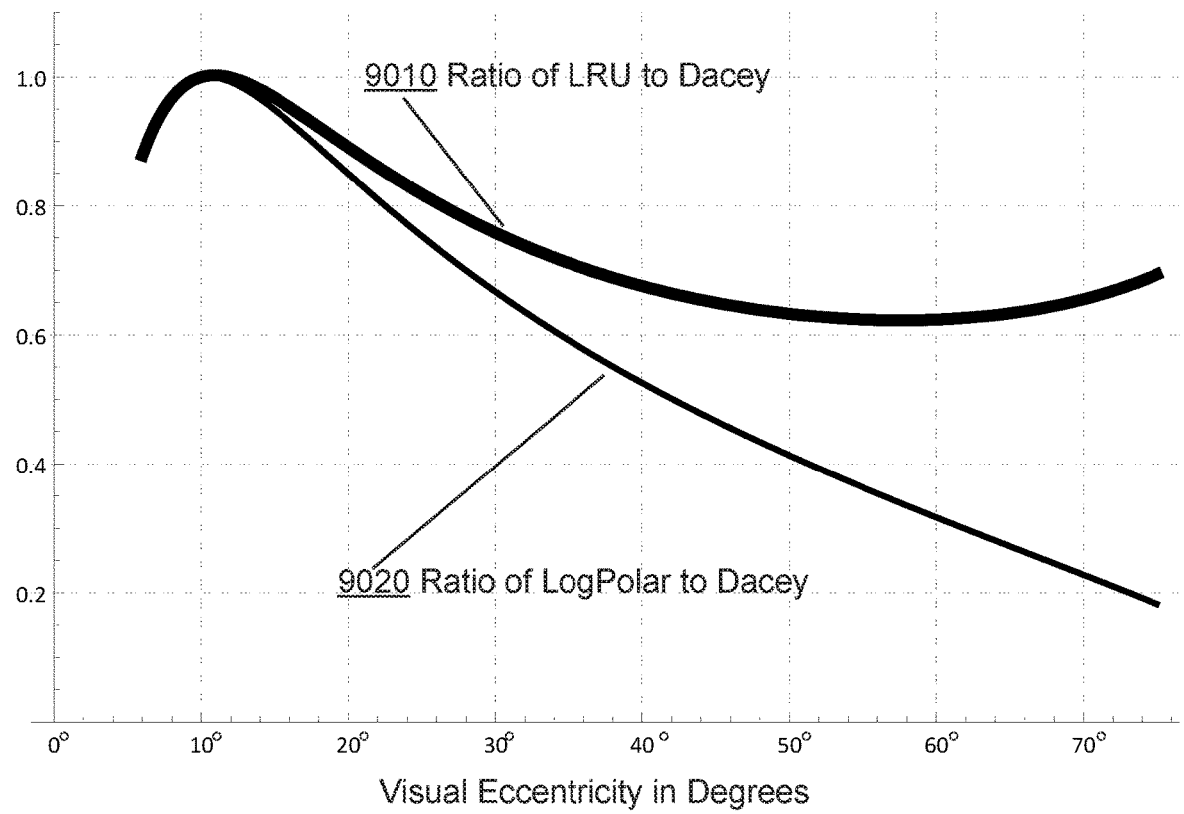
FIG. 90 shows the ratio of the short pitch of the locally uniform resolution mapping to Dacey's model and the ratio of short pitch of the LogPolar mapping to Dacey's model.

We can compare the predictions of the short pitch by the locally uniform resolution mapping against that of Dacey's, as well as the LogPolar mapping. FIG. 90, thick line, element 9010, shows the ratio of the predicted short pitch of locally uniform resolution mapping over Dacey's. FIG. 90, thin line, element 9020, shows the ratio of the predicted short pitch of the LogPolar mapping over Dacey's. Both are shown over the visual eccentricities of 6° to 75°. Both mappings have trouble in the 6° to 10° region. The locally uniform resolution mapping stays within 62% of Dacey over the wide range of 10° to 75°, but the cos [ ] term in the LogPolar mapping to steadily drop to below 20% of Dacey. This again shows that the LogPolar mapping doesn't match very well what seems to be happening in the human eye (and the visual cortex of the brain) at larger angles. Again, in this plot, we are comparing predictions of short pitch length, which is the inverse of resolution. Thus the fact that both mappings fall to lower values than Dacey's empirical measurements means that both are predicting higher resolution than Dacey's data supports. Both mapping models were normalized to unity at the point of highest match to Dacey at 10°. So it is also possible that at least for the locally uniform resolution mapping, it might be predicting lower resolution than Dacey around 10°, and somewhat more consistent numbers at greater visual eccentricities. Another factor to consider is what portion of the visual field in visual longitude are the various models based on. Tyler considers all longitudes, but his model seems to be focused on the nasal quadrant. Dacey takes data from the four major longitudes separately, but his curve fit is to the data from all longitudes. The locally uniform resolution mapping is fit to the nasal quadrant.

Figure 91:
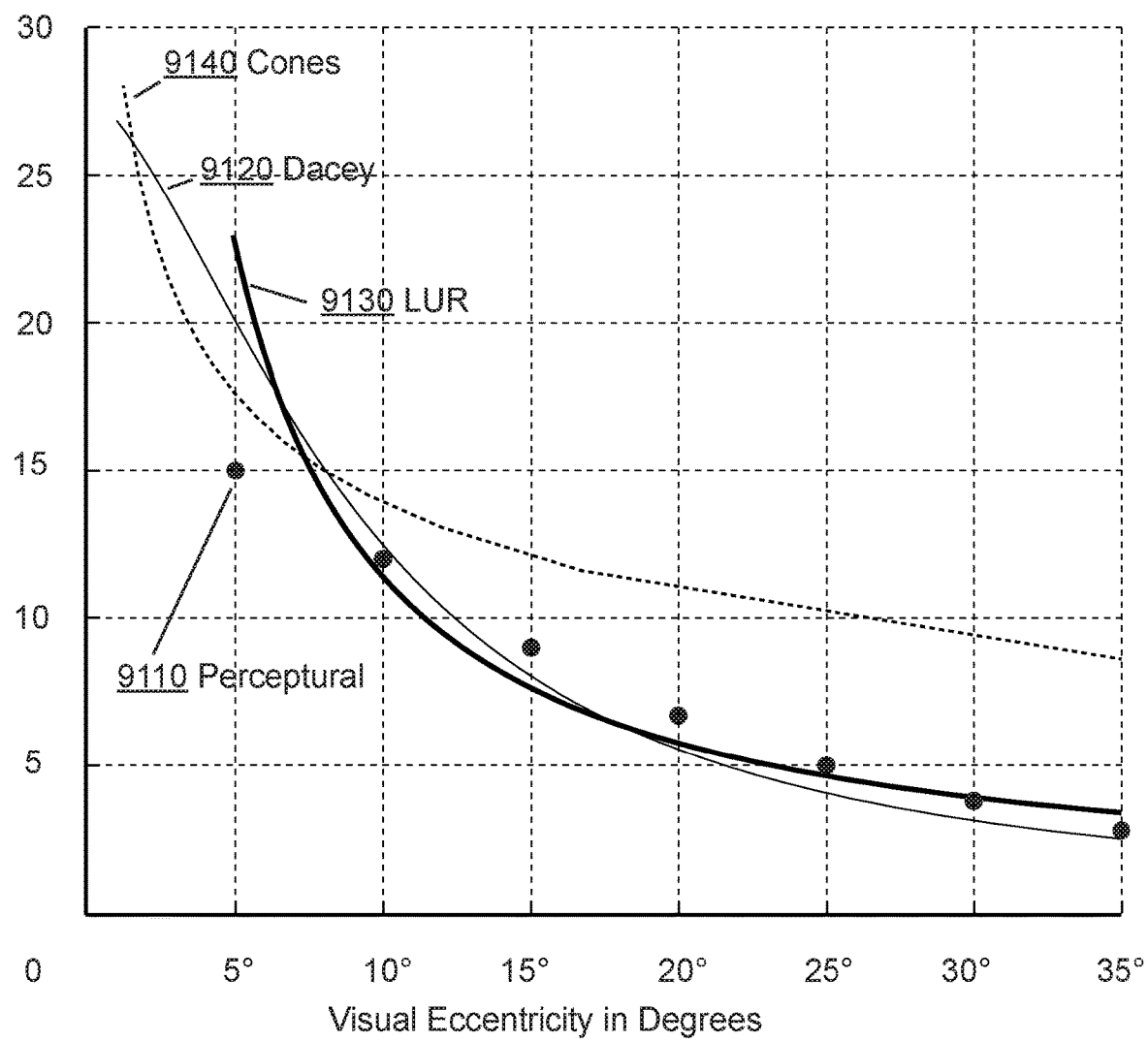
FIG. 91 shows resolution curves from human testing, of the locally uniform resolution mapping, of Dacey's model, and the resolution of cones from Tyler's model.

Now to put all of the data into the form of resolution curves, which will be the inverse of the short pitch prediction curves of the last paragraph. FIG. 91 shows resolution, in units of cycles per degree, on the vertical axis, verses visual eccentricity, in units of degrees, on the horizontal axis. The filled black circles, element 9110, are measurements of human visual resolution from [Anderson S J, Mullen K T, Hess R F (1991) Human peripheral spatial resolution for achromatic and chromatic stimuli: limits imposed by optical and retinal factors. J Physiol (Land) 442:47-64.]. The curved thick line, element 9130, is the resolution of the locally uniform resolution mapping with a SW of 720 equivalent square pixels of resolution. The curved thin line, element 9120, is the resolution of Dacey's midget ganglion cell model. For reference, we include the resolution predicted by the retinal cone mosaic as the curved dashed line, element 9140, based on the cones short pitch from Tyler's model.

In his paper Dacey showed that his model of midget ganglion cell visual angle in "close" approximation with experimental measurements of human perceptual resolution. This can be seen in FIG. 91 in how close his curve 9120 follows all but the 5° lowest visual eccentricity data point. The locally uniform resolution mapping 9130 is also a close fit, except at the same 5° data point. The curve for the cone predicted resolution 9140 overshoots the human experimental perception except at the 5° data point. This is as expected, as beyond 6°, human perceptual resolution is driven by the resolution of the midget ganglion cells, not the cone cells. To avoid over cluttering, the LogPolar mapping's resolution prediction was not included in this figure. For the range of visual eccentricities shown, e.g. below 35°, the LogPolar mapping overshoots the human curve only be a little. As was shown in FIG. 90, at higher visual eccentricities, the cos [ ] term causes the LogPolar mapping to much further overshoot.

This last figure shows the locally uniform resolution mapping in its best light. There was only one parameter to fit, and that was SW. This parameter really just sets the midget ganglion cell density at one point.

The fact that the models over-estimate resolution below 10° of visual eccentricity will be addressed in the next section.

Comments on Estimating Perceptual Resolution Based on Receptor Short Pitch

In the visual science literature it is common to find remarks about how our highest visual acuity at the center of the fovea occurs at the point where the three major factors limiting resolution all meet: the limits imposed by classical optical quality of the eye's optical system, the limits imposed by diffraction at the smallest pupil size, and the limits imposed by the retinal sampling mosaic (e.g., the hexagonally tiled cones). Sometimes a fourth matching limit is added: that of neural noise (though there are several different interpretations of this). All this is quite important, as the mapping implied by the resolution of the eye not only (is thought to) determines the density of the retinal midget ganglion cells, but also the physical organization and structure of most of the visual cortex (one third of the entire human brain). However, there is ample evidence that this triple match point does not actually occur, with the implication that human visual resolution is not (always) determined simply by the density of the retinal midget ganglion cells. This sub-section will describe why the two are somewhat decoupled, especially near the fovea.

In the fields of image processing and computer vision, a big change occurred many years ago when vacuum tube based video cameras (essentially the inverse of a CRT) started to be replaced by discrete digital pixel semiconductor based sensors. These early digital sensors had relatively large pixels with somewhat low fill-factors (gaps between the active area of one pixel to the next), and it was rapidly discovered that processing worked better of the image was slightly defocused. This was usually done optically, but could also be accomplished by an analog low pass filter on the analog video signal (which the early digital cameras still generated), or later, as a digital low pass filter on the digital pixel data. Even with today's much higher resolution digital pixel camera chips, this is still true. Why?

The Nyquist theorem about the maximum frequency component that can be extracted from a (one dimensional) signal comes with a substantial caveat: that signal component must repeat at the same frequency infinitely to the left and right of the sample point. In practice, infinity is not required, but a convolution window of 17 or more pixels is. Why? Consider a one dimensional sine wave whose period exactly matches the spacing of two samples (e.g., at the Nyquist limit). Assuming that the peak of the sine wave occurs centered over all the even sample intervals (a "sample interval" is a one dimensional pixel), and that the trough occurs centered over all the odd sample intervals. What is the digitally sampled result? There sequential digital samples will contain high valued pixels followed by low valued pixels; the signal has successfully been captured (thought at a slight reduction in contrast). However, consider what happens if the sine wave is shifted in phase by half a sample interval. Now all sample intervals will see half of a peak and half of a trough, or vice versa, but all samples will end up sampling the same value (the average of the sine wave). The resultant digital sample stream will be constant, absolutely no evidence of the sine wave will be present in the digital domain. At phase offsets other than exactly half a sample interval, evidence of the underlying sine wave will return, but at reduced to greatly reduced contrast. Practically, a sine wave just a little lower than the Nyquist limit, sampled over 17 sample intervals, and re-constructed over the same range, will bring back most of the signal. But in visual space, one is lucky to get a quarter of a period of a frequency: a rounded step edge between a dark region and a light region. Less frequently, one may encounter half of a period of frequency, e.g., a line: a step up followed by a step down. Thus in practice, the Nyquist limit is too high of bar to set on what peak resolution can be expected to be reliably (e.g., not aliased) extracted from a given sample interval. This is why people defocused the lenses on their digital cameras, to pre-limit the maximum spatial frequency of the image impinging on the digital sensor to something below the Nyquist limit. How far below? At 30% to 50% below the Nyquist limit even step edges now no longer disappear, and the maximum reduction in their contrast is reasonable (e.g. less than 50% or so). A related reason to reduce the maximum spatial frequency present is that the Nyquist theory applies to one dimensional signals, there is not a simple 2D extension. The closest would be to look at sine wave patterns extended in space, presented at all possible angles relative to the underlying tiling of the sensing pixels, and choose which has the lowest resolution. Another way of saying this is that the use of the short pitch of a tiling as the sample interval was a "best case" result. At other orientations, the sample interval is lengthened to the long pitch (the short diagonal), and it can be argued that in the worst case the sample interval could be reduced to the long diagonal of tiling. Considering both factors: the requirement to see reasonable contrast of step edges at all phases, and the lengthening of the sample interval at most orientations, reducing the maximum expected spatial frequency that can be expected to be reliably extracted from a pixel tiling by even as much as 30% over the Nyquist rate implied by the short pitch of the tiling seems a bit optimistic.

There is ample evidence that the human eye does impose such limits by optical means in the foveal region. While aliasing effects have been detected in the periphery, they have never been detected in the fovea under natural viewing conditions. The proof that the retinal image has had the maximum spatial frequency ever present low-passed by the optics of the eye come from experiments that effectively by-pass the eye's natural optical limits. When real-time deformable mirrors are used to correct for the optical imperfection of the human eye with an artificially dilated large pupil (to avoid the limits imposed by diffraction), aliasing has been observed in the fovea. This means that the low-pass filtering is not performed at the neural level of cone outputs (though some charge sharing does occur). Rather, the optics of the human eye appear to be intentionally kept at a slightly lower quality. (Birds, with magnified foveas, have considerably higher quality optical elements than humans do, even though both are formed out of highly modified skin cells.) The amount of low-pass filtering caused by the human eye's optics in the foveal region can be quantified by various experiments, and has been found to be in the 30%+ reduction range over the short pitch Nyquist limit.

What this means for models of the resolution of the human eye is that it should not be expected that human perception resolution in the foveal region should match what the Nyquist limit implied by the short-pitch of the underlying cone tiling would directly predict (and just in the pre-shortened retinal eccentricity direction). The underlying organization of the retinal midget ganglion cells and thus also the implied spatial organization of the visual cortex in the foveal region can still be correctly predicted by the cone tiling; it is only the perceptual resolution in the foveal region that will instead be predicted by a model of the optics of the eye in that region.

What about the resolution in the periphery? Outside the foveal region, the quality of the eye's optics drops relatively fast, but not as fast as the density of the receptor tiling implied by the midget ganglion cells drops. This implies two things: one, aliasing effects should occur in the periphery (they do), and two, the resolution in the periphery should be more directly tied to the Nyquist limit determined by the short pitch of the midget ganglion cells (it is).

What does all this mean for the locally uniform resolution mapping? Because of its local preservation of shape, it still is a good mapping for man-made (display and image processing) applications to use outside of any EndCap, and outside the large foveal region (~8°+ of visual eccentricity), it is still a good candidate for modeling what the human eye's midget ganglion cell mapping is. The "failure" of the locally uniform resolution mapping near the foveal region is thus a non-issue, as it is caused by other factors. Below 6° of visual eccentricity, the retinal density of midget ganglion cells is constrained to be the same as the underlying cone density, as in this region each midget ganglion cell connects to exactly one cone. Starting above 6° of visual eccentricity, midget ganglion cells can attach to multiple (statistically including an integer+fractional) numbers of cone cells, and the density of midget ganglion cells can follow whatever curve evolution wants, relatively independent of the cone density. It makes sense then that the mapping of midget ganglion cells density over all eccentricities is not a single simple function of eccentricity, but at least two, with the locally uniform resolution mapping a good candidate above 8°. (Why 8°, not 6° ? The two mapping functions have to meet at 6°, and the curve is modified in this region.)

Comments on the Biological Plausibility of the Locally Uniform Resolution Mapping The locally uniform resolution mapping may have optimal properties that would make it a good choice for use by biological systems for mapping the midget ganglion cells, but is there a simple way that such systems could "implement" it? It turns out that just setting a biological constraint that the number of midget ganglion cells at placed around all longitudes any retinal eccentricity be constant, and that the cell spacing in the eccentricity direction be the same as in the longitudinal direction, is enough to automatically form a locally uniform resolution mapping. There are also some evolutionary arguments that can be made, but won't be gone into here.

Comments on the Non-Longitudinally Symmetric Resolution of the Human Eye

The locally uniform resolution mapping as presented so far has always been a LinearlyLongitudinal mapping. This is the preferred structure for physical implementations of contact lens displays that must be rotationally symmetric, and is also appropriate for image processing and computer vision applications. It also is integral pixel structure preserving. But it is known that the human eye and human perceptual resolution is not a LinearlyLongitudinal mapping: we have higher resolution in the nasal direction. Full details on how the locally uniform resolution mapping can be extended to be not LinearlyLongitudinal, and can be fit to human perception data in all quadrants, will not be given here. Instead it will just be pointed out that human perceptual resolution (and the underlying density of midget ganglion cells) appears to be close to a locally uniform resolution mapping along at any fixed longitude. It is just that the parameter of the mapping (SW) slowly varies at different longitudes; it is higher in the nasal direction, less so in the temporal, and even less in the superior and oblique directions. So a sketch of how the LinearlyLongitudinal mapping could track this would be one in which pixel columns at different values of u (longitude) would map to smaller amounts of incremental longitudinal angle (outside the symmetric foveal EndCap mapping). This still (mostly) preserves the pixel structure, will allowing the resolution to no longer by constant at the same visual eccentricity at all visual longitudes.

Figure 9:
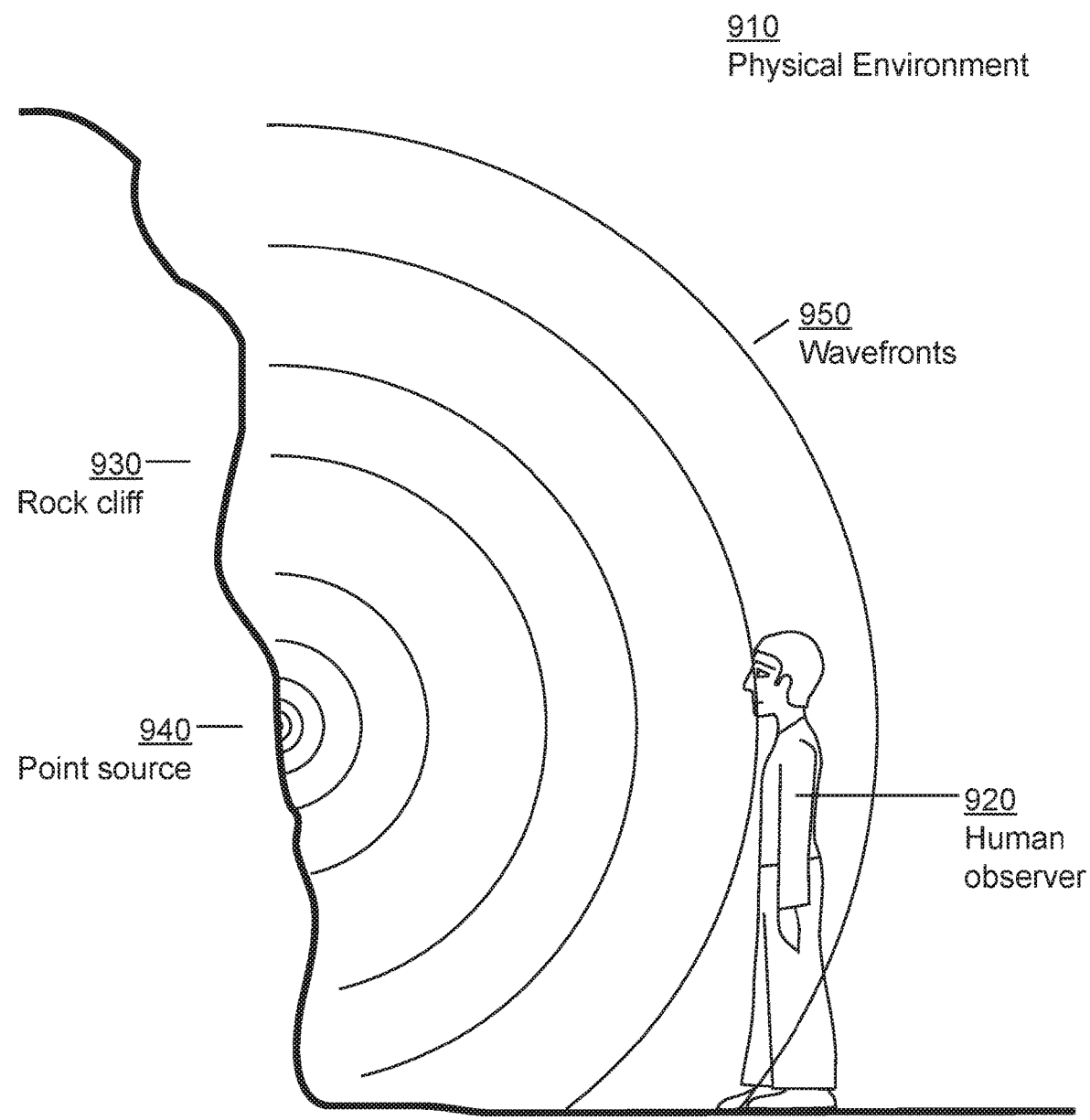
FIG. 9 shows a physical world rock cliff being observed by a human.
Figure 14:
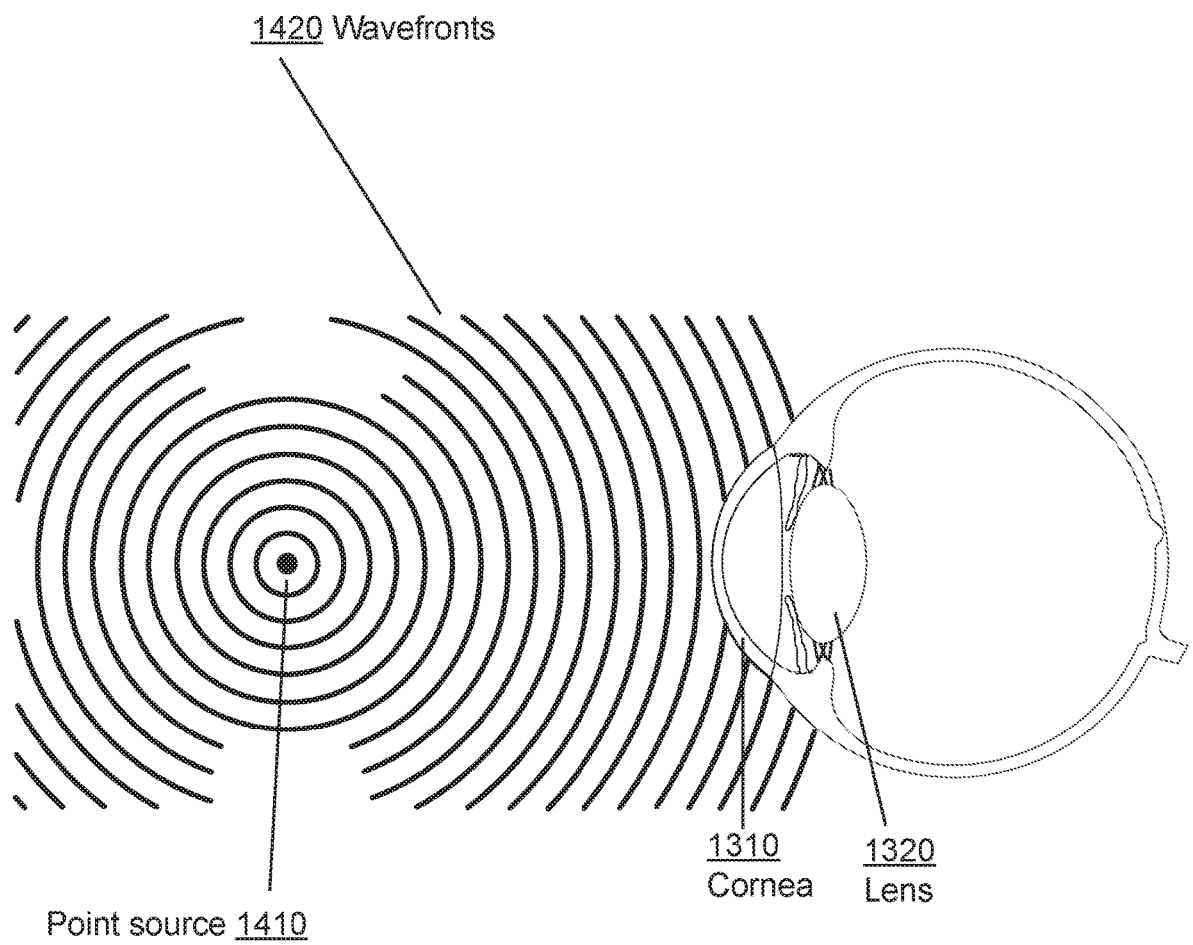
FIG. 14 is a variation of FIG. 9, in which only the point source and the spherical wavefronts of light it generates and the human observer's eye are shown.

V. Optical Function Required for Eye Mounted Displays

Where an eye mounted display is placed: outside, on top of, or within the eye, determines the required optical function of such a display. As shown in FIG. 9 and FIG. 14, in the physical world, and in nearly all previous display technologies, point sources of light 940 and 1410 produce expanding spherical waves of light 950 and 1420. Some of these wavefronts will eventually intersect with the cornea of a human observer's 920 eye. At that point the wavefront will have a radius of curvature equal to the distance between the point source and the viewer's cornea. For very distant point sources, e.g. more than a dozen meters away, the wavefronts are quite flat, and can be treated as plane waves. For very close point sources, e.g. only a foot away, the wavefront is highly curved. Indeed, without external aid, except in high myopias, the human eye cannot focus on objects much closer than a foot away. In summary, in the natural world, wavefronts of light encountering the human eye are expanding spherical wavefronts with a radius at the eye of between one foot and infinity.

Figure 10:
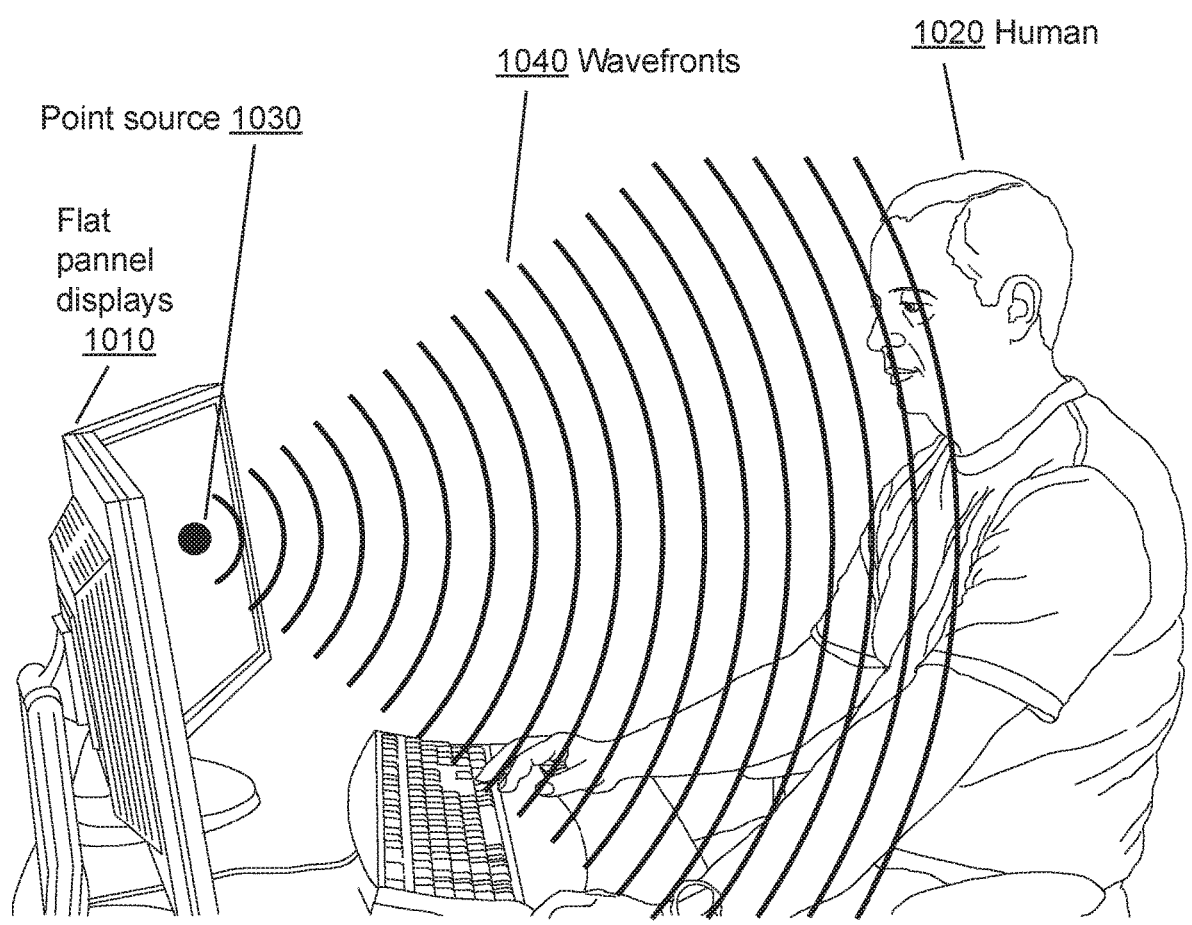
FIG. 10 shows two conventional flat panel displays being observed by a human.
Figure 11:
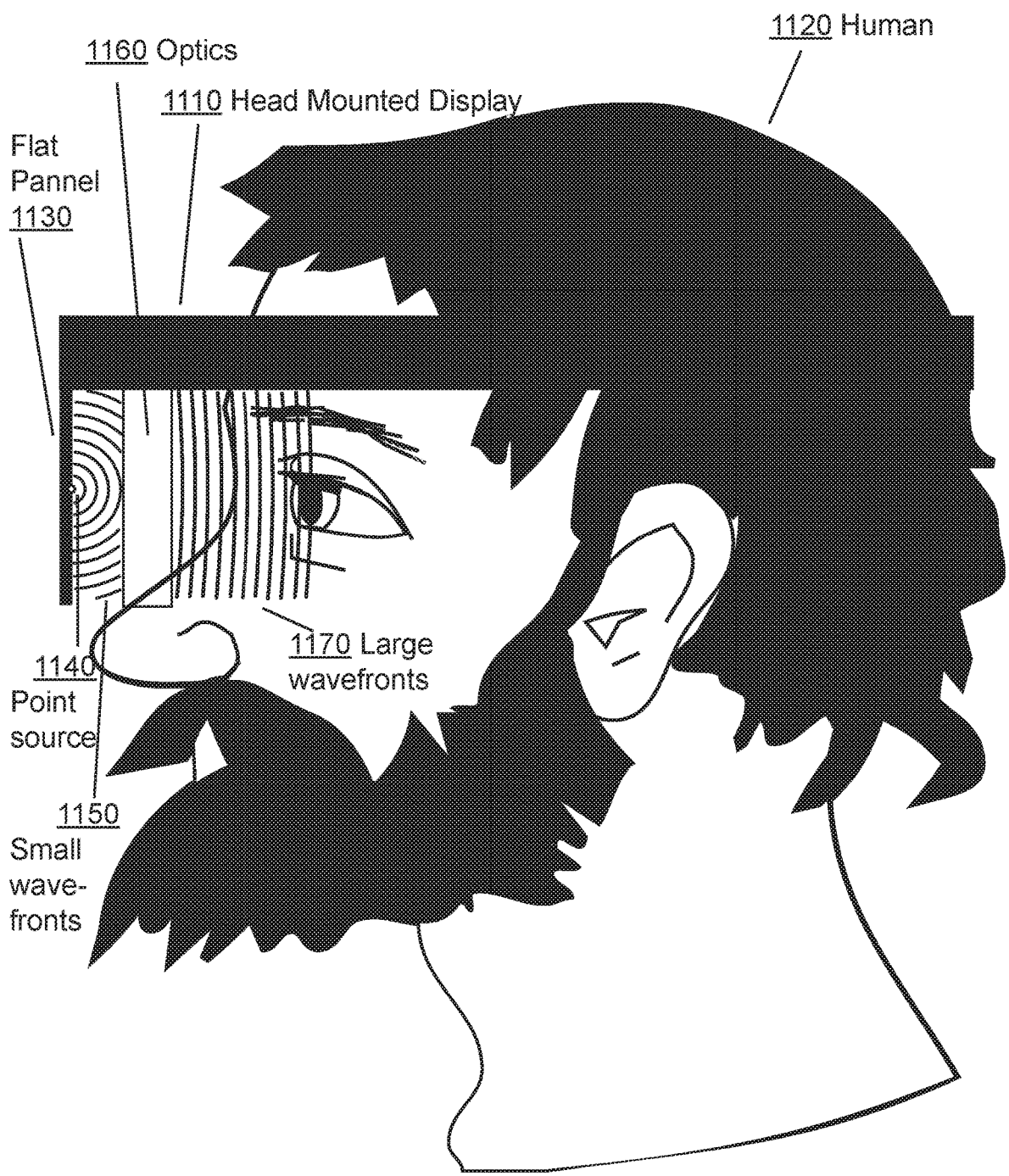
FIG. 11 shows a conventional head mounted display being observed by a human.
Figure 12:
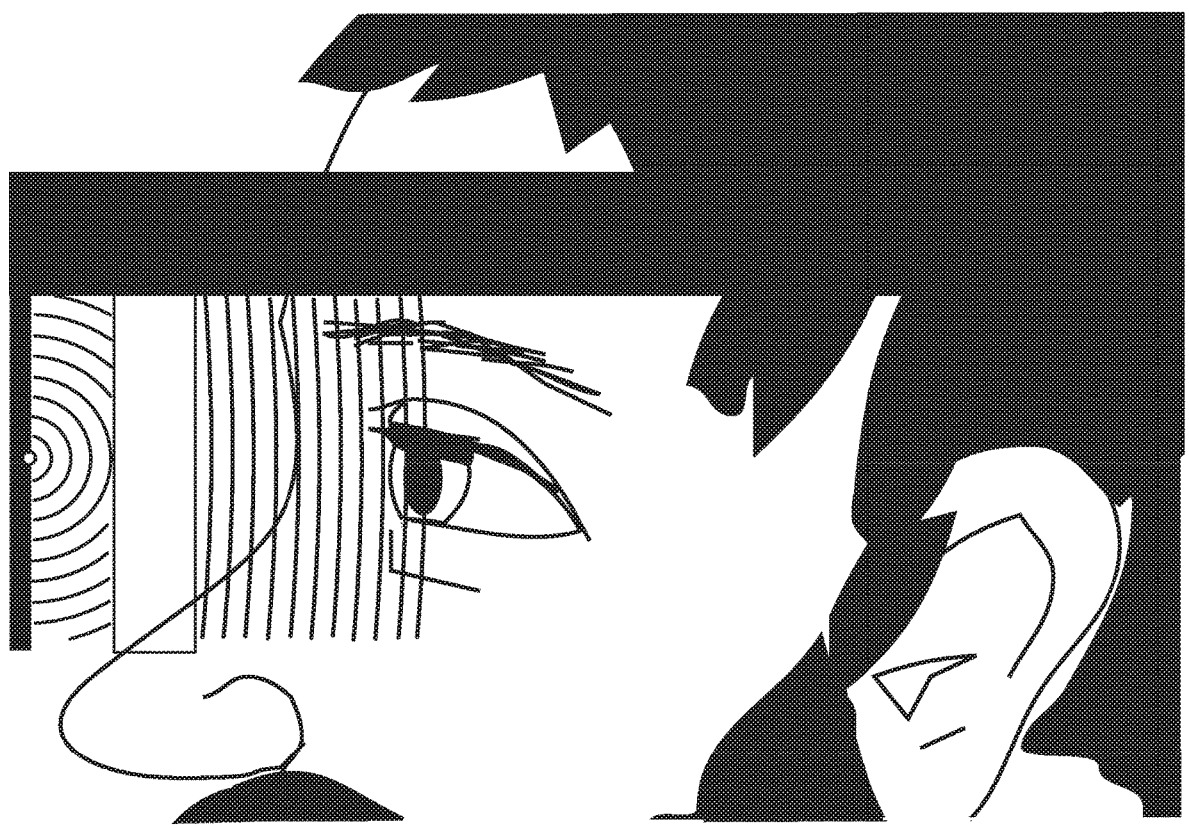
FIG. 12 shows a zoomed view of FIG. 11 to show the details of the change in radius spherical waves.

Most existing display technologies mimic the natural world: they produce similar expanding wavefronts of light. Simplistically, one can imagine each discrete pixel of a display as a different point source. An example of this is shown in FIG. 10, where a human element 1020 is viewing two flat panel displays element 1010, and a pixel on one of the displays creates a point source element 1030, which generates spherical wavefronts of light element 1040. More accurately, each pixel is actually a two dimensional region within which there are many different potential point sources, each with their own unique sub-pixel location. Projection displays are not viewed directly, instead light from them is focused onto some form of screen, either front or rear, and point sources are generated by the screen surface. Head mounted displays differ slightly, in that very small radius wavefront of light from their internal pixels are optically flattened by a large amount before they emerge from the display. This is shown in FIG. 11, where a human element 1120 is wearing a head mounted display element 1110. On a small internal flat panel display element 1130, a pixel produces a point source of light element 1140. This produces small radius spherical wavefronts of light element 1150. But before reaching the viewer's eye, an optical element 1160 within the head mounted display greatly enlarges the radius of curvature of these spherical wavefronts to produce new spherical wavefronts element 1170. These "flattened" wavefronts (now effectively the same as element 1040) are the ones that reach the eye, where they are perceived as object much further away than the flat panel element 1130. The purpose of this flattening is just to mimic the natural world: to ensure that the wavefronts emitted by the display have a radius of curvature somewhere in the human usable range: one foot to infinity. FIG. 12 is a zoom-in of detail of FIG. 11.

An eye mounted display that has an air gap between the display and the cornea is subject to the same laws of physics, and must produce the same radius wavefronts as described above. But an eye mounted display attached to the cornea, or placed further within the eye itself, faces different optical constraints.

Figure 13:
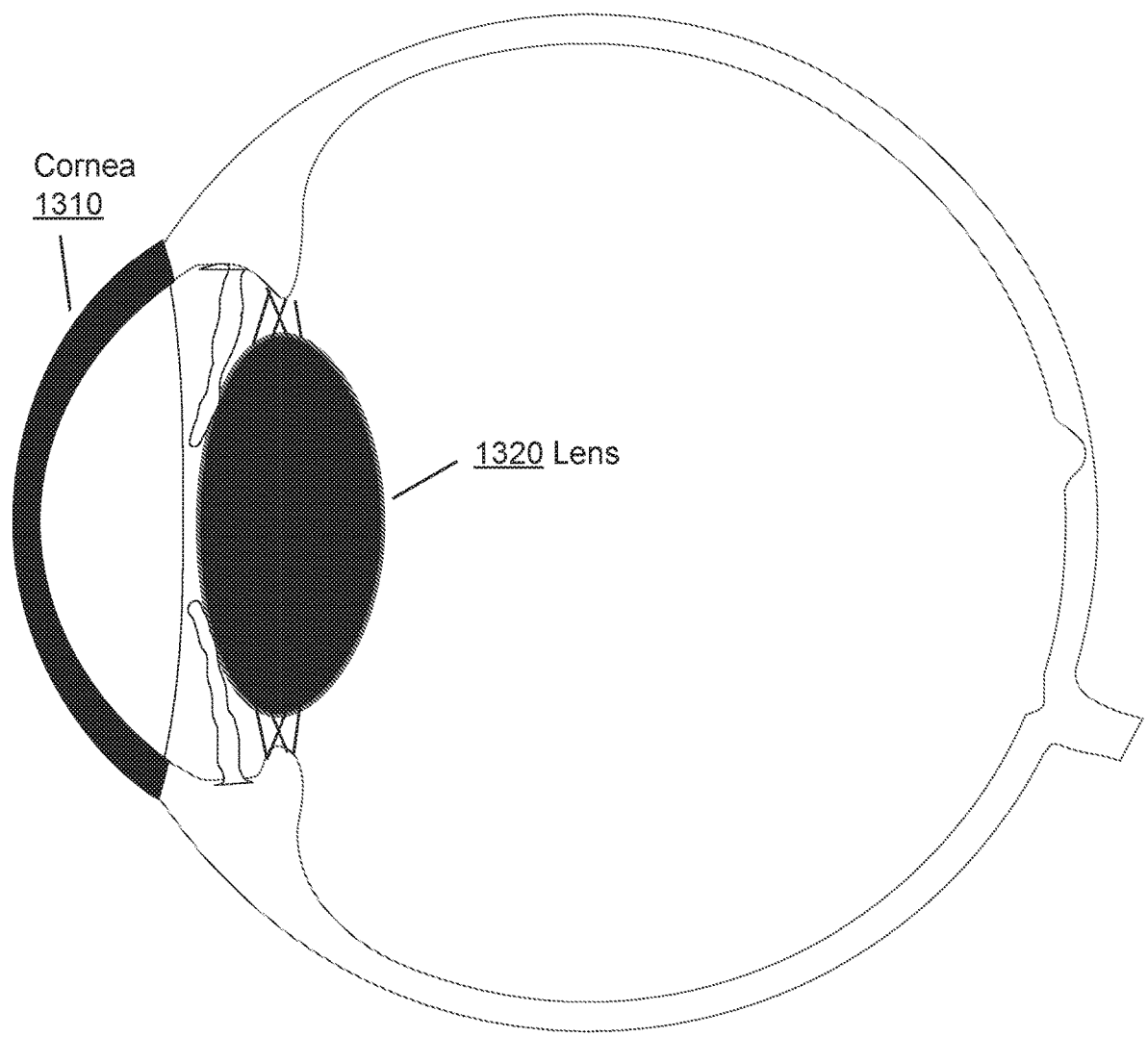
FIG. 13 is a variation of FIG. 5, in which the two optical elements of the human eye have been highlighted.

In the normal un-aided eye, there are just two major optical elements. As shown in FIG. 13 in black, these are the cornea 1310 and the lens 1320. We will next step through how these two elements affect the incoming expanding spherical wavefronts of light from the environment encounter first the cornea 1310 and then the lens 1320.

Figure 15:
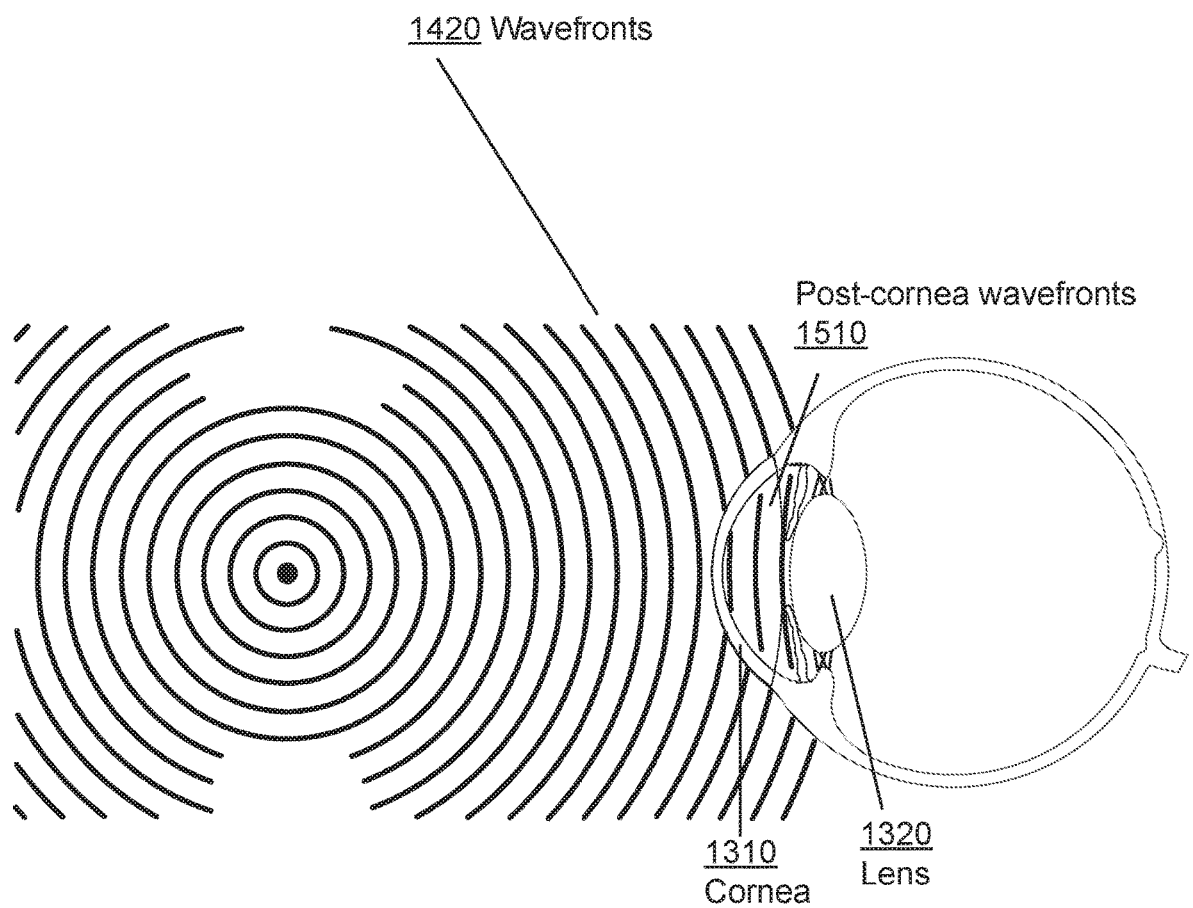
FIG. 15 is a variation of FIG. 14, in which the wavefronts of light as modified by the optical effects of the cornea have been added.
Figure 16:
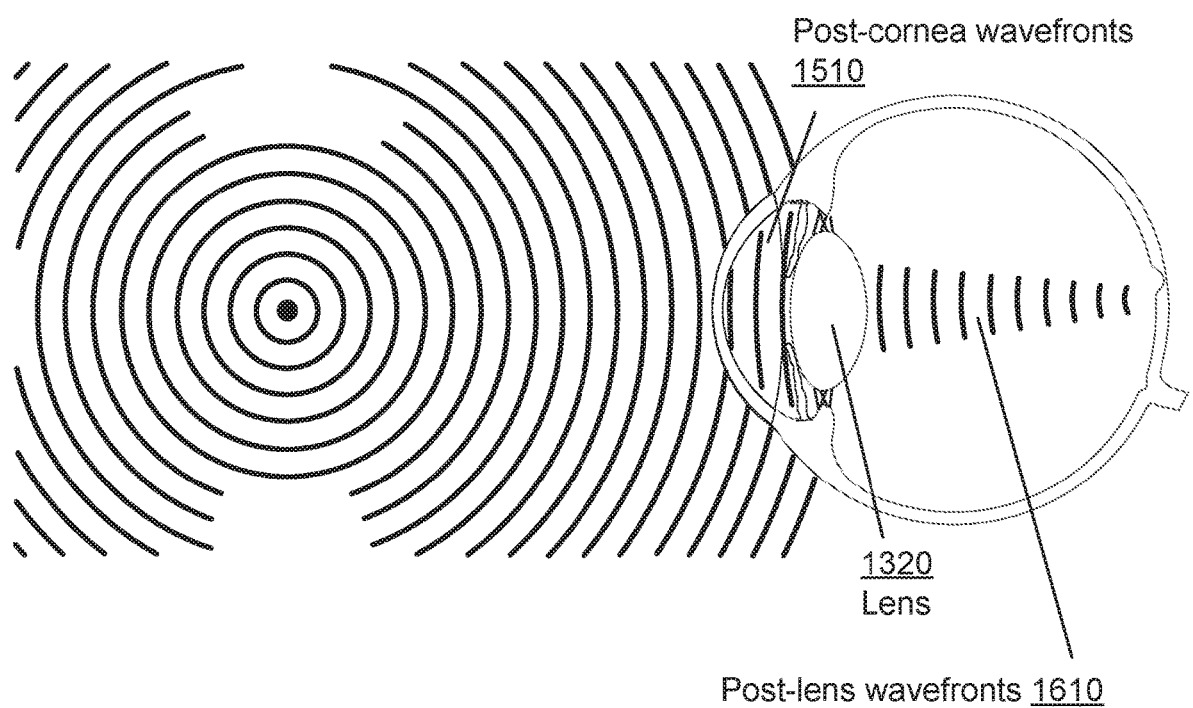
FIG. 16 is a variation of FIG. 15, in which the wavefronts of light as modified by the optical effects of the lens have been added.
Figure 17:
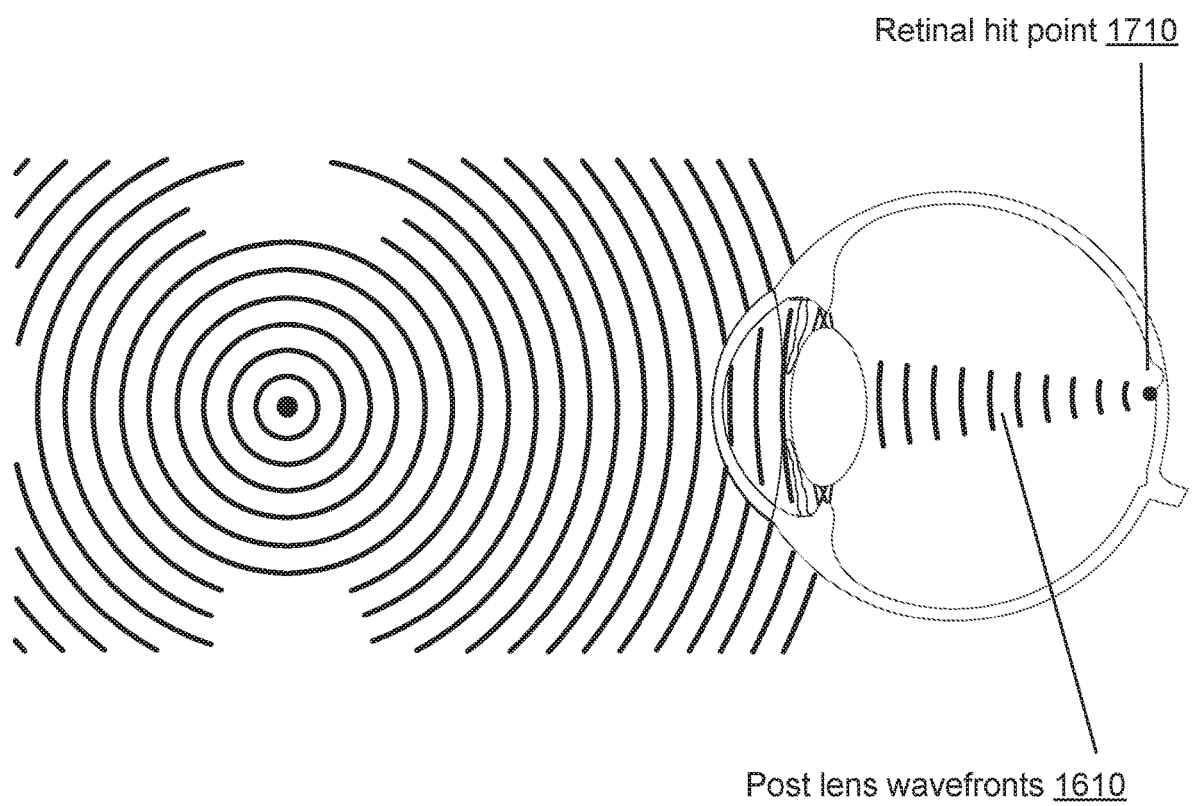
FIG. 17 is a variation of FIG. 16, in which the point on the retinal surface where the wavefronts of light converge is shown.

FIG. 14 shows a point source of light (element 1410) emitting expanding spherical wavefronts of light (element 1420) eventually impacting on the front surface of the cornea (element 1310). (For aid in illustration, the point source as depicted is much closer to the human eye than it can normally focus.) As shown in FIG. 15, when these expanding wavefronts of light from outside the eye pass through the cornea 1310, the optical function of the cornea 1310 is to convert these wavefronts 1420 into post-corneal contracting spherical wavefronts of light 1510. The radius of curvature of these contracting waves is small: slightly more than an inch. This means that without further interference they would contract to a single point slightly behind the eye. The cornea has about two-thirds of the optical power of the eye. The last third is contained in the lens 1320. In FIG. 16 it is shown that when the post-corneal wavefronts 1510 pass through the lens 1320, the optical function of the lens 1320 is to convert these wavefronts 1510 into post-lens contracting spherical wavefronts of light 1610. These wavefronts will have a further reduction in the radius of curvature over those of the post-corneal wavefronts 1510 such that the post-lens wavefronts 1610 will now contract to a point at the surface of the eye's retina (when in focus). This point is shown in FIG. 17 as element 1710.

Figure 18:
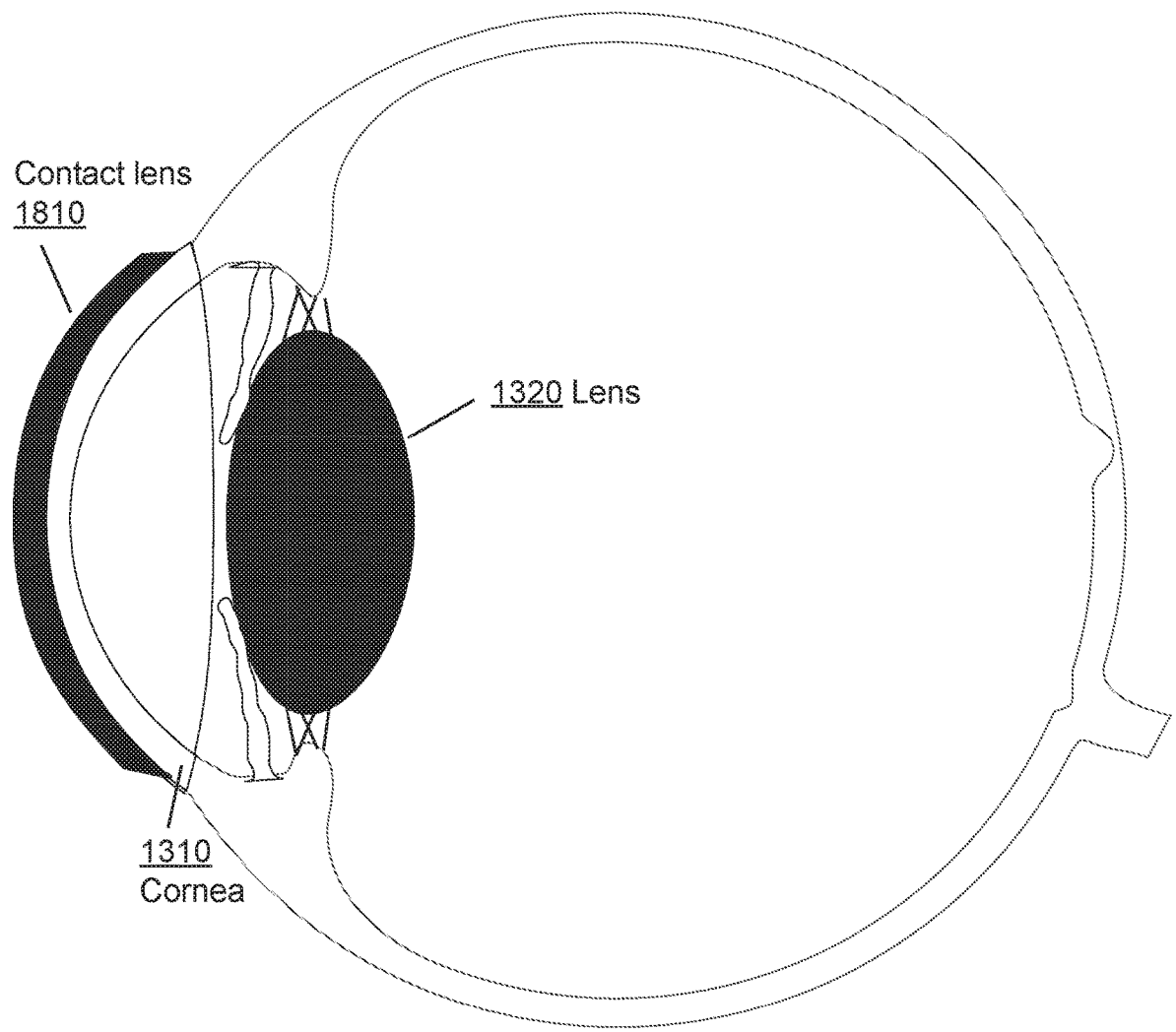
FIG. 18 is a variation of FIG. 13, in which a contact lens is being worn, and in which the resultant two (major) optical elements of the contact lens eye system have been highlighted.
Figure 19:
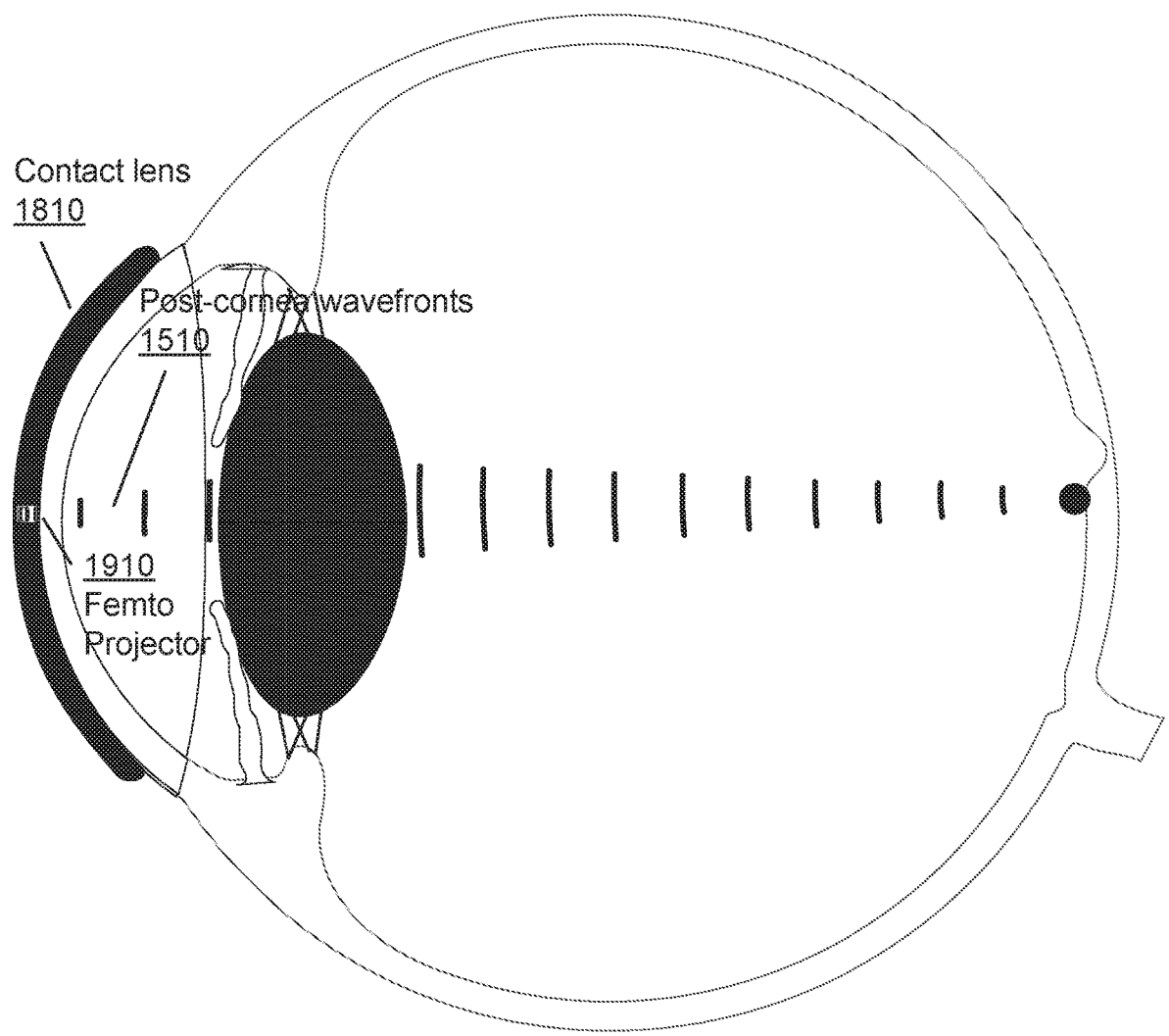
FIG. 19 shows a femto projector embedded in a contact lens and generating post-corneal wavefronts of light.
Figure 20:
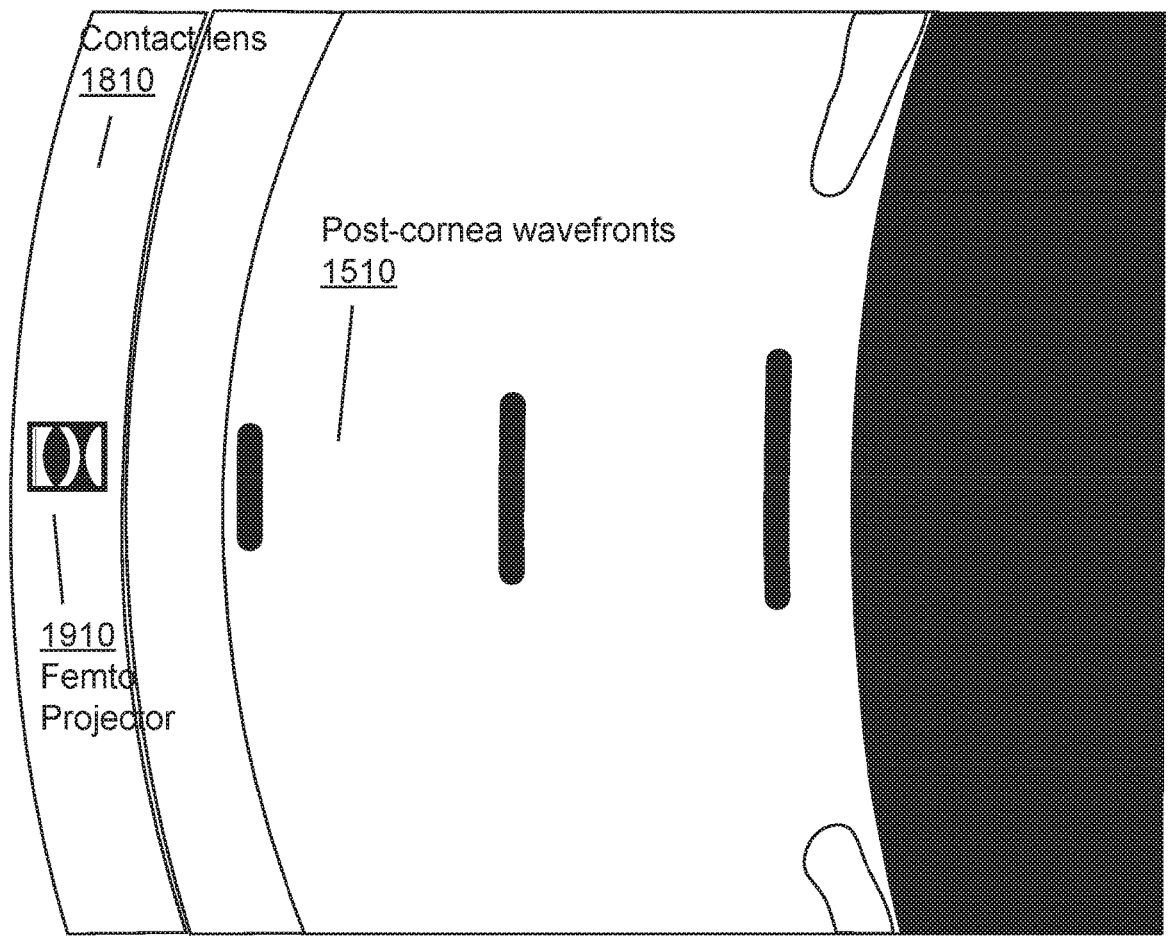
FIG. 20 is a zoom into FIG. 19 and shows detail of a femto projector generating post-corneal wavefronts of light.

To a first approximation, when a contact lens is placed on the eye, it eliminates the cornea as an optical element, replacing that with its own optical properties. This is because the index of refraction of the contact lens, tear fluid, and the cornea are very similar, and so little bending of light is caused by a contact lens covered cornea. The cornea's natural optical function is caused by the large difference in index of refraction between air and the material of the cornea. When a contact lens is present, the large change in optical index is no longer at the surface of the cornea, but at the air-contact lens interface. This is illustrated in FIG. 18, which shows in black the two major optical elements of a contact lens aided eye: the contact lens 1810 and the lens 1320. For a myopic or hyperopia, this allows a properly designed contact lens to correct one's vision. But there are also consequences for a contact lens display: if a display embedded within a contact lens is emitting wavefronts of light, those wavefronts of light will not be modified by the cornea, even though they still pass through it. Instead, the emitted wavefronts of light must match the natural post-corneal wavefronts. As described above, these are rapidly contracting spherical wavefronts of light, and this is what the optical system of a contact lens display must produce. This is illustrated in FIG. 19, where a single femto projector 1910 is shown embedded within the contact lens 1810, and is generating post-corneal wavefronts of light 1510. FIG. 20 is a zoom into FIG. 19, showing the optics in more detail.

Besides residing in an external contact lens, eye mounted displays in general could be placed at many other locations within the eye. Each different placement potentially has a different target type of light wavefront to produce, and thus different optical function requirements. The general rules is the same: produce the same sort of wavefronts that the natural world produces at a given location within the eye's optical system. An eye mounted display placed within the cornea, replacing the cornea, or placed on the posterior of the cornea, all must produce similar optical wavefronts as a contact lens display. Intraocular displays, placed somewhere between the cornea and the lens, have to produce even tighter radius contracting wavefronts of light, the exact radius depends on the exact location of the intraocular display between the cornea and lens. Eye mounted displays placed on the front of the lens, within the lens, replacing the lens, or on the posterior of the lens, have yet different optical function requirements, which can differ between the types. Eye mounted displays placed between the lens and the retina need to produce still tighter radius of curvature for proper function. Eye mounted displays placed on the surface of the retina need to mimic the focused point of light of natural vision, and thus optically can be just point sources. That is, direct emission of light by pixels can be sufficient, without any additional optical modifications.

With the exception of an air-gap eye mounted display, whose required optical function is otherwise well understood, and retinal mounted displays, who may not require any additional optical function at all; all the other cases of possible eye mounted display share the same general requirement: produce contracting small radius spherical wavefronts of light. They only differ in what small radius they must generate. In the general case in which support is to be included is to produce different depths of field, and/or programmable optical prescriptions, rather than a fixed single radius, instead a small range of radii to be produced is the target. Thus without loss of generality, we will expand on the optical implementation of a contact lens display, as the other cases require only slight well understood modifications.

VI. Optical Function of a Contact Lens Display

While there are many different possible way of designing a contact lens display, one method would be to use a planer array of light emitting pixels (point or very small area sources of light), followed by an optical system that converts these very small radius expanding spherical wavefronts of light (because all this is happening within the small confines of a contact lens) into the desired post-corneal contracting wavefronts.

Placed in front of a light emitting pixel array, a single simple convex lens will convert the expanding spherical wavefronts from each pixel into contracting spherical wavefronts of light. Unfortunately the radius of the contracting wavefronts will be similar to the incoming expanding wavefronts, and thus will poses a far smaller radius of curvature than the required post-corneal natural wavefronts. But by placing a simple concave lens just after the convex lens, the resultant radius of curvature is greatly expanded, and the desired wavefronts can be produced. Different numbers and combinations of lenses can produce the same result. These optical systems may include, for example, GRIN lenses, mirror elements, prism elements, Fresnel elements, diffractive elements, holographic elements, negative index materials, etc.

There are several constraints on the physical size and placement of the optics within contact lens display; most of these constraints also apply to other types of eye mounted displays. Physically a comfortable contact lens must be fairly thin—many commercial contact lenses are on the order of 150 microns (0.15 millimeters) thick. Sclera contact lens can be thicker and still comfortable, but the limit is about 500 microns (half a millimeter). The optical zone of a contact lens is only about 8 millimeters in diameter (technically this is a function of the absolute size of the eyeball). This means that any portion of a contact lens display that is emitting light meant to pass into the eye must be located within the 8 millimeter diameter circle. However, other portions of a contact lens display can reside within areas of the contact lens outside this circle.

In traditional optical terminology, the human eye is a very wide field of view device; as much as 165° across. This means that at any particular point on the surface of the cornea, light emitted at that point cannot reach the entire retina, but only a specific portion of it. At the center of the cornea this portion can be as wide as 60° across, but at points with higher eccentricity the addressable portion of the retina narrows considerably. This same optical property means that if a contact lens display is meant to be see-through, the size and shape of any opaque region within the optical zone must be small.

Figure 75:
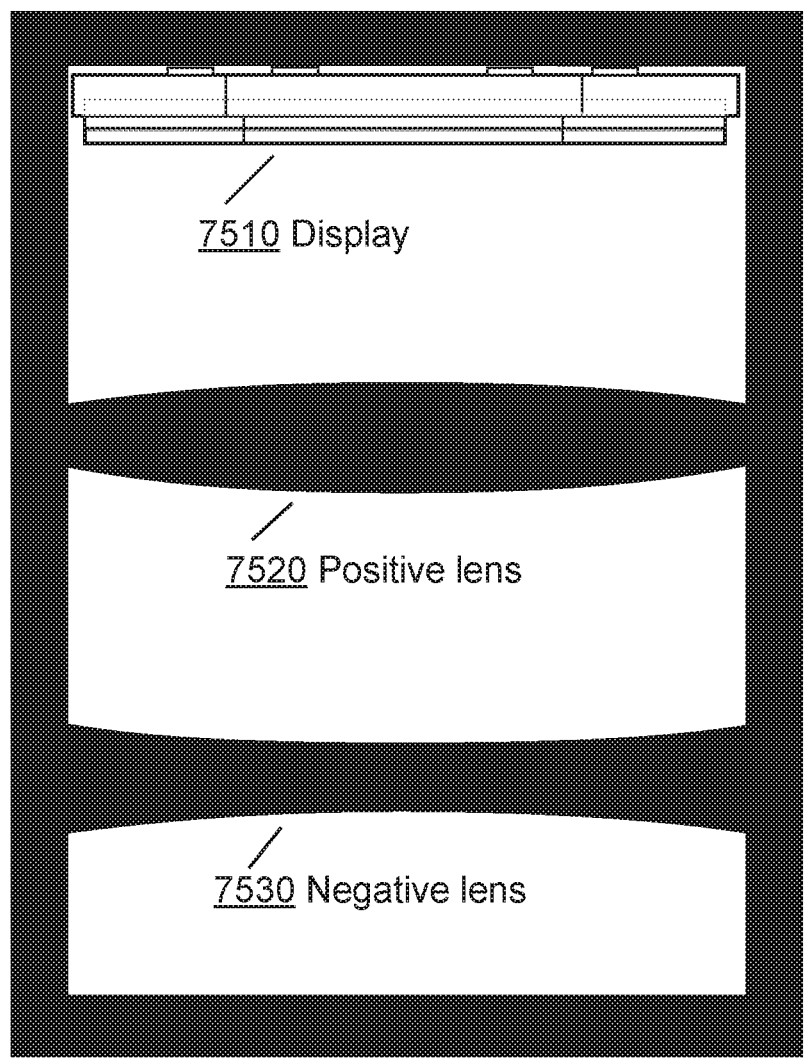
FIG. 75 shows a single femto projector.

The inability of a single point, or small region, to illuminate most of the retina implies that any wide field of view contact lens display must emit light into the eye from several different locations within the optical zone. The see-through requirement implies that each such light emitting component must be fairly small in size: generally less than half a millimeter across. This last constraint precludes many folded optics designs. As shown in FIG. 75, a simple in-line optical design, consisting of the display element (light emitting pixels) 7510, a first (positive) lens 7520, and then a second (negative) lens 7530, has the property that when the diameter of the system is constrained to be less than half a millimeter across, it is possible to design the optical system such that its thickness is less than half a millimeter, thus satisfying the maximum contact lens thickness constraint. Confined to an area less than half a millimeter across, no existing light emitting display technology can contain multiple millions of pixels that larger size displays now commonly do. This means that multiple small displays must be employed to support the desired resolution of a contact lens display.

Definition of term: femto display
Definition of term: femto projector

In this document, the term femto projector, or femto display will refer to any display device that can fit into the half millimeter on a side cube (or less) constraint of fitting into a contact lens, and capable of producing the appropriate post-corneal spherical wavefronts. One specific instance of such a device is the one described previously, in which a planer pixel light emitting element is followed by a positive lens element and then a negative lens element.

It should be noted that traditionally, any self-contained "image projector" device emits contracting spherical wavefronts of light that will all come into focus at a particular (potentially curved) surface in front of the projector. Light re-emitted from the screen will then produce the sort of expanding spherical wavefronts of light that the outside of the human eye is expecting to receive. While we still use the word projector, femto projectors by definition produce contracting spherical wavefronts of light appropriate for the post-corneal expectations of the human eye. One difference here is that there is no separate image forming screen involved.

(The word femto is used, not because of any elements being at the femto-meter scale, but because the terms micro-projector and pico-projector are already in use defining other classes of larger projectors.)

Definition of term: femto projector display die

We need a specific term to refer to the (generally planer) source of light emitting pixels used within a femto projector. In this document we will use the term femto projector display die for this purpose. As described in more detail later, this element can be an OLED on silicon display, or a LED display, or a LCD display, etc. While the word die is use in this term, which will later be defined as a type of integrated circuit, in the general sense intended here the femto projector display die does not have to be an IC die, but any small pixel light emitting element.

VII. Variable Resolution Mappings for Contact Lens Displays

Now that we have an understanding of the variable resolution mapping of the retina, we can start considering how the design of a contact lens display can best take advantage of this.

When a Contact Lens is Fixed to the Cornea

If a contact lens display is fixed to the cornea in both position and orientation (not presently common), from the contact lens' point of view, the varying resolution of the retina is at fixed locations in the display space of the contact lens. That means that the high resolution fovea will appear at just one location (though offset from the center of the contact lens' view), and the contact lens design could be made to only display high resolution pixels there, and progressively lower resolution pixels at locations further from the center of the fovea. And the "progressively lower resolution" function could take into account the different fall-offs in resolution along the different longitudes of the retina. This would truly minimize the total number of display pixels that a contact lens would have to have, while maximizing the displayed resolution from the eye's point of view.

However, there apparently is some variation of the position of the fovea with respect to the corneal optical axis, and of course there is known to be at least a three to one difference in the density of cones (square of resolution) in the foveal maximum cone density zone (e.g., 20/20 people vs. 20/10 people (only about 2% of the population though)). While this could be addressed by fixing the contact lens slightly offset to the cornea, another technique would be to just have a slightly larger highest resolution zone on the contact lens display.

When a Contact Lens is not Fixed to the Cornea

Given the number of practical problems with rigidly fixing a contact lens to the cornea, what would a contact lens display that is free to rotate about the cornea "see" of the retina? First, the center of the fovea, which is nominally offset 5° of visual angle from the corneal optical axis, could appear at any angle of visual longitude. In such a case, a contact lens display would have to place its highest resolution pixels everywhere within a circle of 5° of visual eccentricity from the corneal optical axis, plus a bit more for the width of the high resolution portion of the fovea. Also, because there is a slower drop-off in resolution in the nasal direction, but the contact lens display doesn't know which direction that is, it would have to assume the worst case nasal slower drop off in every direction. That is, outside the greatly enlarged constant resolution foveal display region, the resolution of the contact lens display would have to drop off no faster than the resolution of the retina drops off from the center of the fovea in the nasal direction.

But there is more. A contact lens not fixed to the cornea not only is free to rotate about it, but also to slide off alignment with the corneal apex a bit. The effect of this to a contact lens display design is that one has to add another 2° or so of "enlarged" constant resolution foveal display region.

It should be noted that eye mounted displays implanted into the eye are free of most of these uncertainties, and can be more optimal with how they parcel out their display resolution. But here we want to teach the best methods for non-fixed contact lens displays, so we will describe how to construct contact lens displays that can deal with rotation and slippage with respect to the cornea.

It also should also be noted, though, that at the time of "rendering" any particular variable resolution image to be displayed onto a contact lens display, accurate current knowledge as to the orientation and shift of the contact lens relative to the cornea will always be available. Thus a variable resolution rendering system does not have to render at the same high fixed resolution all over the polar end-cap; instead it can do so only where the fovea is actually located during the frame, and can utilize less rendering resources elsewhere in the majority of the end-cap mapping.

VIII. Means to Display Variable Resolution Pixels

Most all man-made display pixels are all the same size. How are we to construct an eye-mounted display, including contact lens displays, in which the pixel size is not only variable, but potentially continuously variable?

From the discussion describing the constraints on contact lens display optics (as well as that of most other forms of eye mounted displays), we know that multiple different projectors will have to be employed to form the desired image on the retina. Thus one potential way of producing different size pixels on the retina would be to have projectors that project to successively higher bands of eccentricity on the retina have different amounts of optical magnification, even if all the pixel sizes within a given projector would all be the same.

What about the pixels produced by a single projector? Are there any ways to make their sizes change? Optically, one can introduce trapezoidal distortion, where the width of the projected image on the top is wider than the width of the projected image on the bottom. Correspondingly, the width of what were square pixels at the display image source plane would be rectangular pixels at the top of the projected image, wider than high, and less and less wide until the at the bottom of the projected image they would be square. There are two problems with this approach. First, it requires a more complicated tilted optical path than the simple two element optical design that was previously described. Second, we not only want the pixels to be wider at the top, but also taller, e.g., still locally square.

There is another way in which we can apply an arbitrary mapping function to the size and expansion of size of pixels: we can just pre-distort the shape of the pixels that are built from square to the size and position of the pixels of the source image plane device. While modern VLSI fabrication techniques require semiconductor devices to be built as flat, planer objects, the precision of the manufacturing allows pixels to be built of virtually any shape, so long as the scale of the shape is relatively large compared to the smallest feature size of the underlying IC lithography process being used. A figure showing visually what is meant will be given once the topic of pixel shapes and tilings have been discussed.

VIII.A. Pixel Tilings Overview

Most digital devices, both image sensors and displays, are built from square or rectangular, pixel shapes and tilings. But other pixel shapes and tilings, including hexagonal, have been used. The general techniques taught here can be applied to any form of pixel tiling, specifically including square, rectangular, and hexagonal. But for several reasons, the preferred embodiment is to use hexagonal tilings. As previously discussed, hexagonal tilings are 30% more efficient than square pixel tilings in filling a given area with pixels with a given minimum resolution. In a contact lens display that is free to rotate about the corneal axis, the pixels will project to the retina at all angles, and the resolution of square pixel tilings is limited by the length of the diagonal of the square, not the width of the sides. In hexagonal pixel tilings, the resolution is limited by the long width of the hexagon, which is much closer to the width of the short width of the hexagon than is the diagonal of a square pixel relative to its width. The fact that the "pixels of the eye" are also mostly hexagonally tiled is not the reason for our similar choice of tiling of the display source image, but rather an issue of convergent evolution. (Also, hexagonally tiled cells are the most common tiling of biological systems, but instances of square cell tilings occur too.) There are, however, also disadvantages to using hexagonal tilings. Square and/or rectangular tilings are easier and thus usually more efficient for computer graphics and image processing algorithms and techniques to utilize than are hexagonal tilings. When red, green, and blue pixels must be produced in a single source image plane device, it is quite common to place three one third wide by one high rectangular sub pixels together to form a single square RGB pixel (though other designs, including sideways "W" shaped designs, are also in commercial use). There also is a great deal of existing standards, technology, and devices designed around square (or at least rectangular) tilings. But compared to the additional overhead incurred when working in a variable resolution space, the additional penalty due to the use of hexagonal tilings is not great. Because the size of the displayed pixels is so closely matched to that of the underlying cones and groups of cones of the retina, other methods of supporting full color display are possible that are compatible with hexagonal pixel tilings, and will be described later.

VIII.B. Projector Tilings

So far we have only been discussing the tiling of individual pixels. But we already know that we will have multiple projectors that at the individual projected image level also have to tile together. As at the individual pixel level, many different shapes of projected images and tilings of such shapes are possible, specifically including those based on square, rectangular, and hexagonal projector shapes and tilings, but here most of the existing art has been utilized square or rectangular projector image shapes and tilings. The general techniques taught here can be applied to any form of projector shape and tiling, specifically including those based on square, rectangular, and hexagonal shaped projector images and tilings. But for several reasons, again the preferred embodiment is to use hexagonal projector images and tilings.

The idea is to decompose the hexagonal tiling of the rectangular ScreenSurface (hexagonally shaped pixels) into a tiling of n-groups of hexagons (hexagonally shaped projectors). The pixels would be mapped to the surface of the retina via a locally uniform resolution mapping by two techniques, as previously described. First, each ring of projectors would have a different amount of magnification onto the retina. Second, the pixels that form each projector's image would be pre-distorted to match a patch of locally uniform resolution mapping. However, all projectors would have the same number of pixels, and the mapped resolution will closely match that of the retinal receptor fields of the human eye. This is a direct consequence of using the locally uniform resolution mapping. The same will be true for all of the subsequent different parameterizations of projector tilings to be shown.

The decomposition has several parameters and constraints. The choice of parameters many times will be an engineering tradeoff. The previous paragraph describes the choices we have already made about what mapping to use and shape of pixels and projectors. A constraint based choice involves the separate EndCap mapping: what mapping should be used, what $\theta_{min}$ will be used, how will this mapping image interlock (match) that of the locally uniform resolution mapping at the boundaries, and what (constant) resolution should be supported? The decomposition into individual projectors has choices that are the equivalent of choosing a SW and SH of the tiling of the projectors as hexagonal pixels. The SW equivalent will be the number of semi-column pairs of hexagonally shaped projectors (pair of an even and odd semi-column) in tiling. This is the same as the number of projectors per row (even or odd). The SH equivalent will be the number of rows of hexagonally shaped projectors (both even and odd rows) between $\theta_{min}$ and $\theta_{max}$. When mapped to the ViewSphere, each even or odd row of projectors will form a circle of projectors around the center of the contact lens at increasing distances from this center. The distances are constrained by where and how large the entrance pupil for the visual region to be covered by that projector is. Thus each "row" of projectors will be called a "circle" of projectors when viewed after mapping. Thus the parameterization of the decomposition into projectors has four parameters: $\theta_{min}$, $\theta_{max}$, the number of projectors per circle, and the number of concentric circles. As mentioned before, each ring of projectors will have its own particular amount of retinal magnification. Also again, all projectors will have the same number of pixels (as a direct result of the mapping). The actual number of pixels that every projector must have will be a function of just the number of projectors per circle and the number of circles. Thus a different choice in these parameters will affect engineering trade-offs in the number of projectors and the number of pixels per projector.

Figure 56:
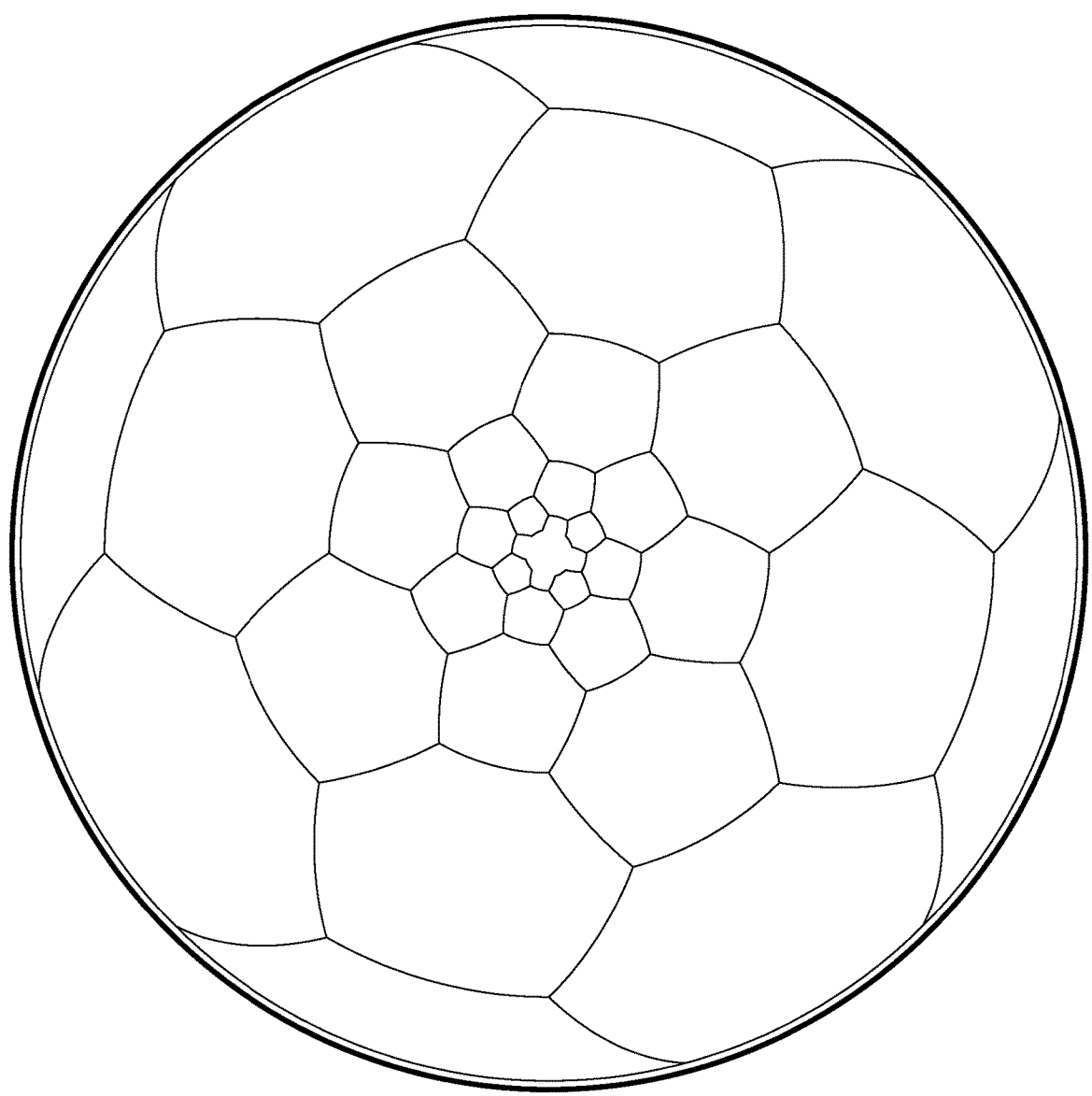
FIG. 56 shows 28 hexagonally shaped projectors in 7 circles of 4.
Figure 57:
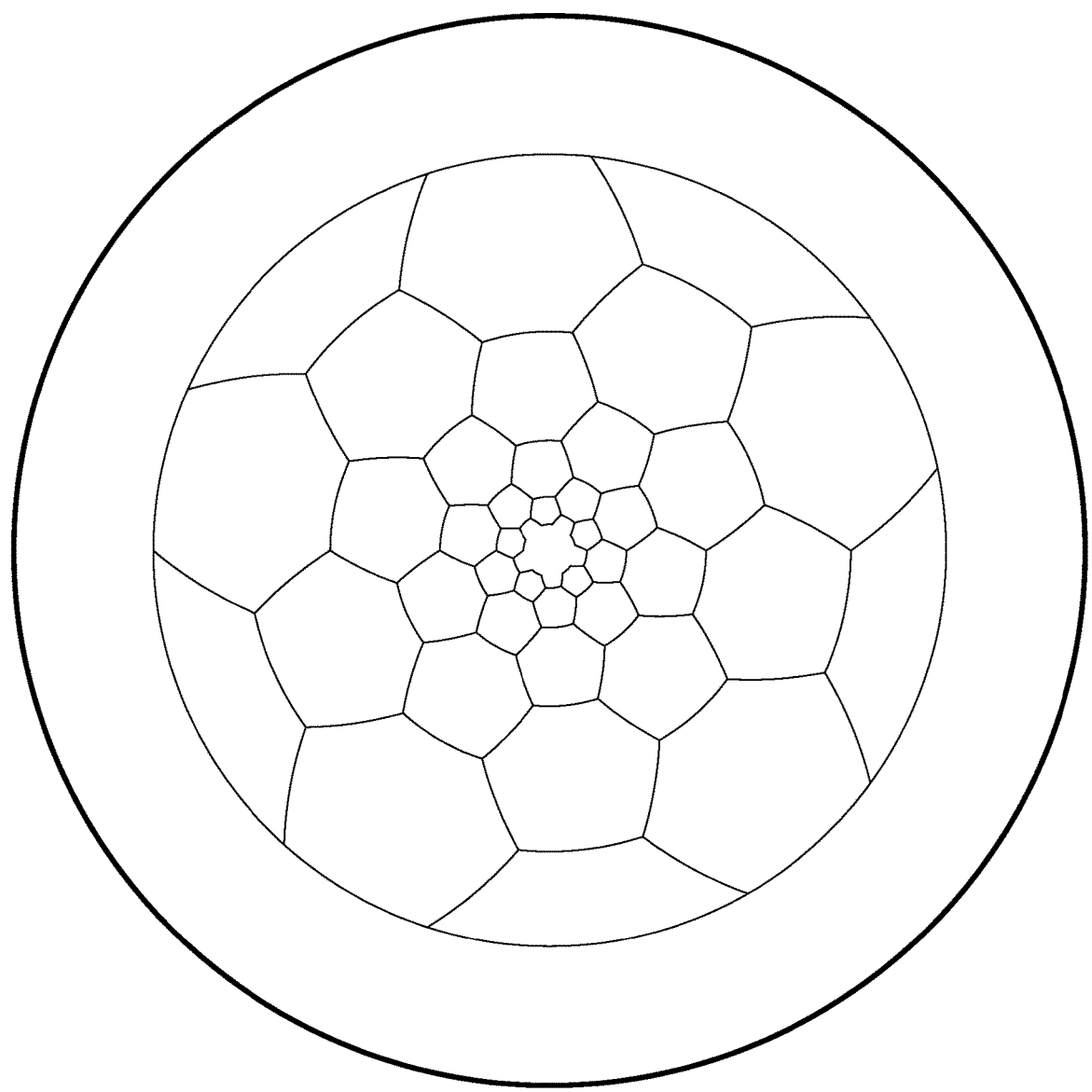
FIG. 57 shows 35 hexagonally shaped projectors in 7 circles of 5.

We will illustrate the effects of different choices of parameters for tiling of the projectors by showing several specific combinations of choices. FIG. 56 shows 28 hexagonally shaped projectors (as pre-distorted to match a patch of locally uniform resolution mapping), mapped as seven circles of four projectors each. Each group of four projectors has the same relative magnification. There are several comments that must be stated about this image that will also apply the several additional variations that will be described next. First, the image is an orthographic polar projection of the areas that each projector projects to. This means that while shapes near the center of the image are represented relatively un-distorted, shapes towards the outer thick edge circle (the silhouette of the ViewSphere) are actually more elongated than they look on the spherical surface. Next, this variable resolution mapping of projector's images stops short of the north pole (the center of the image) to avoid the singularity that is there. This is the "plus sign" shaped region at the center. This will be covered later by a separate EndCap chart, and will left empty in other examples until then. The highest eccentricity that the projectors reach is just shy of 180°, as can be seen by the slight gap between thick circle representing the silhouette of the ViewSphere and the outer circle representing $\theta_{max}$ of this mapping. Also, there are four "half-hexagon" shapes on the outer edge. These represent regions of the mapping with an eccentricity below $\theta_{max}$, but not covered by any of the 28 hexagonally shaped projectors. So the actual portion of the retina covered by the projectors would not include these areas. Alternately, by adding four additional projectors that will only be half utilized, these four half regions could be included. Examining the overall mapping of projectors, it can be seen that the outer ring of four cover too large of longitudinal angle to fit the entrance pupil. Also, the shape of the projectors on different rings varies considerably from the inner to the outer ring Next let us consider what changing to five projectors per ring, still with seven rings, would look like. This uses 35 hexagonally shaped projectors, and is shown in FIG. 57. The portion of the ViewSphere covered is less than in FIG. 56, even though more projectors are used. This is a direct consequence of using more projectors per ring to cover all longitudes. (The required number of pixel per projector, however, would go down.) But the outer ring of projectors still have to cover too large of longitudinal angle.

Figure 58:
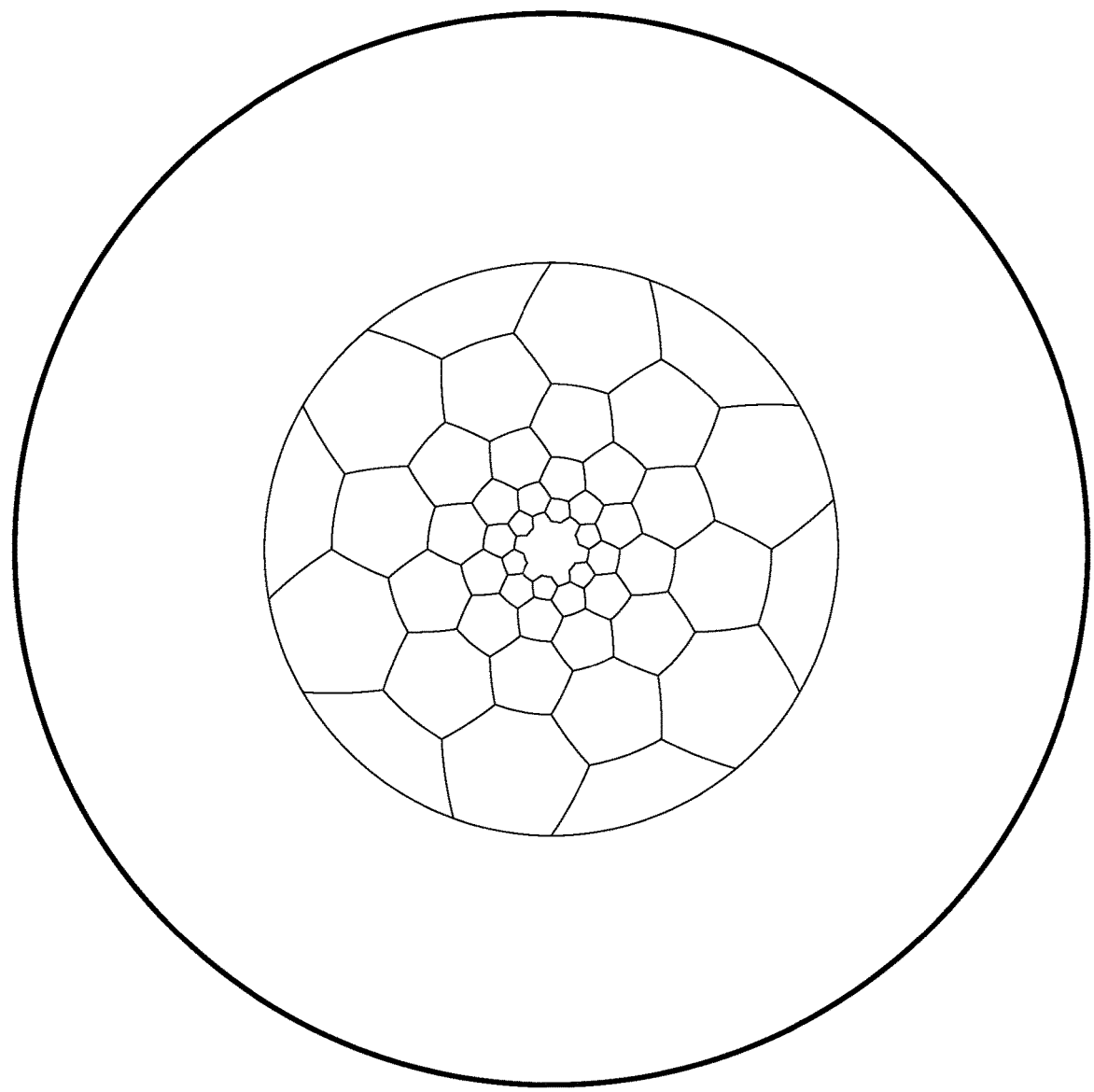
FIG. 58 shows 42 hexagonally shaped projectors in 7 circles of 6.

FIG. 58 shows what happens when there are six projectors per ring. This uses 42 hexagonally shaped projectors.

Figure 59:
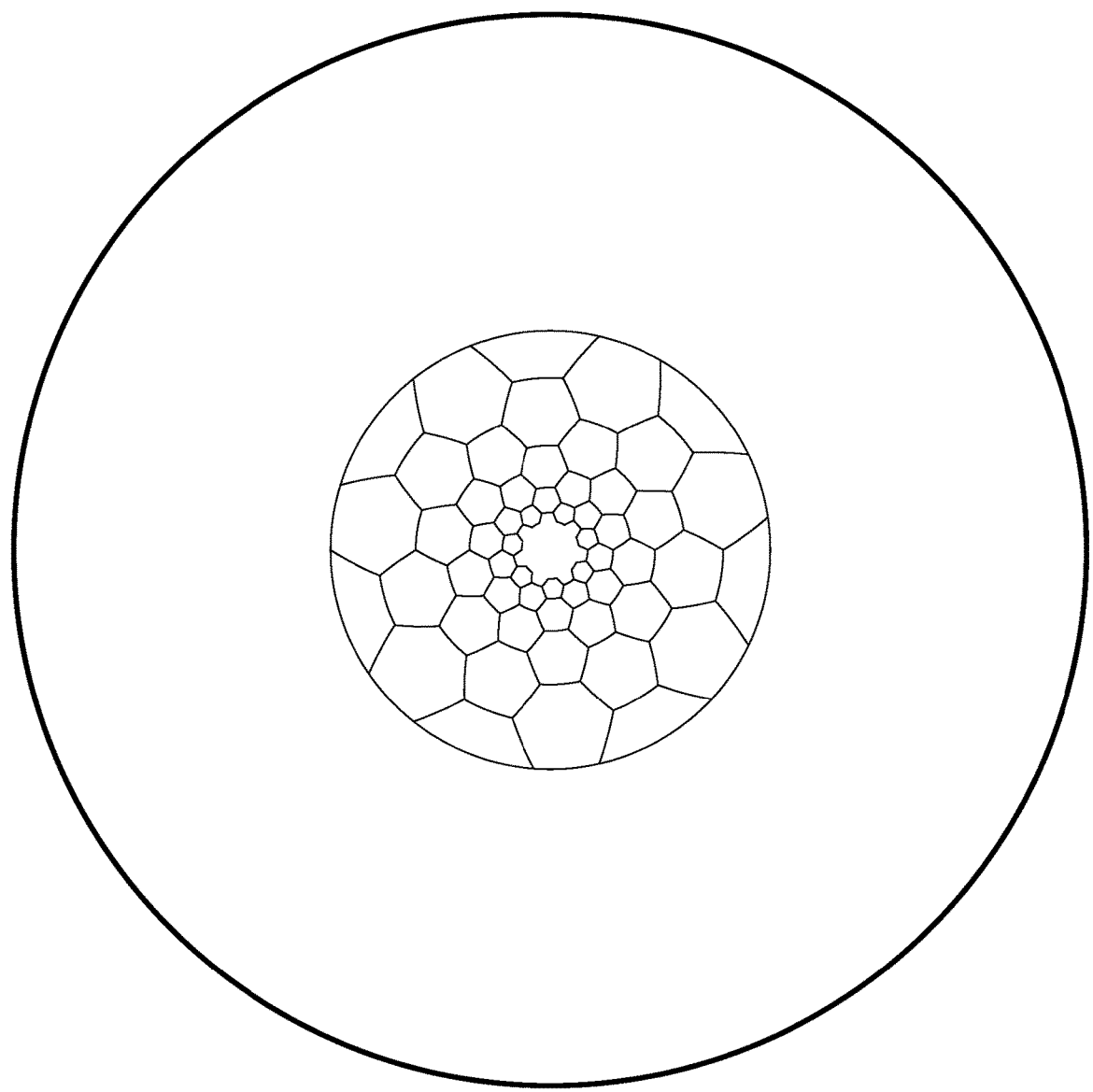
FIG. 59 shows 49 hexagonally shaped projectors in 7 circles of 7.

FIG. 59 shows what happens when there are seven projectors per ring. This uses 49 hexagonally shaped projectors.

Figure 60:
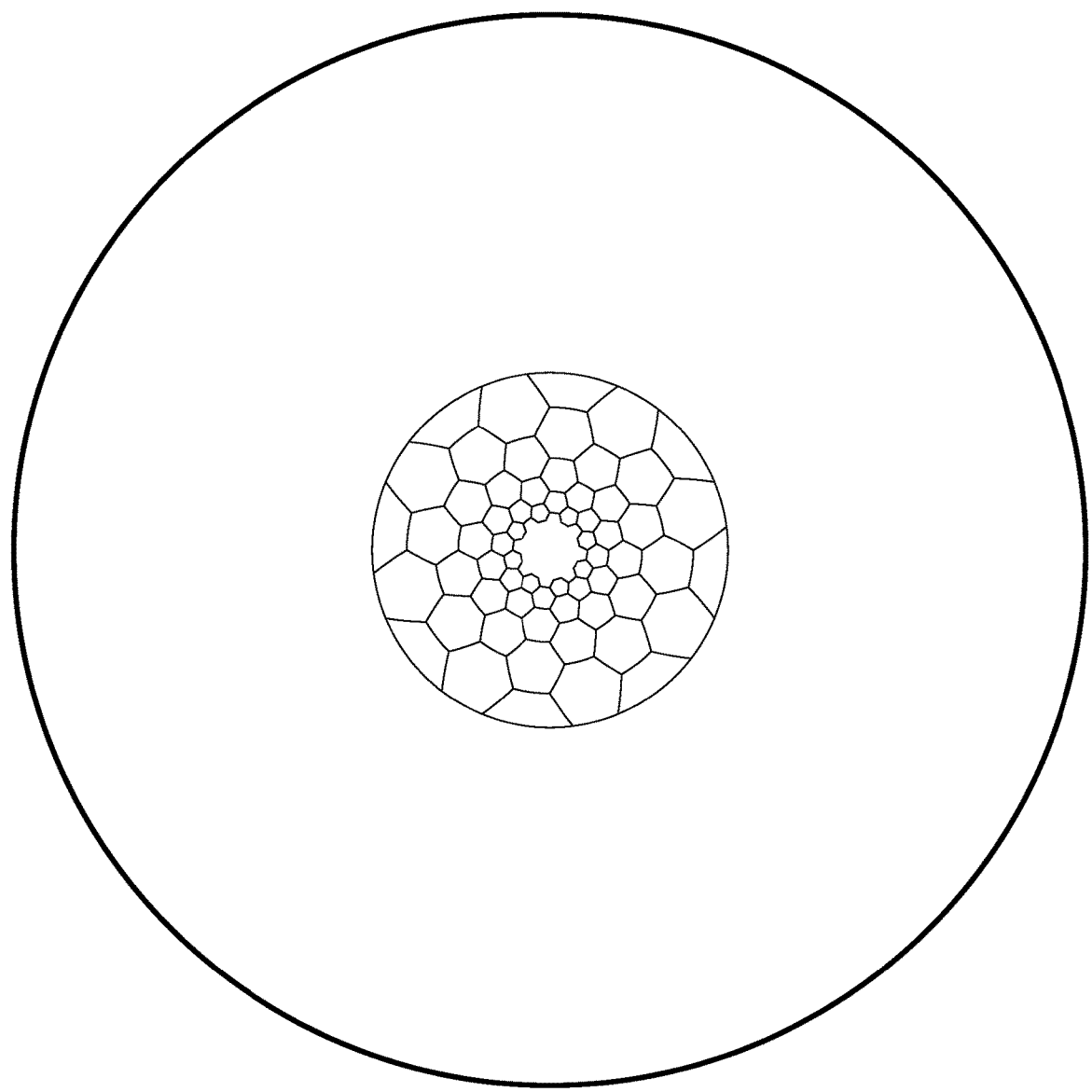
FIG. 60 shows 56 hexagonally shaped projectors in 7 circles of 8.

FIG. 60 shows what happens when there are eight projectors per ring. This uses 56 hexagonally shaped projectors.

Under different circumstances, all of these possible projector tilings, as well as others with more or less rings, are of potential use.

EndCap Projector Tilings

Figure 61:
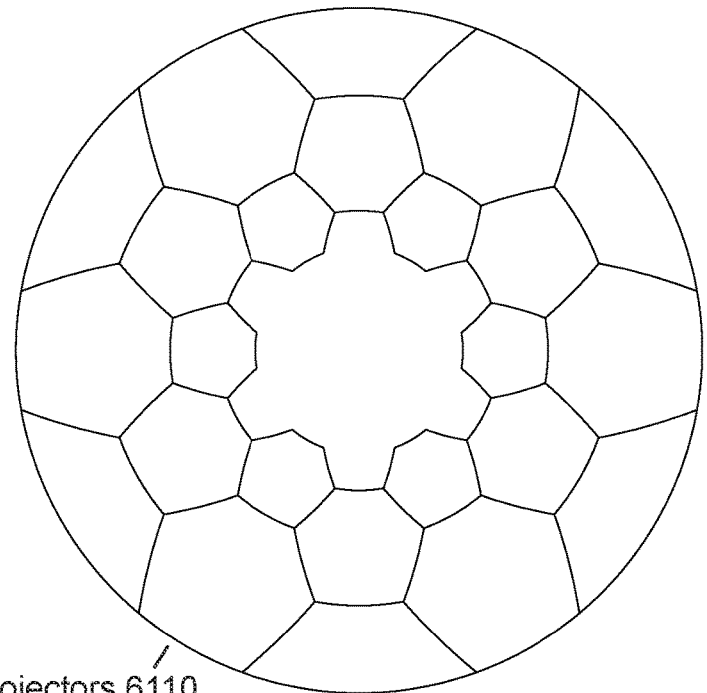
FIG. 61 shows the foveal region of variable resolution projectors, then a combination of variable plus 7 fixed resolution projectors.
Figure 61:
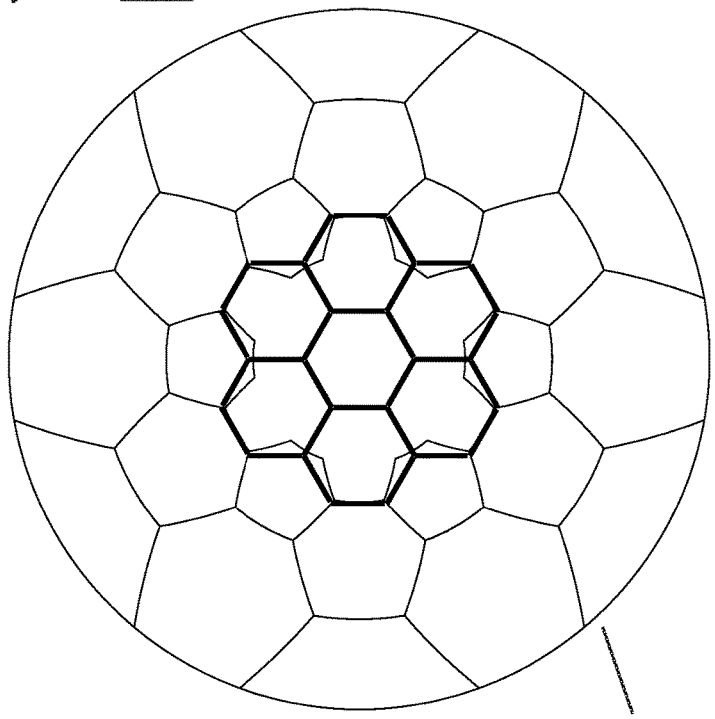
Figure 62:
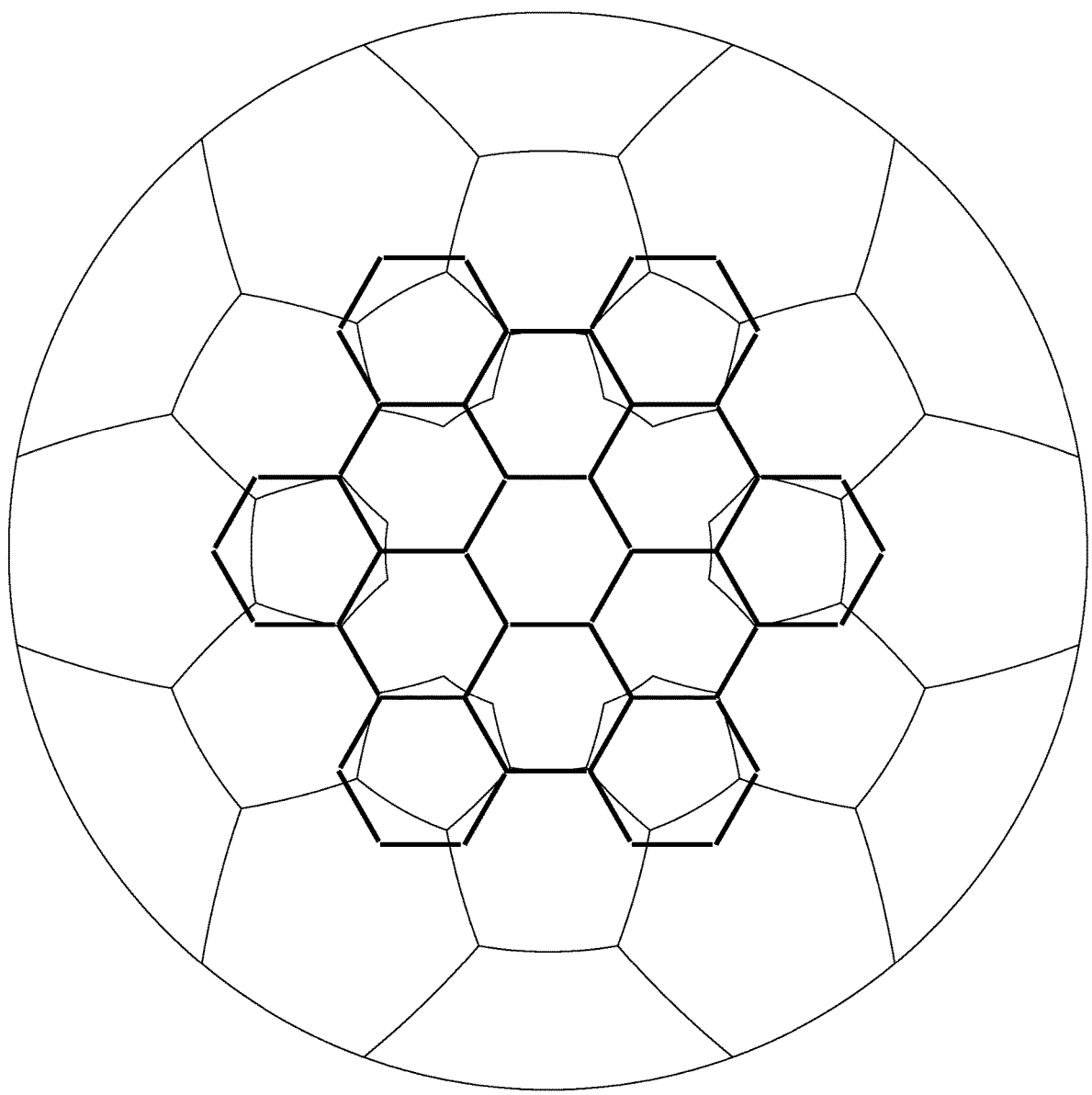
FIG. 62 shows the foveal region of a combination of variable and 13 fixed resolution projectors.

For the EndCap mapping, constant resolution projectors will be used. There is a good match between hexagonally tiled constant resolution projectors and tilings of variable resolution projectors when the number of projectors per ring is six. This way the six-way symmetry of the fixed resolution hexagons "matches" the six-way symmetry of the variable resolution wrap around ring. This is illustrated by first looking at the polar hole in the variable resolution projector mapping, which is shown in FIG. 61 element 6110. This polar hole is due to setting $\theta_{min}$ to a value above zero, in this case about 6°. Otherwise there would have been an infinite number of projectors spiraling in smaller and smaller into the north pole. Now we superimpose over the polar hole six fixed resolution hexagonally tiled hexagonally shaped projectors, shown in FIG. 61 as element 6120. Notice that there is very little overlap between the fixed and variable resolution projectors, yet the entire surface is covered. Note also that the first circle of six variable resolution projectors are similar in shape and size as each of the six fixed resolution projectors. So we can expand the EndCap foveal resolution area by replacing these with six more foveal projectors, if desired. This is shown in the overlap image of FIG. 62. The same sort of levels of overlap can be applied to variable resolution tilings with a different number of projectors per ring, but they won't be as efficient. Since the size (and pixel density) of the fixed resolution projectors is not fixed directly to the size of the variable resolution projectors, their relative scale becomes another design parameter, though the ideal is to have similar pixel densities at the joint boundaries.

Figure 63:
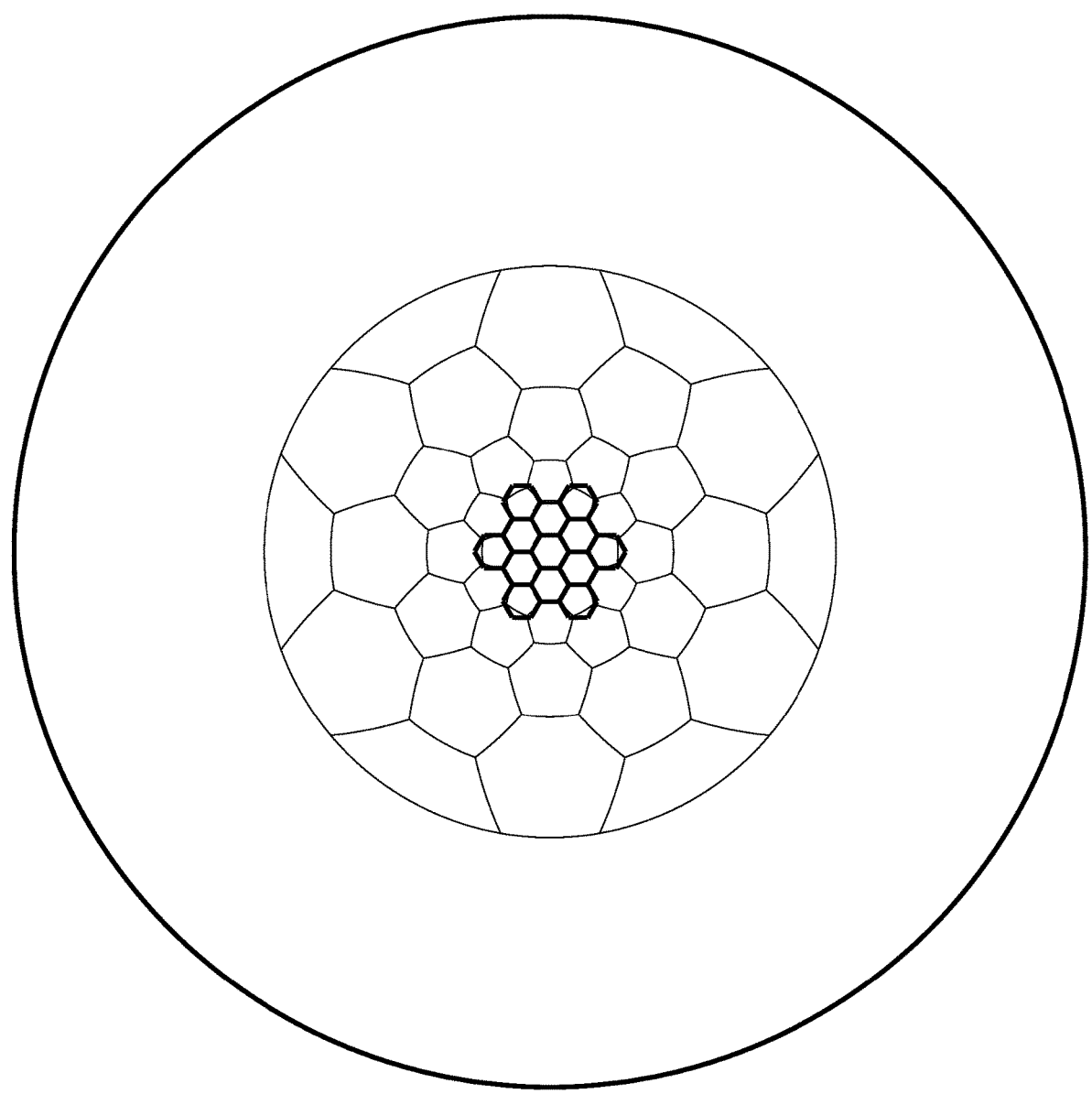
FIG. 63 shows a combination 30 variable resolution plus 13 fixed resolution projectors

Given that a ring size of six seems a good number, with the 13 fixed resolution foveal projectors and 30 variable resolution peripheral projectors, and a $\theta_{max}$ above 65°, FIG. 63 shows a preferred embodiment.

If a larger field of view is desired, more than seven rings can be used. The next two figures shows what this looks like (though back to a seven fixed resolution EndCap).

Figure 64:
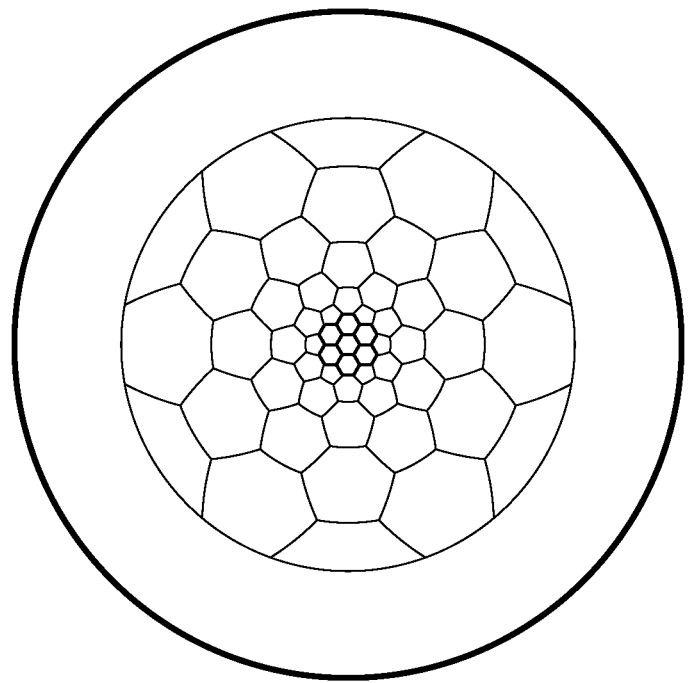
FIG. 64 shows a tiling of 49 and 55 hexagonally shaped projectors.
Figure 64:
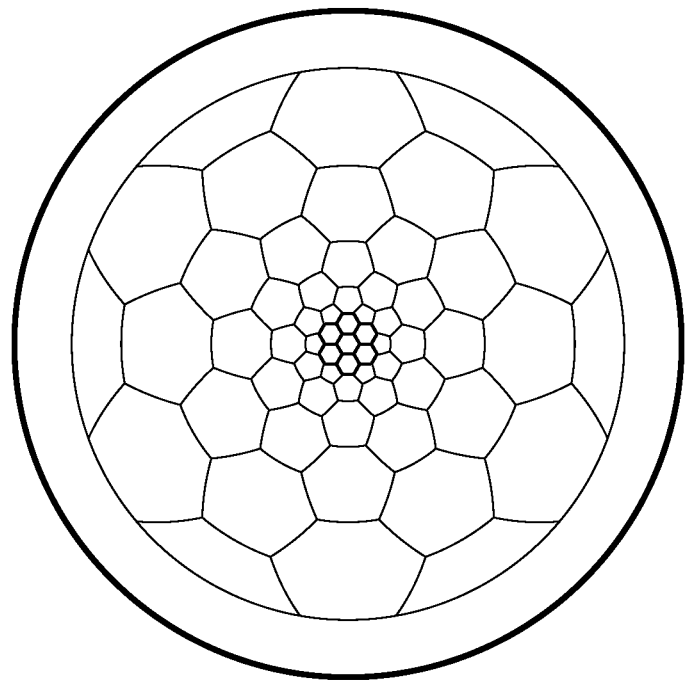

FIG. 64 element 6410 shows what an eight ring tiling with a seven fixed resolution projector EndCap looks like (49 total projectors).

FIG. 64 element 6420 shows what an eight ring tiling with a seven fixed resolution projector EndCap looks like (55 total projectors).

Figure 65:
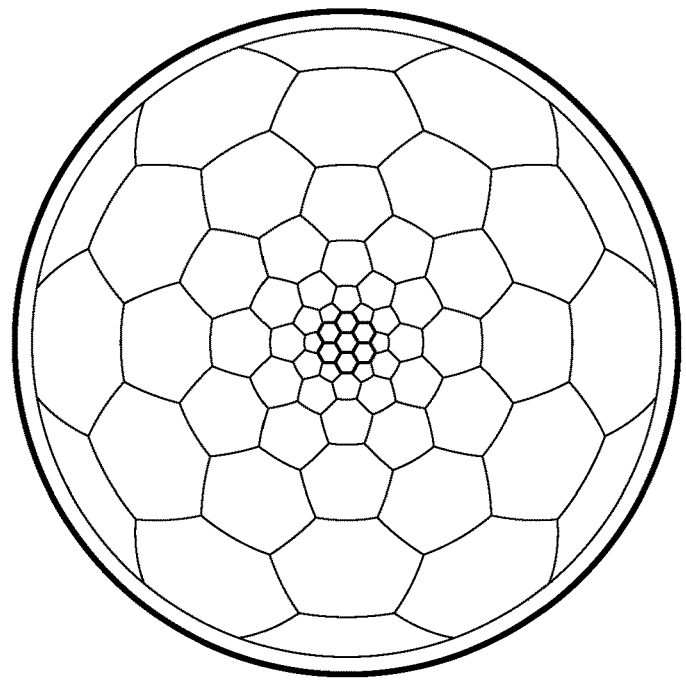
FIG. 65 shows a tiling of 61 and 67 hexagonally shaped projectors.
Figure 65:
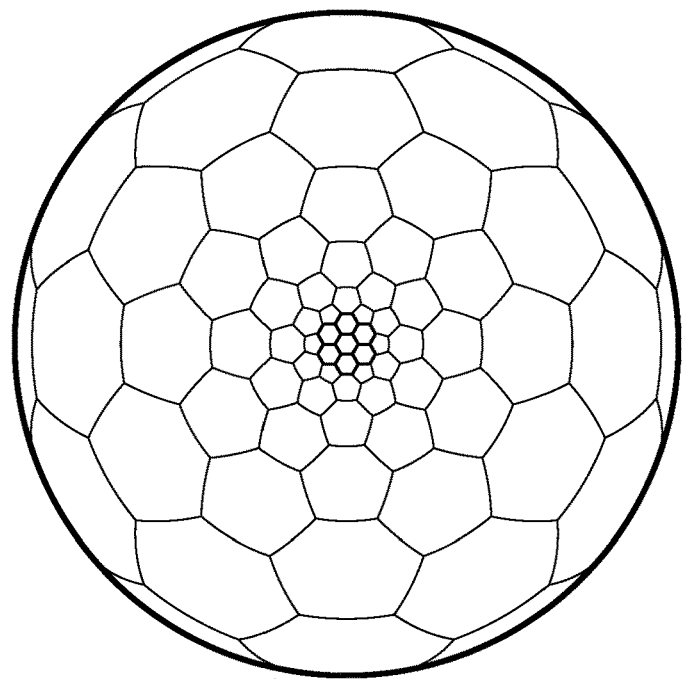

FIG. 65 element 6510 shows what an eight ring tiling with a seven fixed resolution projector EndCap looks like (61 total projectors).

FIG. 65 element 6520 shows what an eight ring tiling with a seven fixed resolution projector EndCap looks like (67 total projectors).

The last configuration has a (circular) field of view of nearly 180° ! The main problem with these additional rings is that their longitudinal subtended angle keeps getting higher and higher while the maximum longitudinal subtended angle entrance pupil keeps getting smaller and smaller. Depending on other optical and efficiency factors, at some point the far peripheral rings would have to transition to a tiling made up of more projectors, but with a smaller number of pixels, and therefore subtended longitudinal angle, once again fitting within the foreshortened entrance pupil of the eye. There is not a hard cut-off, such as at the point where the entrance pupil becomes narrower than the exit pupil of the projector assigned to that region of the retina. This is because at the eye's pupil, the image is still well out of focus, so the effect will at first be a vignetting of the projector's image on the retina, and an associated loss of the total amount of light from the projector that will make it through the pupil, lowering the overall illumination power of the projector. This sort of effect can be countered by having a brighter overall projector with a pre-computed dimming of the center of projection, to pre-correct for the vignetting effects. If, however, a third tiling is needed, then it can be another hexagonal tiling of projectors mapped by locally uniform resolution, it just will have to have a larger number of projectors per ring. What would this look like? That's partially why FIG. 59 and FIG. 60 were included, they show the general form of having more projectors per ring.

Figure 87:
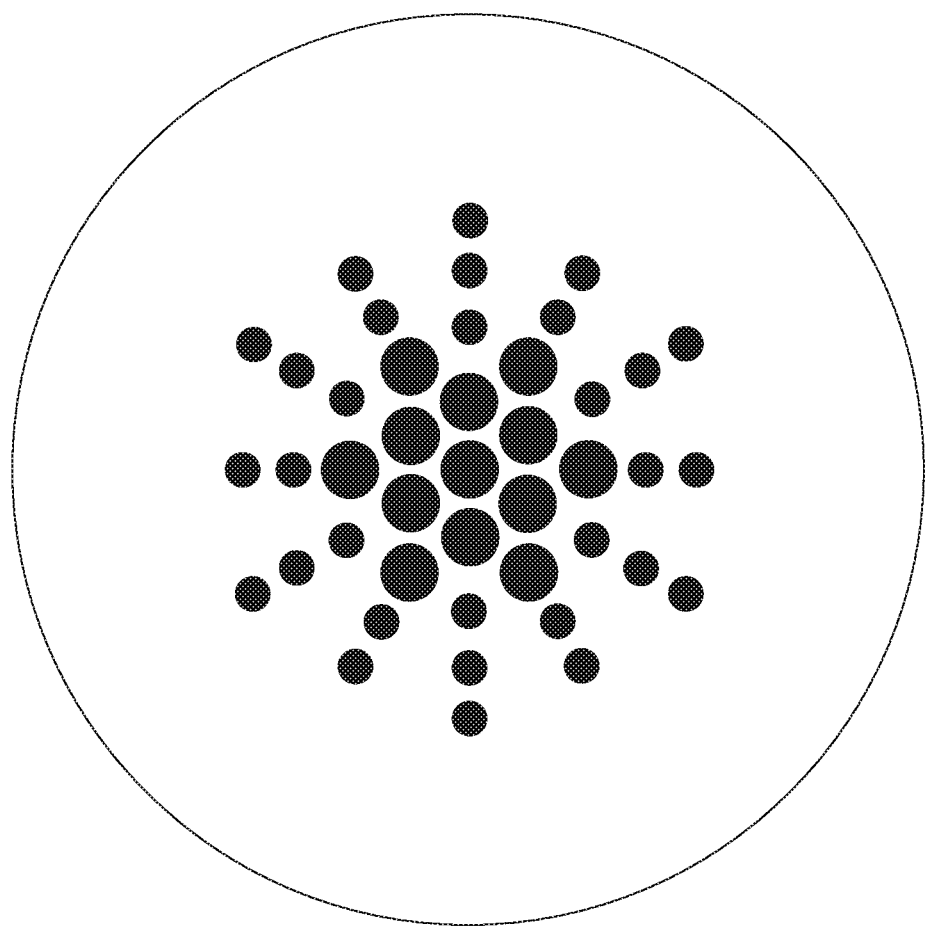
FIG. 87 shows the femto projector blocking portions of contact lens optical zone.
Figure 88:
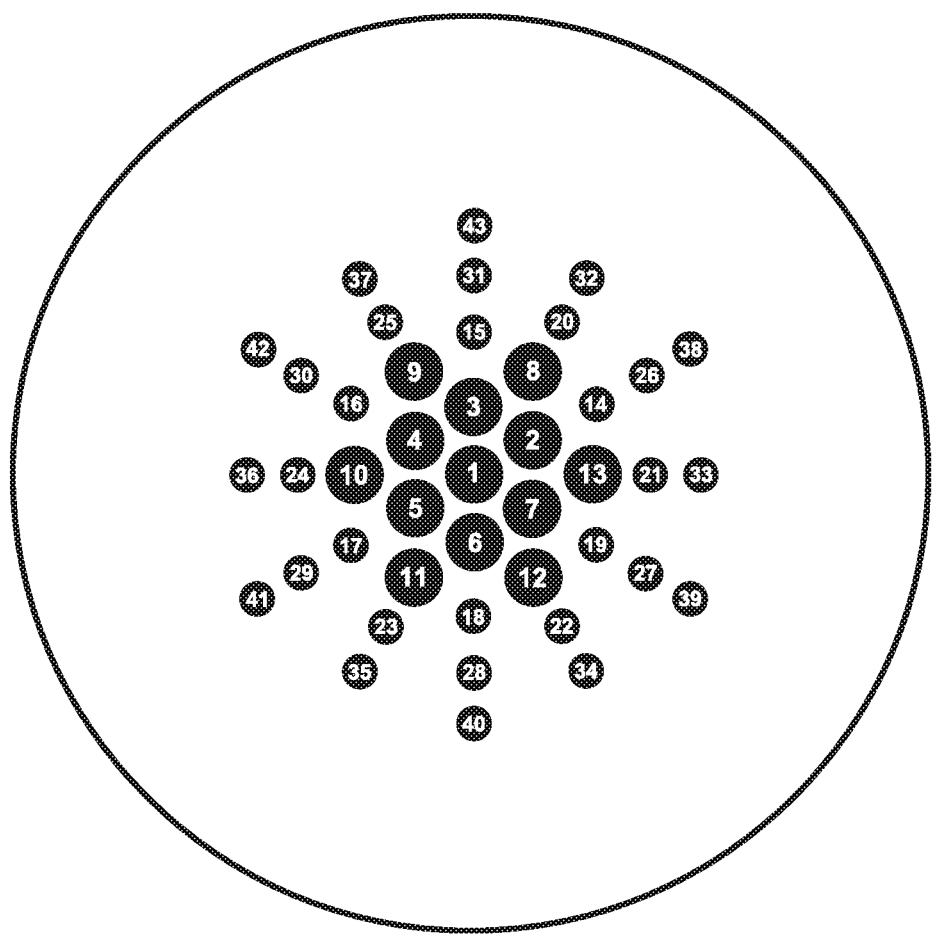
FIG. 88 shows the 43 femto projectors of FIG. 87 individually numbered.

As mentioned before, the entrance pupil of the eye also restricts the locations on the contact lens at which these tiled projectors can be placed. It is not too restrictive for the central projectors, but becomes a tighter and tighter restriction for higher visual eccentricity projectors up to the point where the pupil starts becoming too small to capture the whole display image without excessive vignetting. To see the effects of these constraints on out preferred embodiment of 13 fixed resolution foveal projectors and 30 variable resolution peripheral projectors, FIG. 87 shows one set of placement choices that satisfies the constraints while trying to keep the projectors as far apart as possible. The larger black circles are the fixed resolution projectors; the smaller ones the variable resolution ones. FIG. 88, shows the same image as FIG. 87, except this time inside each black circle there is a projector number starting with one at the center. In both figures the outer circle is the edge of the optical zone of the contact lens, about 8 millimeters in diameter. The fixed resolution projectors are less than half a millimeter across; the variable resolution projectors are less than a third of a millimeter across.

Projector Tiling Overlap

One issue that was not directly addressed in the proceeding discussions was that of building a certain amount of "redundant" overlap between the projected images of projectors on the retina. If all manufacturing and optics was perfect, no such would be needed. But in the slightly imperfect real world of optical design trade-offs and fabrication and assembly tolerances, as will be discussed in more detail later, there is a need to have a certain amount of such built-in overlap between projectors. The easiest way to think of how this effects the details of the tilings just discussed is to assume that each ring of projectors in the existing tilings has its common ring retinal magnification amount set 5 to 10% higher than it otherwise would be. The exact amount of overlap required is a trade-off between the extra costs and hard limits of fabrication and assembly technology (as well as the realities of optical design) versus the costs incurred by having to build more pixels than would otherwise be used. Fortunately the tilings described are easily amenable to such magnification modifications.

VIII.C. Pixel Tilings Details

As previously described, the projectors use hexagonal tilings of hexagonal shaped pixels. The complete shape is that of an n-group of hexagons on their ends, which looks like a single hexagon on its side. In the projectors used for the fixed resolution EndCap mapping all the pixels are the same size, resulting in a uniform tiling. One engineering driven constraint on projectors is that less hardware is used if the number of pixels semi-columns is equal to or just less than a power of two. Since an n-group of hexagons has 2·n+1 hexagons across its widest row, we will illustrate choices of n for which n is one less than a power of two: 3, 7, 15, 31, and 63.

Figure 66:
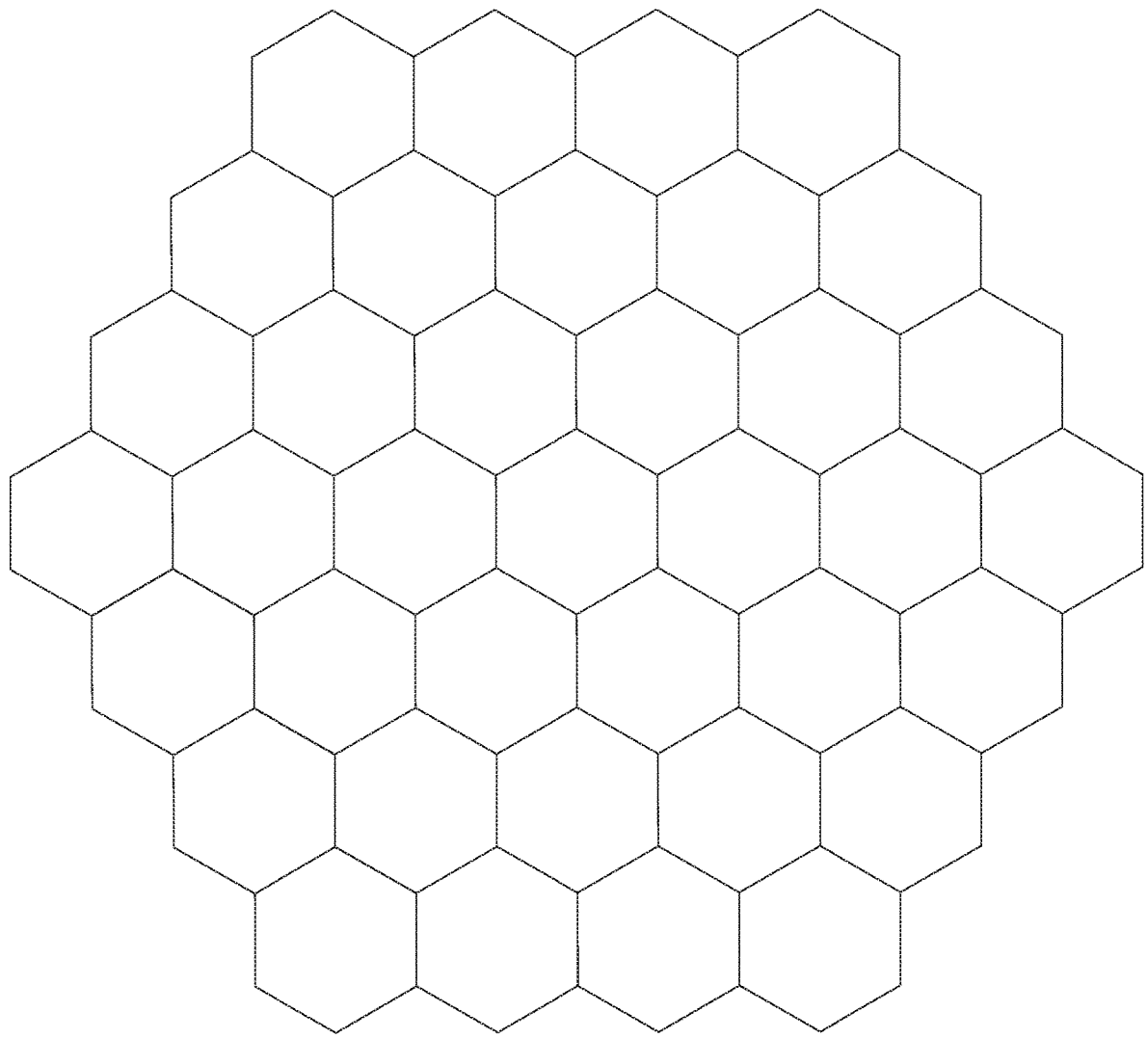
FIG. 66 shows a 3-group (7 hexagon wide) fixed resolution 37 pixel projector.

FIG. 66 shows a 3-group 7 hexagons wide fixed resolution 37 pixel projector.

Figure 67:
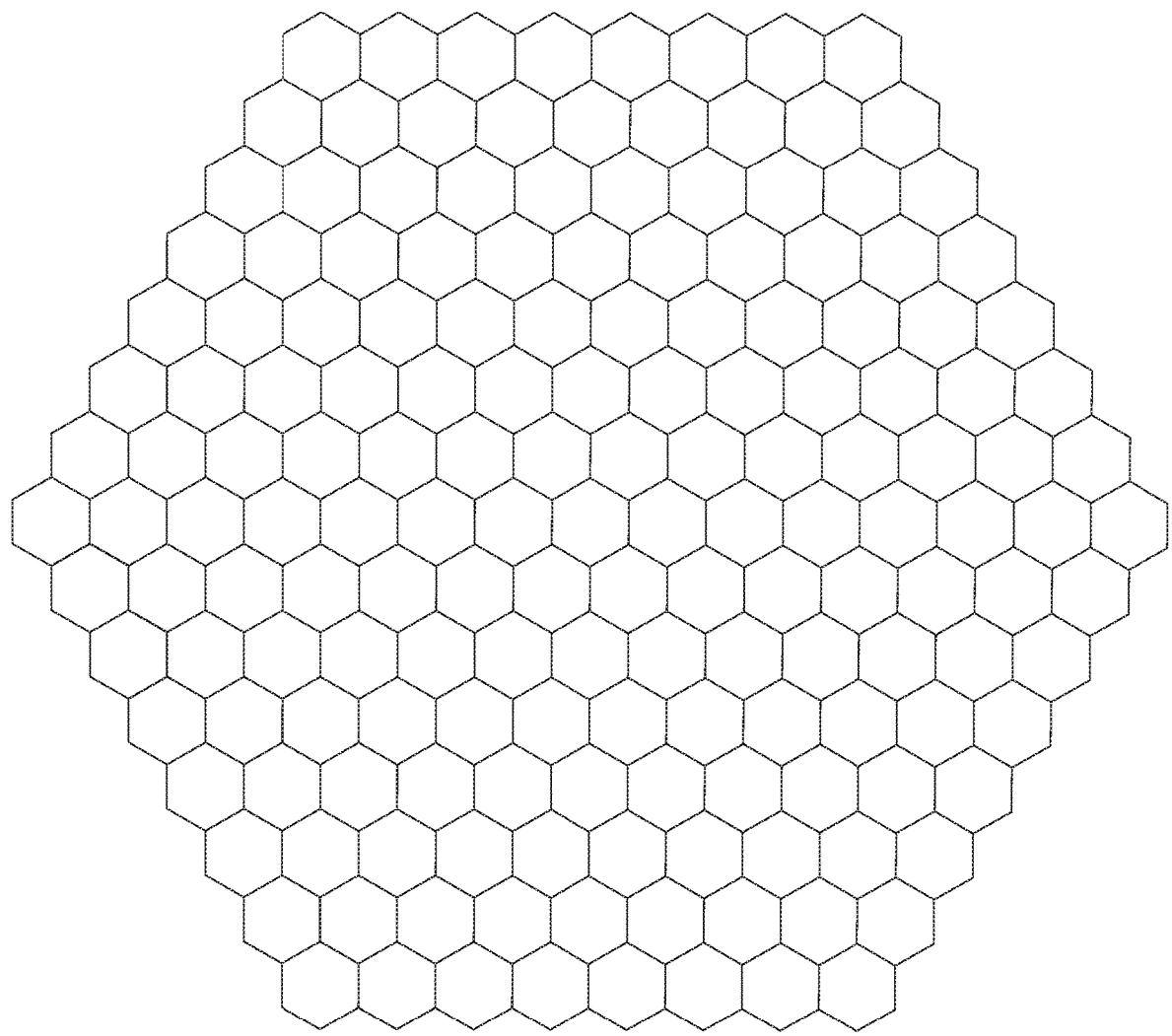
FIG. 67 shows a 7-group (15 hexagon wide) fixed resolution 169 pixel projector.

FIG. 67 shows a 7-group 15 hexagons wide fixed resolution 169 pixel projector.

Figure 68:
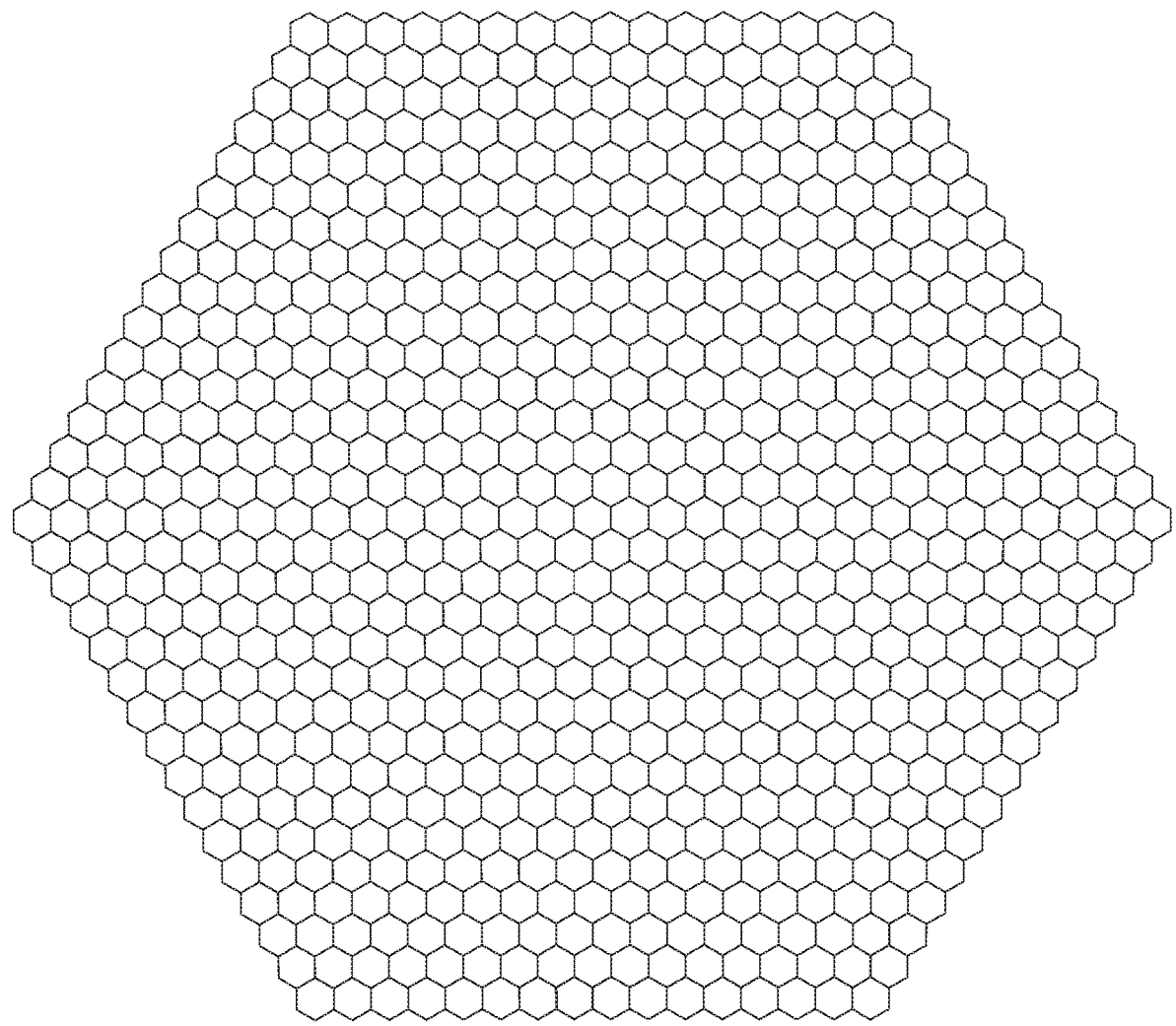
FIG. 68 shows a 15-group (31 hexagon wide) fixed resolution 721 pixel projector.

FIG. 68 shows a 15-group 31 hexagons wide fixed resolution 721 pixel projector.

Figure 69:
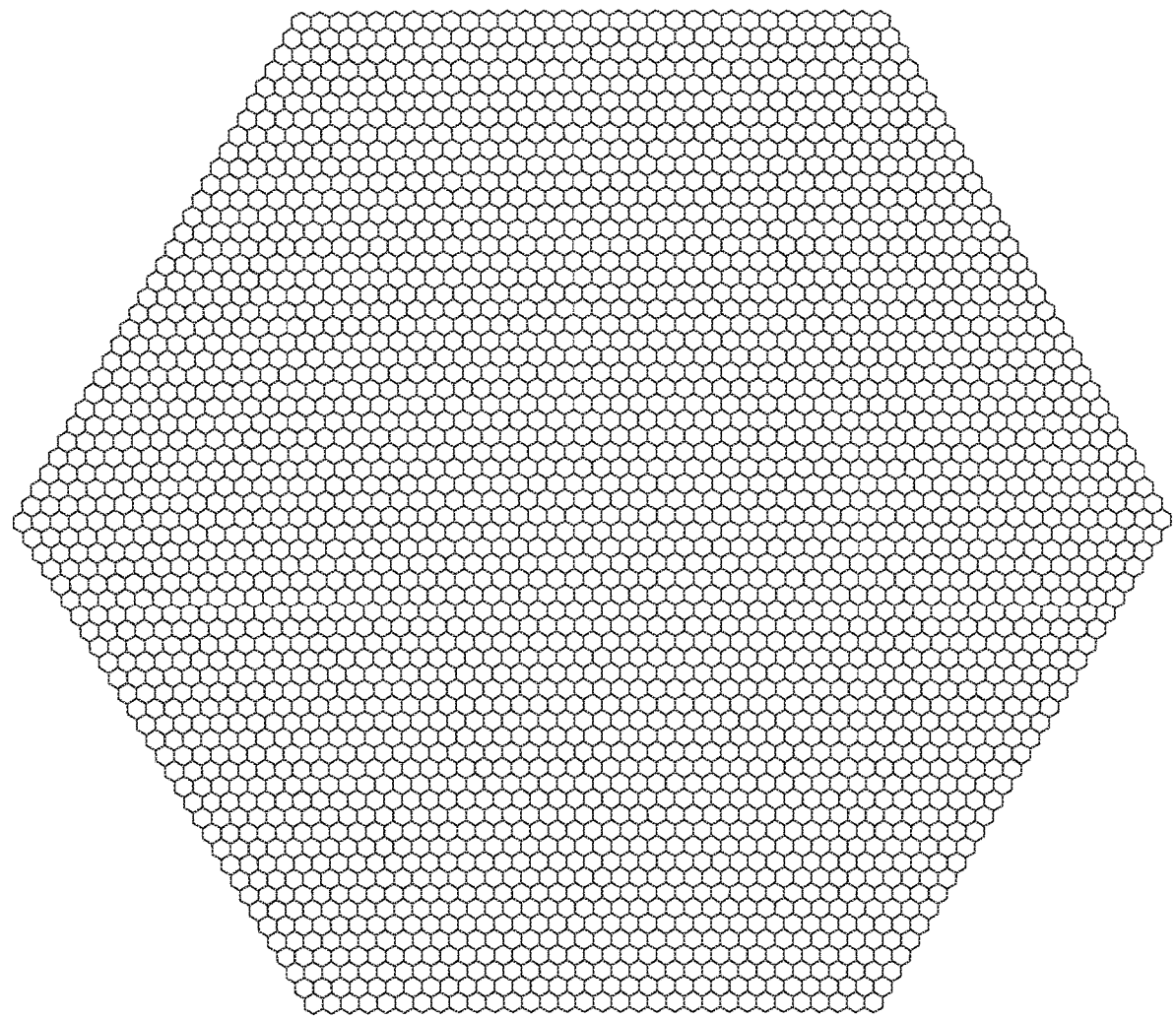
FIG. 69 shows a 31-group (63 hexagon wide) fixed resolution 2,977 pixel projector.

FIG. 69 shows a 31-group 63 hexagons wide fixed resolution 2,997 pixel projector.

Figure 70:
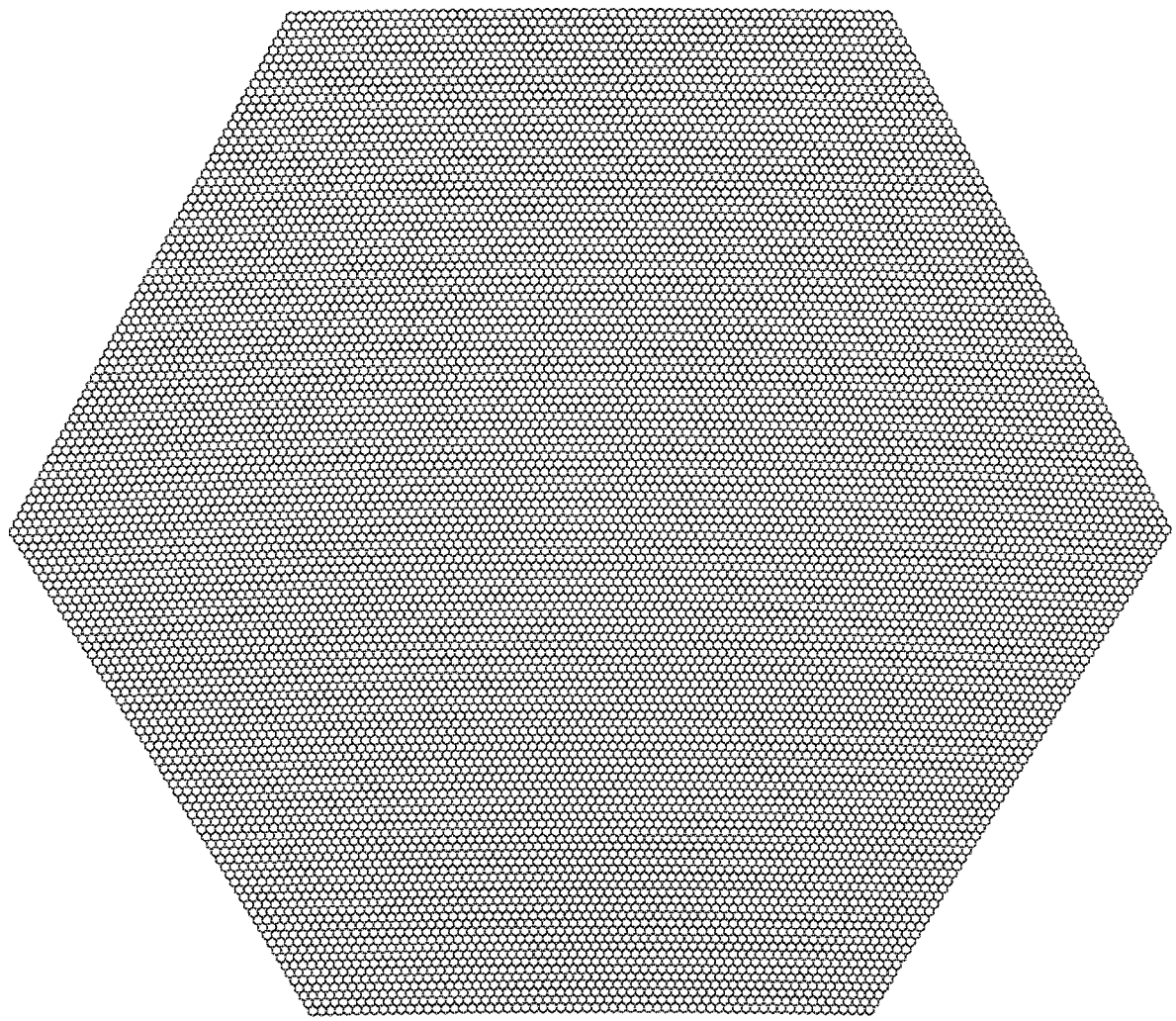
FIG. 70 shows a 63-group (127 hexagon wide) fixed resolution 12,097 pixel projector.

FIG. 70 shows a 63-group 127 hexagons wide fixed resolution 12,097 pixel projector.

Currently the 12,097 pixel projector is the choice of a preferred embodiment for the fixed resolution, foveal projectors, but this is subject to other engineering trade-offs.

For the variable resolution peripheral projectors, many times a lower number of pixels per projector is needed than for fixed resolution projectors. So we will illustrate the variable resolution projectors for values of n of 5, 10, 20, and 40.

Figure 71:
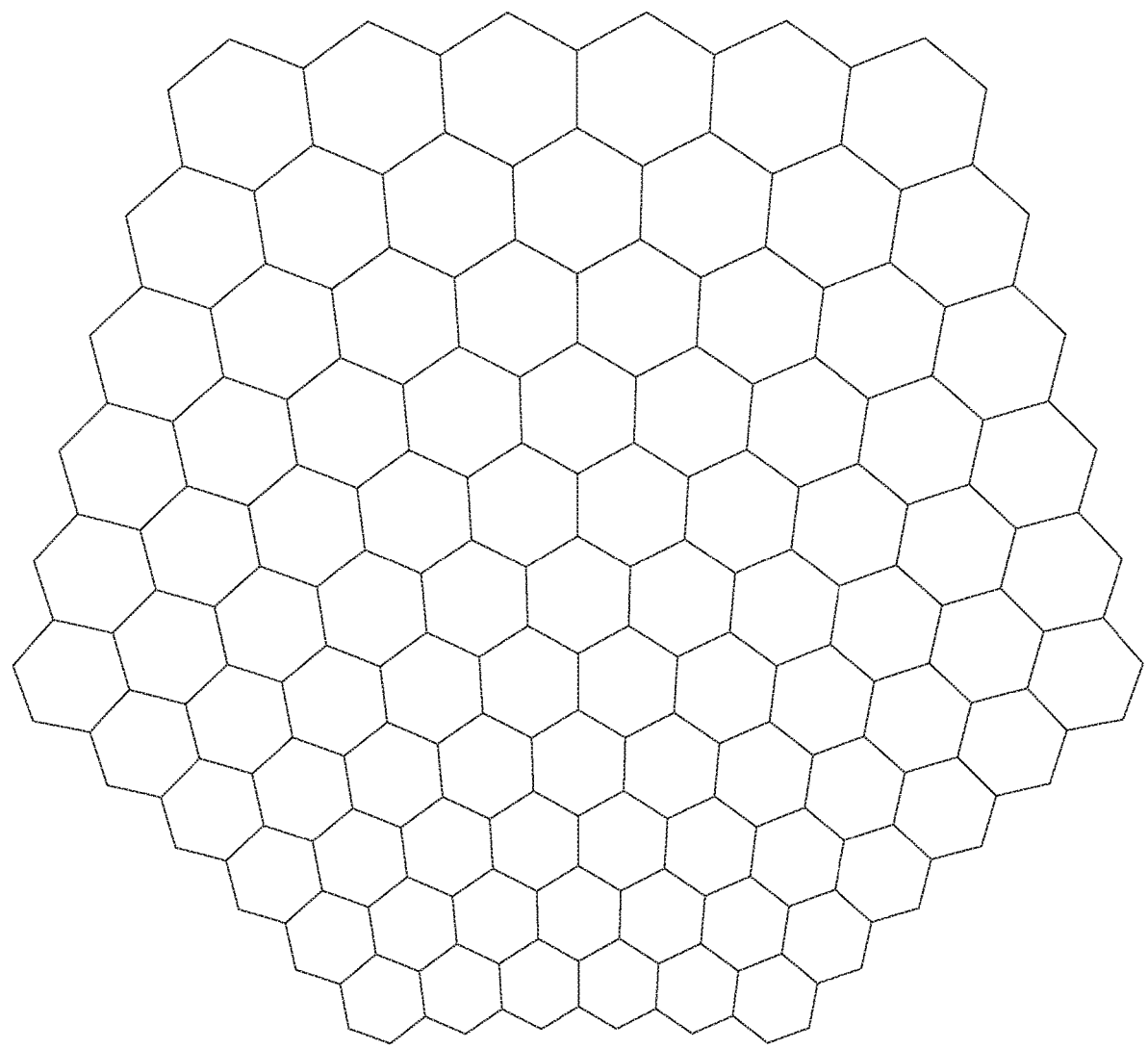
FIG. 71 shows a 5-group (11 hexagon wide) variable resolution 91 pixel projector.

FIG. 71 shows a 5-group 11 hexagons wide variable resolution 91 pixel projector.

Figure 72:
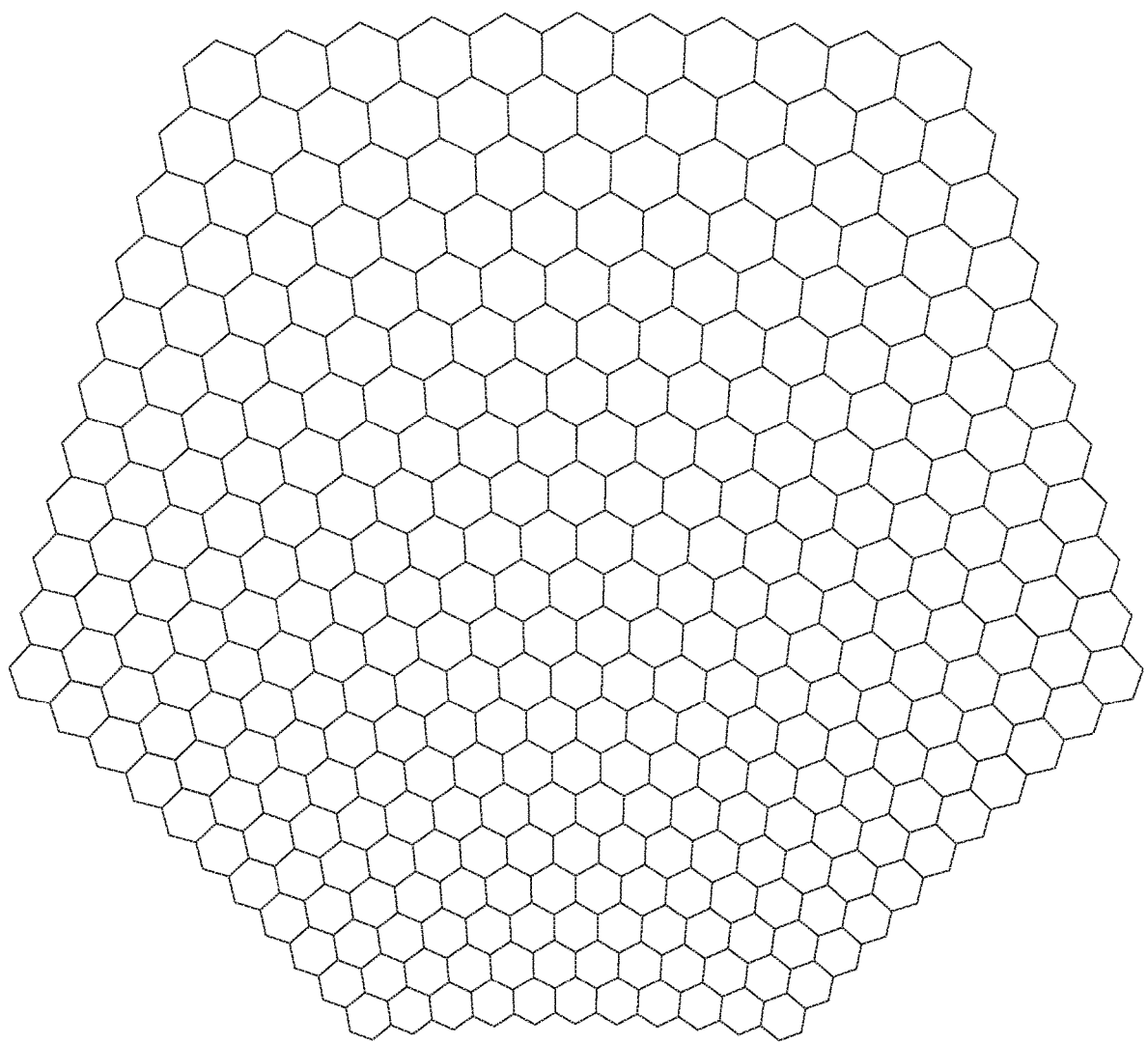
FIG. 72 shows a 10-group (21 hexagon wide) variable resolution 331 pixel projector.

FIG. 72 shows a 10-group 21 hexagons wide variable resolution 331 pixel projector.

Figure 73:
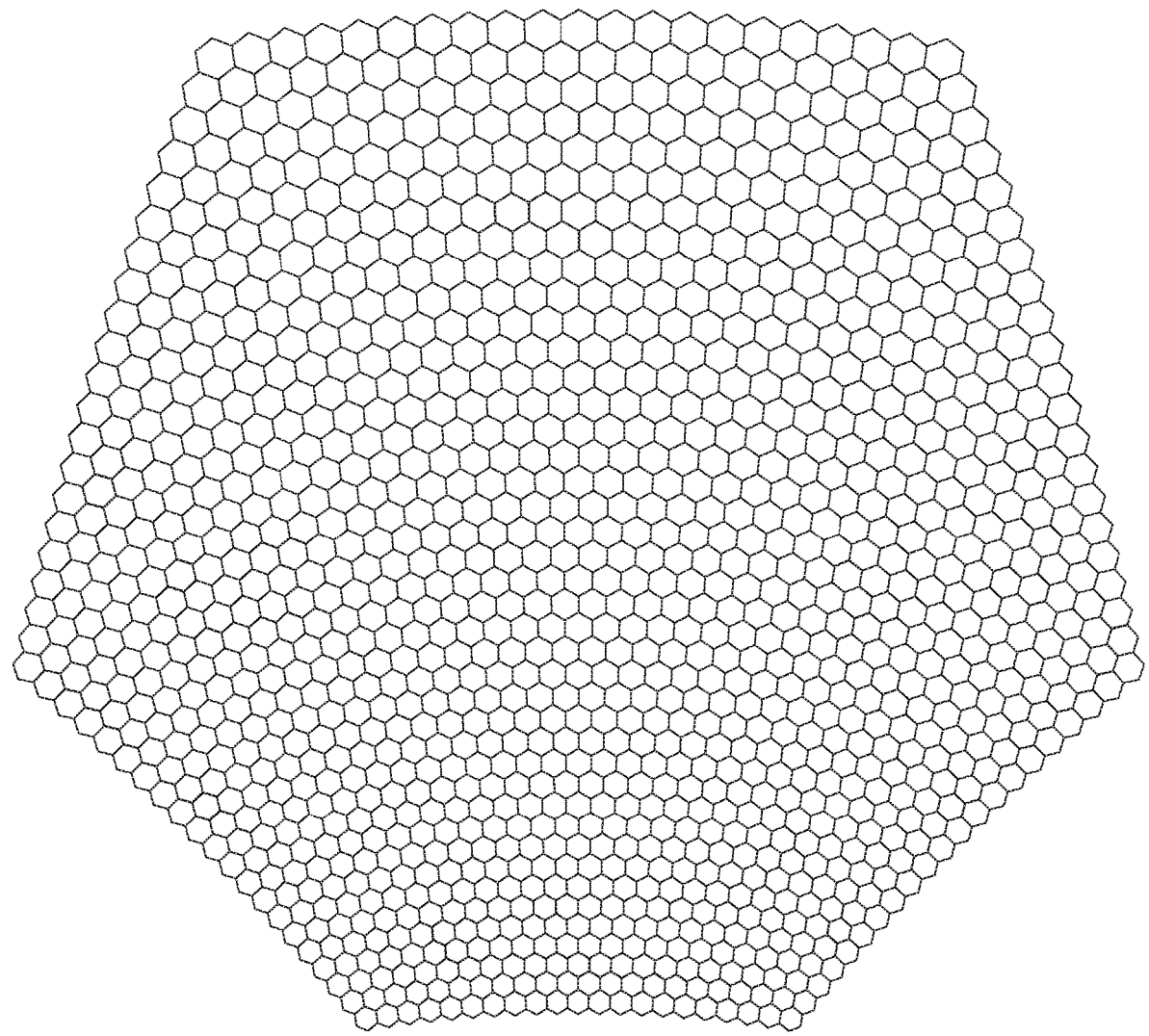
FIG. 73 shows a 20-group (41 hexagon wide) variable resolution 1,261 pixel projector.

FIG. 73 shows a 20-group 41 hexagons wide variable resolution 1,261 pixel projector.

Figure 74:
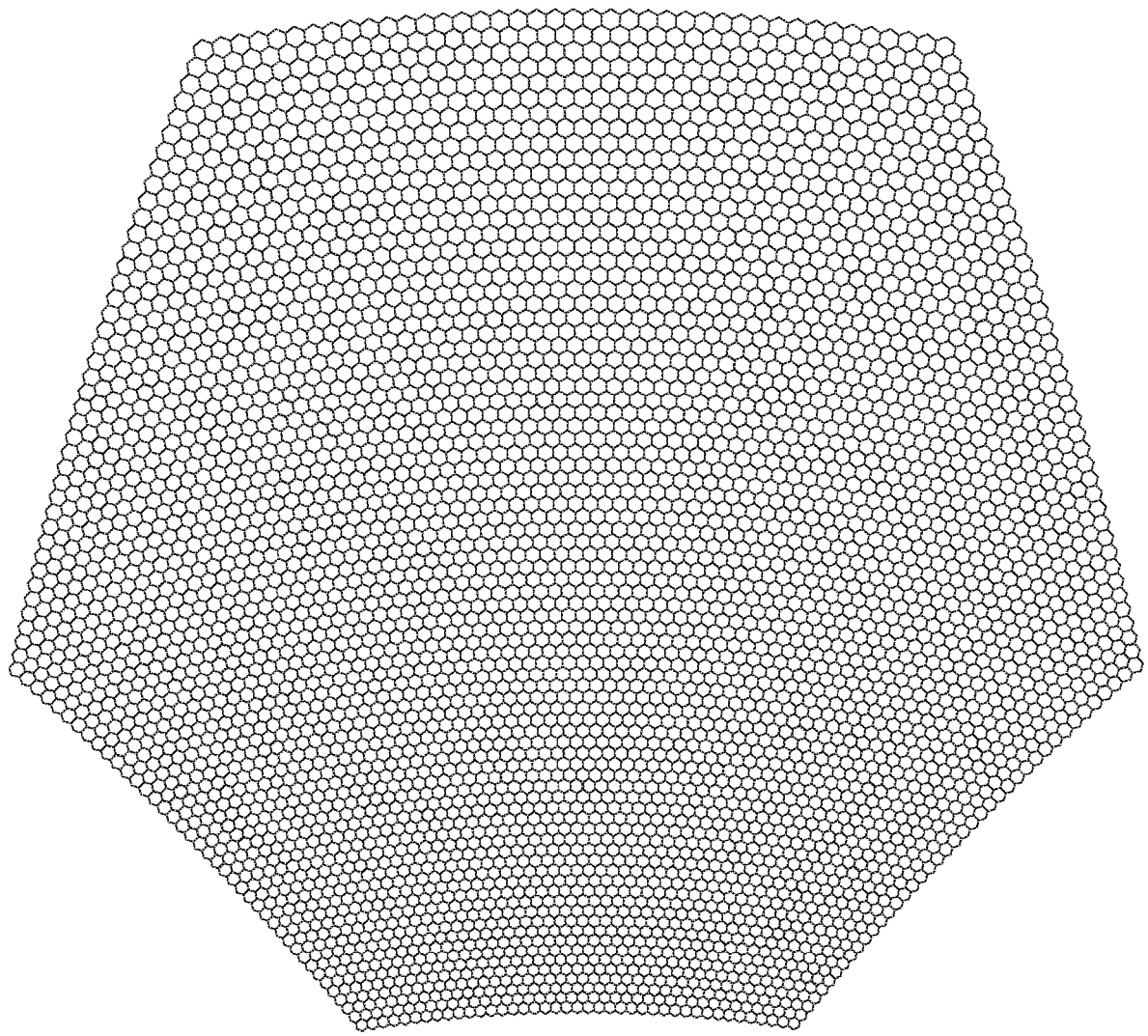
FIG. 74 shows a 40-group (81 hexagon wide) variable resolution 4,921 pixel projector.

FIG. 74 shows a 40-group 81 hexagons wide variable resolution 4,921 pixel projector.

Currently the 4,921 pixel projector is the choice of a preferred embodiment for the variable resolution, peripheral projectors, but this is subject to other engineering trade-offs.

It can be seen that the width of an individual hexagonal shaped pixel changes by almost a factor of two across height of the projector. This is one of the engineering reasons why that in general there is a constraint to have less pixels in total on variable resolution projectors than for fixed.

VIII.D. Sub-Sampling of Color for an Eye-Mounted Display

Color pixels have traditionally been one red, one green, and one blue pixel. However, the color cones of the eye are not evenly distributed: on average, there appears to be twice as many red cones as green cones, and four times as many green cones as blue cones. But there is considerable individual variation, and the different color cones are not evenly distributed. Because the individual pixels of a contact lens display are shifted with time over an average cone integration time, individual pixels can be a single color each. The color of pixels can be somewhat randomly distributed, with, for example, four red pixels and four green pixels for every blue pixel. Many other similar combinations are possible, and there doesn't even have to be a repeating pattern. The main constraint is that the pixel component generation sub-unit has to know which of the three primary colors each individual pixel in a display is.

VIII.E. Computer Graphics Real-Time Variable Resolution Rendering

There are many different techniques for rendering known in computer graphics; while they traditionally have been designed to render to (approximately) fixed resolution pixels of the ViewPlane, most can be adapted to render into a pixel space that has a quite non-linear mapping to the ViewSphere, specifically including the locally uniform resolution mapping.

One class of computer graphics rendering techniques is that of ray tracing. While traditionally rays are traced from the EyePoint through the center of each pixel on the ViewPlane, the rays to be traced can instead be formed by rays from the EyePoint through the center of a pixel mapped back to the ViewSphere by an arbitrary mapping from a ScreenSurface. In a preferred embodiment, the mapping is that of locally uniform resolution. (It is easier when the mapping preserves the pixel structure, such as OrthogonalLongitudeEccentricity mappings.) To perform anti-aliased ray tracing, additional rays at sub-pixel locations are specified and traced for each pixel.

Another class of computer graphics rendering techniques is that of incremental z-buffered rendering of (both 2D and 3D) geometric graphics primitives. Such primitives include, but are not limited to, two and three dimensional points, lines, triangles, and higher order surfaces, such as subdivision surfaces, and NURBS, as well as volumetric primitives. Additional geometric detail is often added to such primitives by use of displacement mapping of the surfaces. In the special case where the ScreenSurface is the ViewPlane, lines and triangles in 3D space project into lines and triangles on the ViewPlane. This simplifies the rendering of such primitives, as they can be rendered by simple linear interpolation on the ViewPlane. However, higher order surfaces need to be tessellated by some means into small triangles, which typically are less than a pixel in size. When rendering to more complex ScreenSurfaces, such as that of locally uniform resolution, rendering of lines and triangles cannot be correctly achieved by linear interpolation on the ScreenSurface. However, if hardware is available that can in real-time tessellate higher order surfaces into sub-pixels triangles, it trivially can do the same for planer 3D triangles. Thus the curved nature of these more complex ScreenSurfaces is no longer an issue, as once primitives have been tessellated in ViewSpace (or an equivalent space) such that the projection of the tessellated triangles produced are all less than a pixel in size on the ScreenSurface, the difference between a planer interpolation of the sub-pixel size triangle and the curved sub-pixel portion of the ScreenSurface is vanishingly small.

As an example of how such a tessellation processes into a highly variable resolution space, such as that of locally uniform resolution, would work, the example of tessellation of subdivision surfaces via subdivision will be worked out in detail.

Subdivision surfaces include those such as the rectangular one of Cattmul-Clark, and the triangular Loop model. We will describe the subdivision process recursively, though actual efficient hardware and software implementations process the work in a more efficient order, as is known to those skilled in the art. An essential element of the subdivision process is the edge subdivision criteria. Given two vertices in ViewSpace that represent the endpoints of the edge, the subdivision criteria will say whether this edge should be subject to further subdivision, or not. This is a criteria based only on the information from one edge within the surface, e.g. just the ViewSpace location and attributes of the two endpoint vertices of the edge. The limitation to this edge-only information for the subdivision criteria, e.g., not taking into account information about any additional edges that are connected to one or the other of the two vertices, allows the decision to subdivide an edge, or not, to be computed anywhere the same edge occurs, without having to have explicit links between different subdivision surfaces that may contain the same edge.

There have historically been many different edge subdivision criteria, applied either in ViewSpace or on the ScreenSurface, including maximum cordial deviation allowed, a maximum edge length allowed, etc. Here we will define two such example criteria: one is the maximum length of an edge on the ScreenSurface, the second is the maximum length that an edge would be on the ScreenSurface if its orientation in ViewSpace had been parallel to the local normal to the ViewSphere, rather than its actual orientation in ViewSpace. The second criteria keeps long thin triangles from being produced near silhouette edges of the subdivision surface, and is especially important if the tessellated subdivision surface is to then subject to displacement mapping.

The length of the edge on the ScreenSurface subdivision test can be described in detail as follows. First, the two three-dimensional vertices of an edge in ViewSpace (or an equivalent space) are mapped to two two-dimensional (2D)

vertices on the ScreenSurface (using the various equations already developed). Before taking a measure of the distance between these two 2D vertices, because many ScreenSurfaces wrap around at the ends of the u range, the two vertices need to be put into an un-wrapped space. Assuming that u1 and u2 are the u coordinates of the two ScreenSurface vertices of the edge, the following pseudo-code fragment defines the un-wrapping procedure:

if (u2>u1 && (u2−u1)>((u1+SW)−u2) then u1=u1+SW
  else if (u1>u2 && (u1−u2)>((u2+SW)−u1) then u2=u2+SW After this, the distance between the two (unwrapped) points on the ScreenSurface can be taken using the distance metric of choice, e.g. Manhattan, Euclidian, Euclidian squared, etc. This distance can then be compared to a (fixed) maximum distance threshold on the ScreenSurface: if it is below the threshold the edge will not be subject to further subdivision; if the edge is equal to or above the threshold, then the edge will be further subdivided. The test for the case when the edge length as projected as if it were oriented parallel to the local normal to the ViewSphere is a straightforward variation of the one given. Although the example threshold of "being smaller than a pixel" has been used earlier, in the general case represented here, the length threshold can be set to any of a range of values, including those actually larger than a single pixel.

However, knowing which edges of a quadrilateral or a triangle should be subject to further subdivision is only the starting part of the algorithm to decide how to subdivide the quadrilateral mesh or a triangle mesh. Fortunately, and this is a great advantage of the subdivision test on the ScreenSurface as described, the details of the mesh sub-division process is the same for the case when we are using the locally uniform resolution mapping as when using the more historical ViewPlane mapping, and thus need not be further detailed here. The resultant images, however, will be quite different. Clipping of subdivision surfaces works a bit differently when using highly variable resolution, as while most portions of the subdivision surface outside the truncated view frustum (or, more accurately, truncated view cone) can be discarded before being subject to much subdivision, some portions will need to be subdivided down to the pixel level to support adjacent portions that are within the view cone. Similar comments apply to the front and rear clipping planes.

It should be noted that more sophisticated subdivision surface primitives include additional subdivision surfaces for texture coordinates, etc. These, however, can be extended in the same way as the positional subdivision was.

In general, any tessellation process that doesn't utilize equal-spaced tessellation, will have a more complex job in computing local derivatives of various quintiles, such as texture address derivatives.

Once a subdivision surface (or even just a planer 3D triangle) has been sub-divided into sub-pixel size triangles, the individual vertices of the triangle, known as microvertices, are subject to the standard programmable pixel shading process, which may first include displacement mapping.

Once the (possibly displacement mapped offset, and possibly then subject to more tessellation to get the microtriangles back down below the desired size) vertices of the sub-pixel size triangles have had color, depth, alpha, and possibly other attributes assigned, the individual triangles can be linearly interpolated on ScreenSurface to the sub-pixel locations of the local super-sample points in the pixels touched, and the results z-buffered into each sample that ends up being covered by the triangle. (When supporting motion blur and/or depth of field, the algorithm is a bit more complex, but otherwise similar to that well known in the art.) The resultant super sample buffer will itself reflect the highly variable resolution of the highly variable resolution mapping involved. But this is the desired results.

The above has described the tessellation via subdivision of subdivision surfaces; similar approaches can be applied to the different tessellation approaches of other higher order surface types and of volumetric primitives.

While the above has described the general case of tessellation of higher order surfaces, the tessellation of simpler geometric primitives, such as curved lines, straight lines, points, and anti-aliased versions of these is a simplified sub-set of the above process.

Another alternative class of rendering algorithms is similar to the one just described, but the programmable shading portion of the process is deferred until after all the z-buffering has taken place. This has the advantage that only visible pixels have to have the programmable shading subprogram run on them, but at the expense of fairly extensive bookkeeping to keep track of the shader context as triangles are produced for z-buffering. This general technique is known as hardware deferred shading [Deering, M., Winner, S., Schediwy, B., Duffy, C and Hunt, N. 1988. The Triangle Processor and Normal Vector Shader: A VLSI system for High Performance Graphics. In Computer Graphics (Proceedings of SIGGRAPH 88), 22 (4) ACM, 21-30.].

The final stage of the rendering process is the conversion of the super-sampled buffer into discrete pixel component values for the target display device, described in the next sub-section.

VIII.F. Generation of Discrete Pixel Component Values from the Super-Sample Buffer Once a sample buffer has been generated for a whole scene of rendering, the sample buffer is converted to discrete pixels for display by application of a convolution of a pixel filtering function centered on where each desired final pixel is to be generated from, with the extent (size) of the filter proportional to the area of the final pixel, though the constant of proportionality depends on the choice of filter. The simplest filters are square box filters, with the extent set to be the same as the final pixel size. (For hexagonally shaped pixels, a hexagonally shaped "box" filter is the most appropriate, but a circular filter will work well too.) The "theoretically" most correct filter is the infinite sync function, which has an infinite extent. The highest quality filter in common use in software renderers is either an 11×11 or a 9×9 pixel size windowed sync filter. The highest quality filter implemented in hardware is generally considered to be the 4×4 Mitchel filter, though the hardware involved can implement any circularly symmetric 5×5 filter [Deering, M., and Naegle, D. 2002. The Sage Graphics Architecture. In Proceedings of SIGGRAPH 2002, ACM Press/ACM SIGGRAPH, New York. Akeley, K., Ed., Computer Graphics Proceedings, Annual Conference Series, ACM, 683-692.]. A 5×5 filter extent is needed in the general case to implement a 4×4 filter when the center location of the final pixel to be produced can be at a location other than the center of a super-sampled pixel.

Such convolution filters are seen as simultaneously performing two functions: an interpolated re-construction of the underlying image function, and a low-pass band filter to remove frequencies higher than are supportable by the Nyquist rate of the final pixel pitch. In the natural world, no such low pass filter occurs before the eye, why? In the natural world, (primarily) the limited quality optics of the eye only pass spatial frequencies below or near the peak Nyquist rate of the underlying photoreceptor mosaic. This doesn't work for most manmade displays, as in general the distance to the viewer, and thus the spatial frequencies produced on the retina, are not known. However, for eye-mounted displays (and head-mounted displays) the distance size that display pixel subtend on the retina is known. For head-mounted displays, however, which portion of the retina is being displayed to generally isn't known, so the relative size of the display pixels to the retinal receptor fields isn't known. But this is known for eye-mounted displays. This means that, in principle, the amount of low-pass spatial filtering that will be caused by the (remaining) optics of the eye (as well as the optics of the projectors) can be known. Blindly applying a traditional anti-aliasing filter can result in an over filtering of the image displayed. Practically, the spatial low pass filtering caused by the eye's (remaining) optics is individual specific, though it is easily determined: to a first approximation it is given by the viewer's maximum acuity (e.g., 20/20, etc.). Thus, depending on the relative size of the displayed pixels to the viewer's spatial frequency perception limit (optically dominated in the fovea, midget ganglion cell visual field center size dominated in the periphery) the appropriate amount of spatial frequency filtering that should be performed by the super-sampled pixel region to display pixel value can be computed, and used to drive the size (and shape) of filtering actually performed, as parameterized by visual eccentricity, of super-samples to final display pixel values. Note that in the limit when display pixels are sufficiently smaller than the midget ganglion cell visual field center size, the correct filter can be the box filter! Again, in practice, the trade-off between aliasing and sharpness is an individual preference, and user level "sharpness" controls should be available to allow the individual user to tune it to personal taste. There is also a content bias to this setting; for antialiased lines, people prefer a lower spatial frequency cut-off, e.g., nearly complete elimination of "jaggies," but at the expense of a slightly blurrier line, whereas for text, the preference is for a higher spatial frequency cut-off that preserves sharpness, e.g., serif's in fonts.

VIII.G. Computer Graphics Real-Time Rendering of Arbitrary Pre-Inverse-Distortion of Pixels General classes of computer graphics rendering algorithms leave their results as a super-sampled image on a ScreenSurface. The final conversion of this data for output to the video display device is a convolution filter that takes in a region of samples and outputs a color component for display. In the simple case, the location of the center of this region is just a simple x-y scan of the sample buffer. In a more complex implementation, the location of the center of each region can be perturbed by a limited amount specified by another function unit. This function unit may be interpolating a spline function, or directly looking up a x-y perturbation value for each pixel to be output to the display. In this way, arbitrary pre-inverse-distortions of the final anti-aliased output image can be performed. Because at least some of the distortions will be slightly different for each color component value, each color component needs to have its own unique perturbations supplied to it. In the special case in which there is only one color component per pixel displayed, only one perturbation per output pixel need be computed, but it has to be the perturbation that is correct for the particular color component presently being displayed.

Technically, if the pre-inverse-distortion involves a change in scale, e.g., a magnification or minification, then the size of the region of super-samples and the associated anti-aliasing convolution filter needs to be changed in a like way. However, if the extent of the change in scale is limited to a few percent, such additional changes may not affect the results sufficiently to be justified. In general, perturbed convolution units can be constructed in either way.

VIII.H. Using Computer Graphics Real-Time Rendering of Arbitrary Pre-Inverse-Distortion of Pixels to Compensate for a Varity of Optical and Manufacturing Based Distortions The two lens per projector display mesh design described will have at least two types of residual optical distortion inherent in the design, and several more likely sources of distortions due to un-avoidable tolerance errors inherent in the fabrication and assembly manufacturing process. The impact of all of these errors on the image quality at the retinal surface can be minimized or eliminated by use of the previously described pre-inverse-distortion of pixels by the computer graphics rendering sub-system. This sub-section will list these likely and potential sources of distortion.

Residual chromatic aberration inherent in the optical design: the simple two lens design has a residual chromatic aberration component larger than that of most commercial optical designs. The "normal" fixes, e.g., use of doublets, or GRIN lenses, and are generally not practical for the small amount of projection optics space available. However the residual chromatic aberration can be greatly reduced by the appropriate color component specific pre-distortion of the image by the sample filtering sub-system.

Residual spherical aberration inherent in the optical design: the simple two lens design has a residual spherical aberration component; this appears as pin-cushion or barrel distortion on the image projected onto the surface of the retina. The amount of such distortion is limited because the display surface is spherical (the inside of the retinal sphere), but some remains because the image production device is (necessarily) planer. Again, this distortion can be greatly reduced or eliminated by the appropriate pre-distortion of the image by the sample filtering sub-system.

Error in the amount of magnification produced by the optics due to optical lens fabrication variation: the projector lenses as actually fabricated will differ in the amount of magnification produced on the retina from the ideal design, due to un-avoidable tolerance errors induced by the fabrication process. There is a trade-off between the cost of fabrication and the magnitude of such errors caused by the fabrication process, and there may be a lower practical limit to how low the errors can be reduced to. By building more pixels on the display device than needed in the ideal case, additional magnification can be provided to compensate to any lost in the fabrication process, again through the appropriate pre-distortion of the image by the sample filtering sub-system. In this case the pre-distortion is just to spread out the image to be displayed over more pixels on the display than would otherwise be the case. Compensating for too much magnification caused by lens fabrication issues can be corrected for in the reverse way.

Errors caused by offset in the lens(es) center position due to either the fabrication or assembly process: slight decentering of the optics as built will cause a corresponding offset of the position of the displayed image on the retina. Once again, by having extra display pixels available at the outer edge of the display device, these sort of errors can be greatly reduced or eliminated by the appropriate pre-distortion of the image by the sample filtering sub-system. In this case the pre-distortion required is the appropriate (simple) shift of where the image is displayed on the display device, though care must be taken to make sure that the desired region of the retina is still projected to.

Errors caused to tilt in the lens(es) due to either the fabrication or assembly process: slight tilt of the as built optics will cause a corresponding elliptical scaling of the displayed image on the retina. Once again, these sort of errors can be greatly reduced or eliminated by the appropriate pre-distortion of the image by the sample filtering sub-system. In this case the pre-distortion required is the appropriate non-uniform scaling of the image displayed on the display device.

Other errors due to either the fabrication or assembly process: There are other types of distortions of the image as displayed on the retina due to manufacturing issues. In general, most all of these sort of errors can be greatly reduced or eliminated by the appropriate pre-distortion of the image by the sample filtering sub-system.

Flatness of field and Vignetting: Another common distortion of optical system is an un-evenness in the intensity of the image at all pixels. In some cases where there are pupil limits within the overall optical path, vignetting can occur. This class of errors can be greatly reduced or eliminated by the appropriate emphasis of the brightness of individual pixels of the image by the sample filtering sub-system. In general, there will be a per display pixel intensity correction factor applied. This can include not only correcting for vignetting effects, but also can per pixel correct for manufactured variations in actual pixel intensities produced by a given physically constructed pixel, as well as correct the intensity of light output from variable resolution pixels to the correct values.

"Feathering" between the edges of adjacent projectors: this is the problem in matching the edges of adjacent projectors while also compensating for all of the above optical distortions. While the appropriate pre-distortion of the image to be display may effectively eliminate all of the potential optical distortions described, the shape of the overall projected image and of the individual pixels on the retina will still be distorted relative to the "ideal." The appropriate corrected pixel display values will be displayed, eliminating the effect of the distortion, but the distortions from one projector to its neighbors will not in general be the same. Thus two projectors that share an edge will not meet at perfect pixel boundaries. "Edge feathering" is a technique that addresses this problem. Here, once again, the display devices are assumed to be slightly over-provisioned in pixels, so that there will always be at least a one pixel overlap between the displayed image on the retina of one projector to any projector that shares an edge with it. By pre-computing how much each pixel contributes to the overlapped area, each pixel component value can have its intensity diminished such that the overall intensity contributed by both pixels to the overlap is similar to what the intensity should had been if only one pixel was displaying to the area. The intensity is "similar" because each pixel also has to display part of its area to a non-overlapped portion of the retina. While in some cases this "feathering" may take place over a number of pixels of overlap, to reduce the amount of over-provisioning of pixels in the display device, the feathering can be reduced to nearly a single pixel of overlap. There are several additional techniques to help with the overlap. First the overall display rate is higher than the light integration time of the cone cells, so that the overlapped pixels will be displayed several times over the time interval that the cones are integrating light. This means that because of (likely) tracked slippage of the contact lens on the cornea (for a contact lens based eye mounted display), the retinal location of the overlap will change several times, reducing its effect. Another effective technique is the use of sub-pixels in the region of the display near the edges. Turning on and off sub-pixels allows for closer matching of the pixels between two adjacent projectors before feathering is applied. At the same time, because such sub-pixels are individually addressed only for the outer edge of the display device, the amount of pixel (and sub-pixel) data that has to be sent to the device is only slightly increased. Finally, while the vast majority of overlapping pixels occur on the boundary edge between just two projectors; at the corners where three projectors meet in a hexagonal projector tiling, or four projectors meet in a rectangular projector tiling, three (four) projector pixels have to all be feathered together. The feathering intensity reduction can be handled by the same super-sample region to pixel component sub-unit that performs the pre-distortions of the image, because it generally will have knowledge of where the overlapping edges between projectors are.

The general solution to producing the desired high quality image on the surface of the retina consists of four parts. First, limiting the maximum amount of errors by appropriate design of the optical components, and tight tolerances in the fabrication and assembly process. Second, the over provisioning of pixels (and optical field area) in the display. Third, the accurate per-manufactured device identification of the combination effect of all the errors present. And finally, the appropriate programmed pre-distortion of the final pixels to be displayed by the super-sample region to pixel component sub-unit. Important note: all the required pre-distortions can be combined together into a single distortion vector per output pixel component. As mentioned before, this distortion field can either be explicit per pixel component location center of convolution offsets, or based on some form of spline interpolation or a similar process. The later can be performed on hardware in real-time from a relatively small number of distortion components, small enough that they can be stored on chip, an explicit vector for every pixel to be output requires enough storage that it may be better streamed in from external RAM every sub-frame.

There is another source of "error": as described before, there is individual variance in the retinal radius of people's eyes. (E.g., each eye in the pair are generally quite similar, but can differ in size from other individuals.) This will show up as a different magnification of the projected images onto the surface of individual's retinas. Some of this is corrected for by individual specific corrective optics in the final portion of the projector optical design, but there will still be some residual error in magnification. If the error were large enough, there could also be an error in focus, but that is generally not the case. The residual individual specific magnification error can be corrected for by the same techniques as have been previously described for other classes of optical errors, once the magnitude of error has been empirically determined.

We have used the term "pre-distortion of pixels" (actually, pre-inverse-distortion) as a general mechanism for correcting for inherent optical design limitations, errors caused by the need for some level of tolerance in the fabrication of optics and other parts, errors caused by the need for some level of tolerance in the mechanical assembly of optics and other parts, errors caused by the need to abut different projector's images on the retina, and errors caused by using the same optical design for people with slight individual variation in eye size, etc. Only errors purely of intensity are corrected for by a companion correction. We so far have defined the method to cause desired distortion in pixels as the appropriate convolution operation on the higher resolution (but also highly aliased) sample buffer, as produced by many computer graphics rendering algorithms. This is indeed the preferred embodiment, as it produces the highest quality final pixels. However, there are simpler, but lower quality methods of producing distorted pixels. Rather that starting with a super sample buffer, one might instead have an image at the pixel level. One could then still compute the intensity value for pixel components that would appear at a sub-pixel offset between the original pixels either via convolution, or simple interpolation (which is really a simplified form of convolution). The site of the interpolated pixels can also be approximated, allowing an alternate mechanism for matching the inherent variable resolution of the retina. Indeed even when the method of convolution of a super sample buffer is employed, the original super-sample values may have been generated by traditional texture mapping techniques from a texture that was a fixed resolution pixel image, such as a frame of incoming traditional video. All of these methods of producing the final pixel component intensity values are subject to trade-offs in design, and compatibility issues with existing content.

VIII.I. Issues of Accommodation and Presbyopia

So far all the optical errors have been passive errors, and thus the corrections can be performed by "passive" mechanisms, e.g. the rendering pre-distortion process. There is an active source of optical changes that it would be desirable to correct in future versions of eye-mounted displays. The source is changes in the focus of the eye's lens due to accommodation. The effects are different in the two optical paths: through the normal outside world imaged onto the retina by the bulk contact lens (independent of any images being displayed), and the displayed virtual image through the optics of the display projectors. As described so far, the virtual image produced by the display will be in focus at a relatively fixed distance from the observer. Due to being a stereo display, portions of the image will be closer or further away than the plane of perfect focus. This is a general issue for most stereo display systems. In an individual with advanced presbyopia, this is not a problem, as they have effectively only one distance at which objects will be in focus. Their problem is the general problem of those who have presbyopia: real world objects at different distances than the single plane of perfect focus will be relatively out of focus; this can only be changed by use of reading glasses or bifocals. In an individual with little or no presbyopia, the accommodation mechanism ensures that when they converge their eyes on portions of the virtual display in front of or behind its plane of perfect focus, their eye's lenses will change focus and cause the virtual image to be out of focus at such points, though real world objects at such locations will be at the correct focus.

For individuals with little or no presbyopia, if the display projectors optics had some ability to change the distance at which they are in focus, then by observing the vergence angle between the two eyes, the virtual image being displayed could be made to come into optical focus at the same distance that the individual viewer's eyes are dynamically focused. (Technically the renderer should only render sharp images for those portions of the virtual world that is relatively near the current dynamic plane of focus; objects further away to either side should be rendered as blurry to match what happens in the physical world.) This does the trick for non-presbyopic individuals. Because the lenses in the currently proposed preferred method projectors are so small (less than half a millimeter across), it is quite feasible for such changes in projector focus to be caused by either piezoelectrical elements, or MEMS elements built within the projector. Other methods include those that directly affect the curvature of the projector lenses.

To improve life for individuals with presbyopia, the opposite is needed: the focus through the optical path through the bulk contact lens needs to be slightly changeable in focus. Since the light from the physical world that forms images on the retina is that which passes through the regions of the contact lens between the display projectors, if focus altering elements are placed between the display projectors, then again by observing in real-time the vergence angle between the individual's two eyes (which any eye-mounted display has to do anyway), the appropriate correction of focus can be dynamically applied to the through the bulk lens optical path. This "cures" presbyopia even when no virtual image is being displayed! Again because of the relatively small size of the lenses involved that would be placed between the display projectors, either piezoelectrical elements or MEMS elements should be able to cause the desired range of dynamic focus.

In the most general case, if the range of diopters of focus that can be dynamically programmed into the bulk contact lens path is large enough, it is possible to have programmable contact lenses. This would be a solution for people with either myopia or hypermetropia. This would be a truly "one size fits all" vision device. Given the ability of a contact lens display to directly image the surface of the retina, such devices could also be auto-prescribing. You put them on, and they just "work." However, given the consequences of failure, especially while an individual is driving a motor vehicle, any such mechanism may include safety locks and features to enhance reliability.

IX. Physical Construction of the Display Mesh

Terminology

In both the technology of integrated circuit chips, and display devices, their ambiguities in terminology. This section more precisely defines what certain terms are meant to mean in this document.

Definition of term: integrated circuit
Definition of term: IC

An integrated circuit (or IC) is generally a single physical object onto/into which a large (to very large) number of electrical circuits have been assembled. While traditionally electrical circuits are thought of, today the circuitry can also be optical and/or mechanical. And the mechanical circuits (such as MEMS) doesn't move just small portions of solid objects, liquids can be moved (or induce movement) as well. Optical circuitry can not only either receive or produce light (or more general electrical magnetic radiation), but also process light directly. Will the most common substrate for ICs is silicon, a variety of other materials, such as Gallium Arsenide, are in use today. And even though the substrate may be comprised of one material, during circuit fabrication, other materials, such as aluminum, or light emitting organic compounds, are frequently deposited on top of the substrate material.

Definition of term: die
Definition of term: bare die
Definition of term: passivated die
Definition of term: hermetically sealed die The single individual IC physical object not including an additional packaging is commonly called a die, or a bare die. It is common for the top and sides of a die to be covered with a protective coating to insulate the sensitive materials of the electronics from the negative effects of oxygen, water, and other possible harmful containments. Many times this encapsulation meets a technical definition of hermetic sealing (simplified meaning protected from air or gas), in which case the die can be considered a hermetically sealed die. Here the term bare die will be used to always have these meanings, implicitly including some form of hermetic sealing when this is required in context. It should be noted that many forms of such sealing can be optically transparent.

Definition of term: wafer
Definition of term: IC wafer

Typically integrated circuit die are not fabricated one at a time, but instead a large number of them are fabricated at the same time on a larger (usually circular) portion of the substrate material called a wafer, or an IC wafer. After (most) fabrication, the wafer is diced up into individual (usually identical) rectangles (or other shapes) which are the bare die.

Definition of term: dicing
Definition of term: diced

While historically the processes of dicing an IC wafer into individual die involves cutting the wafer up along rows and columns, producing rectangular shaped die, it is now possible for individual die to be further trimmed into other shapes, such as hexagonal or octagonal. (Hexagonal is a common shape presently for high power LED die.)

Definition of term: wafer thinning
Definition of term: die thinning

Because wafers are by definition much larger than die, e.g. 6 to 12 to 18 inches in diameter, they usually start out as a fairly thick piece of the substrate material (0.4 to 1.1 millimeters) just for structural support reasons during fabrication. But the active electrical circuitry is contained only in the top two dozen microns or so of the wafer. For various different reasons, this can be too thick. One example is when an optically transparent integrated circuit is desired, such as a micro LCD. Another is when it is desired to place the electrical interconnects to the die on the rear side of the die. Other times there is very little space for the integrated circuit. In all these cases, a much thinner die than standard can be achieved by "thinning" excess material off the rear, allowing final thicknesses to be in the 20 micron range. While the is commonly called wafer thinning, and the thinning can be achieved at the wafer level before dicing, thinning of the individual die after dicing, or die thinning, is also possible.

Definition of term: chip
Definition of term: IC chip
Definition of term: integrated circuit chip
Definition of term: packaged chip When an integrated circuit is wired into and sealed into an exterior package, the complete assembly is commonly referred to as an integrated circuit chip, or an IC chip, or a packaged chip, or just a chip. One has to be careful with the terminology, such as with the phrase "silicon chip", which usually means the completely packaged part, but in other cases might refer to just the bare die. Another case is multi chip module, which multiple bare die are wired into and sealed into a single package.

Definition of term: multi chip module

A multi chip module is the term used to describe a package of integrated circuits in which the package contains more than a single bare die. Thus the use of the term chip in the phrase is misleading. Usually the package contains a miniature printed circuit board that the individual bare die are wired to. In this way, the internal die can be pre-wired to each other as needed, reducing the number of external wires on the package. Modern 3D stacking technology allows one or more bare die to be stacked vertically on top of another, or via an interposer layer. In this case the interposer layer replaces the function of the miniature printed circuit board.

IX.A. Material Considerations

There are issues of construction material properties in building a contact lens display. On one hand, the overall contact lens must have good oxygen permeability, but on the other, the surfaces of the optical elements and their placements have to be ridged. In one extreme, it is possible that some amount of flexing can be tracked in real-time and corrected for (preferably by rendering, but also potentially by mechanical effects such as piezoelectric and/or MEMS). An easier approach would be to have the optical elements and connections between them made out of a fairly ridged material, but with holes in the ridged material, and then have the rest of the contact lens be constructed from a less ridged but more oxygen permeable material. The ridged portion, which we will refer to as the display mesh, will then also serve as a structural skeleton that will keep the less ridged surrounding material from flexing much. So in this case, the optical components that are constructed from the ridged material are the optical components of the femto projectors, but do not include the traditional functional optical component of the contact lens itself, e.g. the correction for normal vision, as seen through the display mesh. In the preferred embodiment being described here, the display mesh also contains the femto projector display die that are the light emitting image element portion 7510 of the femto projectors, as well as other support chips.

IX.B. One Possible Solution: The Display Mesh

Figure 80:
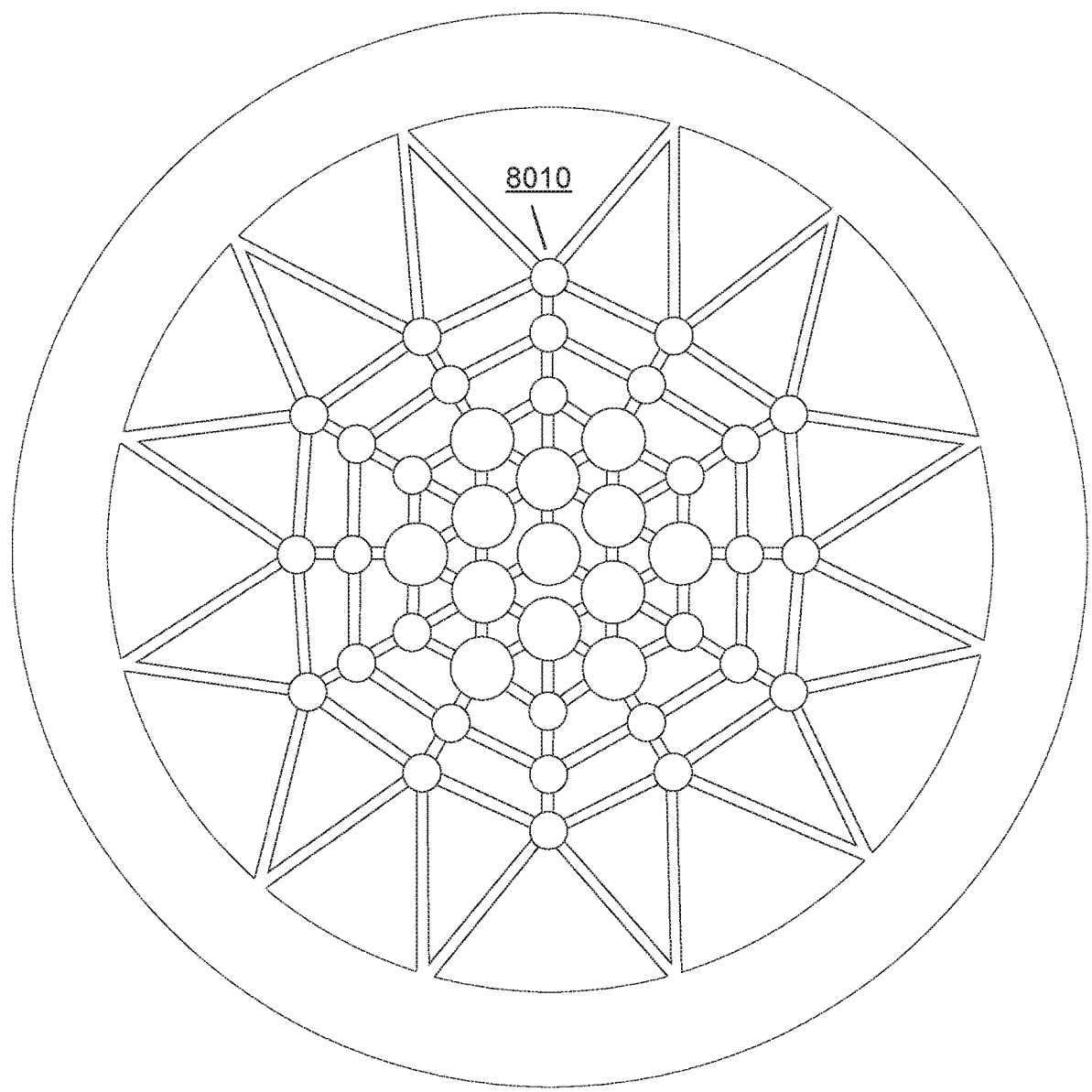
FIG. 80 shows a top view of the display mesh.
Figure 81:
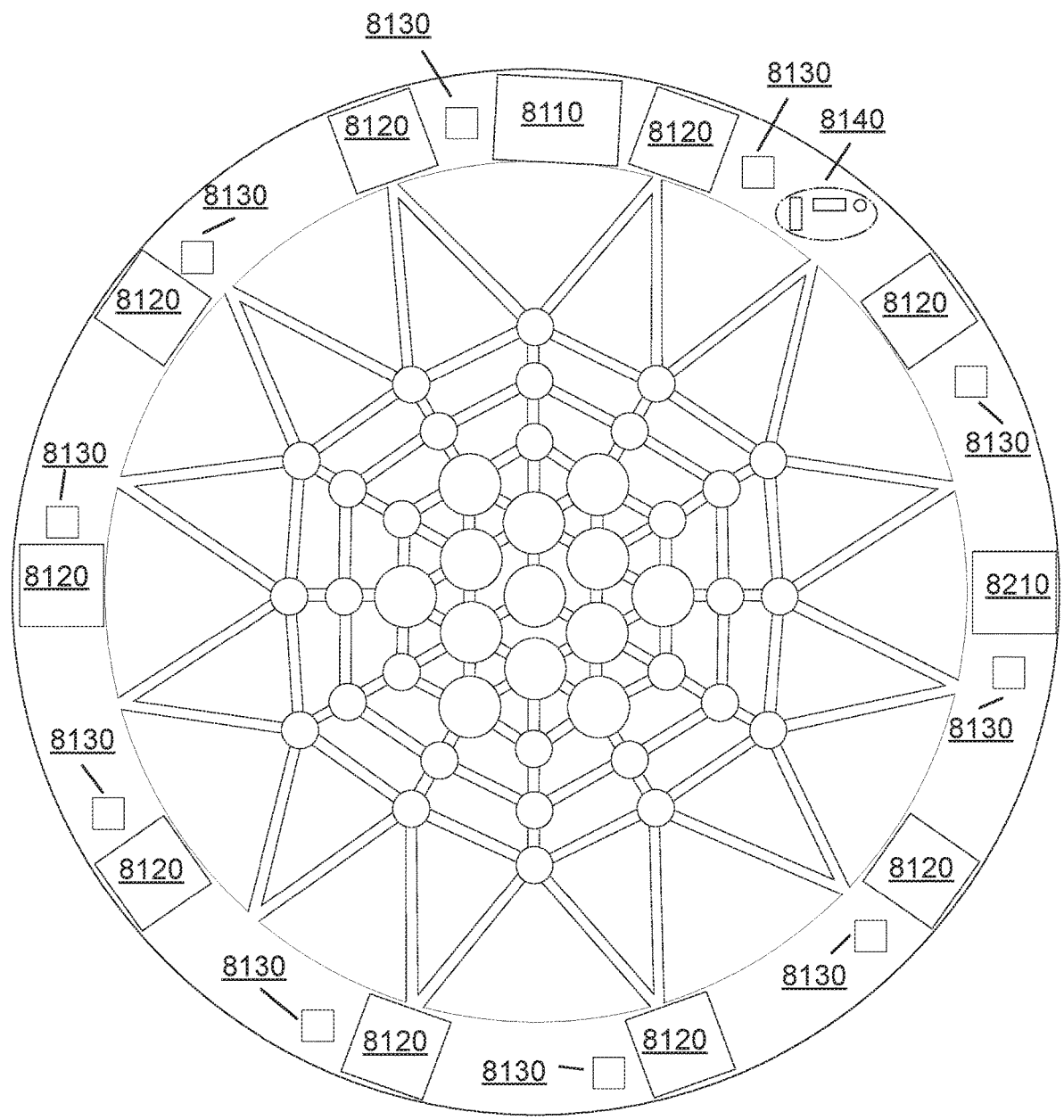
FIG. 81 shows a top view of the display mesh with the outer ring IC die.

An example display mesh is shown from above in FIG. 80. The 43 individual femto projector cylinders are shown as the 43 circular elements 8010 in the figure. FIG. 81 is the same design, but now the IC die have been added in the outer ring area outside the optical zone of the contact lens. Element 8110 is the display controller IC die. Elements 8120 are multiple copies of the Power and Data receiving IC die. Elements 8130 are multiple copies of the Data transmitting IC die. Element 8140 is a multi-axis accelerometer. In the preferred embodiment, the accelerometer is three axis positional and/or three axis orientation sensor, and are generally MEMS based. Sometimes such clusters also include gravitational (down) detectors, as well as magnetic (north) detectors.

Tracking the Contact Lens

Figure 82:
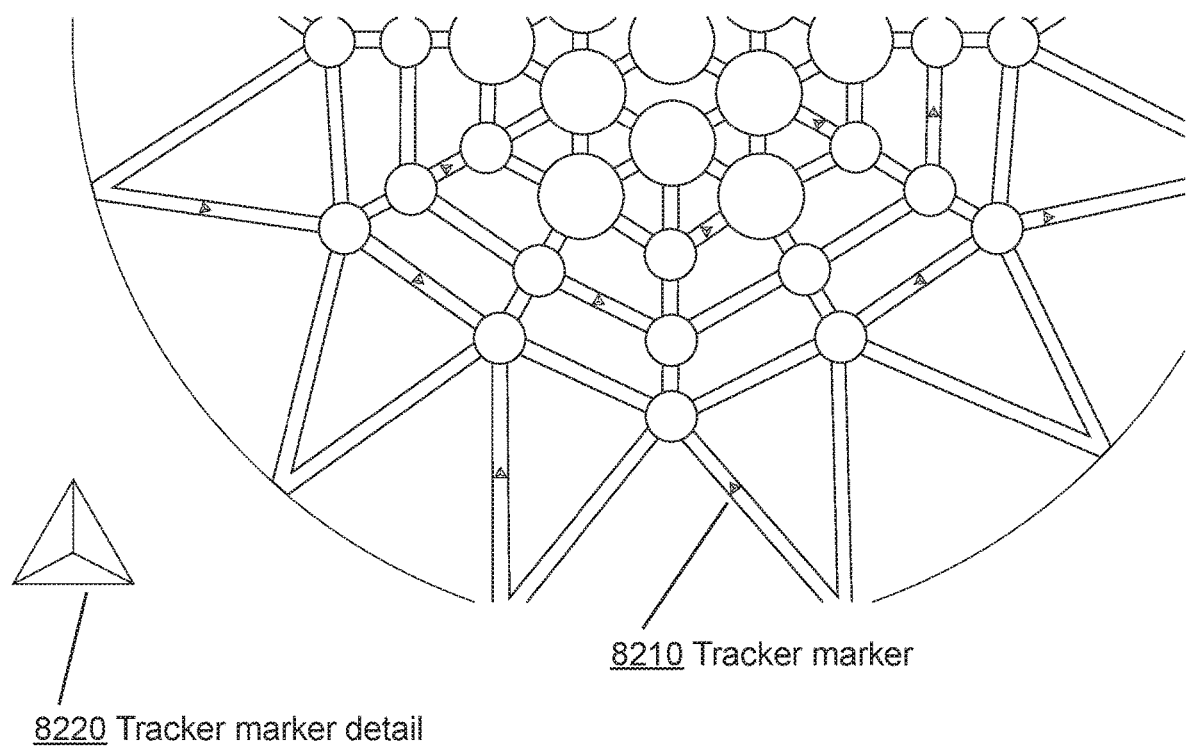
FIG. 82 shows a zoomed top view of the display mesh with the corner reflector detail.

It is vitally important that the location and orientation of the contact lens on the eye be accurately and rapidly tracked in real-time. To help achieve this, some form of fluidal marks can be incorporated into the contact lens display. Ideally, the fluidal marks should be of such a design that they can be both rapidly and highly accurately located by image capture (either linear or array cameras). Examples of such designs are well known to those skilled in the art. In one embodiment, the fluidal marks would be manufactured onto the top surface of the display mesh. These "marks" can be anything that changes the way light (including infrared light) reflects or refracts from the contact lens display. One embodiment of such marks would be light absorbing or light reflecting marks (paint, etc.). Another would be optical indentation, optical extrusion, etc. In the preferred embodiment, the display mesh structure features several strategically placed corner reflectors inscribed into its top surface. Corner reflectors have the advantage that they reflect the vast majority of the light illuminating them back in the same direction as the illumination came from. This allows excellent signal to noise, e.g. a small amount of light will still reflect back a strong point of light, a large amount of light will reflect back an extremely bright point of light. This not only allows smaller (and thus less costly) pixels to be used on the image sensor, it also allows said image sensors to work at a very high frame rate (and still achieve good contrast), e.g. a frame rate of 1,000 Hz or more. Examples of where fluidal marks might be placed on the display mesh are shown in FIG. 82, elements 8210. A zoom into a single corner reflector is shown as element 8220. It is important to note that whatever the placement of the fluidal marks is, it should not be symmetrical to the display mesh, as otherwise it would be impossible to determine which of several possible symmetric rotations of the contact lens had occurred. An alternative to a reflecting mark of a point design would be one of a line design. This allows a larger number of sample points from the mark to be captured by 2D image sensors, or less expensive line sensors to capture at least some portion of the line. Whatever form of fluidal mark, the idea is that the entire area of each eye where the contact lens display might be would be illuminated (preferentially by infrared light) from the eyewear (or similar device), and image sensors would be placed on the eyewear (or similar device) where they can observe any region that the contact lens can be. In the preferred embodiment in which corner reflectors (or something similar for line elements) are used, then the image sensor or sensors for each eye would be placed very near, or mixed optically at, the location on the eyewear where the point of illumination was placed. In the preferred embodiment, not only would an infrared light source be used, but it could be the same infrared light source that is being used to (wirelessly) power the contact lens display (and thus fairly bright), which preferably also is the same infrared light source where a portion of the light intensity is being modulated at a high frequency to provide the digital data (wirelessly) the contact lens display. Alternately, a substantially different frequency of infrared light than is being used for reasons other than illuminating the fluidal marks can be dedicated for the use of illuminating the fluidal marks, and narrow band pass optical filters can be used in various places on both the contact lens and the eyewear to allow only the specific frequency of infrared light of interest to pass as necessary.

More Display Mesh Geometric Detail

Figure 78:
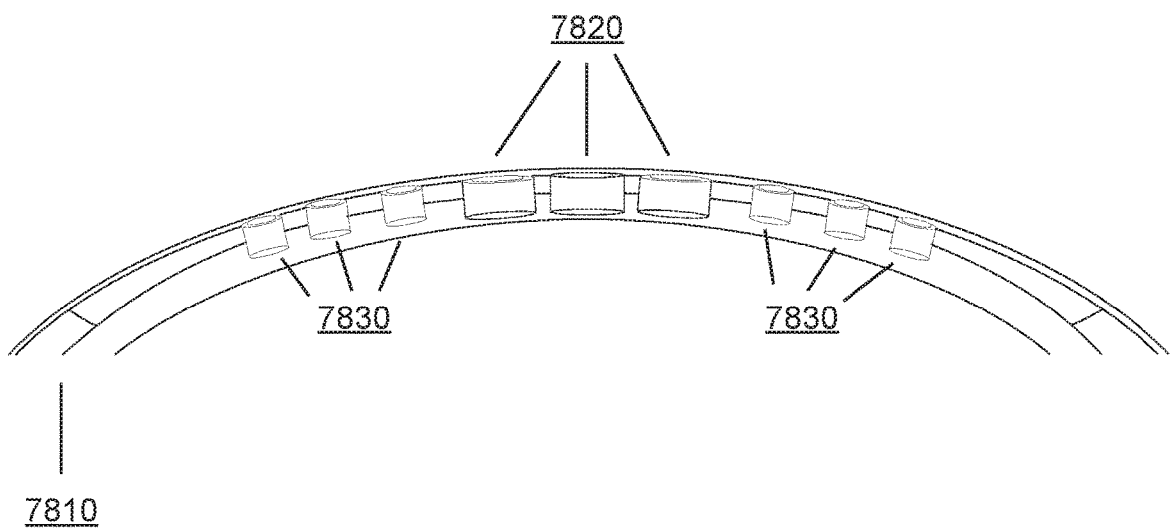
FIG. 78 shows a cross-section through a contact lens display showing three foveal and six peripheral femto projectors as cylinders.
Figure 79:
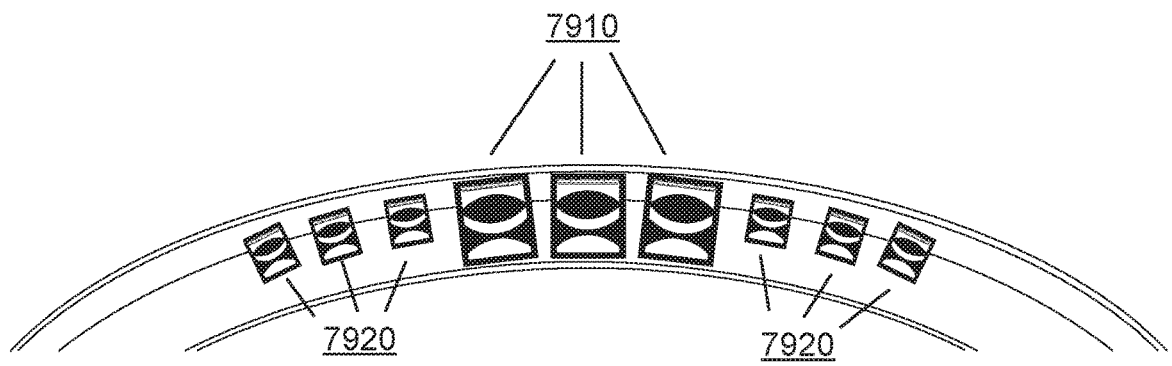
FIG. 79 shows a cross-section through a contact lens display showing three foveal and six peripheral femto projector optics.
Figure 83:
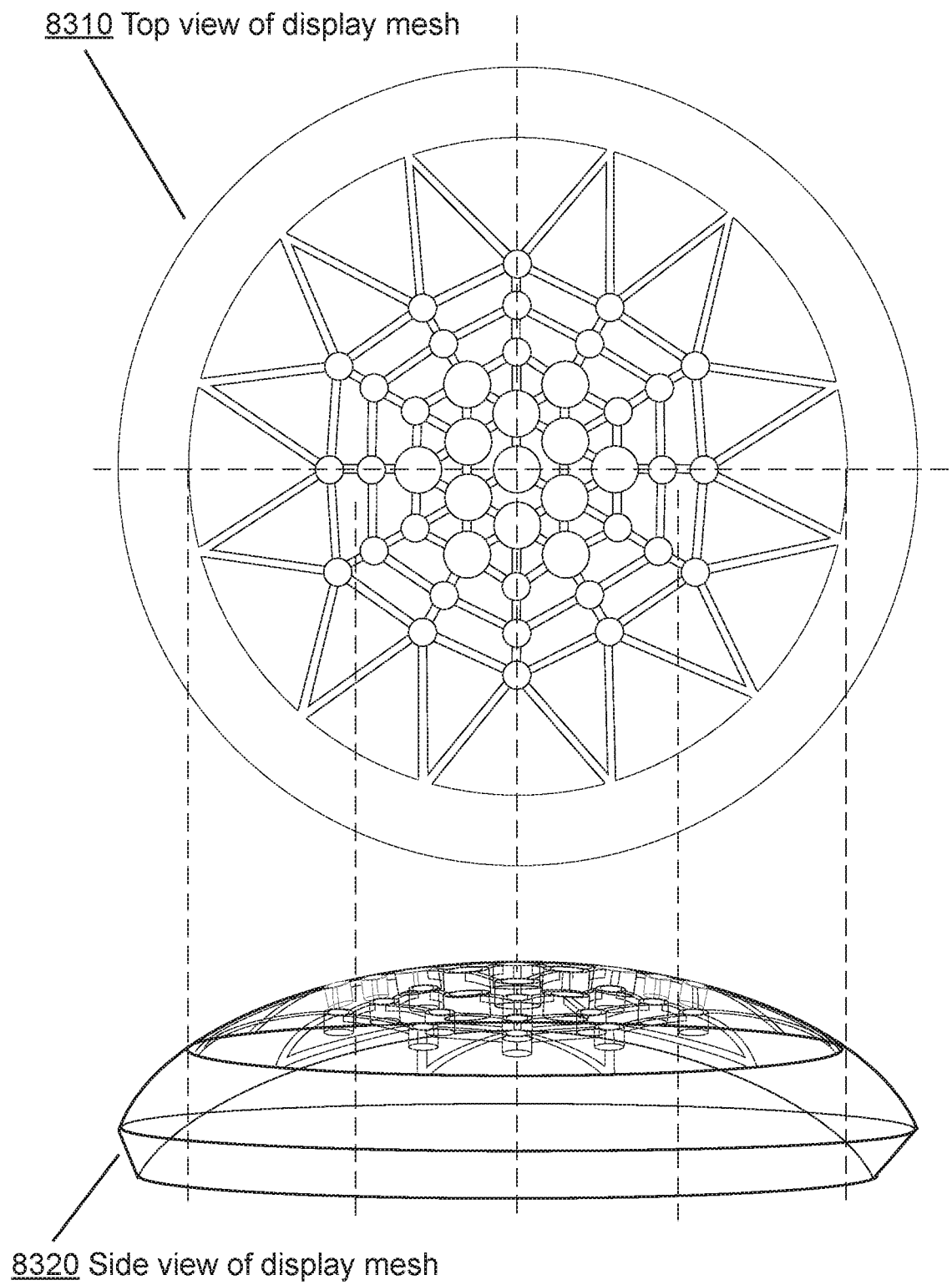
FIG. 83 shows an aligned top and side view of the display mesh.

FIG. 83 shows both a top (element 8310) and side (element 8320) view of the display mesh. To better understand the structure and placement of the femto projectors in the display mesh, a side view central slice view is shown in FIG. 78. The outer edge of the bulk contact lens is shown as element 7810, three foveal femto projectors are shown as cylinders 7820, and six peripheral femto projectors are shown as cylinders 7830. FIG. 79 is the same slice view, except this time we have sliced the femto projectors themselves in half, showing a simplified depiction of the internal optics in black, as elements 7910 for the foveal and 7920 for the peripheral femto projectors.

IX.C. Wiring Up the Display Mesh

An important concern in building an electronic device of this scale is how the individual IC die are wired together. Technically, the collection of die and the display mesh together can be viewed as a form of a hybrid-chip e.g., one "chip" with multiple internal die, and internally wired together. Most hybrid chips of the past were not optically clear, but some have included both opto-electronic die and electronic only die. Also, usually hybrid chips have some external pins for power and data. In the case of the femto projectors, the power and incoming data is received optically as (in the preferred embodiment) infrared light, and data is transmitted back out of the display mesh also as infrared light. (Several alternate means are possible for powering the device, including leaching mechanical energy into electrical energy off of eye blinks.) But, internally, the individual die have some wires running between them. To reduce the number of wires transferring data and clock from the display controller die to the individual femto projector display die, in the preferred embodiment 8b/10b encoding of both clock and data onto a single pair of differentially driven wires is used. This means that there at most has to be a maximum of two wires dedicated to communicating data and clock from the display controller die and each femto projector display die. There is also a requirement for the display controller IC to be able to receive certain data back from the femto projector display die, but because this read-back channel has low bandwidth requirements, a single shared differential pair of wires can serve as a bus from two attachment points on the display controller die to all femto projector display die. Similarly, power and ground can be bussed to all femto projector display die, reducing the number of wires required. In the preferred embodiment described so far, this would mean that each femto projector display die has a maximum of six wire attachment points. (These are not called "pads," as that terminology implies a certain scale and structure of making wire attachments.) Since the display controller die is on the outer non-optical zone ring, but the individual femto projector display die are scatter around the optical zone connected by some common struts, this limits the paths that the wires can take. The scale of the wiring of the die is small. For example, the foveal femto projector display die are less than half a millimeter in diameter, the peripheral femto projector display die are less than a third of a millimeter in diameter, and the struts are even narrower (e.g., on the order of a tenth or a twentieth of a millimeter in width). This means that the total number of wires that can be run along a given strut must be limited, as the wire pitch of wires that can be imprinted here is ten to twenty microns or more at their smallest.

Example Display Mesh Wiring

Figure 84:
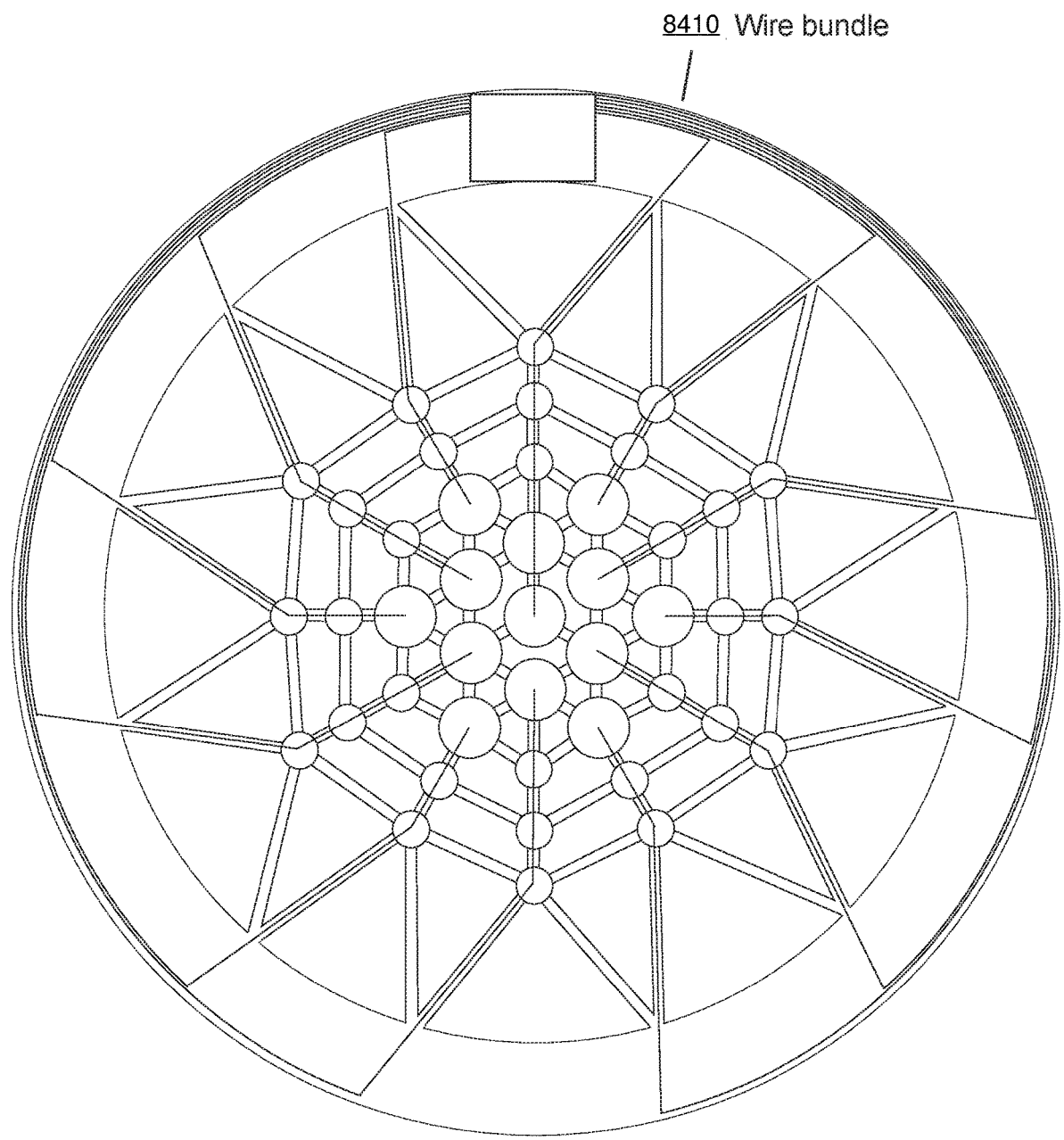
FIG. 84 shows the display mesh display controller die data to individual femto projector display die wiring paths.
Figure 85:
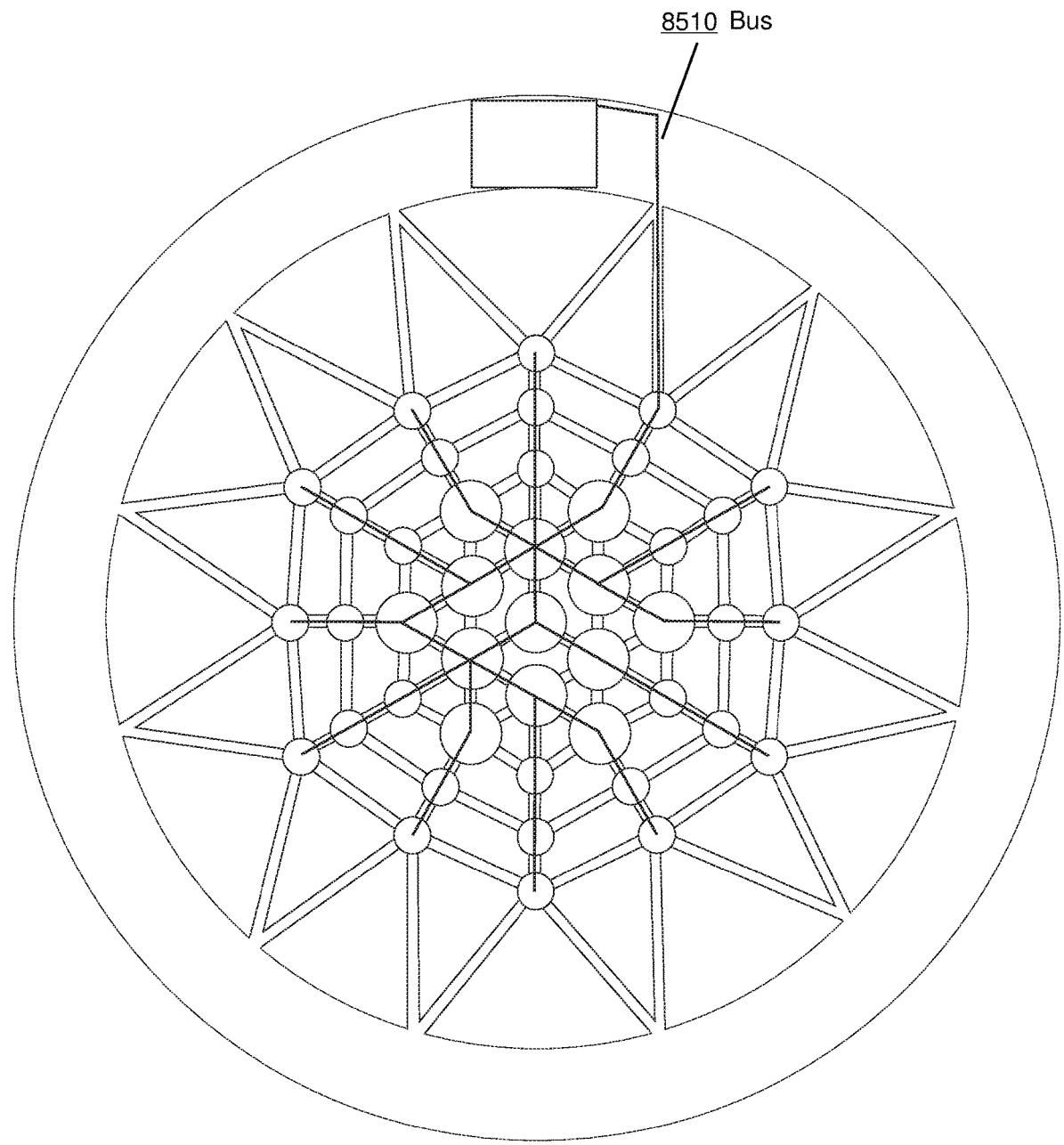
FIG. 85 shows the individual femto projector display die common data back to display controller die wiring path.
Figure 86:
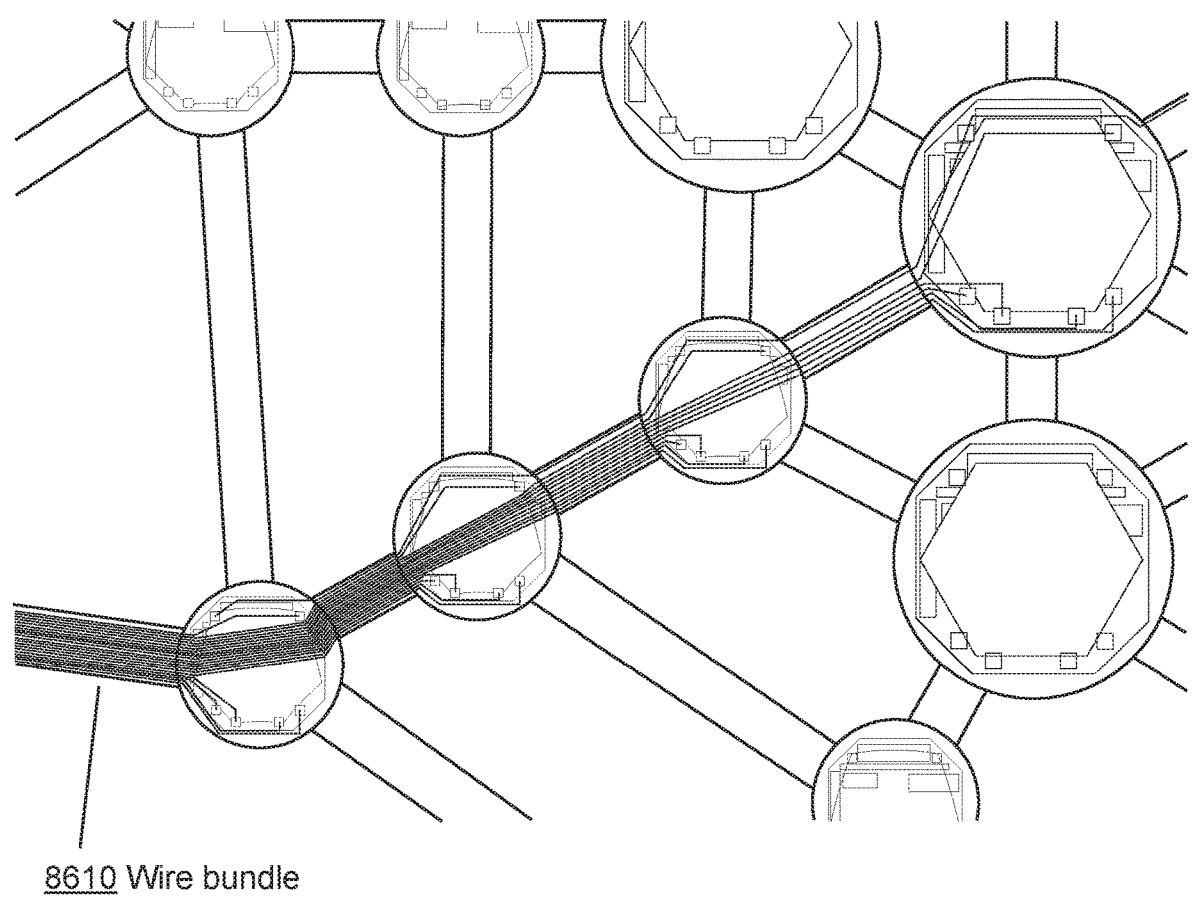
FIG. 86 shows details of the display mesh display controller die data to individual femto projector display die wiring paths.

To see how this can be dealt with, FIG. 84 shows wire bundles 8410 from the display controller die to femto projector display die on separate struts of the display mesh. The advantage of this wiring scheme is that only the wires going to the three, four, or in one case, five femto projector display die along each individual strut need be wired to on that strut. This is a considerable reduction over running all the wires over one strut, which, even using multiple layers of wiring, might be beyond current wire circuit fabrication technologies. FIG. 86 is a zoomed view of how the wire bundle might be decomposed into individual wires that have to connect to four femto projector display die. To reduce the number of wires required on each strut, it is also possible that, rather than a separate pair of differentially encoded data wires for every femto projector display die, the relatively low data speeds required can allow three, four, or five femto projector display die to be connected by a shared bus of just two wires. There are also techniques of providing both power and ground over the same data bus wires, saving another two wires per strut if required. One example of how the return data bus from all the femto projector display die to the display controller die might be wired over the struts is shown in FIG. 85. The two wire bus 8510 (shown as a single line for clarity) gathers the return data from all the femto projector display die in a tree that keeps the wire per strut requirement for this bus to the minimum of two wires. There are also techniques of reversing the data flow on the two data wires going into each femto projector display die from the display controller die into data outputs going back to the display controller die. Because the return data rate is much lower than the input data rate to the femto projector display die, the additional impedance that each femto projector display die will encounter when trying to drive back along the same wires should not be too much of an issue.

Summarizing, the maximum number of wires required to be present on each narrow strut of the display mesh is at a minimum two, which would have to carry the incoming, back going, and power for at most five femto projector display die. If the power bus is separated, then the required number of wires per strut is increased to four. Further decoupling will add more such wires with the benefit of somewhat lower power consumption and higher maximum data rates.

IX.D. Fabricating and Assembling the Display Mesh

Figure 76:
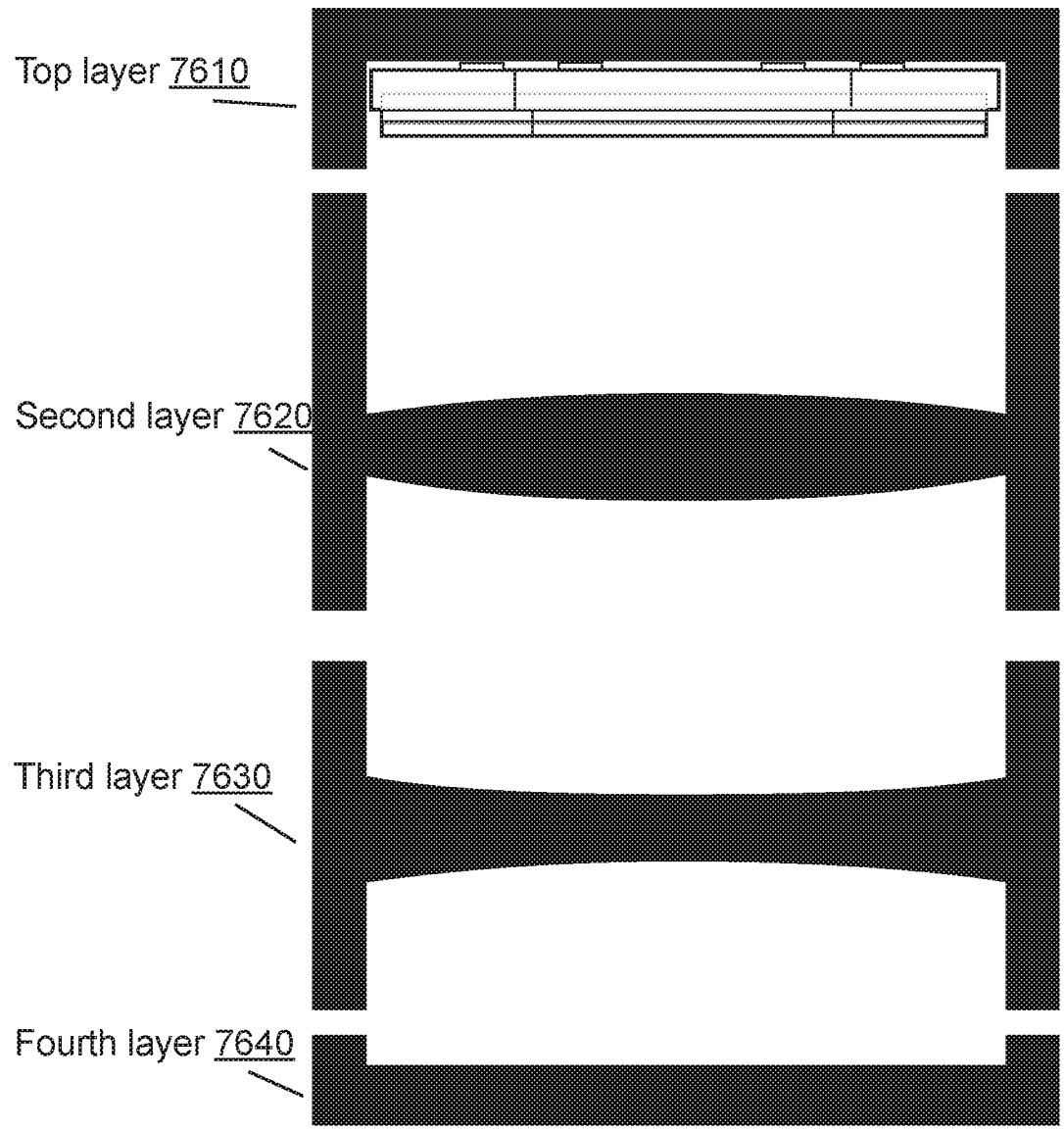
FIG. 76 shows a single femto projector constructed from four pieces.

Each femto projector in the display mesh (43 in the current preferred embodiment) requires two quite small optical lenses, as well as an accurate housing for the femto projector display die, and an optical exit window for the display. The rest of the display mesh consists of multiple struts and the outer ring for placement of additional IC die. It would be advantageous if all these pieces don't have to be separately fabricated and assembled together. In the preferred embodiment, all of the display mesh optical, structural, and mounting portions are fabricated out of just four (or six) single piece layers. To show why multiple layers may be needed for fabrication, examine FIG. 76. This shows just a single femto projector fabricated from four separate pieces such that each piece can be fabricated using standard injection molding techniques, e.g., no undesired holes or voids. Contrast this to FIG. 75, which shows a completely assembled femto projector. Because the volume is closed, it has internal (required) voids. There is no way in which such a shape could be fabricated using traditional injection molding techniques, whereas the four separate pieces of FIG. 76 can be. The idea, however, goes further. The entire display mesh, struts and non-optical zone die mounting region and all can be fabricated out of just four separate parts, again just using standard injection molding techniques. This is not at all infeasible, as the same (generally plastic) materials that are used to make high quality lenses of various sizes are also quite suitable as structural members and die mounting areas. In FIG. 76, it can be seen what the four layers would individually consist of. The topmost layer, element 7610, would form the top of the display mesh, and the underside of it would be the die attach and wire attach surface for the electronics, both the individual femto projector display die, and the outer die attach ring. The outer die attach ring is the portion of the underside of the first layer of the display mesh outside the optical zone of the contact lens. This area is where the display controller die, several instances of power and data receiver die, and several instances of the data transmitter die all attach. The topmost layer would also contain the uppermost portion of the struts between the other elements. The same will be true for the three other layers. The layer second from the top, element 7620, within the femto display areas would form the first (positive) lens of the femto projector optics, as well as part of the cylindrical sides of the projector. The layer third from the top, element 7630, within the femto display areas would form the second (negative) lens of the femto projector optics, as well as more portions of the cylindrical sides of the projector. The lowermost layer, element 7640, would form the encapsulating bottom of the display mesh.

After fabrication, the various IC die would be attached to the underside of the top layer 7610, and then wired together on the same layer, using the underside of the first layer of the structural struts as paths along which portions of the wiring can be run. Then all four layers of the display mesh can be fastened together, using any of various techniques (e.g., various glues). Alternately, the first three layers, which contain no electronics or wiring (in some embodiments), could be pre-assembled, only waiting for the top assembly to be completed before assembling the top layer to the other three. It is advantageous that all of the outer surfaces of the assembled display mesh be "blackened" to light, except for the optical output portion of each femto display on the bottom of the display mesh, and the optical data/power input/output portions above much of the top of the non-optical zone ring. This is to keep stray light from the outside world from getting refracted or reflected by the display mesh itself, potentially lowering external world image quality, as well as to keep such outside light from somehow mixing in with the femto projector display optics. In some cases, the known critical angles of reflection of a specific design and materials may reduce the regions at risk. It is also important that the corner reflectors formed into the top surface of the display mesh are fully functional, which might require not adding (or later removal of) blacking from these areas.

After the display mesh has been assembled (and potentially tested at various interim points), the "bulk" contact lens can be formed around the display mesh resulting in the final contact lens display. The "bulk" contact lens material is most advantageously a plastic material with high oxygen permeability that could be formed by some technique around the fully assembled display mesh without harming the display mesh itself. The existing materials that "soft" contact lenses (e.g., silicon hydrogels, polyacrylamide hydrogels) are formed from is one likely possibility. Because the display mesh will act as an internal skeleton to the softer material, the display mesh should cause the soft material around it to act in a much more ridged manner, potentially acting more like the "hard" central portion of a soft edge scleral contact lens, or like a more traditional "hard" contact lens. The advantage of the central portion of the contact lens being hard is that then astigmatism can be automatically corrected for. The advantage of the edges of the contact lens being softer and more pliable is the potential for a more comfortable fit, more like that of a soft contact lens, or of a soft skirt hard center scleral contact lens.

Figure 77:
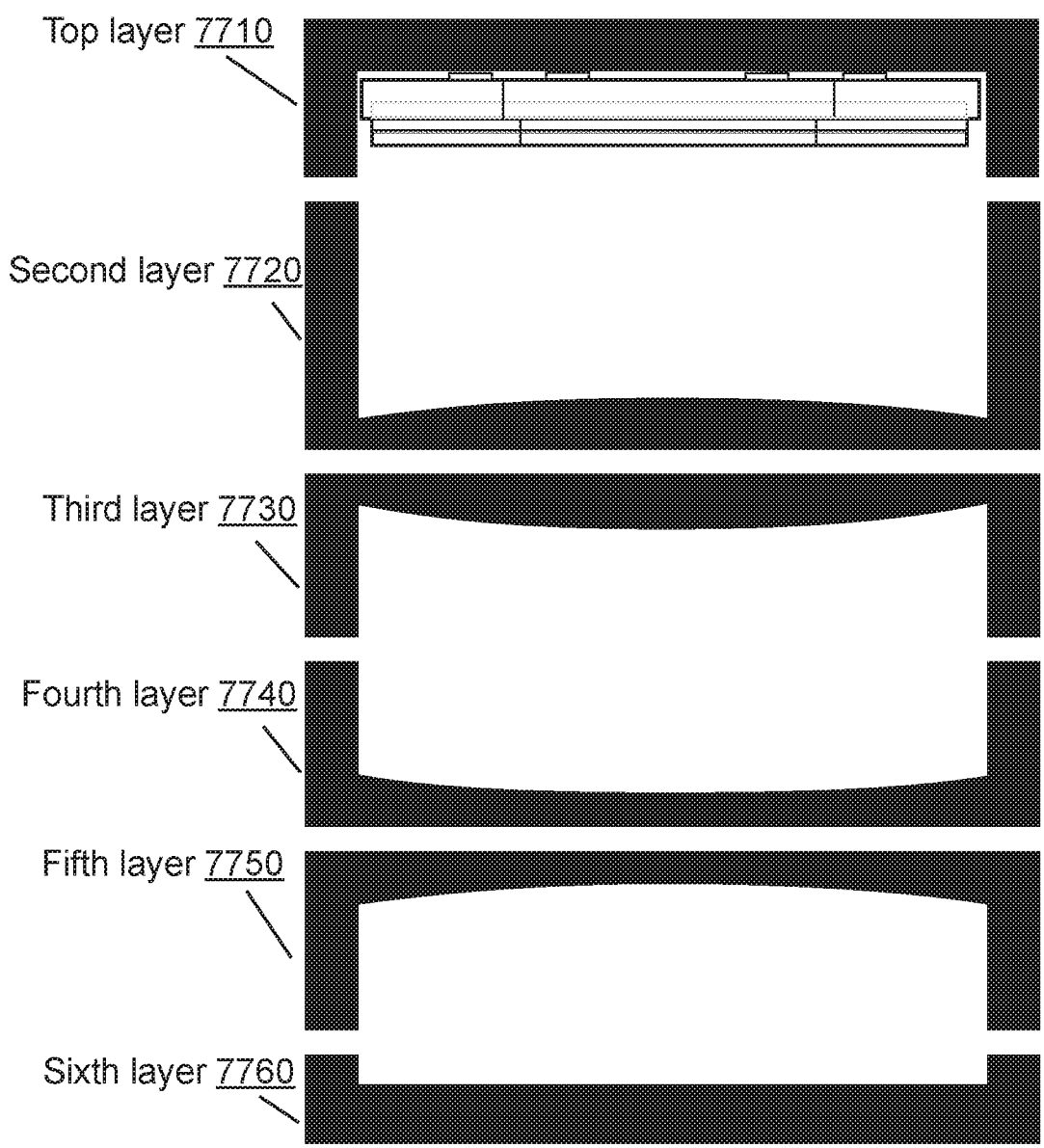
FIG. 77 shows a single femto projector constructed from six pieces.

While current in production injection molding techniques allow optical surfaces to be routinely fabricated to better accuracy than one wavelength of (visible spectrum) light, there are constraints on how thin regions of the molded object can be. The reason is not final structural strength of the molded object, which still can be quite strong over any given area, but the stresses incurred by the newly molded object as the molds are pulled apart. There are, however, some alternate techniques for accurately forming the layers of the display mesh out of a different optically clear material through the use of vapor deposition. Potential materials that could be used here include diamond, silicon nitride, titanium dioxide, silicon dioxide (quartz), and aluminum oxide (sapphire). Front half molds of the negative of the desired optical surface can have the material vapor deposited on them until a sufficient thickness has built up. These molds can be made of any of a large choice of materials, including refractory metals. Then the inaccurate rear side of the single piece of material that was just created can be polished to a smooth (slightly curved) surface by a diamond sander. However, because this technique allows only one non near planer optical surface to be fabricated per piece, six pieces are required to be fabricated to together form a complete display mesh. This is illustrated in FIG. 77, where the optics of a single femto projector have been separated into six pieces that otherwise meet the vapor deposition fabrication technique. The top layer, element 7710, and the bottom layer, element 7760, are essentially the same as their injection mold counterparts 7610 and 7640. The second layer, element 7720, now forms the top half of the first (positive) lens of the femto projector optics, the third layer, element 7730, forms the bottom half. The fourth layer, element 7740, now forms the top half of the second (negative) lens of the femto projector optics, the fifth layer, element 7750, forms the bottom half. The use of diamond as the construction material for the display mesh has several advantages. It is extremely structurally strong, which means even when fabricated to very thin widths, it is unlikely to break during subsequent assembly or forming of the "bulk" contact lens around it. Diamond and the other materials mentioned have high indexes of refraction, making them good optical materials. And unlike plastic materials, which all have some water permeability, diamond and the other materials when glued together creates a hermetic seal, eliminating the possibility of water vapor forming inside the lenses (assuming a zero humidity environment when the portions of the display mesh are fastened together (argon is one such example)), and also eliminating the possibility of condensed water possibly shorting together inter-die wiring. The die themselves in any case would most likely be pre-passivated with an optically clear hermetic seal layer.

Some alteration of the IC dies before construction will be required as well. Normal IC die are quite thick, e.g., half a millimeter or more. That's as thick as the entire contact lens! However, this thickness is not needed for any functioning of the IC, but for structural integrity of the wafer during IC fabrication. After fabrication, "wafer thinning" techniques can be used to make the die 20 microns or less in thickness. (In the following, remember that all die are attached upside down to the bottom surface of the first layer of the display mesh.) A related point is that some die have to be mounted processed side up, pointing out of the contact lens (such as the power & data receiving die, and the data transmitting die), while other die are required to be mounted pointing down, such as the femto projector display die. Depending on how wiring connections are made, this may require one or the other of such groups of die to be able to make wiring connections on the back (non-processed) side of the die. This fits well with wafer thinning, as thinned die can have electrical connections placed on the back of the die (via deep vias).

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

In some embodiments, portions of the invention are implemented in computer hardware, firmware, software, and/or combinations thereof. Apparatus of portions of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

X. Areas of Note

In this portion of the application various embodiments discussed above are highlighted.

In-line display die and multiple optical elements.

Item A. An eye mounted display, comprised of multiple sub-displays, in which each sub display is formed by a flat multi-pixel light emitting display element, followed by a first lens element, followed by a second lens element, and optionally followed by additional lens elements, all parallel to the surface of the eye mounted display.

Item A.1. Item A, in which the first lens element is a positive lens, and the second lens element is a negative lens.

Item A.1.1. Item A.1, in which a third lens element performs ophthalmological correction.

Item A.1.2. Item A.1, in which a third lens element performs additional optical aberration reduction.

Item A.1.2.1. Item A.1.2, in which the third lens element also performs ophthalmological correction.

Item A.2. Item A, in which one or more lens elements can have their position shifted so as to place the display at different depth of field distances from the eye.

Item A.2.1. Item A.2, in which the induced depth of field distance of the display from the eye is determined by a function of the dynamically tracked vergence angle of the two eyes.

Item A.2.1.1. Item A.2.1, in which the function of the vergence angle of the two eyes is one that dynamically places the display at the same optical depth that the vergence angle of the two eyes indicates that normal vision (non-presbyopic) is expecting to have to change the eye's internal lens to accommodate to.

Item A.3. Item A, in which one or more lens elements positioned between the femto projectors can have their position shifted so as to dynamically change the optical power of the corrective lens so as to change the apparent depth of field of the physical world.

Item A.3.1. Item A.3, in which the amount of change in the power of the corrective lens is determined by a function of the dynamically tracked vergence angle of the two eyes.

Item A.3.1.1. Item A.3.1, in which function of the tracked vergence angle of the two eyes causes the power of the corrective lens to bring into focus on the retina objects that are at the distance in the world indicated by the said vergence angle.

Item A.3.1.1.1. Item A.3.1.1, in which it is used to dynamically cure full presbyopia.

Item A.3.1.1.2. Item A.3.1.1, in which it is used to dynamically cure partial presbyopia.

Item A3.2. Item A.3, in which the change in the apparent depth of field of the physical world is fixed such as to correct for known myopia or hypermetropia of an individual's eyes.

Item B. & Item C. Use of the locally uniform resolution mapping as a model of the human (and primate) retinal receptor fields and the physical organization of the human (and primate) visual cortex.

Item B. Using the locally uniform resolution mapping as a model of properties of retinal midget ganglion cells outside the foveal region.

Item B.1 Item B, in which the property of the retinal midget ganglion cells being modeled by the locally uniform resolution mapping is their local density.

Item B.2 Item B, in which the property of the retinal midget ganglion cells being modeled by the locally uniform resolution mapping is local average area of the center portion of their receptor field.

Item B.3 Item B, in which the property of the retinal midget ganglion cells being modeled by the locally uniform resolution mapping is local average area of the surround portion of their receptor field.

Item B.1.1 Item B.1, in which local density of the retinal midget ganglion cells is used as a probability prediction of the specific integral number of retinal cone cells a given modeled retinal midget ganglion cell will connect to create the center portion of its receptor field.

Item C. Using the locally uniform resolution mapping as a model of the spatial organization of the non-foveal portion of the physical human visual cortex.

Item C.1. Item C in which the portion of the physical human visual cortex being modeled by the locally uniform resolution mapping is region V1, V2, and V3.

Item D. Use of the locally uniform resolution mapping for variable resolution display in eye mounted displays, specifically including contact lens displays.

Item D. Use of the locally uniform resolution mapping to define the sizes of pixels displayed on the retina by an eye mounted display, outside the foveal region.

Item D. A eye mounted display device, consisting of multiple pixels, for which the portion of the display meant for outside the foveal region, the pixels have been arraigned such that the number of pixels at any given eccentricity is (approximately) constant, and the aspect ratio of all pixels is (approximately) constant at all eccentricities.

Item D. A eye mounted display device, consisting of multiple pixels, for which the portion of the display meant for outside the foveal region, given any specified direction, the linear pixel density measured in the specified direction divided by the sign of the eccentricity will be the same everywhere.

Item D. A eye mounted display device, consisting of multiple pixels, for which the portion of the display meant for outside the foveal region, at any given eccentricity, the linear pixel density in the longitudinal direction divided by the diameter of the circle on the unit sphere defined by the given eccentricity will be the same as the linear pixel density in the eccentricity direction (not as general).

Item E. In an eye mounted display device comprised of multiple sub-displays, having different sub-displays displaying to different ranges of visual eccentricities magnifying the size of their pixels displayed such that the amount of magnification approximately follows the locally uniform resolution mapping.

Item F. In an eye mounted display device comprised of multiple sub-displays, in which the pixels on individual sub-displays do not have a constant pixel size, but instead the size approximately follows the locally uniform resolution mapping.

Item E+F.

Item G. Optical implementation of the locally uniform resolution mapping for image and video capture onto standard sensor arrays.

An optical system imaging onto a planer image sensor array (still or video) such for any visual longitude in space, the visual eccentricity in space of light coming into the optical system is imaged onto the same longitude on the image sensor, but that light that came from a given visual eccentricity is imaged onto the image sensor at a point at a radial distance r from the center of the image sensor such that r is proportional to log [tan [eccentricity/2]].

Item H. Image processing implementation of the locally uniform resolution mapping for image and video capture onto standard sensor arrays with standard lenses.

An image processing system taking in images from cameras and optics that utilize the standard planer view projection, but that before processing re-samples the input image(s) such that an input pixel coming from a particular visual longitude and visual eccentricity will be used as a sample to contribute to the output value of a pixel with the same longitude, but that has a radial distance in the image plane proportional to log [tan [eccentricity/2]]. Standard output pixel filtering techniques will cause the input pixel to also contribute some amount to nearby neighbors of the said output pixel as well, though usually by a diminished amount.

Pre-distortion of display pixel shapes and sizes on the display die for variable resolution display.

Item I. Pre-distortion of display pixels for correcting for residual imperfections of the femto projector optics.

Item I. Pre-distortion of display pixels for correcting for residual imperfections of the femto projector optics design.

Item I.1. Item I, in which the residual optical imperfections include those of chromatic aberration.

Item I.2. Item I, in which the residual optical imperfections include those of spherical aberration)

Item I.3. Item I, in which the residual optical imperfections include those of keystone aberration.

Item I.4. Item I, in which the residual optical imperfections include those of non-uniformity of image intensity across the field (include the case of vignetting).

Item I.5. Item I, in which the residual optical imperfections include those of pevetisal surface distortion.

Combinations of Items I1-5.

Item J. Pre-distortion of display pixels for correcting for fabrication and assembly errors.

Item J.0. Pre-modification of the intensity of display pixels for correcting for residual imperfections of the pixel intensities produced by the femto projector planer image display element caused by fabrication and assembly errors.

Item J.0.1. Item J.0, in which the intensity of light produced by a specific individual display pixel for any given input digital pixel value differs from what was desired, and the correction is to substitute a different digital pixel value to be displayed that produces the closest actual amount of light as was desired.

Item J.0.1.2. Item J.0.1, in which for most digital input pixel values, the amount of light produced by an individual pixel differs from that which was desired by a linear function of the digital pixel value, and the correction is to pre-multiply the desired digital pixel value by the appropriate inverse linear amount before the pixel is sent to the femto projector.

Item J. Pre-distortion of display pixels for correcting for residual imperfections of the retinal images produced by the femto projector optics caused by fabrication and assembly tolerance errors.

Item J.1. Item J, in which the residual optical imperfections include those that cause in a shift in the retinal position of the image displayed by a femto projector from what was desired, and the correction is to apply an equal but opposite shift to the positions of all pixel data before it is sent to the display.

Item J.2. Item J, in which the residual optical imperfections include those that cause retinal images produced by the femto projector optics to have a different magnification from what was desired, and the correction is to pre-minify or pre-magnify all the pixels of the image to be displayed by the projector by an appropriate inverse amount.

Item J.3. Item J, in which the residual optical imperfections include those that cause undesired keystone distortion in the retinal images produced by the femto projector optics, and the correction is to pre-apply a separate shift in position of each pixel such that the appropriate inverse keystone distortion is applied to the pixel data before it is sent to the projector.

Item J.4. Item J, in which the residual optical imperfections include those that cause an undesired chromatic aberration in the retinal images produced by the femto projector optics, and the correction is to pre-reverse this aberration generally by applying a separate shift offset to each different color of pixel before it is sent to the projector.

Item J.5. Item J, in which the residual optical imperfections include those that cause an undesired spherical aberration in the retinal images produced by the femto projector optics, and the correction is to pre-reverse this aberration.

Item J.6. Item J, in which the residual optical imperfections include those that cause an undesired non-uniformity of image intensity across the field in the retinal images produced by the femto projector optics, and the correction is to pre-reverse this aberration.

Item combo J. Combinations of items J1-6. A combined, separate for each color of pixel, shift, change in magnification, and change in intensity can correct for all the residual imperfections at the same time.

System of items I+J. In an eye mounted display comprised of a number of different femto projectors, perform a post-manufacturing calibration test separately to each said femto projector, capturing undesirable errors in the retinal image produced caused by both residual errors inherent in the optical design as well as those caused by fabrication and assembly tolerance errors, as well as errors in desired pixel light output values caused by fabrication and assembly tolerance errors in the display device, then during operation of the eye mounted display, for each specific femto projector, derived from its specific calibration data, pre-apply the appropriate inverse imaging operation to the pixels that are to be displayed to that specific femto projector.

Feathering outer edges of the images produced by different immediately neighboring femto projectors.

Item I+item J, in which all the absolute positional shifts of pixels displayed by a particular femto projector are known, as part of the overall pre-computation of the pixel corrections to be applied in real-time, from the optical calibration data pre-determine the overlap of the retinal image of adjacent femto projectors, for any pixel of a femto projector whose retinal image overlaps even a portion of the retinal image of a pixel from an adjacent femto projector, either turn off that pixel, or determine an appropriate reduced intensity blend amount to be applied to that pixel, with the inverse of that blend amount to be applied to pixel or pixels that overlap in the adjacent projector, with this per-pixel intensity reduction factor to be pre-combined with any other per pixel intensity pre-correction factors.

Variable Resolution Tiling of Hexagonal Projectors with Different Magnifications.

Tiling of Projectors.

Item K. An eye mounted display, comprised of multiple sub-displays, whose combined projected images on the retina completely cover the retina out to an outer edge, in which the shape of the pixel containing region of the individual sub-displays light emitting element is either a fixed shape that can tile the plane, or similar to the distorted version of that shape produced by mapping that shape by the portion of the locally uniform resolution mapping that applies to the region of the retina that a particular sub-display displays to, which is a shape known to be able to tile a portion of the surface of a sphere.

Item K.1. Item K, in which the fixed shape is rectangular.

Item K.2. Item K, in which the fixed shape is hexagonal.

Item K.3. Item K, in which the fixed shape is triangular.

Item K.2.1, in which a group of centermost sub-displays are hexagonal in shape, and those sub-displays outside this group are those that have a shape similar to the distorted version of a hexagonal shape produced by mapping a hexagonal shape by the portion of the locally uniform resolution mapping that applies to the region of the retina that a particular sub-display displays to.

Item K2.1.1. Item K.2.1, in which the group of displays that are hexagonal in shape are the seven centermost ones.

Item K2.1.2. Item K.2.1, in which the group of displays that are hexagonal in shape are the thirteen centermost ones.

Item K2.1.3. Item K.2.1, in which the group of displays that are hexagonal in shape are the nineteen centermost ones.

Item K.4. Item K, in which the fixed shape sub-displays combined image on the retina covers at least the foveal region.

Item K.5. Item K, in which the eye mounted display is a contact lens display, and in which the fixed shape sub-displays combined image on the retina covers the central portion of the contact lens such that for any normally possible orientation of the contact lens on the cornea, and any normally possible offset of the contact lens from the center of the cornea up to some specified limit, the combined image of the fixed shape sub-displays on the retina will always cover at least the foveal region.

Item K.6. Item K, in which image on the retina produced by each sub-display overlaps by some amount the images on the retina produced by the immediate neighboring sub-displays to the sub-display.

Item K.6.1. Item K.6, in which the amount of sub-projector overlap is sufficient to allow pre-correction of residual errors in the projected image of any sub-projector due to limitations of the optical design, or due to fabrication and assembly tolerance errors, without these corrections resulting in any un-Tillable gaps between sub-projectors.

Same techniques for cameras, including ones constructed on the front of eye mounted displays. (Also, telepresence robotic pair of rotatable camera eyes.)

Variable Resolution Rendering Hardware.

Item L. A hardware 3D computer graphics rendering system in which some portion of the pixels being rendered are rendered in a liner space that is related to the viewing space via the locally linear resolution mapping.

Item L.1. Item L, in which the portion of the pixels are rendered by rendering to a linear sample space that is later converted to the final pixels.

Item L.2. Item L, where geometric graphics primitives are rendered by some method of subdivision, tessellation, or evaluation in 3D space that results smaller and potentially simpler geometric primitives who's bounds in the linear space fall below some threshold, and then can be directly rendered in the linear space.

Item L.1.2. Item L, where geometric graphics primitives are rendered by some method of subdivision, tessellation, or evaluation in 3D space that results smaller and potentially simpler geometric primitives who's bounds in the linear sample space fall below some threshold, and then can be directly rendered in the linear sample space.

Manufacturing: display mesh, multiple layers, fabrication, die thinning, bulk contact lens.

Item M. Constructing a multitude of femto projectors optical paths by fabricating a small number (4, 6, 8) of doubly curved layers of elements meant to be stacked together to form the complete display mesh.

Within the display mesh, leaving holes in the layers between individual femto projectors, so as to allow both light and oxygen through, thus allowing normal vision of the external physical world, as well as appropriate oxygenation of the cornea.

Embedding a display mesh, that may be both light and oxygen impermeable, within a second material that is both light and oxygen permeable, and further forming this second material in a shape such that it can function as a normal contact lens (the "bulk" contact lens).

The previous, in which the "bulk contact lens" may be made of a soft material that is comfortable to the cornea and inside eye-lid.

The previous, in which the display mesh acts as an internal skeleton that will stiffen the bulk contact lens such that it will not bend so as to conform to the shape of the cornea, thus preserving the outer side shape of the bulk contact lens, thus causing any astigmatic errors of the corneal surface to be by-passed, thus correcting for astigmatism.

Item M.0. Item M, in which some form of fluidal marks have been added to the top layer of the display mesh to aid in real-time 3D tracking of the contact lens.

Item M.0.1. Item M.0, in which the fluidal mark is formed by impressing a corner reflector into the top surface of the display mesh.

Item M.0.2. Item M.0, in which the fluidal mark is formed by a retro-reflector embedded into the top of the display mesh.

Item M.0.3. Item M.0, in which the fluidal mark is formed by adding optically absorbing material, such as, but not limited to, ink, in a specific target pattern, onto the top of the display mesh.

Item M.1. Item M, in which an outer ring is present outside the optical zone of the eye mounted display, on which non femto projector die are attached and wired up.

Item M.1.1. Item M.1, in which the wiring to the femto projector image die follows over the bottom (or top) of the structural struts connecting the individual femto projectors together.

Item M.1.2. Item M.1, in which the data wires to and from the femto projector image die along a particular strut path from outside the optical zone to or next to the center of the display mesh carry only data to or from those specific femto projector image die.

Item M.2. Item M, in which all IC die to be included inside the display mesh have been thinned using wafer thing techniques such that the die are thin enough to fit in a prepared gap between two layers of the display mesh.

Item M.3. Item M, in which the femto projector image die has been trimmed from square or rectangular to a shape closer to circular so as to better fit within the circular optical path of the femto projector without making the outer shell of the femto projector larger than it need be.

Item M.3.1. Item M.3, in which the shape closer to circular is octagonal, though not necessarily with all edges of equal length.

Item M.3.2. Item M.3, in which the shape closer to circular is hexagonal, though not necessarily with all edges of equal length.

Item M.4. Item M, in which each of the individual layers has been designed such that it can be formed by a mold with no gaps or voids.

Item M.4.1. Item M.4, in which one side can be formed by a mold with no gaps or voids, but the other side need only be formed by rotational polishing.

Item M.5. Item M, in which all the IC die and associated wiring are attached on one side of one layer of the display mesh.

Item M.5.1. Item M.5, in which the side that all IC die and wires are attached to is the bottom side of the topmost layer of the display mesh.

Item M.6. Item M, in which the material that the individual layers of the display mesh are fabricated from are oxygen permeable.

Item M.7. Item M, in which the material that the individual layers of the display mesh are fabricated from are not oxygen permeable, such that when all the layers have been bonded together, the interior of the display mesh is hermetically sealed.

What is claimed is:

1. An eye mounted display, comprising:
   a contact lens; and
   a plurality of image projectors mounted in the contact lens, each image projector comprising:
   a display element that produces an image; and
   non-folded optics that project the image from the display element onto a retina of a user wearing the contact lens, where the image projector has an in-line optical design; and
   where each of the display elements produces a different image.

2. The eye-mounted display of claim 1 where the image projector has a thickness of not more than 0.5 mm.

3. The eye-mounted display of claim 1 where the image projector has a volume of not more than 0.5 mm×0.5 mm×0.5 mm.

4. The eye-mounted display of claim 1 where the non-folded optics are constructed from at least two layers, each layer including a portion of the non-folded optics for more than one of the image projectors.

5. The eye-mounted display of claim 1 where the image projectors are cylindrically shaped and inserted into the contact lens.

6. The eye-mounted display of claim 1 where the image projectors comprise at least two different optical designs.

7. The eye-mounted display of claim 1 where the plurality of image projectors are peripheral image projectors, and the eye-mounted display further comprises one or more foveal image projectors, the foveal and peripheral image projectors cooperating to tile the retina with projected images, the foveal image projectors projecting images onto the retina with a higher resolution than the peripheral image projectors.

8. The eye-mounted display of claim 1 where the images projected by the image projectors onto the retina are tiled according to a hexagonal tiling.

9. The eye-mounted display of claim 1 where the plurality of image projectors are foveal image projectors, and the eye-mounted display further comprises multiple peripheral image projectors, the foveal and peripheral image projectors cooperating to tile the retina with projected images.

10. The eye-mounted display of claim 1 where the non-folded optics has an optical axis that is perpendicular to a curvature of the contact lens.

11. The eye-mounted display of claim 1 where the non-folded optics comprise one or more refractive lens elements.

12. The eye-mounted display of claim 11 where the non-folded optics further comprises an exit window.

13. The eye-mounted display of claim 11 where the refractive lens element is formed from one of diamond, silicon nitride, titanium dioxide, quartz and sapphire.

14. The eye-mounted display of claim 11 where the refractive lens element is injection molded.

15. The eye-mounted display of claim 11 where the image projector further comprises a housing in which the display element is mounted.

16. The eye-mounted display of claim 13 where the housing is a blackened housing.

17. The eye-mounted display of claim 1 where the non-folded optics comprises a negative lens element and a positive lens element.

18. The eye-mounted display of claim 1 where the display element comprises a wafer thinned die.

19. The eye-mounted display of claim 1 where the display element comprises a wafer thinned die with a thickness of not more than 20 microns.

* * * * *